(12) United States Patent
Yeung et al.

(10) Patent No.: US 9,738,653 B2
(45) Date of Patent: Aug. 22, 2017

(54) FUSED FURANS FOR THE TREATMENT OF HEPATITIS C

(71) Applicant: BRISTOL-MYERS SQUIBB COMPANY, Princeton, NJ (US)

(72) Inventors: Kap-Sun Yeung, Madison, CT (US); Kyle J. Eastman, Killingworth, CT (US); Kyle E. Parcella, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/773,123

(22) PCT Filed: Mar. 12, 2014

(86) PCT No.: PCT/US2014/024181
§ 371 (c)(1),
(2) Date: Sep. 4, 2015

(87) PCT Pub. No.: WO2014/159559
PCT Pub. Date: Oct. 2, 2014

(65) Prior Publication Data
US 2016/0024103 A1   Jan. 28, 2016

Related U.S. Application Data

(60) Provisional application No. 61/784,180, filed on Mar. 14, 2013.

(51) Int. Cl.
   *C07D 491/048* (2006.01)
   *C07D 491/04* (2006.01)
   *C07D 307/84* (2006.01)

(52) U.S. Cl.
   CPC ....... *C07D 491/048* (2013.01); *C07D 307/84* (2013.01); *C07D 491/04* (2013.01)

(58) Field of Classification Search
   None
   See application file for complete search history.

(56) References Cited

U.S. PATENT DOCUMENTS 7,994,171 B2 *  8/2011  Yeung ............... C07D 307/84
                                                 514/252.01
8,048,887 B2    11/2011 Yeung et al.

OTHER PUBLICATIONS

Stepan "Application of the Bicyclo[1.1.1]pentane Motif as a Nonclassical Phenyl Ring Bioisostere in the Design of a Potent and Orally Active γ-Secretase Inhibitor." J. Med. Chem. 2012, 55, 3414-3424.*

* cited by examiner

*Primary Examiner* — David K O'Dell
(74) *Attorney, Agent, or Firm* — James Epperson

(57) ABSTRACT

The disclosure provides compounds of formula I or II, including their salts, as well as compositions and methods of using the compounds. The compounds have activity against hepatitis C virus (HCV) and may be useful in treating those infected with HCV.

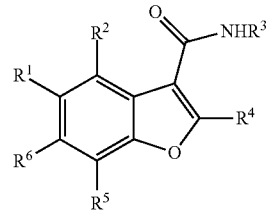

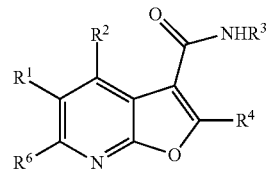

3 Claims, No Drawings

FUSED FURANS FOR THE TREATMENT OF HEPATITIS C

CROSS-REFERENCE TO RELATED APPLICATIONS

This application claims priority to U.S. Provisional Patent Application 61/784,180, filed Mar. 14, 2013, hereby incorporated by reference in its entirety.

BACKGROUND OF THE INVENTION

The disclosure generally relates to the novel compounds of formula I, including their salts, which have activity against hepatitis C virus (HCV) and are useful in treating those infected with HCV. The disclosure also relates to compositions and methods of using these compounds.

Hepatitis C virus (HCV) is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma (Lauer, G. M.; Walker, B. D. *N. Engl. J. Med.* 2001, 345, 41-52).

HCV is a positive-stranded RNA virus. Based on a comparison of the deduced amino acid sequence and the extensive similarity in the 5'-untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B (also referred to as HCV polymerase) is a RNA-dependent RNA polymerase that is involved in the replication of HCV. The HCV NS5B protein is described in "Structural Analysis of the Hepatitis C Virus RNA Polymerase in Complex with Ribonucleotides (Bressanelli; S. et al., *Journal of Virology* 2002, 3482-3492; and Defrancesco and Rice, *Clinics in Liver Disease* 2003, 7, 211-242.

Currently, the most effective HCV therapy employs a combination of alpha-interferon and ribavirin, leading to sustained efficacy in 40% of patients (Poynard, T. et al. *Lancet* 1998, 352, 1426-1432). Recent clinical results demonstrate that pegylated alpha-interferon is superior to unmodified alpha-interferon as monotherapy (Zeuzem, S. et al. *N. Engl. J. Med.* 2000, 343, 1666-1672). However, even with experimental therapeutic regimens involving combinations of pegylated alpha-interferon and ribavirin, a substantial fraction of patients do not have a sustained reduction in viral load. Thus, there is a clear and important need to develop effective therapeutics for treatment of HCV infection.

HCV-796, an HCV NS5B inhibitor, showed an ability to reduce HCV RNA levels in patients. The viral RNA levels decreased transiently and then rebounded during dosing when treatment was with the compound as a single agent but levels dropped more robustly when combined with the standard of care which is a form of interferon and ribavirin. The development of this compound was suspended due to hepatic toxicity observed during extended dosing of the combination regimens. U.S. Pat. No. 7,265,152 and the corresponding PCT patent application WO2004/041201 describe compounds of the HCV-796 class. Other compounds have been disclosed, see for example, WO2009/101022.

The invention provides technical advantages, for example, the compounds are novel and are effective against hepatitis C. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

One aspect of the invention is a compound of formula I or II

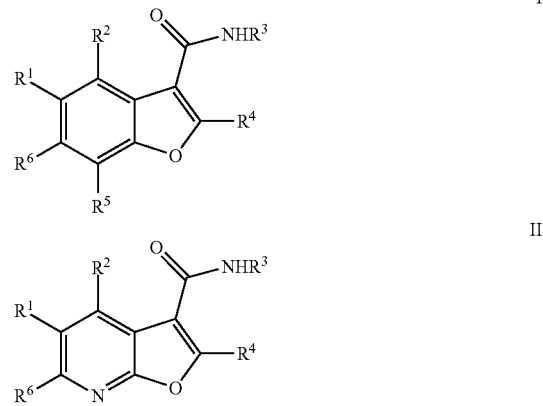

where:
R¹ is cyclohexenyl, phenyl, pyridinyl, or thienyl, and is substituted with 1) CON(R⁹)(R¹⁰) substituent, and is also substituted with 0-3 substituents selected from the group consisting of halo, alkyl, cycloalkyl, haloalkyl, hydroxyalkyl, alkoxyalkyl, alkoxy, cycloalkoxy, hydroxyalkyloxy, and alkoxyalkyloxy;
$R^2$ is hydrogen, halo, alkyl, or alkoxy;
$R^3$ is alkyl;
$R^4$ is phenyl that is independently substituted with 0-2 halo, alkyl, alkoxy, or X—$Ar^1$;
$R^5$ and $R^6$ are independently hydrogen, nitro, halo, alkyl, haloalkyl, hydroxyalkyl, alkoxyalkyl, (benzoyl)alkyl, ($CO_2$ ($R^{11}$))alkyl, (CON($R^{11}$)($R^{12}$))alkyl, ($NHCO_2$($R^{11}$))alkyl, (alkylsulfonyl)alkyl, (alkylsulfonylNH)alkyl, alkoxy, haloalkoxy, nitro, alkylsulfonyl, or N($R^7$)($R^8$);
$R^7$ and $R^8$ are independently hydrogen, alkyl, cyanoalkyl, haloalkyl, (cycloalkyl)alkyl, cycloalkyl, hydroxyalkyl, alkoxyalkyl, alkylcarbonyl, alkoxycarbonyl, haloalkoxycarbonyl, alkylsulfonyl, (alkylsulfonyl)alkyl, or $SO_2$N($R^{11}$)($R^{12}$);
or N($R^7$)($R^8$) taken together is azetidinyl, pyrrolidinyl, piperidinyl, or piperazinyl, and is substituted with 0-2 substituents selected from alkyl, hydroxyalkyl, or hydroxy;
$R^9$ is bicyclo[1.1.1]pentanyl;
$R^{19}$ is hydrogen;
$R^{11}$ is hydrogen or alkyl;
$R^{12}$ is hydrogen or alkyl;
X is —O— or —NH—; and
$Ar^1$ is phenyl or halophenyl;
or a pharmaceutically acceptable salt thereof.
Another aspect of the invention is a compound according to formula I.
Another aspect of the invention is a compound according to formula II.
Another aspect of the invention is a compound of formula I or II where
$R^1$ is phenyl, pyridinyl, or thienyl, and is substituted with 1 CON($R^9$)($R^{10}$) substituent, and is also substituted with 0-3 substituents selected from the group consisting of halo, alkyl, cycloalkyl, haloalkyl, hydroxyalkyl, alkoxyalkyl, alkoxy, cycloalkoxy, hydroxyalkyloxy, and alkoxyalkyloxy;
$R^2$ is hydrogen or halo;
$R^3$ is alkyl;
$R^4$ is halophenyl;
$R^5$ and $R^6$ are independently hydrogen, nitro, halo, alkyl, haloalkyl, hydroxyalkyl, alkoxyalkyl, (benzoyl)alkyl, ($CO_2$ ($R^{11}$))alkyl, (CON($R^{11}$)($R^{12}$))alkyl, ($NHCO_2$($R^{11}$))alkyl, (alkylsulfonyl)alkyl, (alkylsulfonylNH)alkyl, alkoxy, haloalkoxy, nitro, alkylsulfonyl, or N($R^7$)($R^8$);
$R^7$ and $R^8$ are independently hydrogen, alkyl, cyanoalkyl, haloalkyl, (cycloalkyl)alkyl, cycloalkyl, hydroxyalkyl, alkoxyalkyl, alkylcarbonyl, alkoxycarbonyl, haloalkoxycarbonyl, alkylsulfonyl, (alkylsulfonyl)alkyl, or $SO_2$N($R^{11}$)($R^{12}$);
$R^9$ is bicyclo[1.1.1]pentanyl;
$R^{10}$ is hydrogen;
$R^{11}$ is hydrogen or alkyl; and
$R^{12}$ is hydrogen or alkyl;
or a pharmaceutically acceptable salt thereof.
Another aspect of the invention is a compound of formula I where
$R^1$ is phenyl, pyridinyl, or thienyl, and is substituted with 1 CON($R^9$)($R^{10}$) substituent, and is also substituted with 0-3 substituents selected from the group consisting of halo, alkyl, cycloalkyl, haloalkyl, hydroxyalkyl, alkoxyalkyl, alkoxy, cycloalkoxy, hydroxyalkyloxy, and alkoxyalkyloxy;
$R^2$ is hydrogen or halo;
$R^3$ is alkyl;
$R^4$ is halophenyl;

$R^5$ and $R^6$ are independently hydrogen, nitro, halo, alkyl, haloalkyl, hydroxyalkyl, alkoxyalkyl, (benzoyl)alkyl, ($CO_2$ ($R^{11}$))alkyl, (CON($R^{11}$)($R^{12}$))alkyl, ($NHCO_2$($R^{11}$))alkyl, (alkylsulfonyl)alkyl, (alkylsulfonylNH)alkyl, alkoxy, haloalkoxy, nitro, alkylsulfonyl, or N($R^7$)($R^8$);
$R^7$ and $R^8$ are independently hydrogen, alkyl, cyanoalkyl, haloalkyl, (cycloalkyl)alkyl, cycloalkyl, hydroxyalkyl, alkoxyalkyl, alkylcarbonyl, alkoxycarbonyl, haloalkoxycarbonyl, alkylsulfonyl, (alkylsulfonyl)alkyl, or $SO_2$N($R^{11}$)($R^{12}$);
$R^9$ is bicyclo[1.1.1]pentanyl;
$R^{10}$ is hydrogen;
$R^{11}$ is hydrogen or alkyl; and
$R^{12}$ is hydrogen or alkyl;
or a pharmaceutically acceptable salt thereof.
Another aspect of the invention is a compound of formula II where
$R^1$ is phenyl, pyridinyl, or thienyl, and is substituted with 1 CON($R^9$)($R^{10}$) substituent, and is also substituted with 0-3 substituents selected from the group consisting of halo, alkyl, cycloalkyl, haloalkyl, hydroxyalkyl, alkoxyalkyl, alkoxy, cycloalkoxy, hydroxyalkyloxy, and alkoxyalkyloxy;
$R^2$ is hydrogen or halo;
$R^3$ is alkyl;
$R^4$ is halophenyl;
$R^5$ and $R^6$ are independently hydrogen, nitro, halo, alkyl, haloalkyl, hydroxyalkyl, alkoxyalkyl, (benzoyl)alkyl, ($CO_2$ ($R^{11}$))alkyl, (CON($R^{11}$)($R^{12}$))alkyl, ($NHCO_2$($R^{11}$))alkyl, (alkylsulfonyl)alkyl, (alkylsulfonylNH)alkyl, alkoxy, haloalkoxy, nitro, alkylsulfonyl, or N($R^7$)($R^8$);
$R^7$ and $R^8$ are independently hydrogen, alkyl, cyanoalkyl, haloalkyl, (cycloalkyl)alkyl, cycloalkyl, hydroxyalkyl, alkoxyalkyl, alkylcarbonyl, alkoxycarbonyl, haloalkoxycarbonyl, alkylsulfonyl, (alkylsulfonyl)alkyl, or $SO_2$N($R^{11}$)($R^{12}$);
$R^9$ is bicyclo[1.1.1]pentanyl;
$R^{10}$ is hydrogen;
$R^{11}$ is hydrogen or alkyl; and
$R^{12}$ is hydrogen or alkyl;
or a pharmaceutically acceptable salt thereof.
Another aspect of the invention is a compound of formula I or II where $R^1$ is phenyl, pyridinyl, or thienyl, and is substituted with 1 CON($R^9$)($R^{10}$) substituent, and is also substituted with 0-3 substituents selected from the group consisting of halo, alkyl, cycloalkyl, haloalkyl, hydroxyalkyl, alkoxyalkyl, alkoxy, cycloalkoxy, hydroxyalkyloxy, and alkoxyalkyloxy.
Another aspect of the invention is a compound of formula I where $R^1$ is phenyl, pyridinyl, or thienyl, and is substituted with 1 CON($R^9$)($R^{10}$) substituent, and is also substituted with 0-3 substituents selected from the group consisting of halo, alkyl, cycloalkyl, haloalkyl, hydroxyalkyl, alkoxyalkyl, alkoxy, cycloalkoxy, hydroxyalkyloxy, and alkoxyalkyloxy.
Another aspect of the invention is a compound of formula II where $R^1$ is phenyl, pyridinyl, or thienyl, and is substituted with 1 CON($R^9$)($R^{10}$) substituent, and is also substituted with 0-3 substituents selected from the group consisting of halo, alkyl, cycloalkyl, haloalkyl, hydroxyalkyl, alkoxyalkyl, alkoxy, cycloalkoxy, hydroxyalkyloxy, and alkoxyalkyloxy.
Another aspect of the invention is a compound of formula I or II where $R^5$ and $R^6$ are independently hydrogen, nitro, halo, alkyl, haloalkyl, hydroxyalkyl, alkoxyalkyl, (benzoyl) alkyl, ($CO_2$($R^{11}$))alkyl, (CON($R^{11}$)($R^{12}$))alkyl, ($NHCO_2$ ($R^{11}$))alkyl, (alkylsulfonyl)alkyl, (alkylsulfonylNH)alkyl, alkoxy, haloalkoxy, nitro, alkylsulfonyl, or N($R^7$)($R^8$) and $R^7$ and $R^8$ are independently hydrogen, alkyl, cyanoalkyl, haloalkyl, (cycloalkyl)alkyl, cycloalkyl, hydroxyalkyl, alkoxyalkyl, alkylcarbonyl, alkoxycarbonyl, haloalkoxycarbonyl, alkylsulfonyl, (alkylsulfonyl)alkyl, or $SO_2N(R^{11})(R^{12})$.

Another aspect of the invention is a compound of formula I where $R^5$ and $R^6$ are independently hydrogen, nitro, halo, alkyl, haloalkyl, hydroxyalkyl, alkoxyalkyl, (benzoyl)alkyl, $(CO_2(R^{11}))$alkyl, $(CON(R^{11})(R^{12}))$alkyl, $(NHCO_2(R^{11}))$alkyl, (alkylsulfonyl)alkyl, (alkylsulfonylNH)alkyl, alkoxy, haloalkoxy, nitro, alkylsulfonyl, or $N(R^7)(R^8)$ and $R^7$ and $R^8$ are independently hydrogen, alkyl, cyanoalkyl, haloalkyl, (cycloalkyl)alkyl, cycloalkyl, hydroxyalkyl, alkoxyalkyl, alkylcarbonyl, alkoxycarbonyl, haloalkoxycarbonyl, alkylsulfonyl, (alkylsulfonyl)alkyl, or $SO_2N(R^{11})(R^{12})$.

Another aspect of the invention is a compound of formula II where $R^5$ and $R^6$ are independently hydrogen, nitro, halo, alkyl, haloalkyl, hydroxyalkyl, alkoxyalkyl, (benzoyl)alkyl, $(CO_2(R^{11}))$alkyl, $(CON(R^{11})(R^{12}))$alkyl, $(NHCO_2(R^{11}))$alkyl, (alkylsulfonyl)alkyl, (alkylsulfonylNH)alkyl, alkoxy, haloalkoxy, nitro, alkylsulfonyl, or $N(R^7)(R^8)$ and $R^7$ and $R^8$ are independently hydrogen, alkyl, cyanoalkyl, haloalkyl, (cycloalkyl)alkyl, cycloalkyl, hydroxyalkyl, alkoxyalkyl, alkylcarbonyl, alkoxycarbonyl, haloalkoxycarbonyl, alkylsulfonyl, (alkylsulfonyl)alkyl, or $SO_2N(R^{11})(R^{12})$.

Any scope of any variable, including $R^1$, $R^2$, $R^3$, $R^4$, $R^5$, $R^6$, $R^7$, $R^8$, $R^9$, $R^{10}$, $R^{11}$, $R^{12}$, X, and, $Ar^1$, can be used independently with the scope of any other instance of a variable.

Unless specified otherwise, these terms have the following meanings "Halo" means fluoro, chloro, bromo, or iodo. "Alkyl" means a straight or branched alkyl group composed of 1 to 6 carbons. "Alkenyl" means a straight or branched alkyl group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Halo" includes all halogenated isomers from monohalo substituted to perhalo substituted in substituents defined with halo, for example, "Haloalkyl" and "haloalkoxy", "halophenyl", "halophenoxy." Ethylene means ethanediyl or $—CH_2CH_2—$; propylene means propanediyl or $—CH_2CH_2CH_2—$; butylene means butanediyl or $—CH_2CH_2CH_2CH_2—$; pentylene means pentanediyl or $—CH_2CH_2CH_2CH_2CH_2—$. "Aryl" means a monocyclic or bicyclic aromatic hydrocarbon groups having 6 to 12 carbon atoms, or a bicyclic fused ring system wherein one or both of the rings is a phenyl group. Bicyclic fused ring systems consist of a phenyl group fused to a four- to six-membered aromatic or non-aromatic carbocyclic ring. Representative examples of aryl groups include, but are not limited to, indanyl, indenyl, naphthyl, phenyl, and tetrahydronaphthyl. "Heteroaryl" means a 5 to 7 membered monocyclic or 8 to 11 membered bicyclic aromatic ring system with 1-5 heteroatoms independently selected from nitrogen, oxygen, and sulfur. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, camsylate, chloride, citrate, fumarate, glucuronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention possess asymmetric carbon atoms. The invention includes all stereoisomeric forms, including enantiomers and diastereomers as well as mixtures of stereoisomers such as racemates. Some stereoisomers can be made using methods known in the art. Stereoisomeric mixtures of the compounds and related intermediates can be separated into individual isomers according to methods commonly known in the art. The use of wedges or hashes in the depictions of molecular structures in the following schemes and tables is intended only to indicate relative stereochemistry, and should not be interpreted as implying absolute stereochemical assignments.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Pharmaceutical Compositions and Methods of Treatment

The compounds demonstrate activity against HCV NS5B and can be useful in treating HCV and HCV infection. Therefore, another aspect of the invention is a composition comprising a compound, or a pharmaceutically acceptable salt thereof, and a pharmaceutically acceptable carrier.

Another aspect of the invention is a composition further comprising a compound having anti-HCV activity.

Another aspect of the invention is a composition where the compound having anti-HCV activity is an interferon or a ribavirin. Another aspect of the invention is where the interferon is selected from interferon alpha 2B, pegylated interferon alpha, consensus interferon, interferon alpha 2A, interferon lambda, and lymphoblastoid interferon tau.

Another aspect of the invention is a composition where the compound having anti-HCV activity is a cyclosporin. Another aspect of the invention is where the cyclosporin is cyclosporin A.

Another aspect of the invention is a composition where the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is a composition where the compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is a composition comprising a compound, or a pharmaceutically acceptable salt thereof, a pharmaceutically acceptable carrier, an interferon and ribavirin.

Another aspect of the invention is a method of inhibiting the function of the HCV replicon comprising contacting the HCV replicon with a compound or a pharmaceutically acceptable salt thereof.

Another aspect of the invention is a method of inhibiting the function of the HCV NS5B protein comprising contacting the HCV NS5B protein with a compound or a pharmaceutically acceptable salt thereof.

Another aspect of the invention is a method of treating an HCV infection in a patient comprising administering to the patient a therapeutically effective amount of a compound or a pharmaceutically acceptable salt thereof. In another embodiment the compound is effective to inhibit the function of the HCV replicon. In another embodiment the compound is effective to inhibit the function of the HCV NS5B protein.

Another aspect of the invention is a method of treating an HCV infection in a patient comprising administering to the patient a therapeutically effective amount of a compound, or a pharmaceutically acceptable salt thereof, in conjunction with (prior to, after, or concurrently) another compound having anti-HCV activity.

Another aspect of the invention is the method where the other compound having anti-HCV activity is an interferon or a ribavirin.

Another aspect of the invention is the method where the interferon is selected from interferon alpha 2B, pegylated interferon alpha, consensus interferon, interferon alpha 2A, interferon lambda, and lymphoblastoid interferon tau.

Another aspect of the invention is the method where the other compound having anti-HCV activity is a cyclosporin.

Another aspect of the invention is the method where the cyclosporin is cyclosporin A.

Another aspect of the invention is the method where the other compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is the method where the other compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is the method where the other compound having anti-HCV activity is effective to inhibit the function of target in the HCV life cycle other than the HCV NS5B protein.

"Therapeutically effective" means the amount of agent required to provide a meaningful patient benefit as understood by practitioners in the field of hepatitis and HCV infection.

"Patient" means a person infected with the HCV virus and suitable for therapy as understood by practitioners in the field of hepatitis and HCV infection.

"Treatment," "therapy," "regimen," "HCV infection," and related terms are used as understood by practitioners in the field of hepatitis and HCV infection.

The compounds of this invention are generally given as pharmaceutical compositions comprised of a therapeutically effective amount of a compound or its pharmaceutically acceptable salt and a pharmaceutically acceptable carrier and may contain conventional excipients. Pharmaceutically acceptable carriers are those conventionally known carriers having acceptable safety profiles. Compositions encompass all common solid and liquid forms including for example capsules, tablets, lozenges, and powders as well as liquid suspensions, syrups, elixirs, and solutions. Compositions are made using common formulation techniques, and conventional excipients (such as binding and wetting agents) and vehicles (such as water and alcohols) are generally used for compositions. See, for example, *Remington's Pharmaceutical Sciences*, Mack Publishing Company, Easton, Pa., 17th edition, 1985.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regimen, however, will be determined by a physician using sound medical judgment.

The invention also encompasses methods where the compound is given in combination therapy. That is, the compound can be used in conjunction with, but separately from, other agents useful in treating hepatitis and HCV infection. In these combination methods, the compound will generally be given in a daily dose of 1-100 mg/kg body weight daily in conjunction with other agents. The other agents generally will be given in the amounts used therapeutically. The specific dosing regimen, however, will be determined by a physician using sound medical judgment.

Some examples of compounds suitable for compositions and methods are listed in Table 1.

TABLE 1

| Brand Name | Physiological Class | Type of Inhibitor or Target | Source Company |
|---|---|---|---|
| NIM811 | | Cyclophilin Inhibitor | Novartis |
| Zadaxin | | Immuno-modulator | Sciclone |
| Suvus | | Methylene blue | Bioenvision |
| Actilon (CPG10101) | | TLR9 agonist | Coley |

TABLE 1-continued

| Brand Name | Physiological Class | Type of Inhibitor or Target | Source Company |
|---|---|---|---|
| Batabulin (T67) | Anticancer | β-tubulin inhibitor | Tularik Inc., South San Francisco, CA |
| ISIS 14803 | Antiviral | antisense | ISIS Pharmaceuticals Inc, Carlsbad, CA/Elan Pharmaceuticals Inc., New York, NY |
| Summetrel | Antiviral | antiviral | Endo Pharmaceuticals Holdings Inc., Chadds Ford, PA |
| GS-9132 (ACH-806) | Antiviral | HCV Inhibitor | Achillion/Gilead |
| Pyrazolopyrimidine compounds and salts From WO-2005047288 26 May 2005 | Antiviral | HCV Inhibitors | Arrow Therapeutics Ltd. |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | monoclonal antibody | XTL Biopharmaceuticals Ltd., Rehovot, Isreal |
| Telaprevir (VX-950, LY-570310) | Antiviral | NS3 serine protease inhibitor | Vertex Pharmaceuticals Inc., Cambridge, MA/Eli Lilly and Co. Inc., Indianapolis, IN |
| HCV-796 | Antiviral | NS5B Replicase Inhibitor | Wyeth/Viropharma |
| NM-283 | Antiviral | NS5B Replicase Inhibitor | Idenix/Novartis |
| GL-59728 | Antiviral | NS5B Replicase Inhibitor | Gene Labs/Novartis |
| GL-60667 | Antiviral | NS5B Replicase Inhibitor | Gene Labs/Novartis |
| 2'C MeA | Antiviral | NS5B Replicase Inhibitor | Gilead |
| PSI 6130 | Antiviral | NS5B Replicase Inhibitor | Roche |
| R1626 | Antiviral | NS5B Replicase Inhibitor | Roche |
| 2'C Methyl adenosine | Antiviral | NS5B Replicase Inhibitor | Merck |
| JTK-003 | Antiviral | RdRp inhibitor | Japan Tobacco Inc., Tokyo, Japan |
| Levovirin | Antiviral | ribavirin | ICN Pharmaceuticals, Costa Mesa, CA |
| Ribavirin | Antiviral | ribavirin | Schering-Plough Corporation, Kenilworth, NJ |
| Viramidine | Antiviral | Ribavirin Prodrug | Ribapharm Inc., Costa Mesa, CA |
| Heptazyme | Antiviral | ribozyme | Ribozyme Pharmaceuticals Inc., Boulder, CO |
| BILN-2061 | Antiviral | serine protease inhibitor | Boehringer Ingelheim Pharma KG, Ingelheim, Germany |
| SCH 503034 | Antiviral | serine protease inhibitor | Schering Plough |
| Zadazim | Immune modulator | Immune modulator | SciClone Pharmaceuticals Inc., San Mateo, CA |

TABLE 1-continued

| Brand Name | Physiological Class | Type of Inhibitor or Target | Source Company |
|---|---|---|---|
| Ceplene | Immunomodulator | immune modulator | Maxim Pharmaceuticals Inc., San Diego, CA |
| CellCept | Immunosuppressant | HCV IgG immunosuppressant | F. Hoffmann-La Roche LTD, Basel, Switzerland |
| Civacir | Immunosuppressant | HCV IgG immunosuppressant | Nabi Biopharmaceuticals Inc., Boca Raton, FL |
| Albuferon - α | Interferon | albumin IFN-α2b | Human Genome Sciences Inc., Rockville, MD |
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| Rebif | Interferon | IFN-β1a | Serono, Geneva, Switzerland |
| Roferon A | Interferon | IFN-α2a | F. Hoffmann-La Roche LTD, Basel, Switzerland |
| Intron A | Interferon | IFN-α2b | Schering-Plough Corporation, Kenilworth, NJ |
| Intron A and Zadaxin | Interferon | IFN-α2b/α1-thymosin | RegeneRx Biopharma. Inc., Bethesda, MD/ SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/ Valentis |
| Wellferon | Interferon | Lympho-blastoid IFN-αn1 | Glaxo SmithKline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |
| Pegasys and Ceplene | Interferon | PEGylated IFN-α2a/ immune modulator | Maxim Pharmaceuticals Inc., San Diego, CA |
| Pegasys and Ribavirin | Interferon | PEGylated IFN-α2a/ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/ Ribavirin | Interferon | PEGylated IFN-α2b/ribavirin | Schering-Plough Corporation, Kenilworth, NJ |
| IP-501 | Liver protection | antifibrotic | Indevus Pharmaceuticals Inc., Lexington, MA |
| IDN-6556 | Liver protection | caspase inhibitor | Idun Pharmaceuticals Inc., San Diego, CA |
| ITMN-191 (R-7227) | Antiviral | serine protease inhibitor | InterMune Pharmaceuticals Inc., Brisbane, CA |
| GL-59728 | Antiviral | NS5B Replicase Inhibitor | Genelabs |

TABLE 1-continued

| Brand Name | Physiological Class | Type of Inhibitor or Target | Source Company |
| --- | --- | --- | --- |
| ANA-971 | Antiviral | TLR-7 agonist | Anadys |
| Boceprevir | Antiviral | serine protease inhibitor | Schering Plough |
| TMS-435 | Antiviral | serine protease inhibitor | Tibotec BVBA, Mechelen, Belgium |
| BI-201335 | Antiviral | serine protease inhibitor | Boehringer Ingelheim Pharma KG, Ingelheim, Germany |
| MK-7009 | Antiviral | serine protease inhibitor | Merck |
| PF-00868554 | Antiviral | replicase inhibitor | Pfizer |
| ANA598 | Antiviral | Non-Nucleoside NS5B Polymerase Inhibitor | Anadys Pharmaceuticals, Inc., San Diego, CA, USA |
| IDX375 | Antiviral | Non-Nucleoside Replicase Inhibitor | Idenix Pharmaceuticals, Cambridge, MA, USA |
| BILB 1941 | Antiviral | NS5B Polymerase Inhibitor | Boehringer Ingelheim Canada Ltd R&D, Laval, QC, Canada |
| PSI-7851 | Antiviral | Nucleoside Polymerase Inhibitor | Gilead (formerly from Pharmasset) |
| PSI-7977 sofosbuvir | Antiviral | Nucleotide NS5B Polymerase Inhibitor | Gilead (formerly from Pharmasset) |
| VCH-759 | Antiviral | NS5B Polymerase Inhibitor | ViroChem Pharma |
| VCH-916 | Antiviral | NS5B Polymerase Inhibitor | ViroChem Pharma |
| GS-9190 | Antiviral | NS5B Polymerase Inhibitor | Gilead |
| Peg-interferon lamda | Antiviral | Interferon | ZymoGenetics/Bristol-Myers Squibb |
| asunaprevir | Antiviral | serine protease inhibitor | Bristol-Myers Squibb |
| BMS-791325 | Antiviral | NS5B Polymerase Inhibitor | Bristol-Myers Squibb |
| daclatasvir | Antiviral | HCV NS5A replication complex inhibitor | Bristol-Myers Squibb |
| GS-5885 | Antiviral | HCV NS5A replication complex inhibitor | Gilead |

Synthetic Methods

The compounds may be made by methods known in the art including those described below. Some reagents and intermediates are known in the art. Other reagents and intermediates can be made by methods known in the art using commercially available materials. The variables (e.g. numbered "R" substituents) used to describe the synthesis of the compounds are intended only to illustrate how to make and are not to be confused with variables used in the claims or in other sections of the specification. Abbreviations used within the schemes generally follow conventions used in the art.

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "DMSO" for dimethylsulfoxide; "h" for hours; "rt" or "RT" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine; TEA for triethylamine; DCM for dichloromethane Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "A" for microliter or microliters, "N" for normal, "M" for molar, "mmol" for millimole or millimoles, "min" for minute or minutes, "h" for hour or hours, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "¹H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Methods- to prepare compounds of the invention are shown below.

DESCRIPTION OF SPECIFIC EMBODIMENTS

Experimentals for Benzofuran [1.1.1]-Amides

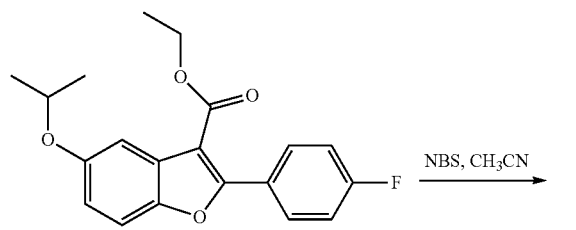

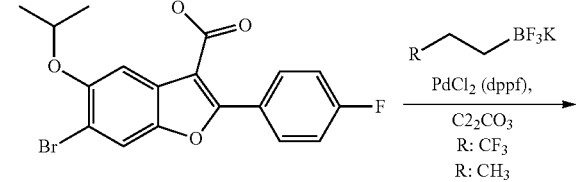

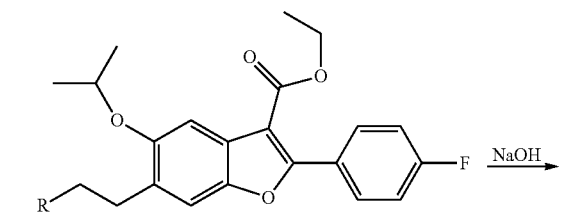

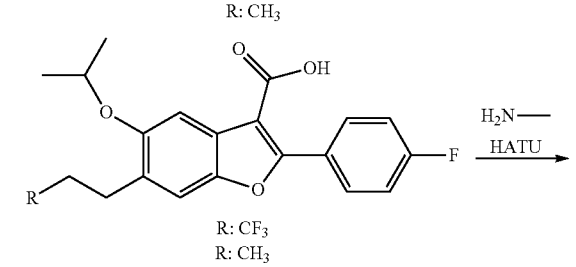

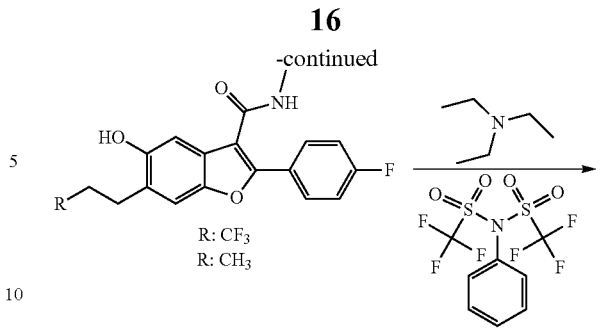

Ethyl 6-bromo-2-(4-fluorophenyl)-5-isopropoxybenzofuran-3-carboxylate

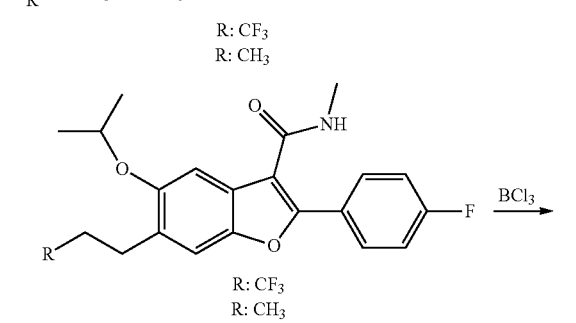

N-Bromosuccinimide (624 mg, 3.51 mmol) was added to a solution of ethyl 2-(4-fluorophenyl)-5-isopropoxybenzofuran-3-carboxylate (1000 mg, 2.92 mmol) in acetonitrile (100 mL). The mixture was stirred at room temperature for 19 hrs. The solvent was removed and the residue was purified by column chromatography (Biotage 25 s, $CH_2Cl_2$/Hexane=0 to 20%) to give 764 mg (62%) of the target compound.

¹H NMR (500 MHz, CHLOROFORM-d) δ 8.05 (dd, J=8.9, 5.4 Hz, 2H), 7.75 (s, 1H), 7.64 (s, 1H), 7.20 (t, J=8.7 Hz, 2H), 4.45-4.45 (m, 1H), 4.42 (q, J=7.1 Hz, 2H), 1.53-1.36 (m, 9H).

$R_t$ (retention time)=4.545 min., m/z 421 (M+H).

The LC/MS data was obtained on a Shimadzu analytical LC/Micromass Platform LC (ESI+) at 220 nm using The following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute. LCMS

Ethyl 2-(4-fluorophenyl)-5-isopropoxy-6-(3,3,3-trifluoropropyl)benzofuran-3-carboxylate

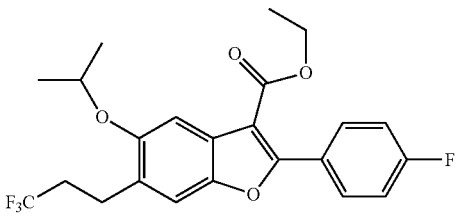 [SMILES: CCOC(=O)c1c(-c2ccc(F)cc2)oc2cc(CCC(F)(F)F)c(OC(C)C)cc12]

A mixture of ethyl 6-bromo-2-(4-fluorophenyl)-5-isopropoxybenzofuran-3-carboxylate (1.14 g, 2.71 mmol), potassium trifluoro(3,3,3-trifluoropropyl)borate (0.828 g, 4.06 mmol), $PdCl_2$(dppf) (0.297 g, 0.406 mmol) and cesium carbonate (3.97 g, 12.18 mmol) in toluene (40 mL) and water (13 mL) was flushed with $N_2$ and then stirred at 90° C. for 4 hrs, and then at room temperature overnight. The mixture was diluted with $CH_2Cl_2$ and filtered. The solution was washed with water and brine, and concentrated. The residue was purified by column chromatography (Biotage 25 m, $CH_2Cl_2$/Hexane=0 to 20%) to give 0.988 g (83%) of the product as an off white solid.

$^1$H NMR (400 MHz, CHLOROFORM-d) δ 8.09-8.01 (m, 2H), 7.54 (s, 1H), 7.32 (s, 1H), 7.23-7.15 (m, 2H), 4.75-4.63 (m, 1H), 4.42 (q, J=7.1 Hz, 2H), 3.02-2.94 (m, 2H), 2.53-2.37 (m, 2H), 1.50-1.39 (m, 9H).

LCMS $R_t$=4.626 min., m/z 439 (M+H).

The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

Ethyl 2-(4-fluorophenyl)-5-isopropoxy-6-propylbenzofuran-3-carboxylate

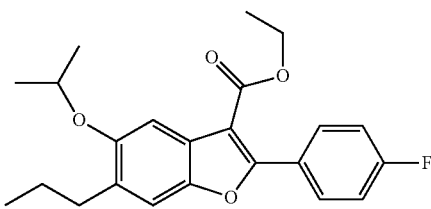 [SMILES: CCCc1cc2oc(-c3ccc(F)cc3)c(C(=O)OCC)c2cc1OC(C)C]

Ethyl 2-(4-fluorophenyl)-5-isopropoxy-6-propylbenzofuran-3-carboxylate was prepared by using the same methodology for ethyl 2-(4-fluorophenyl)-5-isopropoxy-6-(3,3,3-trifluoropropyl)benzofuran-3-carboxylate, from ethyl 6-bromo-2-(4-fluorophenyl)-5-isopropoxybenzofuran-3-carboxylate (1.5 g, 3.56 mmol) and potassium trifluoro(propyl)borate (0.801 g, 5.34 mmol). The product was isolated in 88% yield (1.20 g) as an off white solid.

$^1$H NMR (400 MHz, CHLOROFORM-d) δ 8.08-8.01 (m, 2H), 7.52 (s, 1H), 7.30 (s, 1H), 7.18 (t, J=8.7 Hz, 2H), 4.64 (m, 1H), 4.42 (q, J=7.2 Hz, 2H), 2.75-2.68 (m, 2H), 1.75-1.64 (m, 2H), 1.49-1.40 (m, 9H), 1.00 (t, J=7.4 Hz, 3H).

LCMS $R_t$=4.868 min., m/z 385 (M+H).

The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

2-(4-Fluorophenyl)-5-isopropoxy-6-(3,3,3-trifluoropropyl)benzofuran-3-carboxylic acid

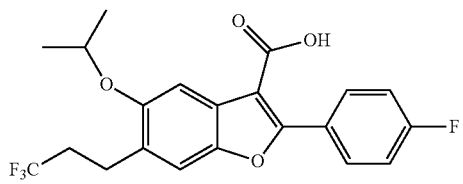

A 1M solution of sodium hydroxide (6.76 mL, 6.76 mmol) was added into a solution of ethyl 2-(4-fluorophenyl)-5-isopropoxy-6-(3,3,3-trifluoropropyl)benzofuran-3-carboxylate (988 mg, 2.254 mmol) in a mixture of MeOH (10 mL) and THF (10 mL). The mixture was stirred with gentle heating overnight at 40° C. The mixture was cooled to 0° C. and ice cold 1M HCl (10 mL) was added. The resulting yellow solid was filtered, washed with water and dried to obtain 830 mg (90%) of the target compound.

$^1$H NMR (400 MHz, CHLOROFORM-d) δ 8.10-8.03 (m, 2H), 7.57 (s, 1H), 7.35 (s, 1H), 7.21 (t, J=8.8 Hz, 2H), 4.75 (m, 1H), 3.03-2.95 (m, 2H), 2.46 (m, 2H), 1.44 (d, J=6.0 Hz, 6H).

LCMS $R_t$=4.020 min., m/z 411 (M+H).

The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

2-(4-Fluorophenyl)-5-isopropoxy-6-propylbenzofuran-3-carboxylic acid

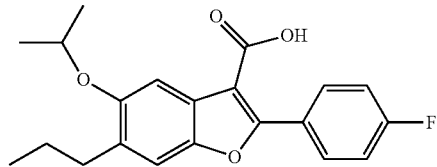 [SMILES: CCCc1cc2oc(-c3ccc(F)cc3)c(C(=O)O)c2cc1OC(C)C]

2-(4-Fluorophenyl)-5-isopropoxy-6-propylbenzofuran-3-carboxylic acid was prepared by using the same methodology for 2-(4-fluorophenyl)-5-isopropoxy-6-(3,3,3-trifluoropropyl)benzofuran-3-carboxylic acid from ethyl 2-(4-fluorophenyl)-5-isopropoxy-6-propylbenzofuran-3-carboxylate (1.2 g, 3.12 mmol). The product was isolated in 99% yield (1.112 g) as an off white solid.

$^1$H NMR (400 MHz, CHLOROFORM-d) δ 8.10-8.03 (m, 2H), 7.56 (s, 1H), 7.33 (s, 1H), 7.21 (m, 2H), 4.71 (m, 1H), 2.76-2.69 (m, 2H), 1.76-1.64 (m, 2H), 1.42 (d, J=6.0 Hz, 6H), 1.01 (t, J=7.3 Hz, 3H).

LCMS $R_t$=4.223 min., m/z 357 (M+H).

The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

2-(4-fluorophenyl)-5-isopropoxy-N-methyl-6-(3,3,3-trifluoropropyl)benzofuran-3-carboxamide

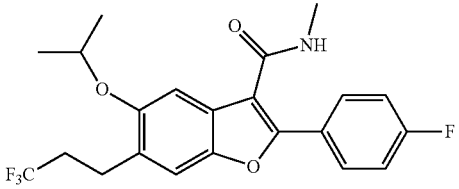

2-(3H-[1,2,3]triazolo[4,5-b]pyridin-3-yl)-1,1,3,3-tetramethylisouronium hexafluorophosphate(V) (1230 mg, 3.24 mmol) was added to a solution of 2-(4-fluorophenyl)-5-isopropoxy-6-(3,3,3-trifluoropropyl)benzofuran-3-carboxylic acid (830 mg, 2.023 mmol), methanamine hydrochloride (205 mg, 3.03 mmol) and N-ethyl-N-isopropylpropan-2-amine (1.762 mL, 10.11 mmol) in DMF (25 mL). The reaction mixture was stirred at rt for 2 hrs, and then added with 100 g of ice-water. The solid was filtered, washed with water, and died to give 843 mg (95%) of the crude product.

$^1$H NMR (500 MHz, CHLOROFORM-d) δ 7.90-7.85 (m, 2H), 7.33 (s, 1H), 7.31 (s, 1H), 7.24-7.17 (m, 2H), 5.81-5.72 (br, 1H), 4.74-4.66 (m, 1H), 3.01 (d, J=4.9 Hz, 3H), 2.99-2.94 (m, 2H), 2.50-2.38 (m, 2H), 1.40 (d, J=6.0 Hz, 6H).

LCMS $R_t$=3.881 min., m/z 424 (M+H).

The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

2-(4-Fluorophenyl)-5-isopropoxy-N-methyl-6-propylbenzofuran-3-carboxamide

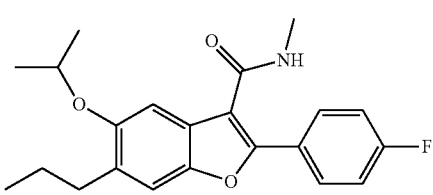 [SMILES: CCCc1cc2oc(-c3ccc(F)cc3)c(C(=O)NC)c2cc1OC(C)C]

2-(4-Fluorophenyl)-5-isopropoxy-N-methyl-6-propylbenzofuran-3-carboxamide was prepared by using the same methodology for the 6-(3,3,3-trifluoropropyl) analog from 2-(4-Fluorophenyl)-5-isopropoxy-6-propylbenzofuran-3-carboxylic acid (1.1 g, 3.09 mmol). The crude product was isolated in 96% yield (1.14 g).

$^1$H NMR (400 MHz, CHLOROFORM-d) δ 7.93-7.86 (m, 2H), 7.29 (s, 2H)), 7.19 (t, J=8.7 Hz, 2H), 5.77 (br. s., 1H), 4.68-4.60 (m, 1H), 3.01 (d, J=4.8 Hz, 3H), 2.74-2.67 (m, 2H), 1.74-1.62 (m, 2H), 1.39 (d, J=6.0 Hz, 6H), 0.99 (t, J=7.4 Hz, 3H).

LCMS $R_t$=4.088 min., m/z 370 (M+H).

The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

2-(4-Fluorophenyl)-5-hydroxy-N-methyl-6-(3,3,3-trifluoropropyl)benzofuran-3-carboxamide

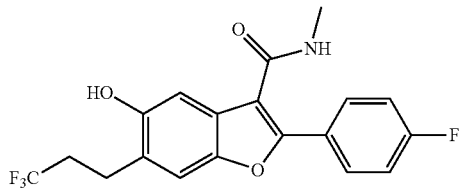 [SMILES: CNC(=O)c1c(-c2ccc(F)cc2)oc2cc(CCC(F)(F)F)c(O)cc12]

Trichloroborane (5.97 mL, 5.97 mmol) in DCM (25 mL) was added dropwise to a solution of 2-(4-fluorophenyl)-5-isopropoxy-N-methyl-6-(3,3,3-trifluoropropyl)benzofuran-3-carboxamide (843 mg, 1.991 mmol) in DCM (100 mL) at 0° C. for 20 min. The reaction mixture was stirred for 0.5 h slowly reaching to rt. The mixture was continued stirred overnight. Methanol (15 mL) was added dropwise to the reaction mixture at 0° C., upon which the red suspension turned to yellow solution. The solvent was removed, and methanol (50 mL×2) was added to the residue respectively. The solvent was removed, and 775 mg (crude, 102%) of the compound as a yellow solid was yielded.

$^1$H NMR (400 MHz, DMSO-$d_6$) δ 9.63 (s, 1H), 8.37 (m, 1H), 7.97-7.89 (m, 2H), 7.49 (s, 1H), 7.37 (t, J=8.9 Hz, 2H), 7.05 (d, J=2.5 Hz, 1H), 2.95-2.86 (m, 2H), 2.83 (d, J=4.5 Hz, 3H), 2.63-2.50 (m, 2H).

LCMS $R_t$=2.763 min., m/z 382 (M+H).

The LC/MS data was obtained on a Shimadzu analytical LC/Micromass Platform LC (ESI+) at 220 nm using the following set of conditions: Phenomenex Luna 3 nm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

2-(4-Fluorophenyl)-5-hydroxy-N-methyl-6-propyl-benzofuran-3-carboxamide

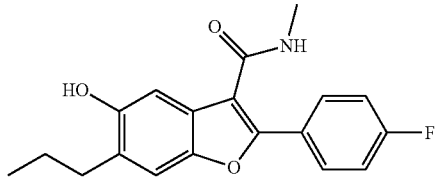 [SMILES: CCCc1cc2oc(-c3ccc(F)cc3)c(C(=O)NC)c2cc1O]

2-(4-Fluorophenyl)-5-hydroxy-N-methyl-6-propylbenzofuran-3-carboxamide was prepared by using the same methodology for the 6-(3,3,3-trifluoropropyl) analog from 2-(4-fluorophenyl)-5-isopropoxy-N-methyl-6-propylbenzofuran-3-carboxamide (1.097 g, 2.97 mmol). The crude product was isolated in 102% yield (0.989 g).

$^1$H NMR (400 MHz, DMSO-d$_6$) δ 9.32 (s, 1H), 8.35 (d, J=4.5 Hz, 1H), 7.98-7.89 (m, 2H), 7.42-7.32 (m, 3H), 7.01 (s, 1H), 2.83 (d, J=4.5 Hz, 3H), 2.67-2.60 (m, 2H), 1.68-1.56 (m, 2H), 0.94 (t, J=7.3 Hz, 3H).

LCMS R$_t$=3.138 min., m/z 328 (M+H).

The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

2-(4-Fluorophenyl)-3-(methylcarbamoyl)-6-(3,3,3-trifluoropropyl)benzofuran-5-yl trifluoromethanesulfonate

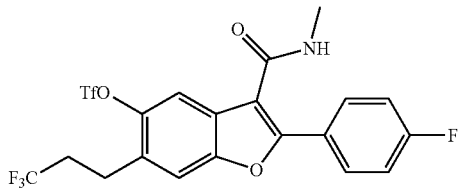 [SMILES: CNC(=O)c1c(-c2ccc(F)cc2)oc2cc(CCC(F)(F)F)c(OS(=O)(=O)C(F)(F)F)cc12]

Triethylamine (0.555 mL, 3.98 mmol) was added dropwise to a suspension of 2-(4-fluorophenyl)-5-hydroxy-N-methyl-6-(3,3,3-trifluoropropyl)benzofuran-3-carboxamide (0.759 g, 1.99 mmol) in DCM (65 mL) at room temperature under N$_2$. 1,1,1-trifluoro-N-phenyl-N-((trifluoromethyl)sulfonyl)methanesulfonamide (0.853 g, 2.388 mmol) was added portionwise to the mixture at 0° C. The yellow slurry mixture was then allowed to warm to room temperature, and stirred over the weekend. Additional 1,1,1-trifluoro-N-phenyl-N-((trifluoromethyl)sulfonyl)methanesulfonamide (0.2 g) and triethylamine (0.15 mL) were added. The mixture was stirred at room temperature for 20 hrs. The reaction mixture was washed with water, and water solution was extracted with CH$_2$Cl$_2$. The combined organic layer was washed with brine, dried over MgSO$_4$, filtered and concentrated to give the crude product as a dark yellow solid. This compound was purified by column chromatography (Biotage 25 m, EtOAc/Hexanes=0 to 25%) to give 996 mg (97%) of the target compound as a white solid $^1$H NMR (500 MHz, DMSO-d$_6$) δ 8.49 (m, 1H), 8.01 (s, 1H), 7.98-7.93 (m, 2H), 7.64 (s, 1H), 7.46-7.39 (m, 2H), 3.08-3.02 (m, 2H), 2.83 (d, J=4.6 Hz, 3H), 2.78-2.67 (m, 2H).

LCMS R$_t$=3.768 min., m/z 514 (M+H).

The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

2-(4-Fluorophenyl)-3-(methylcarbamoyl)-6-propyl-benzofuran-5-yl trifluoromethanesulfonate

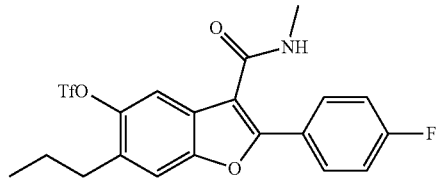

2-(4-Fluorophenyl)-3-(methylcarbamoyl)-6-propylbenzofuran-5-yl trifluoromethanesulfonate was prepared by using the same methodology for the 6-(3,3,3-trifluoropropyl) analog from 2-(4-fluorophenyl)-5-hydroxy-N-methyl-6-propylbenzofuran-3-carboxamide (0.972 g, 2.97 mmol). The product was isolated in 88% yield (1.206 g) as a white solid.

$^1$H NMR (500 MHz, DMSO-d$_6$) δ 8.47 (dd, J=4.6 Hz, 1H), 7.98-7.93 (m, 2H), 7.85 (s, 1H), 7.58 (s, 1H), 7.46-7.39 (m, 2H), 2.83 (d, J=4.6 Hz, 3H), 2.79-2.73 (m, 2H), 1.73-1.64 (m, 2H), 0.95 (t, J=7.3 Hz, 3H).

LCMS R$_t$=3.903, m/z 460 (M+H).

The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4

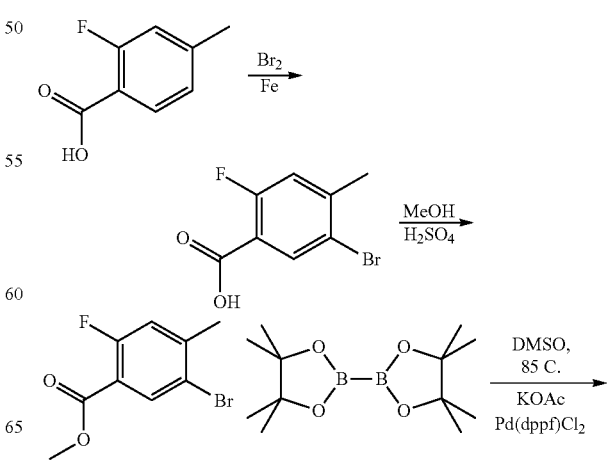

-continued

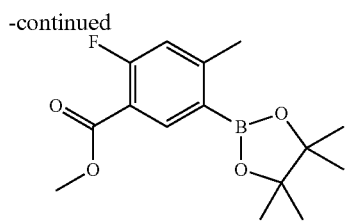

5-Bromo-2-fluoro-4-methylbenzoic acid

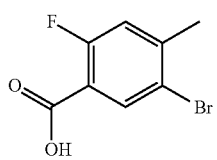

To a cold (0° C.) stirred solution of bromine (25.07 ml, 487 mmol) and iron powder (2.72 g, 48.7 mmol) was added 2-fluoro-4-methylbenzoic acid (5.00 g, 32.4 mmol) portionwise and the resulting red solution was allowed to reach room temperature and stirred for 1 hour. The mixture was cooled to 0° C. and quenched with 250 mL of aq. 1M sodium thiosulfate. The crude product was diluted with ethyl acetate, extracted, washed with water, brine, dried over magnesium sulfate, filtered and evaporated to a yellow solid. The crude solid was re-crystallized in 150 mL of cyclohexane to give 6.65 g (76% yield) of 5-bromo-2-fluoro-4-methylbenzoic acid.

$^1$H NMR (500 MHz, DMSO-d$_6$) δ ppm 13.44 (br. s., 1H), 7.98 (d, J=7.09 Hz, 1H), 7.41 (d, J=11.51 Hz, 1H), 2.40 (s, 3H).

LCMS R$_t$=2.925 min., m/z 232.91 (M−H).

The LC/MS data was obtained on a Shimadzu analytical LC/Micromass Platform LC (ESI+/−) at 220 nm using the following set of conditions: Phenomenex Luna 3 m C18, 2×50 mm column, with a gradient of 0-100% B (B=95% HPLC grade methanol/10 Mm ammonium acetate/5% HPLC grade water), (A=5% HPLC grade methanol/10 Mm ammonium acetate/95% HPLC grade water), in 4 minutes with a 1 minute hold at a rate of 0.8 mL/minute.

Methyl 5-bromo-2-fluoro-4-methylbenzoate

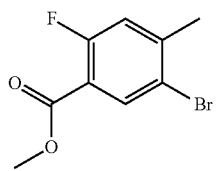

To a 250 mL RBF was added 5-bromo-2-fluoro-4-methylbenzoic acid (2.330 g, 10 mmol), methanol (50.0 ml) and sulfuric acid (1.066 ml, 20.00 mmol). The mixture was heated at 55° C. for 3 hours. The mixture was cooled and volatiles were removed on the rotovap. The resulting crude mixture was taken up in 75 mL of diethyl ether, washed with 20 mL of 1N NaOH, brine, dried over magnesium sulfate, filtered and evaporated to a white solid. The crude solid was pushed through a plug of silica gel (0-5% ethyl acetate/hexane) giving 2.1 grams (80% yield) of methyl 5-bromo-2-fluoro-4-methylbenzoate.

$^1$H NMR (400 MHz, CDCl$_3$) δ ppm 8.10 (d, J=6.78 Hz, 1H), 7.04 (d, J=11.04 Hz, 1H), 3.93 (s, 3H), 2.43 (s, 3H).

LCMS R$_t$=3.291 min., m/z 247.1 (M), m/z 249.1 (M+2H).

The LC/MS data was obtained on a Shimadzu analytical LC/Micromass Platform LC (ESI+) at 220 nm using the following set of conditions: Phenomenex Luna 3 m C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

Methyl 2-fluoro-4-methyl-5-(4,4,5,5-tetramethyl-1,3,2-dioxaborolan-2-yl)benzoate

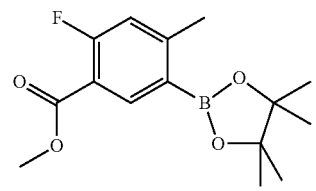 [SMILES: COC(=O)c1cc(B2OC(C)(C)C(C)(C)O2)c(C)cc1F]

To a sealed tube was added methyl 5-bromo-2-fluoro-4-methylbenzoate (750 mg, 3.04 mmol), DMSO (20 mL), 4,4,4',4',5,5,5',5'-octamethyl-2,2'-bi(1,3,2-dioxaborolane) (1542 mg, 6.07 mmol), potassium acetate (894 mg, 9.11 mmol) and PdCl$_2$(dppf) (74.9 mg, 0.091 mmol). The mixture was de-gassed and flushed with nitrogen five times and then heated to 85° C. for 20 hours. The mixture was cooled to room temperature, pushed through a plug of celite, diluted with 100 mL of DCM, washed with water, brine, dried over magnesium sulfate, filtered, and evaporated to give an oily solid. The solid was pushed through a plug of silica gel (50 mL hexane×2, 50 mL DCM×2) to give 1.07 g of methyl 2-fluoro-4-methyl-5-(4,4,5,5-tetramethyl-1,3,2-dioxaborolan-2-yl)benzoate (90% yield).

$^1$H NMR (400 MHz, CDCl$_3$) δ ppm 8.30 (d, J=8.53 Hz, 1H), 6.80-6.96 (d, J=12.30 Hz, 1H), 3.89 (s, 3H), 2.54 (s, 3H), 1.32 (s, 12H).

LCMS R$_t$=3.795 min., m/z 295.3 (M+2H).

The LC/MS data was obtained on a Shimadzu analytical LC/Micromass Platform LC (ESI+) at 220 nm using the following set of conditions: Phenomenex Luna 3 mm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

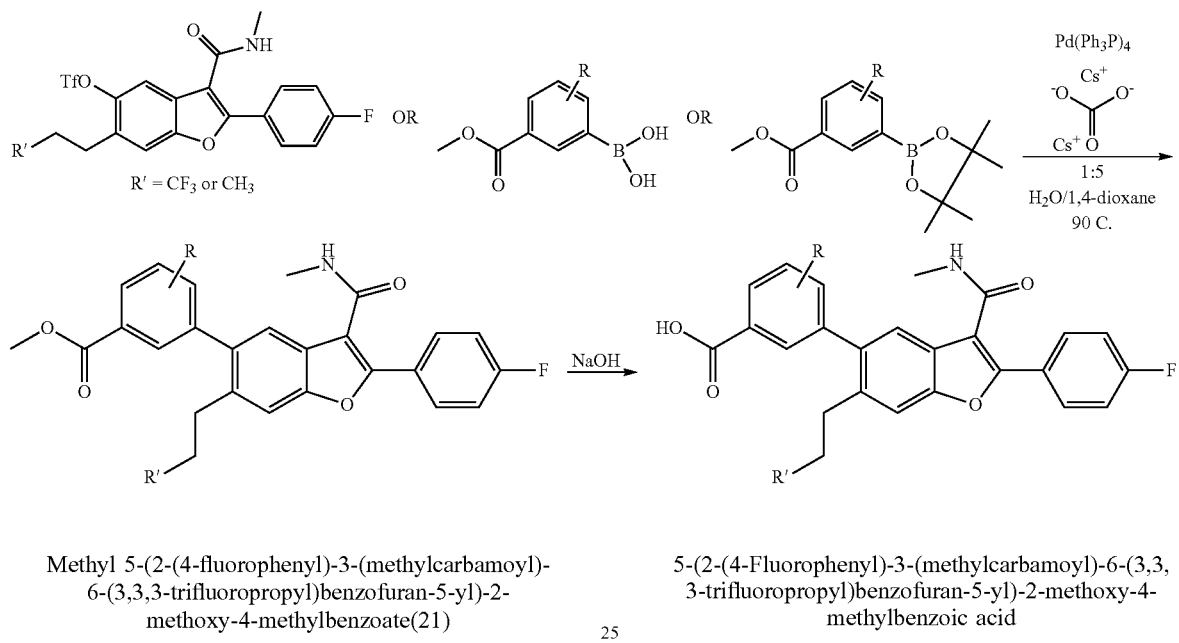

Methyl 5-(2-(4-fluorophenyl)-3-(methylcarbamoyl)-6-(3,3,3-trifluoropropyl)benzofuran-5-yl)-2-methoxy-4-methylbenzoate(21)

5-(2-(4-Fluorophenyl)-3-(methylcarbamoyl)-6-(3,3,3-trifluoropropyl)benzofuran-5-yl)-2-methoxy-4-methylbenzoic acid

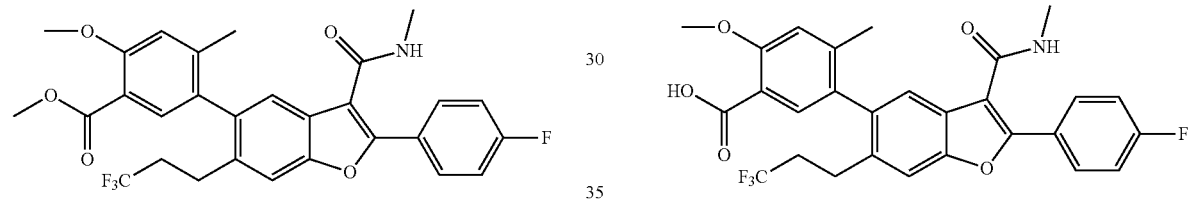

A mixture of 2-(4-fluorophenyl)-3-(methylcarbamoyl)-6-(3,3,3-trifluoropropyl)benzofuran-5-yl trifluoromethanesulfonate (150 mg, 0.292 mmol) in dioxane (10 mL) along with water (1 mL), cesium carbonate (162 mg, 0.497 mmol), (4-methoxy-5-(methoxycarbonyl)-2-methylphenyl)boronic acid (98.8 mg, 0.441 mmol) and palladium tetrakis(triphenyl)phosphine (33.8 mg, 0.029 mmol) was degassed and then heated at 90° C. for 3 hrs. The solvent was evaporated, and the residue was dissolved in $CH_2Cl_2$ (150 mL) and added with 1N HCl (3 mL). The mixture was washed with water, brine, dried over $MgSO_4$, filtered and concentrated to give a solid. The solid was triturated with ether (20 mL×2), dried, and purified by column chromatography (Biotage 25 s, EtOAc/Hexane=0 to 30%) to give 115 mg (72%) of the target compound as an off white solid.

$^1$H NMR (400 MHz, METHANOL-$d_4$) δ 8.01-7.94 (m, 2H), 7.63 (d, J=6.0 Hz, 2H), 7.41 (s, 1H), 7.28 (t, J=8.8 Hz, 2H), 7.14 (s, 1H), 3.97 (s, 3H), 3.86 (s, 3H), 2.96-2.92 (m, 3H), 2.89-2.79 (m, 1H), 2.73-2.63 (m, 1H), 2.39-2.24 (m, 2H), 2.15 (s, 3H).

LCMS $R_f$=3.600, m/z 544 (M+H).

The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

A solution of 1M sodium hydroxide (0.618 mL, 0.618 mmol) was added to a solution of ethyl 5-(2-(4-fluorophenyl)-3-(methylcarbamoyl)-6-(3,3,3-trifluoropropyl)benzofuran-5-yl)-2-methoxybenzoate (112 mg, 0.206 mmol) in a mixture of MeOH (2 mL) and THF (2 mL). The reaction mixture was stirred at room temperature overnight. The mixture was added with 1N HCl (0.9 mL). The organic solvent was removed, and water was sucked out from the solid. The solid was washed with water, and dried to give 107 mg (98%) of crude target product as a white solid.

$^1$H NMR (400 MHz, DMSO-$d_6$) δ 8.39 (dd, J=4.5 Hz, 1H), 8.03-7.96 (m, 2H), 7.79 (s, 1H), 7.48 (s, 1H), 7.41 (t, J=8.9 Hz, 2H), 7.34 (s, 1H), 7.15 (s, 1H), 3.90 (s, 3H), 2.81 (d, J=4.5 Hz, 3H), 2.79-2.67 (m, 1H), 2.63-2.42 (m, 3H), 2.09 (s, 3H).

LCMS $R_f$=3.325, m/z 530 (M+H).

The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

The Following Intermediates were Prepared by the General Procedure:

To a small sealed tube was added 2-(4-fluorophenyl)-3-(methylcarbamoyl)-6-(3,3,3-trifluoropropyl)benzofuran-5-yltrifluoromethanesulfonate (100 mg, 0.195 mmol) or (90 mg, 0.195 mmol)2-(4-fluorophenyl)-3-(methylcarbamoyl)-6-propylbenzofuran-5-yltrifluoromethanesulfonate (100 mg, 0.218 mmol), dioxane (4 mL), water (800 L), 2.5 eq. cesium carbonate (159 mg, 0.487 mmol), 1.3 eq boronic acid or ester (0.253 mmol) and 0.1 eq palladium tetrakis(triphenyl)phosphine (22.51 mg, 0.019 mmol). The mixture was degassed/flushed with nitrogen five times and then heated for 5 hours at 90° C. The product solution was cooled to room temperature and filtered through celite. The dioxane solution was added to 50 mL of aq. 0.1M HCl and the resulting fine white solids were filtered to give 55-80% yield of methyl ester.

Methyl 2-fluoro-5-(2-(4-fluorophenyl)-3-(methylcarbamoyl)-6-propylbenzofuran-5-yl)benzoate

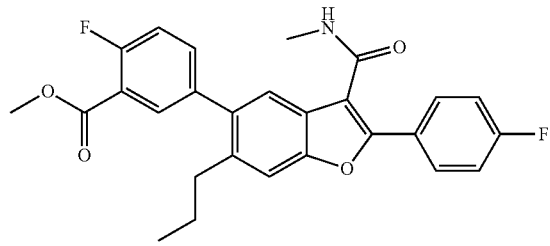 [SMILES: CCCc1cc2oc(-c3ccc(F)cc3)c(C(=O)NC)c2cc1-c1ccc(F)c(C(=O)OC)c1]

55% yield as a white solid.

$^1$H NMR (400 MHz, DMSO-d$_6$) δ ppm 8.41 (d, J=4.77 Hz, 1H), 7.97-8.05 (m, 2H), 7.83 (dd, J=6.90, 2.38 Hz, 1H), 7.64-7.72 (m, 2H), 7.36-7.52 (m, 4H), 3.90 (s, 3H), 2.82 (d, J=4.52 Hz, 3H), 2.58-2.66 (m, 2H), 1.39-1.55 (m, 2H), 0.79 (t, J=7.28 Hz, 3H).

LCMS R$_t$=3.906 min., m/z 464.4 (M+H).

The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

Methyl 2-fluoro-5-(2-(4-fluorophenyl)-3-(methylcarbamoyl)-6-(3,3,3-trifluoropropyl)benzofuran-5-yl)benzoate

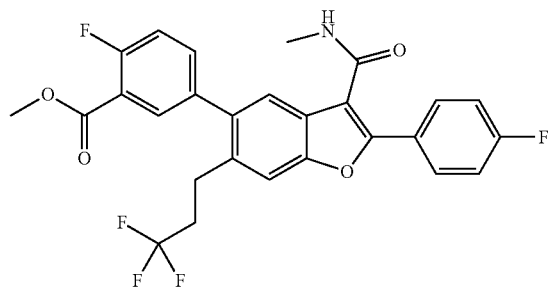 [SMILES: CNC(=O)c1c(-c2ccc(F)cc2)oc2cc(CCC(F)(F)F)c(-c3ccc(F)c(C(=O)OC)c3)cc12]

68% yield as a white solid.

$^1$H NMR (400 MHz, DMSO-d$_6$) δ ppm 8.43 (m, 1H), 7.98-8.05 (m, 2H), 7.85 (dd, J=6.90, 2.38 Hz, 1H), 7.81 (s, 1H), 7.73 (m, 1H), 7.46-7.53 (m, 2H), 7.41 (t, J=8.91 Hz, 2H), 3.88-3.92 (m, 3H), 2.85-2.93 (m, 2H), 2.82 (d, J=4.52 Hz, 3H), 2.42-2.50 (m, 1H).

LCMS R$_t$=3.708 min., m/z 518.3 (M+H).

The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

Methyl 2-fluoro-5-(2-(4-fluorophenyl)-3-(methylcarbamoyl)-6-propylbenzofuran-5-yl)-4-methylbenzoate

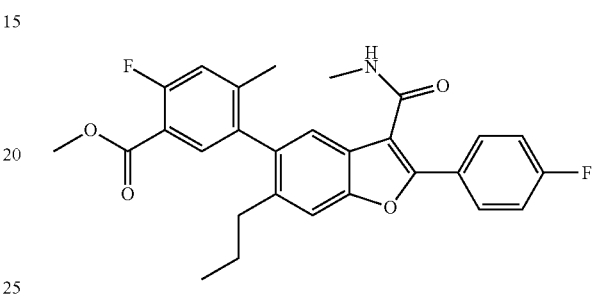

79% yield as a white solid.

$^1$H NMR (500 MHz, DMSO-d$_6$) δ ppm 8.39 (m, 1H), 7.96-8.03 (m, 2H), 7.62-7.68 (m, 2H), 7.36-7.44 (m, 3H), 7.32 (s, 1H), 3.85 (s, 3H), 2.80 (d, J=4.73 Hz, 3H), 2.44-2.49 (m, 1H), 2.24-2.34 (m, 1H), 2.09 (s, 3H), 1.37-1.49 (m, 2H), 0.75 (t, J=7.33 Hz, 3H).

LCMS R$_t$=4.035 min., m/z 478.3 (M+H).

The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

Methyl 2-fluoro-5-(2-(4-fluorophenyl)-3-(methylcarbamoyl)-6-(3,3,3-trifluoropropyl)benzofuran-5-yl)-4-methylbenzoate

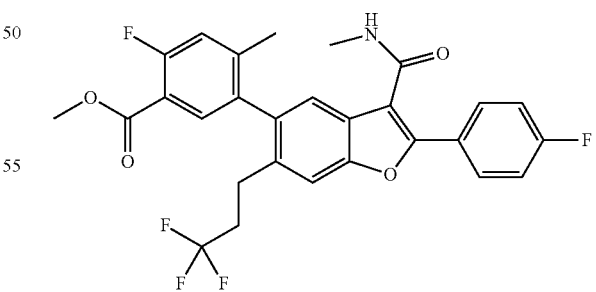

64% yield as a white solid.

$^1$H NMR (400 MHz, DMSO-d$_6$) δ ppm 8.40 (m, 1H), 8.01 (m, 2H), 7.82 (s, 1H), 7.66 (m, 1H), 7.36-7.49 (m, 4H), 3.86 (s, 3H), 2.83 (d, J=4.52 Hz, 3H), 2.67-2.78 (m, 1H), 2.54-2.61 (m, 2H), 2.38-2.48 (m, 1H), 2.10 (s, 3H).

LCMS R$_t$=3.976 min., m/z 532.25 (M+H).

The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

Methyl 5-(2-(4-fluorophenyl)-3-(methylcarbamoyl)-6-propylbenzofuran-5-yl)-2-methoxy-4-methylbenzoate

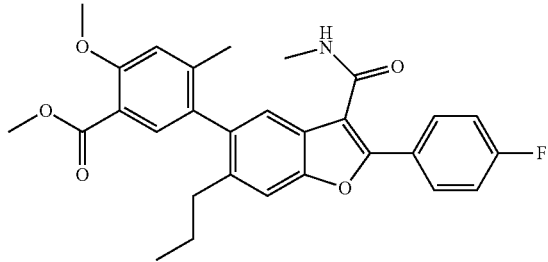 [SMILES: CCCc1cc2oc(-c3ccc(F)cc3)c(C(=O)NC)c2cc1-c1cc(C(=O)OC)c(OC)cc1C]

63% yield as a white solid.
$^1$H NMR (500 MHz, DMSO-$d_6$) δ ppm 8.39 (m, 1H), 7.99 (m, 2H), 7.63 (s, 1H), 7.45 (s, 1H), 7.39 (t, J=8.83 Hz, 2H), 7.28 (s, 1H), 7.15 (s, 1H), 3.89 (s, 3 H), 3.77 (s, 3H), 2.80 (d, J=4.57 Hz, 3H), 2.45-2.49 (m, 1H), 2.26-2.39 (m, 1H), 2.08 (s, 3H), 1.36-1.52 (m, 2H), 0.75 (t, J=7.25 Hz, 3H).
LCMS $R_t$=3.826 min., m/z 490.3 (M+H).

The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

The Following Intermediates were Prepared by the General Procedure:

To a small round-bottom flask (RBF) was added the methyl ester (0.150 mmol), a 1:1 mixture of methanol (2.5 mL)/THF (2.5 mL), and 4.0 eq. 1N aq sodium hydroxide (600 L, 0.600 mmol). The mixture was stirred at room temperature for 5 hours. The product solution was diluted with 75 mL of ethyl acetate and 700 μL of aq. 1M HCl, extracted, washed with water, brine, dried over sodium sulfate, filtered and evaporated to a white solid of the acid product (average yield >96%).

2-Fluoro-5-(2-(4-fluorophenyl)-3-(methylcarbamoyl)-6-(3,3,3-trifluoropropyl)benzofuran-5-yl)benzoic acid

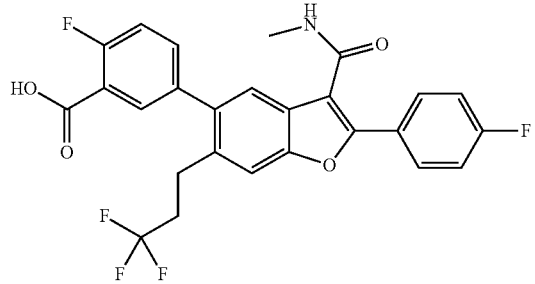 [SMILES: CNC(=O)c1c(-c2ccc(F)cc2)oc2cc(CCC(F)(F)F)c(-c3ccc(F)c(C(=O)O)c3)cc12]

$^1$H NMR (500 MHz, DMSO-$d_6$) δ ppm 13.38 (br.s., 1H), 8.45 (m, 1H), 8.00 (m, 2H), 7.78-7.85 (m, 2H), 7.64-7.70 (m, 1H), 7.35-7.50 (m, 4H), 2.85-2.92 (m, 2H), 2.81 (d, J=4.57 Hz, 3H), 2.42-2.49 (m, 2H).
LCMS $R_t$=3.231 min., m/z 504.25 (M+H).

The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

2-Fluoro-5-(2-(4-fluorophenyl)-3-(methylcarbamoyl)-6-propylbenzofuran-5-yl)benzoic acid

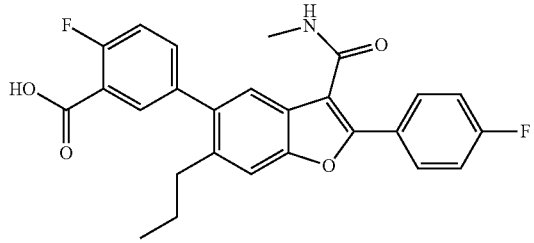 [SMILES: CCCc1cc2oc(-c3ccc(F)cc3)c(C(=O)NC)c2cc1-c1ccc(F)c(C(=O)O)c1]

$^1$H NMR (400 MHz, DMSO-$d_6$) δ ppm 13.35 (br.s., 1H), 8.41 (m, 1H), 7.96-8.05 (m, 2H), 7.77 (dd, J=7.03, 2.26 Hz, 1H), 7.65 (s, 1H), 7.58 (m, 1H), 7.33-7.45 (m, 4H), 2.82 (d, J=4.77 Hz, 3H), 2.58-2.66 (m, 2H), 1.44-1.55 (m, 2H), 0.79 (t, J=7.28 Hz, 3H).
LCMS $R_t$=3.380 min., m/z 450.3 (M+H).

The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

2-Fluoro-5-(2-(4-fluorophenyl)-3-(methylcarbamoyl)-6-(3,3,3-trifluoropropyl)benzofuran-5-yl)-4-methylbenzoic acid

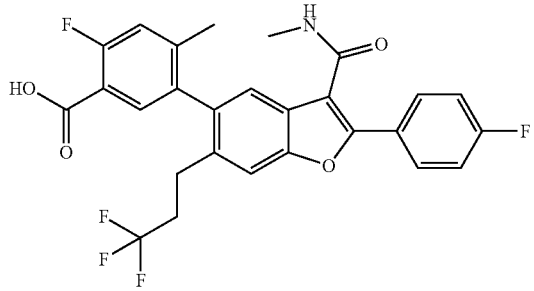 [SMILES: CNC(=O)c1c(-c2ccc(F)cc2)oc2cc(CCC(F)(F)F)c(-c3cc(C(=O)O)c(F)cc3C)cc12]

$^1$H NMR (400 MHz, DMSO-$d_6$) δ ppm 13.17 (br. s., 1H), 8.39 (m, 1H), 7.95-8.05 (m, 2H), 7.82 (s, 1H), 7.65 (d, J=7.53 Hz, 1H), 7.32-7.48 (m, 4H), 2.81 (d, J=4.52 Hz, 3H), 2.69-2.78 (m, 1H), 2.55-2.62 (m, 1H), 2.55-2.63 (m, 1H), 2.38-2.49 (m, 1H), 2.09 (s, 3H).

LCMS $R_t$=3.350 min., m/z 518.3 (M+H).

The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

2-Fluoro-5-(2-(4-fluorophenyl)-3-(methylcarbamoyl)-6-propylbenzofuran-5-yl)-4-methylbenzoic acid

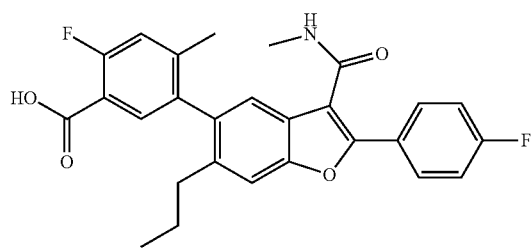 [SMILES: CCCc1cc2oc(-c3ccc(F)cc3)c(C(=O)NC)c2cc1-c1cc(C(=O)O)c(F)cc1C]

$^1$H NMR (500 MHz, DMSO-d$_6$) δ ppm 13.11 (br.s., 1H), 8.39 (m, 1H), 7.96-8.02 (m, 2H), 7.65 (s, 1H), 7.61 (d, J=7.72 Hz, 1H), 7.37-7.43 (m, 2H), 7.29-7.35 (m, 2H), 2.80 (d, J=4.73 Hz, 3H), 2.45-2.49 (m, 1H), 2.25-2.34 (m, 1H), 2.07 (s, 3H), 1.39-1.50 (m, 2H), 0.75 (t, J=7.33 Hz, 3H).

LCMS $R_t$=3.495 min., m/z 464.3 (M+H).

The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

5-(2-(4-Fluorophenyl)-3-(methylcarbamoyl)-6-propylbenzofuran-5-yl)-2-methoxy-4-methyl benzoic acid

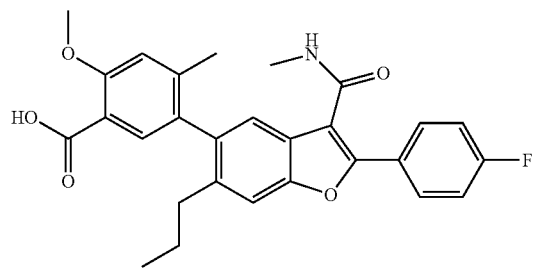

$^1$H NMR (400 MHz, DMSO-d$_6$) δ ppm 12.42 (br. s., 1H), 8.37 (m, 1H), 7.95-8.05 (m, 2H), 7.63 (s, 1H), 7.46 (s, 1H), 7.36-7.43 (m, 2H), 7.29 (s, 1H), 7.12 (s, 1H), 3.90 (s, 3H), 2.81 (d, J=4.77 Hz, 3H), 2.45-2.50 (m, 1H), 2.28-2.40 (m, 1H), 2.05-2.13 (m, 3H), 1.46 (m, 2H), 0.77 (t, J=7.28 Hz, 3H).

LCMS $R_t$=3.445 min., m/z 476.3 (M+H).

The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4

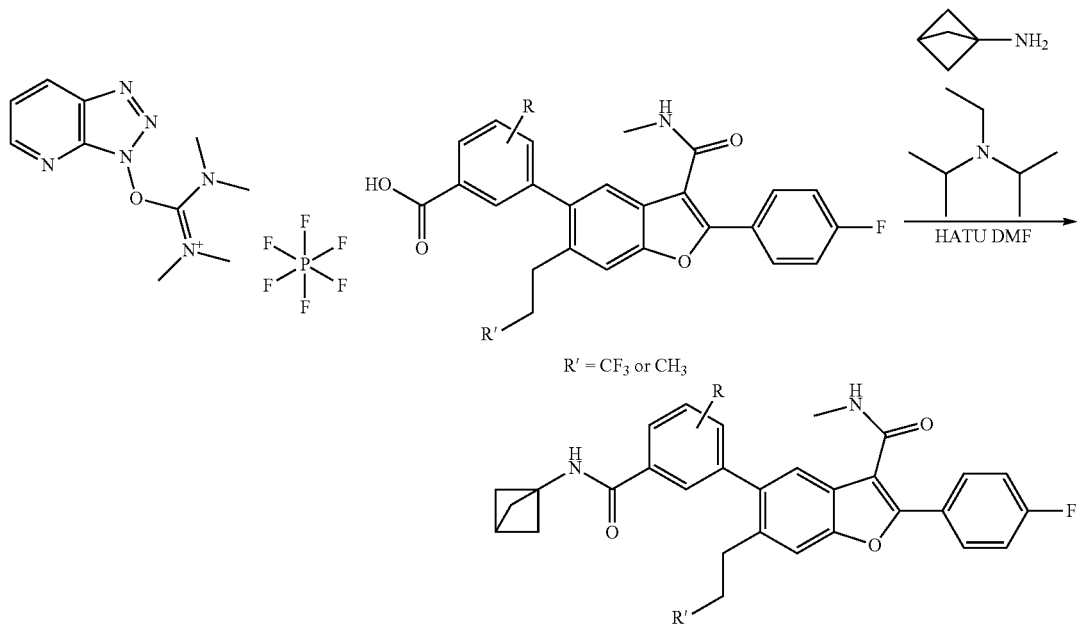

R' = CF$_3$ or CH$_3$

The Following Examples were Prepared by the General Procedure:

To a scintillation vial or small RBF was added the benzoic acid (0.133 mmol), DMF (4 mL), 6.0 eq of N-ethyl-N,N- diisopropylpropan-2-amine (0.140 mL, 0.801 mmol), 2.5 eq of bicyclo[1.1.1]pentan-1-amine HCl (39.9 mg, 0.334 mmol) and 3.0 eq of HATU (152 mg, 0.400 mmol). The vial or flask was sealed and the mixture stirred overnight at room temperature.

5-(3-(Bicyclo[1.1.1]pentan-1-ylcarbamoyl)-4-fluorophenyl)-2-(4-fluorophenyl)-N-methyl-6-(3,3,3-trifluoropropyl)benzofuran-3-carboxamide

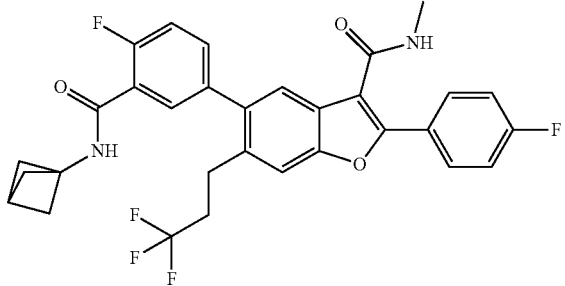 [SMILES: CNC(=O)c1c(-c2ccc(F)cc2)oc2cc(CCC(F)(F)F)c(-c3ccc(F)c(C(=O)NC45CC(C4)C5)c3)cc12]

The product was purified using a Shimadzu preparative HPLC employing acetonitrile/water/TFA where solvent A was 10% acetonitrile/90% water/0.1% trifluoroacetic acid and solvent B was 10% water/90% acetonitrile/0.1% trifluoroacetic acid with a XTERRA 5 mC18, 30×100 mm column at a gradient of 40-100% B and a flow rate of 40 mL/min. over 15 minutes with a 5 minute hold. 70% Yield.

$^1$H NMR (400 MHz, DMSO-d$_6$) δ ppm 8.92 (s, 1H), 8.43 (m, 1H), 7.96-8.05 (m, 2H), 7.80 (s, 1H), 7.51-7.58 (m, 2H), 7.46 (s, 1H), 7.34-7.44 (m, 3H), 2.86-2.93 (m, 2H), 2.82 (d, J=4.52 Hz, 3H), 2.45-2.54 (m, 3H), 2.10 (br.s., 6H).

LCMS R$_t$=3.796 min, m/z 569.4 (M+H).

HPLC R$_t$=11.336 min. (Sunfire C18), 100% purity and 12.108 min. (XBridge Phenyl), 100% purity.

HPLC purity was determined using a Shimadzu analytical LC at 254 nm and 256 nm with a Waters Sunfire C18, 3.5 μm 4.6×150 mm column employing water/acetonitrile/0.1% trifluoroacetic acid with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Waters XBridge Phenyl 3.5 m, 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute.

The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

5-(3-(Bicyclo[1.1.1]pentan-1-ylcarbamoyl)-4-fluorophenyl)-2-(4-fluorophenyl)-N-methyl-6-propylbenzofuran-3-carboxamide

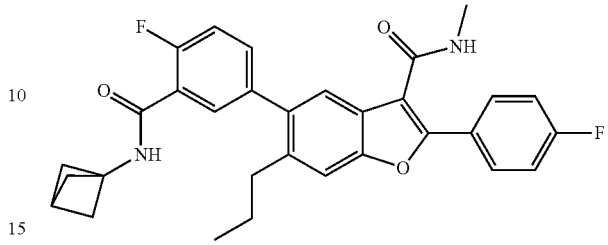

The product was purified using preparative LC/MS employing acetonitrile/water/20 mM ammonium acetate where solvent A was water/20 mM ammonium acetate and solvent B was 95/5 acetonitrile/water/20 mM ammonium acetate with a Waters XBridge C18, 5 μm 19×200 mm column at a gradient of 65-100% B over 12 minutes with a 5 minute hold at 20 mL/min. 57% Yield.

$^1$H NMR (500 MHz, DMSO-d$_6$) δ ppm 8.94 (s, 1H), 8.45 (m, 1H), 7.95-8.05 (m, 2H), 7.65 (s, 1H), 7.46-7.53 (m, 2H), 7.31-7.44 (m, 4H), 2.82 (d, J=4.58 Hz, 3H), 2.57-2.65 (m, 2H), 2.47 (s, 1H), 2.10 (br.s., 6H), 1.43-1.53 (m, 2H), 0.79 (t, J=7.17 Hz, 3H).

(Injection 1) LCMS R$_t$=3.59 min, m/z 515.3 (M+H), 98.0% purity.

(Injection 2) LCMS R$_t$=4.49 min, m/z 515.3 (M+H), 98.0% purity.

The analytical LC/MS data was obtained using the following set of conditions: (Injection 1) Waters BEH 1.7 μm C18, 2.0×50 mm column employing acetonitrile/water/10 mM ammonium acetate with a gradient of 0-100% B over 4 minutes with a 1 minute hold (where solvent A was 5/95 acetonitrile/water/10 mM ammonium acetate and solvent B was 95/5 acetonitrile/water/10 mM ammonium acetate) at a flow rate of 0.5 mL/min. and (Injection 2) Waters BEH 1.7 μm C18, 2.0×50 mm column employing methanol/water/10 mM ammonium acetate with a gradient of 0-100% B over 4 minutes with a 1 minute hold (where solvent A was 5/95 methanol/water/10 mM ammonium acetate and solvent B was 95/5 methanol/water/10 mM ammonium acetate) at a flow rate of 0.5 mL/min.

5-(5-(Bicyclo[1.1.1]pentan-1-ylcarbamoyl)-4-fluoro-2-methylphenyl)-2-(4-fluorophenyl)-N-methyl-6-(3,3,3-trifluoropropyl)benzofuran-3-carboxamide

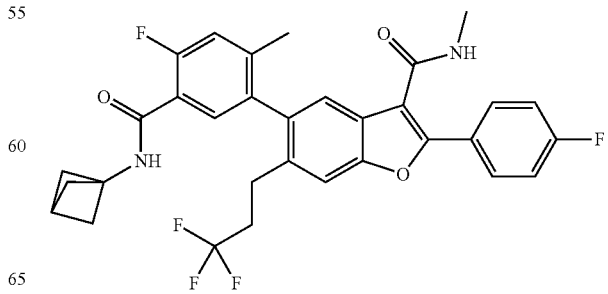

The product was purified using preparative LC/MS employing acetonitrile/water/20 mM ammonium acetate where solvent A was water/20 mM ammonium acetate and solvent B was 95/5 acetonitrile/water/20 mM ammonium acetate with a Waters XBridge C18, 19×100 mm 5 μm column at a gradient of 20-95% B over 11 minutes with a 4 minute hold at 25 mL/min. 53% Yield.

$^1$H NMR (500 MHz, DMSO-$d_6$) δ ppm 8.80 (s, 1H), 8.43 (m, 1H), 7.94-8.03 (m, 2H), 7.81 (s, 1H), 7.41 (m, 2H), 7.39 (m, 1H), 7.34 (s, 1H), 7.31 (m, 1H), 2.80 (d, J=4.58 Hz, 3H), 2.71 (m, 1H), 2.54-2.63 (m, 1H), 2.44-2.50 (m, 3H), 2.08 (br.s., 6H), 2.05 (s, 3H).

(Injection 1) LCMS $R_t$=3.54 min, m/z 583.4 (M+H), 95.0% purity.

(Injection 2) LCMS $R_t$=4.42 min, m/z 583.4 (M+H), 95.0% purity.

The analytical LC/MS data was obtained using the following set of conditions: (Injection 1) Waters BEH 1.7 μm C18, 2.0×50 mm column employing acetonitrile/water/10 mM ammonium acetate with a gradient of 0-100% B over 4 minutes with a 1 minute hold (where solvent A was 5/95 acetonitrile/water/10 mM ammonium acetate and solvent B was 95/5 acetonitrile/water/10 mM ammonium acetate) at a flow rate of 0.5 mL/min. and (Injection 2) Waters BEH 1.7 μm C18, 2.0×50 mm column employing methanol/water/10 mM ammonium acetate with a gradient of 0-100% B over 4 minutes with a 1 minute hold (where solvent A was 5/95 methanol/water/10 mM ammonium acetate and solvent B was 95/5 methanol/water/10 mM ammonium acetate) at a flow rate of 0.5 mL/min.

5-(5-(Bicyclo[1.1.1]pentan-1-ylcarbamoyl)-4-methoxy-2-methylphenyl)-2-(4-fluorophenyl)-N-methyl-6-(3,3,3-trifluoropropyl)benzofuran-3-carboxamide

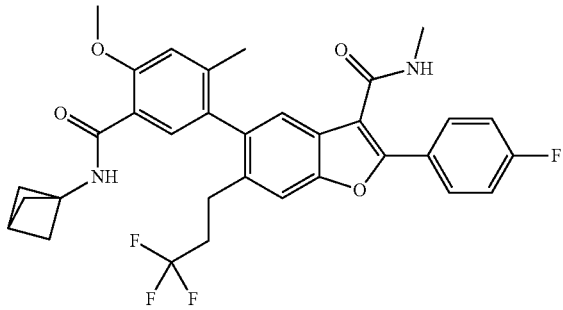 [SMILES: CNC(=O)c1c(-c2ccc(F)cc2)oc2cc(CCC(F)(F)F)c(-c3cc(C(=O)NC45CC(C4)C5)c(OC)cc3C)cc12]

The product was purified using preparative LC/MS employing acetonitrile/water/20 mM ammonium acetate where solvent A was water/20 mM ammonium acetate and solvent B was 95/5 acetonitrile/water/20 mM ammonium acetate with a Waters XBridge C18, 19×200 mm 5 μm column at a gradient of 60-100% B over 20 minutes with a 4 minute hold at 20 mL/min. 65% Yield.

$^1$H NMR (500 MHz, DMSO-$d_6$) δ ppm 8.48 (s, 1H), 8.43 (m, 1H), 7.96-8.03 (m, 2H), 7.79 (s, 1H), 7.55 (s, 1H), 7.41 (m, 2H), 7.31 (s, 1H), 7.15 (s, 1H), 3.96 (s, 3H), 2.80 (d, J=4.58 Hz, 3H), 2.70-2.77 (m, 1H), 2.55-2.63 (m, 1H), 2.36-2.49 (m, 3H), 2.09 (br. s., 6H), 2.07 (s, 3H).

(Injection 1) LCMS $R_t$=3.55 min, m/z 595.4 (M+H), 100% purity.

(Injection 2) LCMS $R_t$=4.45 min, m/z 595.4 (M+H), 100% purity.

The analytical LC/MS data was obtained using the following set of conditions: (Injection 1) Waters BEH 1.7 μm C18, 2.0×50 mm column employing acetonitrile/water/10 mM ammonium acetate with a gradient of 0-100% B over 4 minutes with a 1 minute hold (where solvent A was 5/95 acetonitrile/water/10 mM ammonium acetate and solvent B was 95/5 acetonitrile/water/10 mM ammonium acetate) at a flow rate of 0.5 mL/min. and (Injection 2) Waters BEH 1.7 μm C18, 2.0×50 mm column employing methanol/water/10 mM ammonium acetate with a gradient of 0-100% B over 4 minutes with a 1 minute hold (where solvent A was 5/95 methanol/water/10 mM ammonium acetate and solvent B was 95/5 methanol/water/10 mM ammonium acetate) at a flow rate of 0.5 mL/min.

5-(5-(bicyclo[1.1.1]pentan-1-ylcarbamoyl)-4-fluoro-2-methylphenyl)-2-(4-fluorophenyl)-N-methyl-6-propylbenzofuran-3-carboxamide

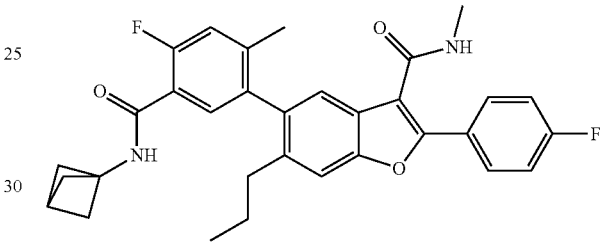

The product was purified using preparative LC/MS employing acetonitrile/water/20 mM ammonium acetate where solvent A was water/20 mM ammonium acetate and solvent B was 95/5 acetonitrile/water/20 mM ammonium acetate with a Waters XBridge C18, 19×200 mm 5 μm column at a gradient of 60-100% B over 20 minutes with a 4 minute hold at 20 mL/min. 65% yield.

$^1$H NMR (500 MHz, DMSO-$d_6$) δ ppm 8.77 (s, 1H), 8.38 (m, 1H), 7.95 (m, 2H), 7.62 (s, 1H), 7.37 (m, 2H), 7.31 (d, J=7.63 Hz, 1H), 7.22-7.28 (m, 2H), 2.78 (d, J=4.58 Hz, 3H), 2.39-2.48 (m, 2H), 2.24-2.33 (m, 1H), 2.06 (br.s., 6H), 2.02 (s, 3H), 1.36-1.48 (m, 2H), 0.74 (t, J=7.32 Hz, 3H).

(Injection 1) LCMS $R_t$=3.70 min, m/z 529.4 (M+H), 100% purity.

(Injection 2) LCMS $R_t$=4.55 min, m/z 529.4 (M+H), 100% purity.

The analytical LC/MS data was obtained using the following set of conditions: (Injection 1) Waters BEH 1.7 μm C18, 2.0×50 mm column employing acetonitrile/water/10 mM ammonium acetate with a gradient of 0-100% B over 4 minutes with a 1 minute hold (where solvent A was 5/95 acetonitrile/water/10 mM ammonium acetate and solvent B was 95/5 acetonitrile/water/10 mM ammonium acetate) at a flow rate of 0.5 mL/min. and (Injection 2) Waters BEH 1.7 μm C18, 2.0×50 mm column employing methanol/water/10 mM ammonium acetate with a gradient of 0-100% B over 4 minutes with a 1 minute hold (where solvent A was 5/95 methanol/water/10 mM ammonium acetate and solvent B was 95/5 methanol/water/10 mM ammonium acetate) at a flow rate of 0.5 mL/min.

5-(5-(bicyclo[1.1.1]pentan-1-ylcarbamoyl)-4-methoxy-2-methylphenyl)-2-(4-fluorophenyl)-N-methyl-6-propylbenzofuran-3-carboxamide

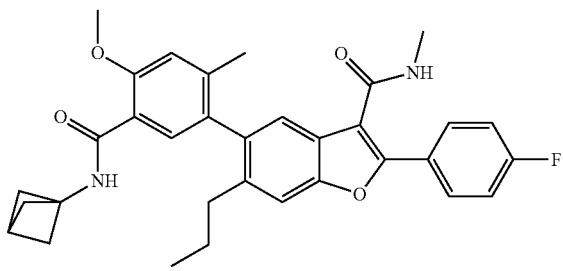 [SMILES: CCCc1cc2oc(-c3ccc(F)cc3)c(C(=O)NC)c2cc1-c1cc(C(=O)NC23CC(C2)C3)c(OC)cc1C]

The product was purified using preparative LC/MS employing acetonitrile/water/20 mM ammonium acetate where solvent A was water/20 mM ammonium acetate and solvent B was 95/5 acetonitrile/water/20 mM ammonium acetate with a Waters XBridge C18, 19×200 mm 5 μm column at a gradient of 60-100% B over 20 minutes with a 4 minute hold at 20 mL/min. 50% yield.

$^1$H NMR (500 MHz, DMSO-d$_6$) δ ppm 8.47 (s, 1H), 8.39 (m, 1H), 7.95 (m, 2H), 7.60 (s, 1H), 7.51 (s, 1H), 7.37 (m, 2H), 7.22 (s, 1H), 7.09 (s, 1H), 3.93 (s, 3H), 2.77 (d, J=4.58 Hz, 3H), 2.40-2.48 (m, 2H), 2.24-2.33 (m, 1H), 2.07 (br.s., 6H), 2.04 (s, 3H), 1.31-1.49 (m, 2H), 0.72 (t, J=7.32 Hz, 3H).

(Injection 1) LCMS R$_t$=3.72 min, m/z 541.4 (M+H), 100% purity.

(Injection 2) LCMS R$_t$=4.57 min, m/z 541.4 (M+H), 100% purity.

The analytical LC/MS data was obtained using the following set of conditions: (Injection 1) Waters BEH 1.7 μm C18, 2.0×50 mm column employing acetonitrile/water/10 mM ammonium acetate with a gradient of 0-100% B over 4 minutes with a 1 minute hold (where solvent A was 5/95 acetonitrile/water/10 mM ammonium acetate and solvent B was 95/5 acetonitrile/water/10 mM ammonium acetate) at a flow rate of 0.5 mL/min. and (Injection 2) Waters BEH 1.7 μm C18, 2.0×50 mm column employing methanol/water/10 mM ammonium acetate with a gradient of 0-100% B over 4 minutes with a 1 minute hold (where solvent A was 5/95 methanol/water/10 mM ammonium acetate and solvent B was 95/5 methanol/water/10 mM ammonium acetate) at a flow rate of 0.5 mL/min.

The preparation of 5-(5-(bicyclo[1.1.1]pentan-1-ylcarbamoyl)-4-methoxy-2-methylphenyl)-4-fluoro-2-(4-fluorophenyl)-6-(methoxymethyl)-N-methyl-benzofuran-3-carboxamide

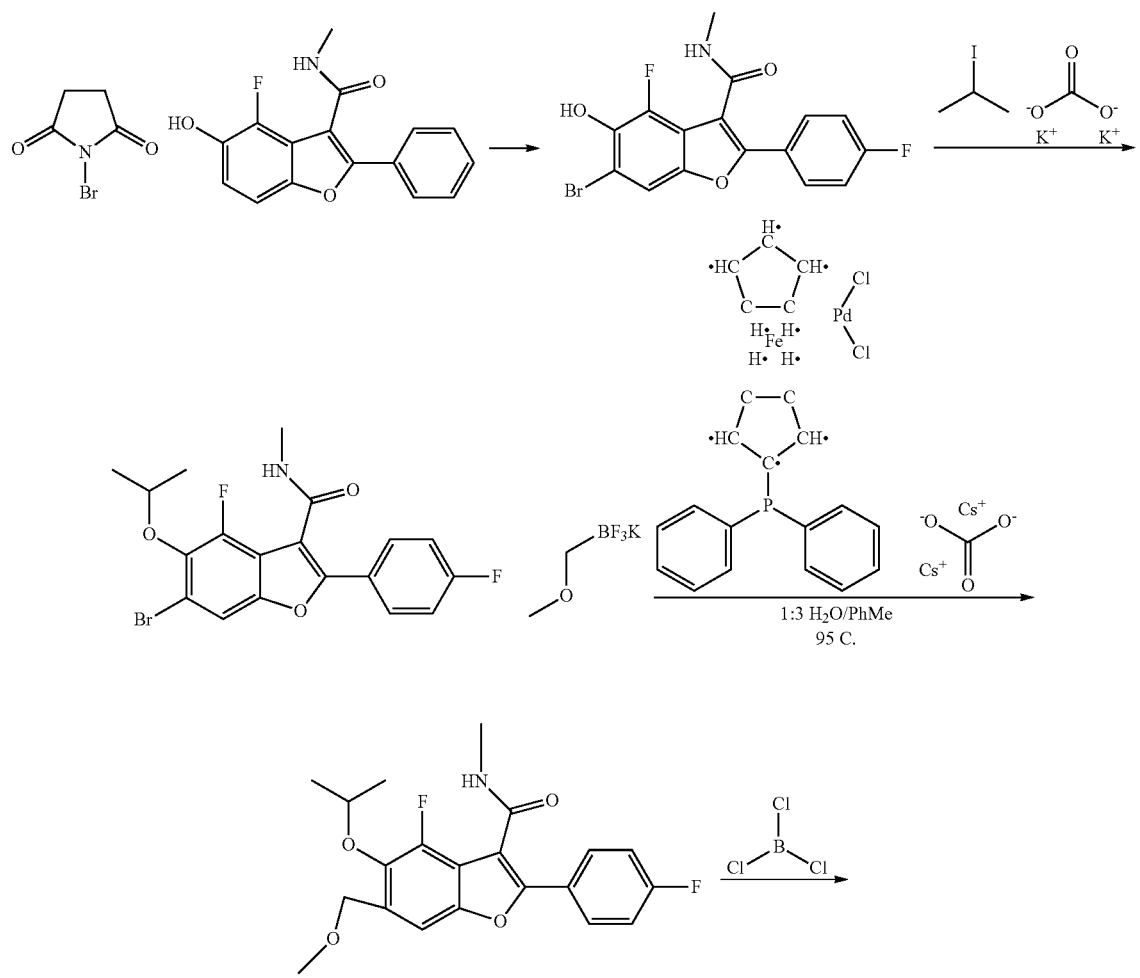

-continued
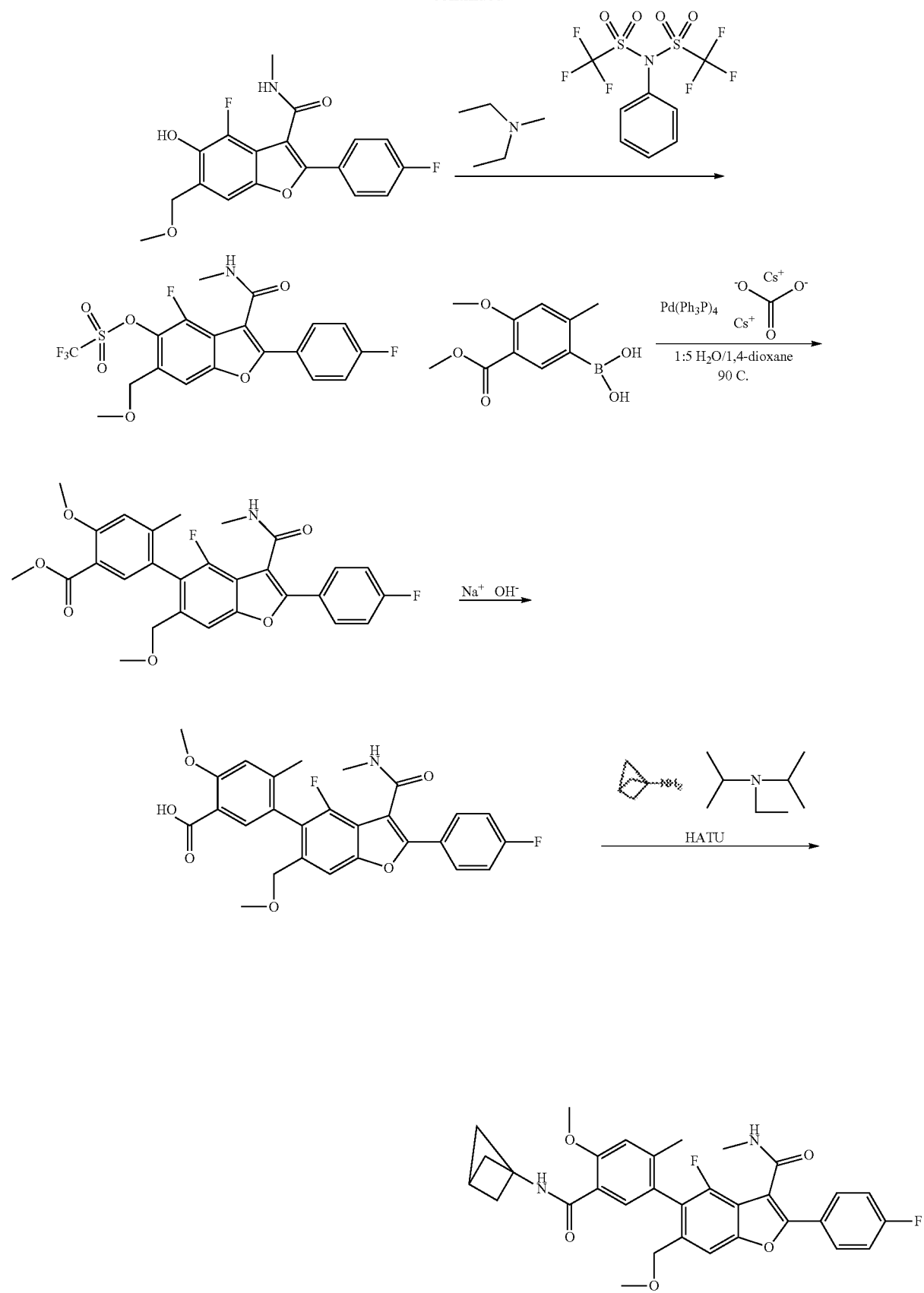

6-Bromo-4-fluoro-2-(4-fluorophenyl)-5-hydroxy-N-methylbenzofuran-3-carboxamide

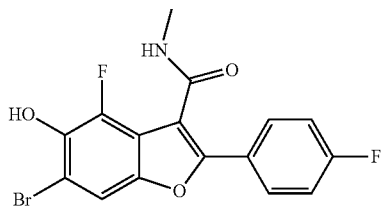 [SMILES: CNC(=O)c1c(-c2ccc(F)cc2)oc2cc(Br)c(O)c(F)c12]

N-Bromosuccinimide (4.93 g, 27.7 mmol) was added to a solution of 4-fluoro-2-(4-fluorophenyl)-5-hydroxy-N-methylbenzofuran-3-carboxamide (7 g, 23.08 mmol) in acetonitrile (700 mL). The mixture was stirred at room temperature for 19 hrs. The precipitate was collected and washed with acetonitrile to give 5.35 g of the product (61%).

$^1$H NMR (400 MHz, DMSO-$d_6$) δ 10.2 (br, 1H), 8.66 (m, 1H), 7.92-7.85 (m, 2H), 7.81 (d, J=1.3 Hz, 1H), 7.46-7.37 (m, 2H), 2.83 (d, J=4.8 Hz, 3H).

LCMS $R_t$ (retention time)=2.725 min., m/z 384 (M+2H).

The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

6-Bromo-4-fluoro-2-(4-fluorophenyl)-5-isopropoxy-N-methylbenzofuran-3-carboxamide

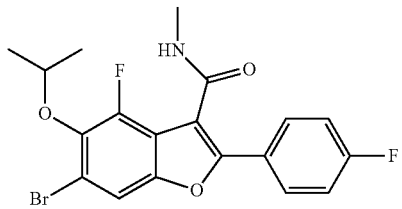 [SMILES: CNC(=O)c1c(-c2ccc(F)cc2)oc2cc(Br)c(OC(C)C)c(F)c12]

A mixture of 6-bromo-4-fluoro-2-(4-fluorophenyl)-5-hydroxy-N-methylbenzofuran-3-carboxamide (2.3 g, 6.02 mmol), iso-propyl iodide (3.01 mL, 30.1 mmol), and potassium carbonate (4.16 g, 30.1 mmol) in acetonitrile (170 mL) was stirred for 4 hrs at 85° C. The solvent was removed. The residue was dissloved in $CH_2Cl_2$ (300 mL), which was washed with water and brine, dried over $MgSO_4$, and concentrated to give 2.56 g (100%) of the target compound as an off white solid.

$^1$H NMR (500 MHz, DMSO-$d_6$) δ 8.71 (m 1H), 7.94 (d, J=1.1 Hz, 1H), 7.92-7.86 (m, 2H), 7.45-7.39 (m, 2H), 4.49-4.42 (m, 1H), 2.82 (d, J=4.6 Hz, 3H), 1.34 (d, J=6.1 Hz, 6H).

LCMS $R_t$=3.580 min., m/z 426 (M+2H).

The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

4-Fluoro-2-(4-fluorophenyl)-5-isopropoxy-6-(methoxymethyl)-N-methylbenzofuran-3-carboxamide

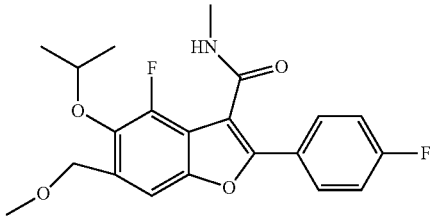 [SMILES: CNC(=O)c1c(-c2ccc(F)cc2)oc2cc(COC)c(OC(C)C)c(F)c12]

A mixture of 6-bromo-4-fluoro-2-(4-fluorophenyl)-5-isopropoxy-N-methylbenzofuran-3-carboxamide (600 mg, 1.414 mmol), potassium methoxymethyltrifluoroborate (2149 mg, 14.14 mmol), $PdCl_2$(dppf) (310 mg, 0.424 mmol) and cesium carbonate (2074 mg, 6.36 mmol) in a mixture of toluene (60 mL) and water (20 ml) was flushed with $N_2$ and then stirred at 85° C. for 48 hrs. The mixture was diluted with EtOAc (200 mL). The water layer was removed. The organic layer was filtered and then concentrated to give a crude solid, which was purified by column chromatography (Biotage 25 m, EtOAc/Hexane=0 to 30%) to give 280 mg (51%) of the product as a white solid.

$^1$H NMR (400 MHz, CHLOROFORM-d) δ 7.99-7.92 (m, 2H), 7.41 (s, 1H), 7.21-7.13 (m, 2H), 6.12 (br. s., 1H), 4.62 (d, J=0.5 Hz, 2H), 4.56-4.47 (m, 1H), 3.51-3.47 (m, 3H), 3.07 (d, J=5.0 Hz, 3H), 1.37 (m, 6H).

LCMS $R_t$=3.151 min., m/z 390 (M+H).

The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

4-Fluoro-2-(4-fluorophenyl)-5-hydroxy-6-(methoxymethyl)-N-methylbenzofuran-3-carboxamide

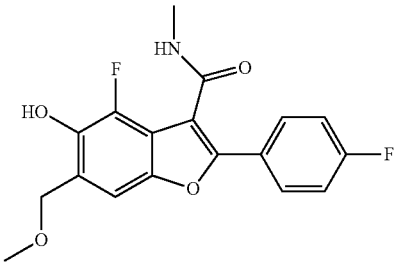 [SMILES: CNC(=O)c1c(-c2ccc(F)cc2)oc2cc(COC)c(O)c(F)c12]

Trichloroborane (2.134 mL, 2.134 mmol) was added dropwise to a solution of 4-fluoro-2-(4-fluorophenyl)-5-isopropoxy-6-(methoxymethyl)-N-methylbenzofuran-3-carboxamide (277 mg, 0.711 mmol) in DCM (50 mL) at −10°

C. The reaction mixture was stirred for 30 min at −10° C., and then added with methanol (20 mL) and stirred at rt over weekend. The solvent was removed to give the crude product (202 mg), which was directly used in the next reaction without further purification.

$^1$H NMR (400 MHz, METHANOL-$d_4$) δ 7.94-7.86 (m, 2H), 7.34 (s, 1H), 7.25 (t, J=8.8 Hz, 2H), 4.64 (s, 2H), 3.47 (s, 3H), 2.96 (s, 3H).

LCMS $R_t$=2.422 min., m/z 348 (M+H).

The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

4-Fluoro-2-(4-fluorophenyl)-6-(methoxymethyl)-3-(methylcarbamoyl)benzofuran-5-yl trifluoromethanesulfonate

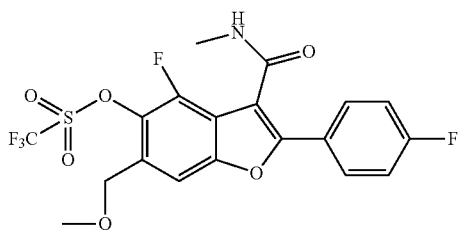 [SMILES: CNC(=O)c1c(-c2ccc(F)cc2)oc2cc(COC)c(OS(=O)(=O)C(F)(F)F)c(F)c12]

Triethylamine (0.162 mL, 1.163 mmol) was added dropwise to a suspension of 4-fluoro-2-(4-fluorophenyl)-5-hydroxy-6-(methoxymethyl)-N-methylbenzofuran-3-carboxamide (202 mg, 0.582 mmol) in DCM (100 mL) at room temperature under $N_2$. 1,1,1-trifluoro-N-phenyl-N-((trifluoromethyl)sulfonyl)methanesulfonamide (249 mg, 0.698 mmol) was added portionwise to the mixture at 0° C. The mixture was then allowed to warm to rt, and stirred overnight. Additional 1,1,1-trifluoro-N-phenyl-N-((trifluoromethyl)sulfonyl)methanesulfonamide (249 mg, 0.698 mmol) and triethylamine (0.162 mL, 1.163 mmol) were added. The mixture was stirred at room temperature for 12 hrs. The reaction mixture was washed with water, and water solution was extracted with $CH_2Cl_2$. The combined organic layer was washed with brine, dried over $MgSO_4$, filtered and concentrated to give the crude product as a dark yellow solid, which was purified by column chromatography (Biotage 25 s, EtOAc/Hexanes=0 to 25%) to give 238 mg of the product.

$^1$H NMR (400 MHz, CHLOROFORM-d) δ 7.98-7.88 (m, 2H), 7.53-7.50 (m, 1H), 7.22-7.15 (m, 2H), 6.17 (br. s., 1H), 4.67 (s, 2H), 3.53-3.50 (m, 3H), 3.05 (d, J=5.0 Hz, 3H).

LCMS $R_t$=3.436 min., m/z 480 (M+H).

The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

Methyl 5-(4-fluoro-2-(4-fluorophenyl)-6-(methoxymethyl)-3-(methylcarbamoyl)benzofuran-5-yl)-2-methoxy-4-methylbenzoate

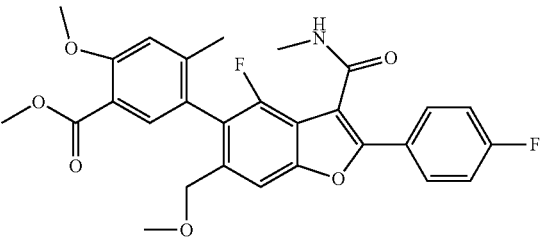 [SMILES: CNC(=O)c1c(-c2ccc(F)cc2)oc2cc(COC)c(-c3cc(C(=O)OC)c(OC)cc3C)c(F)c12]

To a mixture of 4-fluoro-2-(4-fluorophenyl)-6-(methoxymethyl)-3-(methylcarbamoyl)benzofuran-5-yl trifluoromethanesulfonate (71.4 mg, 0.149 mmol) in dioxane (3 mL) along with water (0.3 mL), cesium carbonate (83 mg, 0.253 mmol), (4-methoxy-5-(methoxycarbonyl)-2-methylphenyl)boronic acid (45.1 mg, 0.201 mmol) and palladium tetrakis(triphenyl)phosphine (33.8 mg, 0.029 mmol) were added. The resulted mixture was degassed and then heated at 90° C. for 3 hrs. The solvent was evaporated. The residue was purified by column chromatography (Biotage 25 s, EtOAc/Hexane=0 to 30%) to give 43 mg (56%, two steps) of the target compound as an off white solid.

$^1$H NMR (400 MHz, CHLOROFORM-d) δ 8.03-7.96 (m, 2H), 7.65 (s, 1H), 7.58 (s, 1H), 7.21-7.14 (m, 2H), 6.96 (s, 1H), 6.22 (br. s., 1H), 4.25-4.11 (m, 2H), 3.98 (s, 3H), 3.87 (s, 3H), 3.31 (s, 3H), 3.00 (d, J=5.0 Hz, 3H), 2.14 (s, 3H).

LCMS $R_t$=3.190 min., m/z 510 (M+H).

The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

5-(4-Fluoro-2-(4-fluorophenyl)-6-(methoxymethyl)-3-(methylcarbamoyl)benzofuran-5-yl)-2-methoxy-4-methylbenzoic acid

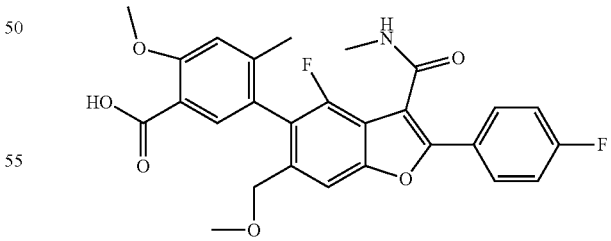

A solution of 1M sodium hydroxide (0.253 mL, 0.253 mmol) was added to a solution of methyl 5-(4-fluoro-2-(4-fluorophenyl)-6-(methoxymethyl)-3-(methylcarbamoyl)benzofuran-5-yl)-2-methoxy-4-methylbenzoate (43 mg, 0.084 mmol) in MeOH (1 mL) and THF (1 mL). The reaction mixture was stirred at room temperature overnight. 1N HCl (0.6 mL) was added to the mixture. The organic solvent was removed, and water was sucked out from the solid. The solid was washed with water, and dried to give 38 mg of the crude target product as white solid.

LCMS $R_t$=2.870 min., m/z 496 (M+H).

The LC/MS data was obtained on a Shimadzu analytical LC/Micromass Platform LC (ESI+) at 220 nm using the following set of conditions: Phenomenex Luna 3 µm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

5-(5-(Bicyclo[1.1.1]pentan-1-ylcarbamoyl)-4-methoxy-2-methylphenyl)-4-fluoro-2-(4-fluorophenyl)-6-(methoxymethyl)-N-methylbenzofuran-3-carboxamide

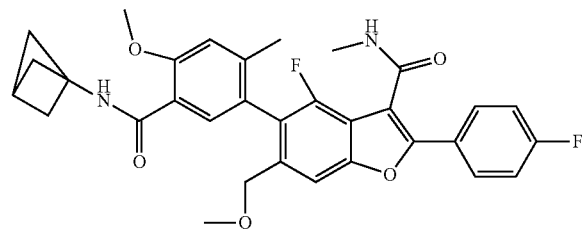 [SMILES: CNC(=O)c1c(-c2ccc(F)cc2)oc2cc(COC)c(-c3cc(C(=O)NC45CC(C4)C5)c(OC)cc3C)c(F)c12]

A mixture of 5-(4-fluoro-2-(4-fluorophenyl)-6-(methoxymethyl)-3-(methylcarbamoyl)benzofuran-5-yl)-2-methoxy-4-methylbenzoic acid (38 mg, 0.077 mmol), DMF (1 mL), N-ethyl-N-isopropylpropan-2-amine (0.080 mL, 0.460 mmol), bicyclo[1.1.1]pentan-1-amine HCl (22.93 mg, 0.192 mmol) and HATU (87 mg, 0.230 mmol) was stirred at room temperature for 3 hrs. The reaction mixture was purified via preparative LC/MS to yield 33.5 mg (98%) of the product and the purity is 100% by analytical LCMS analysis.

$^1$H NMR (500 MHz, DMSO-$d_6$) δ 8.69 (d, J=4.9 Hz, 1H), 8.48 (s, 1H), 7.93 (dd, J=8.9, 5.5 Hz, 2H), 7.64 (s, 1H), 7.49 (s, 1H), 7.42 (t, J=8.9 Hz, 2H), 7.16 (s, 1H), 4.18-4.08 (m, 2H), 3.95 (s, 3H), 3.19 (s, 3H), 2.78 (d, J=4.6 Hz, 3H), 2.45 (s, 1H), 2.12-2.02 (m, 9H).

Method 1: LCMS $R_t$=3.31 min., m/z 561 (M+H), 100% purity.

Method 2: LCMS $R_t$=4.17 min., m/z 561 (M+H), 100% purity.

The preparative LC/MS was performed with the following conditions: Column: Waters XBridge C18, 19×200 mm, 5-µm particles; Guard Column: Waters XBridge C18, 19×10 mm, 5-µm particles; Mobile Phase A: water with 20-mM ammonium acetate; Mobile Phase B: 95:5 acetonitrile:water with 20-mM ammonium acetate; Gradient: 55-95% B over 12 minutes, then a 5-minute hold at 100% B; Flow: 20 mL/min. Fractions containing the desired product were combined and dried via centrifugal evaporation.

The final purity was determined by two analytical LC/MS methods. Method 1 conditions: Column: Waters BEH C18, 2.0×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Method 2 conditions: Column: Waters BEH C18, 2.0×50 mm, 1.7-µm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min.

The preparation of 5-(3-(bicyclo[1.1.1]pentan-1-ylcarbamoyl)phenyl)-4-fluoro-2-(4-fluorophenyl)-6-(methoxymethyl)-N-methylbenzofuran-3-carboxamide

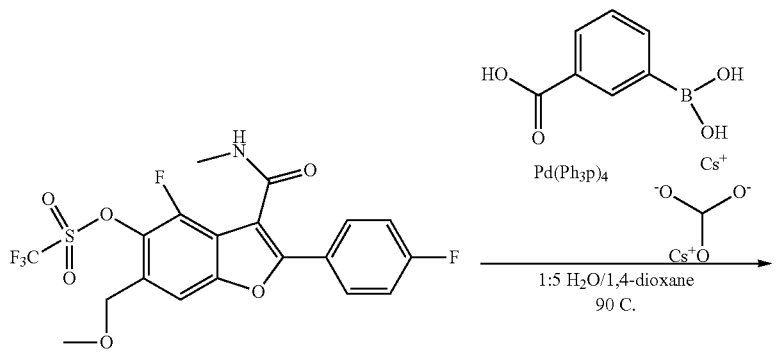

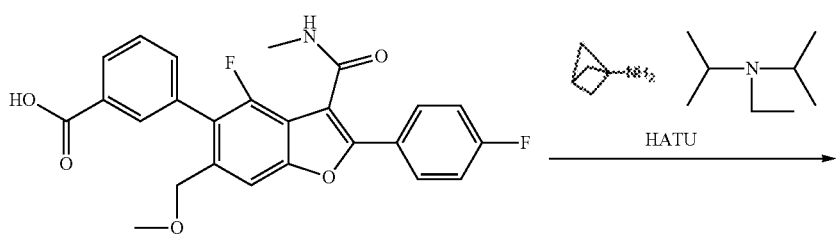

-continued

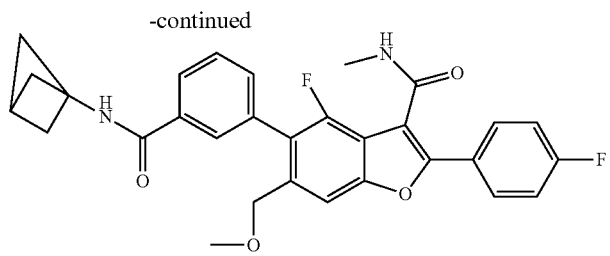

3-(4-Fluoro-2-(4-fluorophenyl)-6-(methoxymethyl)-3-(methylcarbamoyl)benzofuran-5-yl)benzoic acid 5-(3-(Bicyclo[1.1.1]pentan-1-ylcarbamoyl)phenyl)-4-fluoro-2-(4-fluorophenyl)-6-(methoxymethyl)-N-methylbenzofuran-3-carboxamide

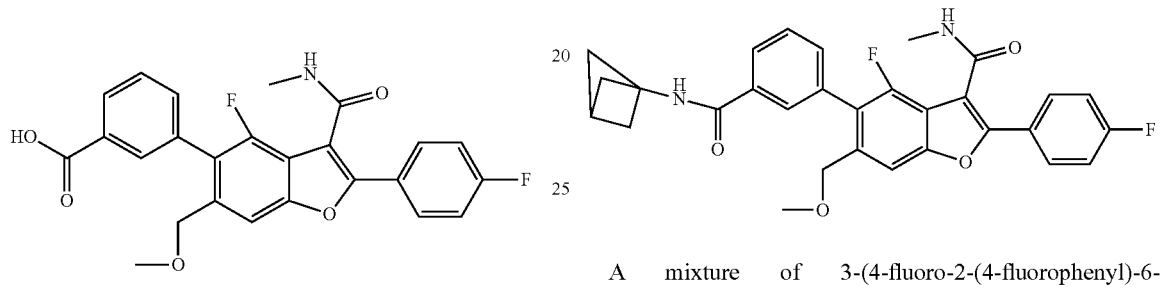

A mixture of 4-fluoro-2-(4-fluorophenyl)-6-(methoxymethyl)-3-(methylcarbamoyl)benzofuran-5-yltrifluoromethanesulfonate (238 mg, 0.496 mmol) in dioxane (12 mL) along with Water (1.2 mL), cesium carbonate (275 mg, 0.844 mmol), 3-boronobenzoic acid (111 mg, 0.670 mmol) and palladium tetrakis(triphenyl)phosphine (57.4 mg, 0.050 mmol) was degassed and then heated at 90° C. for 3 hrs. The solvent was removed. The residue was dissolved in $CH_2Cl_2$ (150 mL) and added with 1N HCl (5 mL). The mixture was washed with water, brine, dried over $MgSO_4$, filtered and concentrated to give a solid. The solid was triturated with ether (6 mL) and dried to give 150 mg (67%) of the crude target compound as a yellowish solid. This compound was directly used in the next reaction without further purification.

$^1$H NMR (400 MHz, METHANOL-$d_4$) δ 8.14-8.11 (m, 1H), 8.03 (s, 1H), 7.99-7.94 (m, 2H), 7.64-7.61 (m, 3H), 7.33-7.26 (m, 2H), 4.30 (s, 2H), 3.30 (s, 3H), 2.96-2.93 (m, 3H).

LCMS $R_t$=2.940 min., m/z 452 (M+H).

The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

A mixture of 3-(4-fluoro-2-(4-fluorophenyl)-6-(methoxymethyl)-3-(methylcarbamoyl)benzofuran-5-yl) benzoic acid (30 mg, 0.066 mmol), DMF (1 mL), N-ethyl-N-isopropylpropan-2-amine (0.069 mL, 0.399 mmol), bicyclo[1.1.1]pentan-1-amine HCl (19.87 mg, 0.166 mmol) and HATU (76 mg, 0.199 mmol) was stirred at rt for 3 hrs. The reaction mixture was purified via preparative LC/MS to yield 20.4 mg (59.4%) of the product and the purity is 100% by LCMS analysis.

$^1$H NMR (500 MHz, DMSO-$d_6$) δ 9.06 (s, 1H), 8.70 (d, J=4.6 Hz, 1H), 7.96-7.88 (m, 3H), 7.79 (s, 1H), 7.65 (s, 1H), 7.58 (t, J=7.8 Hz, 1H), 7.49 (d, J=7.6 Hz, 1H), 7.41 (t, J=8.9 Hz, 2H), 4.25 (s, 2H), 3.19 (s, 3H), 2.78 (d, J=4.6 Hz, 3H), 2.46 (s, 1H), 2.08 (s, 6H).

Method 1: LCMS $R_t$=3.06 min., m/z 517 (M+H), 100% purity.

Method 2: LCMS $R_t$=3.99 min., m/z 517 (M+H), 100% purity.

The preparative LC/MS was performed with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 30-95% B over 19 minutes, then a 3-minute hold at 100% B; Flow: 20 mL/min. Fractions containing the desired product were combined and dried via centrifugal evaporation.

Two analytical LC/MS methods were used to determine the final purity. Method 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Method 2 conditions: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min.

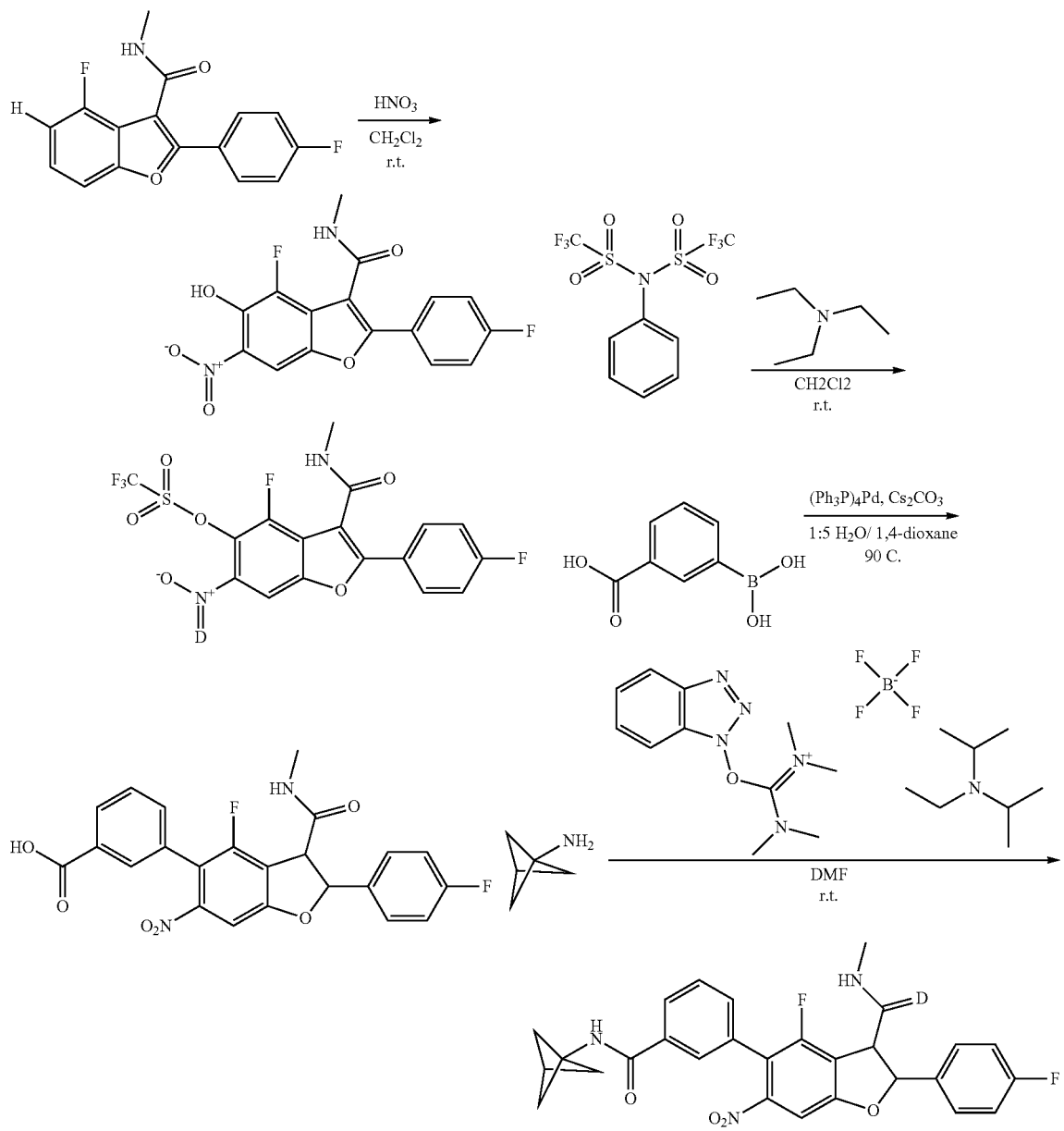

4-Fluoro-2-(4-fluorophenyl)-5-hydroxy-N-methyl-6-nitrobenzofuran-3-carboxamide

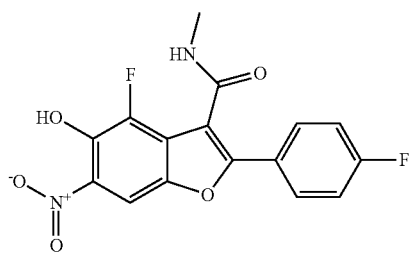

To a white suspension of 4-fluoro-2-(4-fluorophenyl)-5-hydroxy-N-methylbenzofuran-3-carboxamide (2 g, 6.59 mmol) in $CH_2Cl_2$ (20 mL) at r.t. under $N_2$ was added dropwise nitric acid (0.712 mL, 15.83 mmol, 70%). The mixture was stirred at r.t., and solid precipitated out within 3 min. The mixture was then stirred at r.t. for another 2 min after the solid formed and until the mixture was difficult to stir, added with 100 mL $H_2O$ and filtered. The solid residue was washed with $H_2O$ (3×40 mL) and dried. The solid after drying was dissolved in 50 mL DMF, and then the mixture was added with 110 mL $H_2O$ slowly (slightly exothermic). The yellow precipitates were filtered and washed with $H_2O$ (3×40 mL) and dried to give the product (1.572 g, 68%).

$^1$H NMR (400 MHz, DMSO-$d_6$, J in Hz) δ 10.83 (broad s, 1H), 8.79-8.76 (m, 1H), 8.23 (d, J=1.5, 1H), 7.96-7.92 (m, 2H), 7.45 (appeared as t, J=8.9, 2H), 2.84 (d, J=4.6, 3H). $^{19}$F NMR (376.46 MHz, DMSO-$d_6$) δ −108.93, −139.26 (The $^{19}$F chemical shift was referenced to $CFCl_3$ at 0.0 ppm).

LCMS (ES+) m/z (M+H)$^+$=349.14, $R_f$=1.167 min.

LC/MS were performed by using Shimadzu-VP instrument with UV detection at 220 nm and Waters Micromass. HPLC method: Solvent A=10% MeOH/90% H₂O/0.1% TFA, Solvent B=90% MeOH/10% H₂O/0.1% TFA, Start % B=40, Final % B=100, Gradient time=2 min, Stop time=3 min, Flow Rate=1 ml/min, Column: Phenomenex-Luna, 2.0×30 mm, 3 um.

4-Fluoro-2-(4-fluorophenyl)-3-(methylcarbamoyl)-6-nitrobenzofuran-5-yl trifluoromethanesulfonate

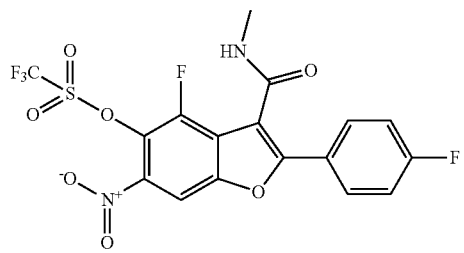

To a mixture of 4-fluoro-2-(4-fluorophenyl)-5-hydroxy-N-methyl-6-nitrobenzofuran-3-carboxamide (750 mg, 2.154 mmol) in CH₂Cl₂ (22 mL) at r.t. under N₂ was added triethylamine (0.600 mL, 4.31 mmol) dropwise. The mixture was cooled in an ice-water bath and stirred until it turned from a suspension to a reddish brown solution. The mixture was then added with 1,1,1-trifluoro-N-phenyl-N-((trifluoromethyl)sulfonyl)methanesulfonamide (1154 mg, 3.23 mmol) portion-wise. The mixture was then stirred at r.t. overnight. Another amount of triethylamine (0.600 mL, 4.31 mmol) followed by 1,1,1-trifluoro-N-phenyl-N-((trifluoromethyl)sulfonyl)methanesulfonamide (1154 mg, 3.23 mmol) were added to the reaction mixture, which was stirred for another 4 hours. The mixture was evaporated to dryness and then added with 55 ml H₂O. The light brown solid was filtered and washed with H₂O (3×15 mL) and dried. The solid was further washed with Et₂O (2×15 mL) to give the product as a beige solid (938 mg, 91%).

¹H NMR (400 MHz, DMSO-d₆) δ 8.91-8.88 (m, 1H), 8.79 (d, J=1.2, 1H), 8.00-7.96 (m, 2H), 7.50 (appeared as t, J=8.9, 2H), 2.85 (d, J=4.9, 3H). ¹⁹F NMR (376.46 MHz, DMSO-d₆) −72.83, −107.76, −130.66.

LCMS (ES+) m/z (M+H)⁺=481.08, R$_t$=1.735 min.

LC/MS were performed by using Shimadzu-VP instrument with UV detection at 220 nm and Waters Micromass. HPLC method: Solvent A=10% MeOH/90% H₂O/0.1% TFA, Solvent B=90% MeOH/10% H₂O/0.1% TFA, Start % B=40, Final % B=100, Gradient time=2 min, Stop time=3 min, Flow Rate=1 ml/min, Column: Phenomenex-Luna, 2.0×30 mm, 3 um.

3-(4-Fluoro-2-(4-fluorophenyl)-3-(methylcarbamoyl)-6-nitrobenzofuran-5-yl)benzoic acid

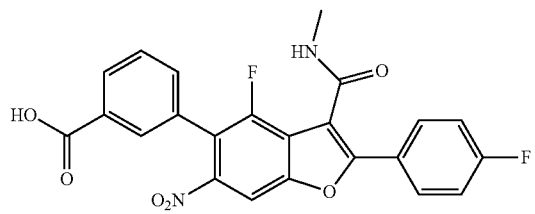 [SMILES: CNC(=O)c1c(-c2ccc(F)cc2)oc2cc([N+](=O)[O-])c(-c3cccc(C(=O)O)c3)c(F)c12]

A mixture of 4-fluoro-2-(4-fluorophenyl)-3-(methylcarbamoyl)-6-nitrobenzofuran-5-yltrifluoromethanesulfonate (250 mg, 0.520 mmol), 3-boronobenzoic acid (130 mg, 0.781 mmol), (Ph₃P)₄Pd (60.1 mg, 0.052 mmol) and cesium carbonate (288 mg, 0.885 mmol) in a mixture of water (1.2 mL)/dioxane (6 mL) under N₂ was stirred at 90° C. for 4 hours, and then left standing at r.t. for 14 hours. The mixture was diluted with 4 mL 1,4-dioxane, added with 4 ml 1N HCl, and diluted with 40 ml H₂O. The brown solid was filtered, washed with 3×4 ml H₂O and dried. The solid was further washed with Et₂O (3×2 mL) and then with a 1:10 mixture of MeOH/Et₂O (2×2 mL) and dried.

LCMS (ES+) m/z (M+H)⁺=453.14, R$_t$=1.723 min.

LC/MS were performed by using Shimadzu-VP instrument with UV detection at 220 nm and Waters Micromass. HPLC method: Solvent A=10% MeOH/90% H₂O/0.1% TFA, Solvent B=90% MeOH/10% H₂O 0.1% TFA, Start % B=40, Final % B=100, Gradient time=2 min, Stop time=3 min, Flow Rate=1 ml/min, Column: Phenomenex-Luna, 2.0×30 mm, 3 um.

5-(3-(Bicyclo[1.1.1]pentan-1-ylcarbamoyl)phenyl)-4-fluoro-2-(4-fluorophenyl)-N-methyl-6-nitrobenzofuran-3-carboxamide

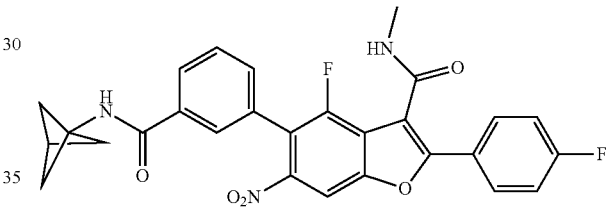

To a mixture of 3-(4-fluoro-2-(4-fluorophenyl)-3-(methylcarbamoyl)-6-nitrobenzofuran-5-yl)benzoic acid (133 mg, 0.294 mmol) (crude assumed 0.294 mmol), bicyclo[1.1.1]pentan-1-amine HCl (70.3 mg, 0.588 mmol) and 2-(1H-benzo[d][1,2,3]triazol-1-yl)-1,1,3,3-tetramethylisouronium tetrafluoroborate (236 mg, 0.735 mmol) in DMF (3 mL) at r.t. under N₂ was added N-ethyl-N-isopropylpropan-2-amine (0.308 mL, 1.764 mmol). The mixture was stirred at r.t. for 18 hours. The mixture was added with 12 mL H₂O. The solid filtered and washed with H₂O (3×3 mL) and dried. The solid was further washed with Et₂O (2×2 mL) and dried to give the crude product as a brown solid (108 mg). The ethereal filtrate which still contained the product was evaporated and the residue purified by preparative LC/MS using the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 50-90% B over 12 minutes, then a 5-minute hold at 100% B; Flow: 20 mL/min. Fractions containing the desired product were combined and dried via centrifugal evaporation.

¹H NMR (500 MHz, DMSO-d₆) δ 9.09 (s, 1H), 8.84-8.81 (m, 1H), 8.49 (s, 1H), 7.99-7.97 (m, 2H), 7.93 (d, J=7.6, 1H), 7.83 (s, 1H), 7.53 (d, J=7.6, 1H), 7.46 (appeared as t, J=8.7, 2H), 7.61-7.58 (m, 1H), 2.80 (d, J=4.6, 3H), 2.46 (s, 1H), 2.09 (s, 6H).

Method 1: LCMS (ES+) m/z (M+H)⁺=518.2, R$_t$=2.98 min., 99% purity.

Method 2: LCMS (ES+) m/z (M+H)+=518.2, $R_f$=3.91 min., 99% purity.

Two analytical LC/MS methods were used to determine the final purity. Method 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0.5 min hold at 0% B, 0-100% B over 4 minutes, then a 0.5-minute hold at 100% B; Flow: 1 mL/min. Method 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0.5 min hold at 0% B, 0-100% B over 4 minutes, then a 0.5-minute hold at 100% B; Flow: 0.5 mL/min.

Preparation of bicyclo[1.1.1]pentan-1-amine hydrochloride Methods from Literature Reference: Kevin D. Bunker et. al. Organic Letters 2011, 13 (17), 4746-4748 and Associated Supplementary Information

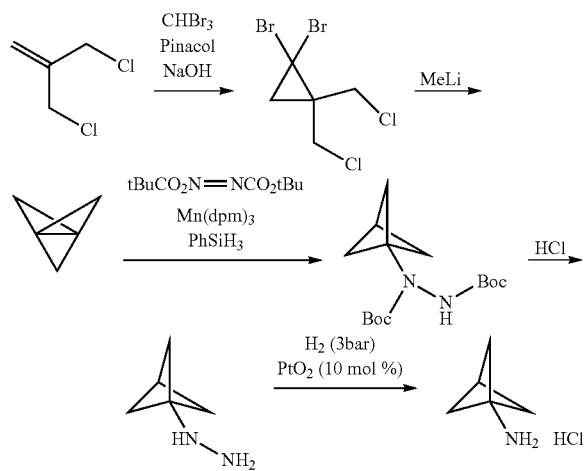

1,1-dibromo-2,2-bis(chloromethyl)cyclopropane

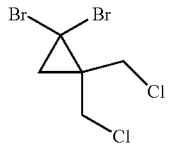

A mixture of 3-chloro-2-(chloromethyl)prop-1-ene (50 g, 400 mmol), bromoform (70.0 ml, 800 mmol), pinacol (1.749 g, 14.80 mmol) and 6,7,9,10,17,18,20,21-octahydrodibenzo[b,k][1,4,7,10,13,16]hexaoxacyclo-octadecin (1.442 g, 4.00 mmol) was very vigorously stirred. To the mixture was added in one portion a 50% aqueous sodium hydroxide (304 g, 3800 mmol) solution that had been pre-cooled to 15° C. The color of the reaction mixture turned to orange, and then brown and black within 5 min. The internal temperature of the reaction mixture rose to 49-50° C. within 20 min. At which point, the reaction mixture was cooled to 20° C. by using a water bath. After 1 hr, the water bath was removed and the mixture was stirred at 40° C. for 4 days. The reaction mixture was cooled to room temperature, and diluted with water (500 mL), then filtered through a pad of Celite on a glass-fritted funnel (pore size C) and washed with water (1.5 L). The dark brown solid was transferred to a beaker using hexane/acetone (1/1, 500 mL×3). The Combined organic solution was dried over $MgSO_4$, filtered and concentrated. The residue was triturated with hexanes to give 1,1-dibromo-2,2-bis(chloromethyl)cyclopropane (77.58 g, 65%).

$^1$H NMR (400 MHz, $CDCl_3$) δ 3.99 (d, J=6.0 Hz, 4H), 1.85 (s, 2H). $^{13}$C NMR (100.6 MHz, $CDCl_3$) δ: 47.31, 34.92, 33.62, 31.63.

Tricyclo[1.1.1.0$^{1,3}$]pentane

Methyllithium (46.3 mL, 74.1 mmol, 1.6M in diethyl ether) was added to a solution of 1,1-dibromo-2,2-bis(chloromethyl)cyclopropane (10 g, 33.7 mmol) in pentane (10 mL) stirred at −78° C. for 15 min. After the reaction mixture was maintained at −78° C. for 15 min, the reaction flask was removed from the dry ice/acetone bath and placed in an ice-water bath. The reaction mixture was stirred at that temperature for 2 hrs. The volatiles, which was warmed at 40° C. by using an oil bath, were collected via a shortpath distillation condenser under a dry-ice-acetone environment. The condensed material was used in next reaction without further purification.

Di-tert-butyl 1-(bicyclo[1.1.1]pentan-1-yl)hydrazine-1,2-dicarboxylate

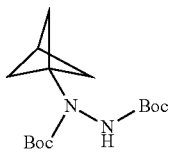

Under a nitrogen atmosphere tris(2,2,6,6-tetramethyl-3,5-heptanedionato)manganese (III) (0.300 g, 0.496 mmol) was dissolved in 2-propanol (100 mL) at rt, and then the solution cooled to 0° C. A mixture of phenylsilane (2.68 g, 24.80 mmol) and di-tert-butylazodicarboxylate (8.57 g, 37.2 mmol) in DCM (100 mL) was slowly added to the above mixture to maintain the temperature at 0° C. The mixture was then added with tricyclo[1.1.1.0$^{1,3}$]pentane (1.639 g, assumed 24.8 mmol). The resulting mixture was stirred at 0° C. for 19 hrs. The reaction was quenched by adding water (10 ml) and brine (25 mL). The mixture was stirred for 5 min and then extracted with EtOAc. The combined organic extracts were dried ($MgSO_4$), filtered and the volatiles removed under reduced pressure. The crude residue was then purified by flash chromatography (Biotage 40 m, 0 to 25% EtOAc/Hexanes) to give di-tert-butyl 1-(bicyclo[1.1.1]pentan-1-yl)hydrazine-1,2-dicarboxylate (6.18 g, 84%) as a white solid.

$^1$H NMR (400 MHz, CDCl$_3$) δ 6.29 (br, 0.64H), 6.01 (br, 0.36H), 2.41 (s, 1H), 2.06 (s, 6H), 1.49 (s, 18H).

Bicyclo[1.1.1]pentan-1-ylhydrazine

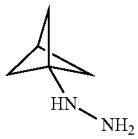

To a solution of di-tert-butyl 1-(bicyclo[1.1.1]pentan-1-yl)hydrazine-1,2-dicarboxylate (18.9 g, 63.3 mmol) in ethyl acetate (100 mL) at room temperature was added hydrochloric acid (158 mL, 633 mmol, 4M in dioxane). The reaction mixture was stirred at room temperature for 20 hrs. The solvent was concentrated to ⅓ of the volume, and solid was collected and washed with ether, and then dried to give the hydrochloride salt of bicyclo[1.1.1]pentan-1-ylhydrazine (9.56 g, 88%) as a white solid.

$^1$H NMR (400 MHz, DMSO-d$_6$) δ 2.47 (s, 1H), 1.84 (s, 6H).

$^{13}$C NMR (100.6 MHz, DMSO-d$_6$) δ 53.96, 49.41, 21.56.

Bicyclo[1.1.1]pentan-1-amine hydrochloride

Platinum(IV) oxide (1.269 g, 5.59 mmol) was added to solution of bicyclo[1.1.1]pentan-1-ylhydrazine (9.56 g, 55.9 mmol, assumed 2 HCl) in MeOH (200 mL). The mixture was placed under 3 bar of hydrogen at room temperature for 20 hrs. The mixture was filtered through a cake of celite, and the filtrate was concentrated. The solid was washed with ether, and then triturated with a mixture of isopropyl alcohol/DCM (10/1) (260 mL), and filtered. The filtrate was evaporated to provide bicyclo[1.1.1]pentan-1-amine hydrochloride (6.4 g, 96%) as an off white solid.

$^1$H NMR (400 MHz, DMSO-d$_6$) δ 8.73 (br. s., 3H), 2.61 (s, 1H), 1.99 (s, 6H).

$^{13}$C NMR (100.6 MHz, DMSO-d$_6$) δ 50.35, 44.79, 22.98.

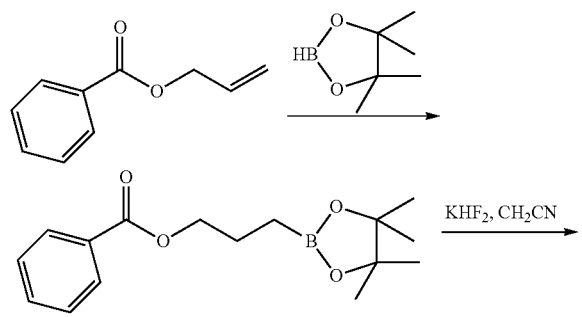

3-(4,4,5,5-Tetramethyl-1,3,2-dioxaborolan-2-yl)propyl benzoate

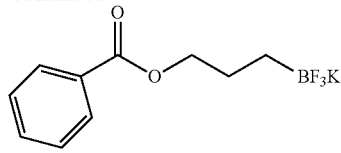

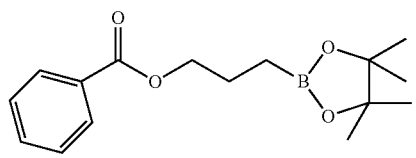 [SMILES: CC1(C)OB(CCCOC(=O)c2ccccc2)OC1(C)C]

To a solution of allyl benzoate (6 g, 37.0 mmol) in dichloromethane (100 mL) in the presence of Tris(triphenylphosphine)rhodium(I) chloride (0.685 g, 0.740 mmol) catalyst at 0° C. was added 4,4,5,5-tetramethyl-1,3,2-dioxaborolane (7.10 g, 55.5 mmol). The reaction mixture was allowed to warm to room temperature, and stirred for 18 hrs. The mixture was then added with dichloromethane, and washed with water and brine, dried over MgSO$_4$, and concentrated to give a residue. Purification of the residue by column chromatography (Biotage 45 m, 0 to 10% EtOAc/Hexanes) gave 3-(4,4,5,5-tetramethyl-1,3,2-dioxaborolan-2-yl)propyl benzoate (5.73 g, 53%).

$^1$H NMR (400 MHz, CHLOROFORM-d) δ 8.10-8.04 (m, 2H), 7.60-7.54 (m, 1H), 7.48-7.42 (m, 2H), 4.32 (t, J=6.8 Hz, 2H), 1.96-1.86 (m, 2H), 1.28 (m, 12H), 0.99-0.91 (m, 2H).

LCMS Rt=3.601 min., m/z 291 (M+H), 96.21% purity.

The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

Potassium (3-(benzoyloxy)propyl)trifluoroborate

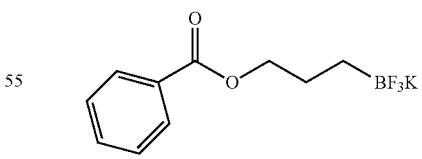

3-(4,4,5,5-Tetramethyl-1,3,2-dioxaborolan-2-yl)propyl benzoate (5.73 g, 19.75 mmol) was dissolved in acetonitrile (100 mL) and potassium bifluoride (4.78 g, 61.2 mmol) was added at room temperature followed by the addition of water (12 mL) over 1 hr. The reaction mixture was stirred at room temperature for 1 hr. The mixture was added with water (12 mL), and extracted with acetone (40 and 3×10 mL). The combined acetone extracts was concentrated and then dried under high vacuum for 1 hr. The resulting white solid was purified by dissolving in hot (70° C.) acetonitrile (60 mL), and precipitation by adding Et₂O (300 mL). The suspension was left standing at room temperature for 0.5 hr and 0° C. for 0.5 hr. The solid was filtered and dried to provide potassium (3-(benzoyloxy)propyl)trifluoroborate (5.33 g, 100%) as a white solid.

¹H NMR (500 MHz, Acetone-d₆) δ 8.06-8.02 (m, 2H), 7.64-7.60 (m, 1H), 7.54-7.48 (m, 2H), 4.26 (t, J=7.6 Hz, 2H), 1.77-1.69 (m, 2H), 0.22 (m, 2H).

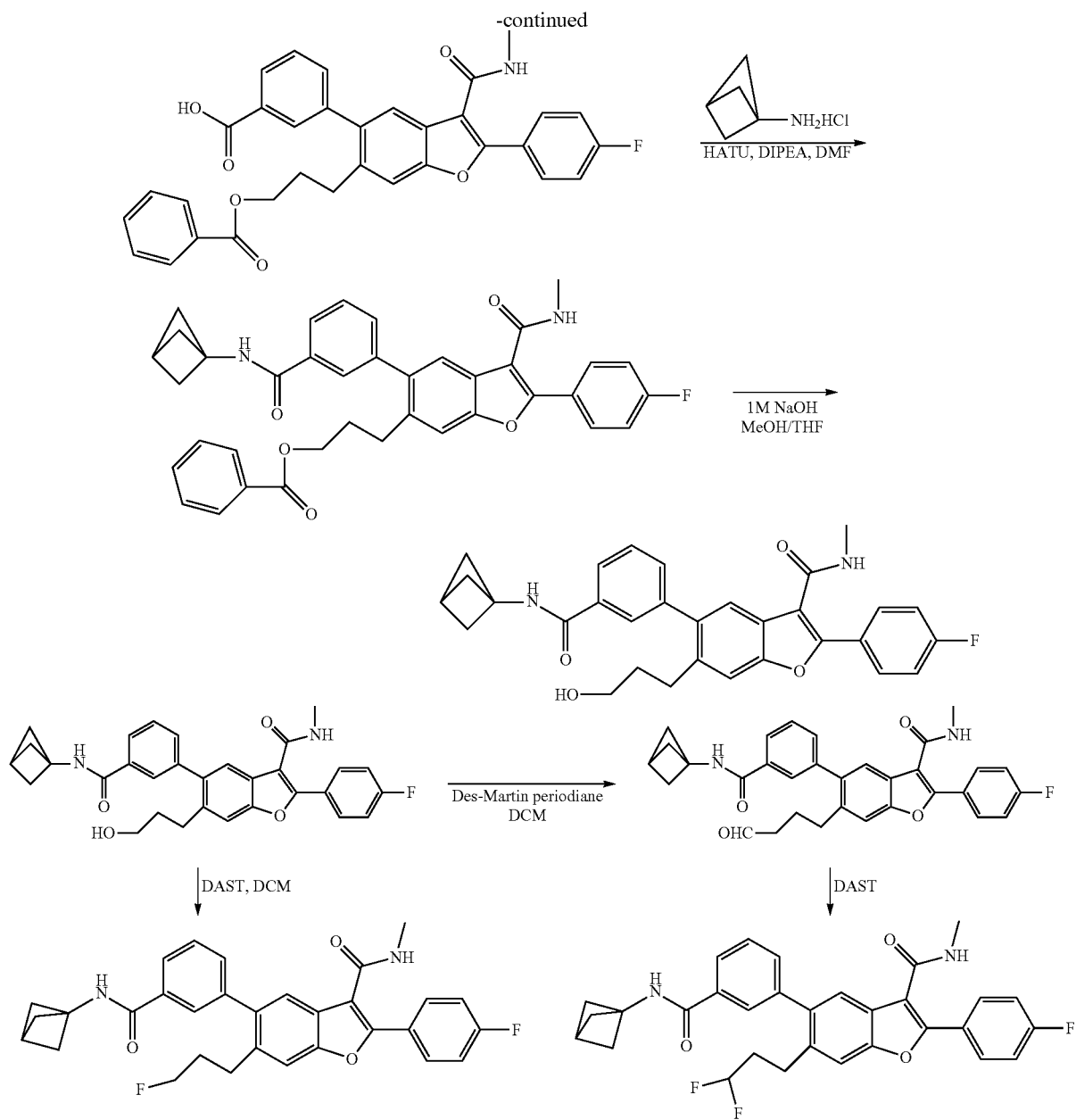

6-Bromo-2-(4-fluorophenyl)-5-isopropoxybenzofuran-3-carboxylic acid

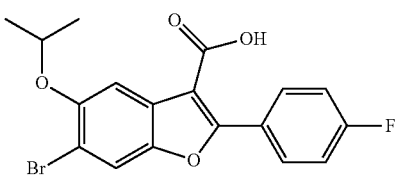 [SMILES: CC(C)Oc1cc2c(C(=O)O)c(-c3ccc(F)cc3)oc2cc1Br]

A 1M solution of sodium hydroxide (24.21 mL, 24.21 mmol) was added into a solution of ethyl 6-bromo-2-(4-fluorophenyl)-5-isopropoxybenzofuran-3-carboxylate (3.4 g, 8.07 mmol) in 1:1 MeOH (34 mL)/THF (34 mL). The mixture was stirred with gentle heating at 40° C. overnight. The mixture was cooled to 0° C. and ice-cold 1M HCl (100 mL) was added. The resulting yellow solid was filtered, washed with water and dried under vacuum for three days. A 3.137 g (99%) of 6-bromo-2-(4-fluorophenyl)-5-isopropoxybenzofuran-3-carboxylic acid was obtained.

$^1$H NMR (400 MHz, DMSO-$d_6$) δ 8.10-8.03 (m, 3H), 7.63 (s, 1H), 7.45-7.37 (m, 2H), 4.69-4.61 (m, 1H), 1.36 (d, J=6.0 Hz, 6H).

LCMS Rt=3.77 min., m/z 393 (M+1), 92.7% purity.

The LC/MS data was obtained on a Shimadzu analytical LC/Micromass Platform LC (ESI+) at 220 nm using The following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

6-Bromo-2-(4-fluorophenyl)-5-isopropoxy-N-methylbenzofuran-3-carboxamide

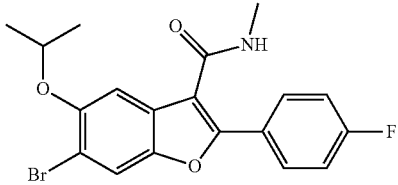 [SMILES: CNC(=O)c1c(-c2ccc(F)cc2)oc2cc(Br)c(OC(C)C)cc12]

HATU (4.85 g, 12.76 mmol) was added to a mixture of 6-bromo-2-(4-fluorophenyl)-5-isopropoxybenzofuran-3-carboxylic acid (3.137 g, 7.98 mmol), methylamine hydrochloride (0.808 g, 11.97 mmol), and N,N-diisopropylethylamine (6.95 mL, 39.9 mmol) in DMF (50 mL). The reaction mixture was stirred at room temperature for 2 hrs. Ice-water (200 g) was then added to the mixture. The solid was filtered, washed with water and dried to give 6-bromo-2-(4-fluorophenyl)-5-isopropoxy-N-methylbenzofuran-3-carboxamide (3.175 g, 98%).

$^1$H NMR (400 MHz, CHLOROFORM-d) δ 7.90-7.83 (m, 2H), 7.73 (s, 1H), 7.43 (s, 1H), 7.25-7.18 (m, 2H), 5.79 (br. s., 1H), 4.63 (dt, J=12.2, 6.1 Hz, 1H), 3.00 (d, J=5.0 Hz, 3H), 1.43 (d, J=6.0 Hz, 6H).

LCMS Rt=3.571 min., m/z 407 (M+1), 97.77% purity.

The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

3-(2-(4-Fluorophenyl)-5-isopropoxy-3-(methylcarbamoyl)benzofuran-6-yl)propyl benzoate

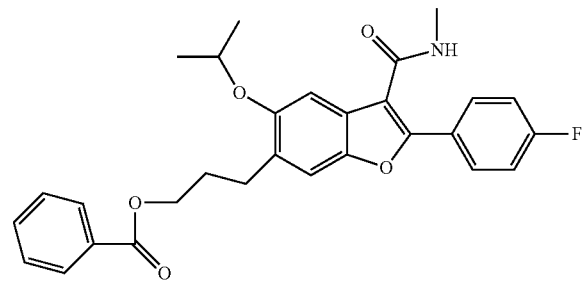 [SMILES: CNC(=O)c1c(-c2ccc(F)cc2)oc2cc(CCCOC(=O)c3ccccc3)c(OC(C)C)cc12]

A mixture of 6-bromo-2-(4-fluorophenyl)-5-isopropoxy-N-methylbenzofuran-3-carboxamide (1.4 g, 3.45 mmol), potassium (3-(benzoyloxy)propyl)trifluoroborate (1.396 g, 5.17 mmol), PdCl$_2$(dppf) (0.378 g, 0.517 mmol) and cesium carbonate (5.05 g, 15.51 mmol) was added toluene (50 mL) and water (17 mL). The mixture was flushed with N$_2$ and then stirred at 90° C. for 4 hrs. The mixture was diluted with ethyl acetate, and filtered. The filtrate was washed with water and brine, and then concentrated. The residue was purified by column chromatography (Biotage 25 m, 0 to 30% EtOAc/Hexane) to give the product (1.234 g, 73%).

$^1$H NMR (500 MHz, CHLOROFORM-d) δ 8.08-8.05 (m, 2H), 7.90-7.86 (m, 2H), 7.60-7.56 (m, 1H), 7.48-7.43 (m, 2H), 7.33 (s, 1H), 7.30 (s, 1H), 7.23-7.17 (m, 2H), 5.76 (br, 1H), 4.70-4.64 (m, 1H), 4.39 (t, J=6.4 Hz, 2H), 3.01 (d, J=5.0 Hz, 3H), 2.91 (t, J=7.4 Hz, 2H), 2.18-2.11 (m, 2H), 1.40-1.37 (m, 6H).

LCMS Rt=3.923 min., m/z 490 (M+H), 97.1% purity.

The LC/MS data was obtained on a Shimadzu analytical LC/Micromass Platform LC (ESI+) at 220 nm using The following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

3-(2-(4-Fluorophenyl)-5-hydroxy-3-(methylcarbamoyl)benzofuran-6-yl)propyl benzoate

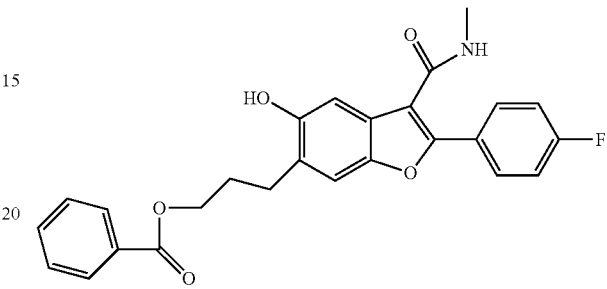

Trichloroborane (2.451 mL, 2.451 mmol) was added dropwise to a solution of 3-(2-(4-fluorophenyl)-5-isopropoxy-3-(methylcarbamoyl)benzofuran-6-yl)propyl benzoate (400 mg, 0.817 mmol) in dichloromethane (70 mL) at −20° C. The reaction mixture was stirred for 1.5 hrs at −20 to −10° C. Methanol (20 mL) was added to the mixture and evaporated, and additional methanol (30 mL×2) was added. The solvent was evaporated to give the crude product (340 mg) which was used directly in the next reaction without further purification.

$^1$H NMR (400 MHz, DMSO-d$_6$) δ 9.48 (s, 1H), 8.41 (d, J=4.8 Hz, 1H), 7.99-7.95 (m, 2H), 7.95-7.89 (m, 2H), 7.66 (d, J=7.3 Hz, 1H), 7.57-7.51 (m, 2H), 7.43 (s, 1H), 7.37 (t, J=8.9 Hz, 2H), 7.04-7.01 (m, 1H), 4.31 (t, J=6.4 Hz, 2H), 2.86-2.80 (m, 5H), 2.11-2.03 (m, 2H)

LCMS Rt=3.335 min., m/z 448 (M+1), 87.2% purity.

The LC/MS data was obtained on a Shimadzu analytical LC/Micromass Platform LC (ESI+) at 220 nm using The following set of conditions: PhenomenexLuna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

3-(2-(4-Fluorophenyl)-3-(methylcarbamoyl)-5-(((trifluoromethyl)sulfonyl)oxy)benzofuran-6-yl)propyl benzoate

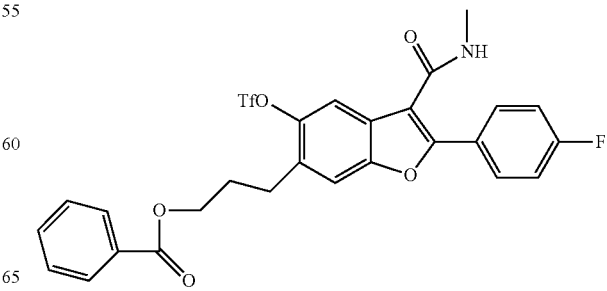

Triethylamine (0.199 mL, 1.430 mmol) was added dropwise to a suspension of 3-(2-(4-fluorophenyl)-5-hydroxy-3-(methylcarbamoyl)benzofuran-6-yl)propyl benzoate (320 mg, 0.715 mmol) (crude, assumed 0.715 mmol) in dichloromathane (120 mL) at room temperature under $N_2$. 1,1,1-Trifluoro-N-phenyl-N-((trifluoromethyl)sulfonyl)methanesulfonamide (307 mg, 0.858 mmol) was added portionwise to the mixture at 0° C. The mixture was then allowed to warm to room temperature. After stirring for 16 hrs, additional 3-(2-(4-fluorophenyl)-5-hydroxy-3-(methylcarbamoyl)benzofuran-6-yl)propyl benzoate (320 mg, 0.715 mmol) and triethylamine (0.199 mL, 1.430 mmol) were added, and the mixture was stirred over 48 hrs. The reaction mixture was washed with water, and the aqueous solution was extracted with dichloromethane. The combined organic layers was washed with brine, dried over $MgSO_4$, filtered and concentrated to give the crude product as a dark yellow solid, which was purified by column chromatography (Biotage 25 s, 0 to 40% EtOAc/Hexanes) to give 3-(2-(4-fluorophenyl)-3-(methylcarbamoyl)-5-(((trifluoromethyl)sulfonyl)oxy)benzofuran-6-yl)propyl benzoate (405 mg, 98%).

$^1$H NMR (400 MHz, CHLOROFORM-d) δ 8.08-8.03 (m, 2H), 7.93-7.87 (m, 2H), 7.82 (s, 1H), 7.61-7.56 (m, 1H), 7.51 (s, 1H), 7.49-7.43 (m, 2H), 7.27-7.21 (m, 2H), 5.77 (br. s., 1H), 4.42 (t, J=6.1 Hz, 2H), 3.08-3.00 (m, 5H), 2.26-2.18 (m, 2H).

LCMS Rt=3.901 min., m/z 580 (M+H), 97.31% purity.

The LC/MS data was obtained on a Shimadzu analytical LC/Micromass Platform LC (ESI+) at 220 nm using the following set of conditions: PhenomenexLuna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

3-(6-(3-(Benzoyloxy)propyl)-2-(4-fluorophenyl)-3-(methylcarbamoyl)benzofuran-5-yl)benzoic acid

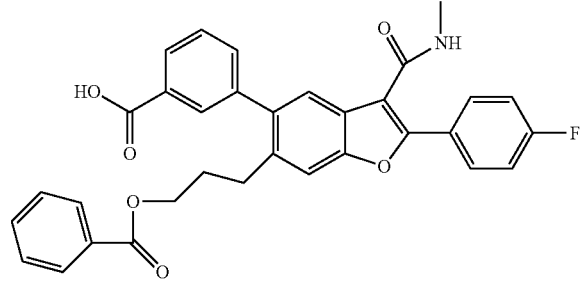 [SMILES: CNC(=O)c1c(-c2ccc(F)cc2)oc2cc(CCCOC(=O)c3ccccc3)c(-c3cccc(C(=O)O)c3)cc12]

A mixture of 3-(2-(4-fluorophenyl)-3-(methylcarbamoyl)-5-(((trifluoromethyl)sulfonyl)oxy)benzofuran-6-yl) propyl benzoate (405 mg, 0.699 mmol) in dioxane (20 mL) along with water (2 mL), cesium carbonate (387 mg, 1.188 mmol), 3-boronobenzoic acid (157 mg, 0.943 mmol) and $(Ph_3P)_4Pd$ (81 mg, 0.070 mmol) was degassed and then heated at 90° C. for 4 hrs. The solvent was then evaporated. The residue was dissolved in $CH_2Cl_2$ (150 mL) and added with 1N HCl (5 mL). The mixture was washed with water and brine, dried over $MgSO_4$, and concentrated to give a solid. The solid was triturated with ether (6 mL), and dried to give the crude target compound (370 mg, 96%) as a light grey solid. This compound was used directly in the next reaction without further purification.

$^1$H NMR (400 MHz, METHANOL-$d_4$) δ 8.03 (m, 1H), 8.01-7.95 (m, 3H), 7.80-7.75 (m, 2H), 7.70-7.65 (m, 1H), 7.65-7.63 (m, 1H), 7.62-7.57 (m, 3H), 7.52-7.41 (m, 4H), 7.31-7.24 (m, 2H), 4.21 (t, J=5.9 Hz, 2H), 2.98-2.91 (m, 5H), 2.02-1.93 (m, 2H).

LCMS Rt=3.486 min., m/z 552 (M+1), 81.2% purity.

The LC/MS data was obtained on a Shimadzu analytical LC/Micromass Platform LC (ESI+) at 220 nm using the following set of conditions: PhenomenexLuna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

3-(5-(3-(Bicyclo[1.1.1]pentan-1-ylcarbamoyl)phenyl)-2-(4-fluorophenyl)-3-(methylcarbamoyl)benzofuran-6-yl)propyl benzoate

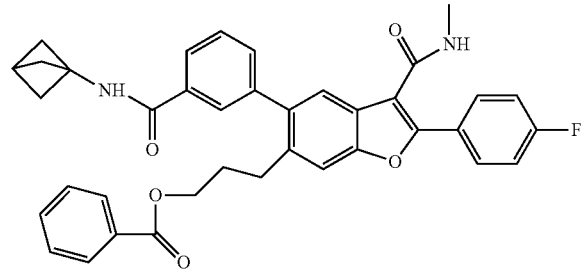 [SMILES: CNC(=O)c1c(-c2ccc(F)cc2)oc2cc(CCCOC(=O)c3ccccc3)c(-c3cccc(C(=O)NC45CC(C4)C5)c3)cc12]

A mixture of 3-(6-(3-(benzoyloxy)propyl)-2-(4-fluorophenyl)-3-(methylcarbamoyl)benzofuran-5-yl)benzoic acid (15 mg, 0.027 mmol), N,N-diisopropylethylamine (0.028 mL, 0.163 mmol), bicyclo[1.1.1]pentan-1-amine HCl salt (8.13 mg, 0.068 mmol) and HATU (31.0 mg, 0.082 mmol) in DMF (1 mL) in a sealed vessel was stirred at rt overnight. The solvent was removed, and the residue purified via preparative LC/MS with the following conditions: Column: Waters XBridge C18, 19×100 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 55-95% B over 12 minutes, then a 5-minute hold at 100% B; Flow: 20 mL/min. Fractions containing the desired product were combined and dried via centrifugal evaporation to give 7.5 mg (45%) of the product.

$^1$H NMR (500 MHz, DMSO-$d_6$) δ 9.02 (s, 1H), 8.42 (d, J=4.6 Hz, 1H), 7.96 (dd, J=7.9, 5.5 Hz, 2H), 7.84 (br. s., 2H), 7.74-7.66 (m, 3H), 7.62 (d, J=6.7 Hz, 1H), 7.53-7.43 (m, 4H), 7.43-7.33 (m, 3H), 4.13 (m., 2H), 2.84-2.2.79 (m, 5H), 2.44 (s, 1H), 2.07 (s, 6H), 1.92-1.83 (m, 2H).

LCMS (Injection 1 conditions: acetonitrile:water with 10 mM ammonium acetate)

Rt=3.47 min, m/z 617 (M+1), m/z 615 (M−1), 100% purity

LCMS (Injection 2 conditions: methanol:water with 10 mM ammonium acetate)

Rt=4.40 min, m/z 617 (M+1), m/z 615 (M−1), 100% purity.

Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min.

5-(3-(Bicyclo[1.1.1]pentan-1-ylcarbamoyl)phenyl)-2-(4-fluorophenyl)-6-(3-hydroxypropyl)-N-methyl-benzofuran-3-carboxamide

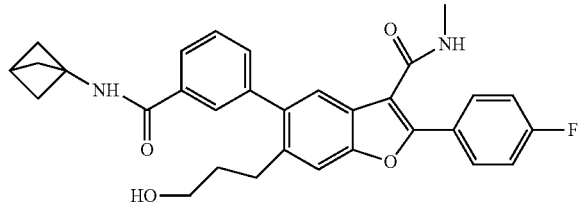 [SMILES: CNC(=O)c1c(-c2ccc(F)cc2)oc2cc(CCCO)c(-c3cccc(C(=O)NC45CC(C4)C5)c3)cc12]

A 1M solution of sodium hydroxide (0.063 mL, 0.063 mmol) was added to a solution of 3-(5-(3-(bicyclo[1.1.1]pentan-1-ylcarbamoyl)phenyl)-2-(4-fluorophenyl)-3-(methylcarbamoyl)benzofuran-6-yl)propyl benzoate (13 mg, 0.021 mmol) in MeOH (1 mL)/THF (1 mL). The resulting solution was stirred at room temperature overnight. 1M HCl (4 mL) was added to the mixture and the solvent was removed. The residue was dissolved in CH$_2$Cl$_2$. The mixture was washed with aqueous Na$_2$CO$_3$ solution, water, and then brine, dried over MgSO$_4$, and concentrated. The residue was purified via preparative LC/MS with the following conditions: Column: Waters XBridge C18, 19×100 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 55-95% B over 12 minutes, then a 5-minute hold at 100% B; Flow: 20 mL/min. Fractions containing the desired product were combined and dried via centrifugal evaporation to give 8.1 mg (75%) of the product.
$^1$H NMR (500 MHz, DMSO-d$_6$) δ 9.05 (s, 1H), 8.43 (d, J=4.0 Hz, 1H), 7.99 (d, J=7.6 Hz, 2H), 7.86 (d, J=7.3 Hz, 1H), 7.81 (br. s., 1H), 7.63 (s, 1H), 7.58-7.47 (m, 2H), 7.43-7.34 (m, 3H), 3.31-3.27 (m, 2H), 2.80 (d, J=4.0 Hz, 3H), 2.67 (t, J=7.2 Hz, 2H), 2.46 (s, 1H), 2.09 (s, 7H), 1.64-1.55 (m, 2H).
LCMS (Injection 1 conditions: acetonitrile:water with 10 mM ammonium acetate)
Rt=2.70 min, m/z 513 (M+1), m/z 511 (M−1), 100% purity
LCMS (Injection 2 conditions: methanol:water with 10 mM ammonium acetate) Rt=3.76 min, m/z 513 (M+1), m/z 511 (M−1), 100% purity.
Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min.

5-(3-(Bicyclo[1.1.1]pentan-1-ylcarbamoyl)phenyl)-2-(4-fluorophenyl)-6-(3-fluoropropyl)-N-methylbenzofuran-3-carboxamide (12)

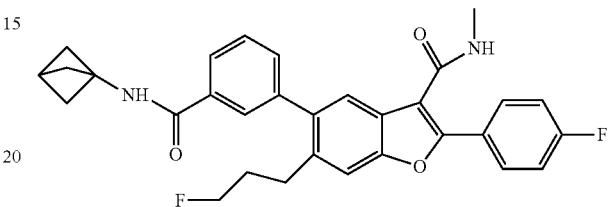

A solution of 5-(3-(bicyclo[1.1.1]pentan-1-ylcarbamoyl)phenyl)-2-(4-fluorophenyl)-6-(3-hydroxypropyl)-N-methyl-benzofuran-3-carboxamide (51 mg, 0.099 mmol) in dichloromethane (5 mL) under N$_2$ was stirred at −78° C., and added with (diethylamino)sulfur trifluoride (0.039 mL, 0.298 mmol). The mixture was then allowed to warm slowly to room temperature and stirred overnight. The reaction mixture was cooled to −10° C. and water (2 mL) was added. The aqueous phase was separated and extracted with dichloromethane. The combined organic layers was washed with water and brine, dried over MgSO$_4$, filtered and the solvent was evaporated. The residue was purified by preparative LC/MS with the following conditions: Column: Waters XBridge C18, 19×100 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 55-95% B over 12 minutes, then a 5-minute hold at 100% B; Flow: 20 mL/min. Fractions containing the desired product were combined and dried via centrifugal evaporation to yield 21.2 mg (40%) of the product.
$^1$H NMR (500 MHz, DMSO-d$_6$) δ 9.05 (s, 1H), 8.44 (d, J=4.6 Hz, 1H), 8.03-7.93 (m, 2H), 7.87 (d, J=7.0 Hz, 1H), 7.82 (br. s., 1H), 7.68 (s, 1H), 7.59-7.47 (m, 2H), 7.45-7.34 (m, 3H), 4.39-4.23 (dt, J=4.3, 47.3 Hz, 2H), 2.80 (d, J=4.0 Hz, 3H), 2.74 (t, J=7.5 Hz, 2H), 2.46 (s, 1H), 2.09 (s, 6H), 1.87-1.72 (m, 2H).
LCMS (Injection 1 conditions: acetonitrile:water with 10 mM ammonium acetate)
Rt=3.15 min, m/z 515 (M+1), m/z 513 (M−1), 98% purity
LCMS (Injection 2 conditions: methanol:water with 10 mM ammonium acetate)
Rt=4.13 min, m/z 515 (M+1), m/z 513 (M−1), 97% purity
Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min.

5-(3-(Bicyclo[1.1.1]pentan-1-ylcarbamoyl)phenyl)-2-(4-fluorophenyl)-N-methyl-6-(3-oxopropyl)benzofuran-3-carboxamide (13)

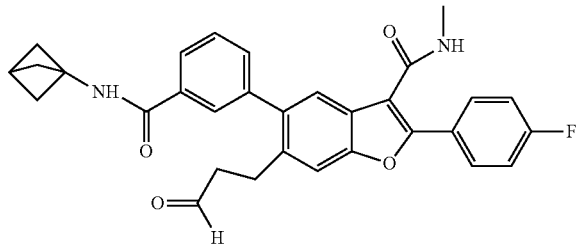 [SMILES: CNC(=O)c1c(-c2ccc(F)cc2)oc2cc(CCC=O)c(-c3cccc(C(=O)NC45CC(C4)C5)c3)cc12]

To a stirred suspension of Dess-Martin periodinane (148 mg, 0.349 mmol) in dichloromethane (5 mL) was added a solution of 5-(3-(bicyclo[1.1.1]pentan-1-ylcarbamoyl)phenyl)-2-(4-fluorophenyl)-6-(3-hydroxypropyl)-N-methylbenzofuran-3-carboxamide (143 mg, 0.279 mmol) in dichloromehtane (5 mL) within 5 min at room temperature. After stirring for 4 hrs, 20% aq. $Na_2S_2O_3$ (3 mL) and $NaHCO_3$ (10 mL) were added. The resulting mixture was extracted with $CH_2Cl_2$ (3×20 mL). The combined organic extracts was dried over $MgSO_4$ and concentrated to give a residue, which was purified by column chromatography (25 s, 0 to 30% EtOAc/hexanes) to give 112 mg (79%) of the target compound as a white solid.

$^1$H NMR (400 MHz, CHLOROFORM-d) δ 9.67 (t, J=1.3 Hz, 1H), 8.03-7.95 (m, 2H), 7.79 (dt, J=7.1, 1.7 Hz, 1H), 7.74 (s, 1H), 7.64 (s, 1H), 7.56-7.44 (m, 3H), 7.26-7.18 (m, 2H), 6.67 (br s, 1H), 5.86 (br. s., 1H), 3.08-2.99 (m, 5H), 2.62 (td, J=7.5, 1.1 Hz, 2H), 2.55 (s, 1H), 2.24 (s, 6H)

LCMS Rt=3.248 min., m/z 511 (M+H), 95% purity.

The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

5-(3-(Bicyclo[1.1.1]pentan-1-ylcarbamoyl)phenyl)-6-(3,3-difluoropropyl)-2-(4-fluorophenyl)-N-methyl-benzofuran-3-carboxamide (14)

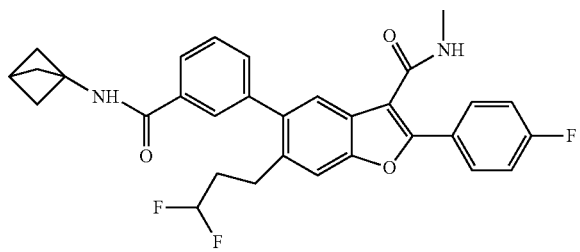 [SMILES: CNC(=O)c1c(-c2ccc(F)cc2)oc2cc(CCC(F)F)c(-c3cccc(C(=O)NC45CC(C4)C5)c3)cc12]

A solution of 5-(3-(bicyclo[1.1.1]pentan-1-ylcarbamoyl)phenyl)-2-(4-fluorophenyl)-N-methyl-6-(3-oxopropyl)benzofuran-3-carboxamide (51 mg, 0.100 mmol) in dichloromethane (5 mL) under $N_2$ was stirred at −78° C., and added with (diethylamino)sulfur trifluoride (0.046 mL, 0.350 mmol). The mixture was then allowed to warm slowly to room temperature and stirred for 5 hrs. The reaction mixture was cooled to −10° C. and water (2 mL) was added. The aqueous phase was separated and extracted with DCM. The combined organic layers was washed with water and brine, dried over $MgSO_4$, and the solvent removed. The residue was purified via preparative LC/MS with the following conditions: Column: Waters XBridge C18, 19×100 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 55-95% B over 12 minutes, then a 5-minute hold at 100% B; Flow: 20 mL/min. Fractions containing the desired product were combined and dried via centrifugal evaporation to yield 45.9 mg (86%) of the product.

$^1$H NMR (500 MHz, DMSO-$d_6$) δ 9.05 (s., 1H), 8.43 (s., 1H), 7.98 (t, J=5.5 Hz, 2H), 7.93-7.86 (m, 1H), 7.83 (s., 1H), 7.73 (s, 1H), 7.60-7.49 (m, 2H), 7.46-7.34 (m, 3H), 6.11-5.81 (t, J=48 Hz, 1H), 2.85-2.72 (m, 5H), 2.46 (s, 1H), 2.10 (s, 6H), 1.99 (br. s., 2H).

LCMS (Injection 1 conditions: acetonitrile:water with 10 mM ammonium acetate)

Rt=3.15 min, m/z 533 (M+1), m/z 531 (M−1), 100% purity

LCMS (Injection 2 conditions: methanol:water with 10 mM ammonium acetate)

Rt=4.12, m/z 533 (M+1), m/z 531 (M−1), 100% purity

Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min.

Intermediate Synthesis.

6-(sec-Butyl)-2-(4-fluorophenyl)-3-(methylcarbamoyl)benzofuran-5-yl trifluoromethanesulfonate was synthesized in the following manner.

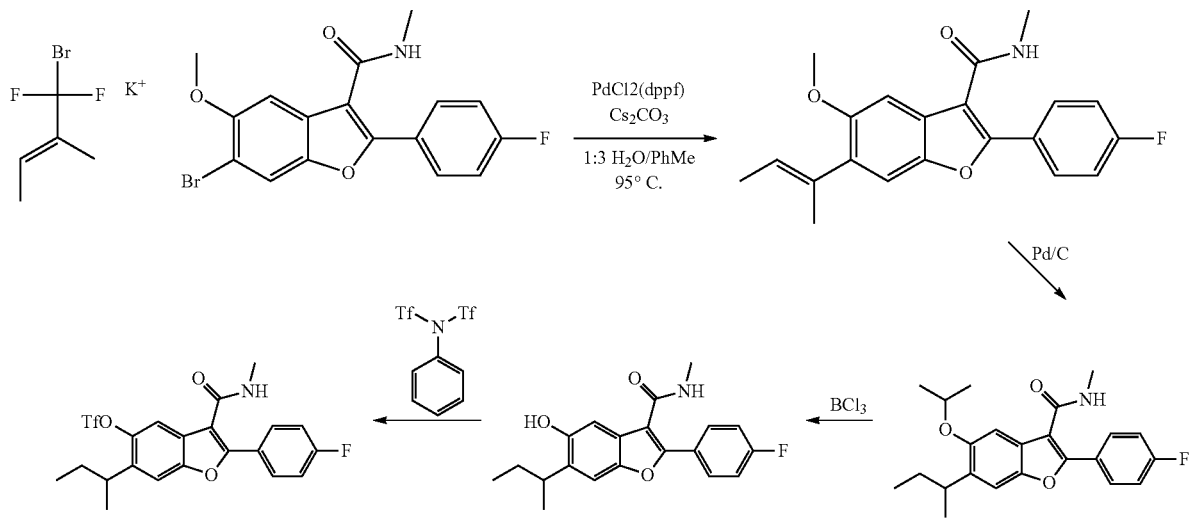

To a small sealed tube was added 6-bromo-2-(4-fluorophenyl)-5-isopropoxy-N-methylbenzofuran-3-carboxamide (300 mg, 0.738 mmol), a 40 mL 3:1 mixture of toluene and water, cesium carbonate (1083 mg, 3.32 mmol), potassium (Z)-but-2-en-2-yltrifluoroborate (359 mg, 2.215 mmol), and 1,1'-bis(diphenylphosphino)ferrocenepalladium(II) dichloride (182 mg, 0.222 mmol). The vessel was sealed, the mixture de-gassed/flushed with nitrogen over 15 minutes, then heated at 90° C. for 10 hours. The crude product was cooled, diluted with 100 mL of DCM, washed with 10 mL of aq 0.1M HCl, water, brine, pushed through a plug of sodium sulfate/celite and concentrated. Purification on silica gel using 0-50% EtOAc/hexane gave a 78% yield of 6-(but-2-en-2-yl)-2-(4-fluorophenyl)-5-isopropoxy-N-methylbenzofuran-3-carboxamide as a yellow solid.

$^1$H NMR (400 MHz, DMSO-d$_6$) δ ppm 8.37 (m, 1H), 7.90-8.00 (m, 2H), 7.31-7.44 (m, 3H), 7.08 (s, 1H), 5.51-5.60 (m, 1H), 4.60 (m, 1H), 2.85 (d, J=4.52 Hz, 3H), 1.98 (br. s., 3H), 1.76 (dd, J=6.78, 0.75 Hz, 3H), 1.30 (d, J=6.02 Hz, 6H).

LCMS Rt (Retention time)=3.860 min., m/z 382.3 (M+H), purity 100%.

The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

To a 250 mL RBF was added 6-(but-2-en-2-yl)-2-(4-fluorophenyl)-5-isopropoxy-N-methylbenzofuran-3-carboxamide (156.4 mg, 0.410 mmol) and ethanol (68 mL). The solution was de-gassed and flushed with nitrogen ×3. To the solution was added palladium, 10% on carbon (43.6 mg, 0.041 mmol) and the flask was fitted with a balloon of hydrogen. The black mixture was stirred overnight at room temperature. At this point the mixture was filtered through celite and concentrated to give a 99% yield of racemic 6-(sec-butyl)-2-(4-fluorophenyl)-5-isopropoxy-N-methylbenzofuran-3-carboxamide as a white solid.

$^1$H NMR (500 MHz, DMSO-d$_6$) δ ppm 8.37 (m, 1H), 7.90-7.97 (m, 2H), 7.45 (s, 1H), 7.34-7.40 (m, 2H), 7.09 (s, 1H), 4.63 (m, 1H), 3.16 (m, 1H), 2.84 (d, J=4.73 Hz, 3H), 1.54-1.68 (m, 2H), 1.32 (d, J=5.99 Hz, 6H), 1.19-1.22 (m, 3H), 0.81 (t, J=7.41 Hz, 3H).

LCMS Rt=3.973 min., m/z 384.3 (M+H), 100% purity.

The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

1M Trichloroborane in DCM (1.2 mL, 1.2 mmol) was added dropwise to a solution of racemic 6-(sec-butyl)-2-(4-fluorophenyl)-5-isopropoxy-N-methylbenzofuran-3-carboxamide (157.6 mg, 0.411 mmol) in DCM (15 mL) at 0° C. After 60 minutes the icebath was removed and the reaction mixture was allowed to slowly warm to room temperature. The mixture was re-cooled to 0° C. and 15 mL of methanol was added dropwise. Volatiles were removed and to the residue was added methanol (50 mL×3) then diethyl ether respectively followed by evaporation to give 142 mgs (100% yield) of 6-(sec-butyl)-2-(4-fluorophenyl)-5-hydroxy-N-methylbenzofuran-3-carboxamide as a light yellow solid.

$^1$H NMR (400 MHz, DMSO-d6) δ ppm 9.34 (s, 1H), 8.38 (m, 1H), 7.88-7.99 (m, 2H), 7.29-7.43 (m, 3H), 7.01 (s, 1H), 3.13 (m, 1H), 2.83 (d, J=4.52 Hz, 3H), 1.52-1.74 (m, 2H), 1.20 (d, J=7.03 Hz, 3H), 0.83 (t, J=7.40 Hz, 3H).

LCMS Rt=3.183 min., m/z 342.3 (M+H), 95% purity.

The LC/MS data was obtained on a Shimadzu analytical LC/Micromass Platform LC (ESI+) at 220 nm using the following set of conditions: Phenomenex Luna 3 mm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

Under a nitrogen atmosphere was added racemic 6-(sec-butyl)-2-(4-fluorophenyl)-5-hydroxy-N-methylbenzofuran-3-carboxamide (138.7 mg, 0.406 mmol) in DCM (15 mL) and triethylamine (0.113 mL, 0.813 mmol). The mixture was cooled to 0° C. and 1,1,1-trifluoro-N-phenyl-N-((trifluoromethyl)sulfonyl)methanesulfonamide (174 mg, 0.488 mmol) was slowly added portion-wise. The resulting mixture was allowed to warm to room temperature and stir for 18 hours. To the mixture was added DCM (5 mL) and additional triethylamine (0.113 mL, 0.813 mmol) and 1,1,1-trifluoro-N-phenyl-N-((trifluoromethyl)sulfonyl)methanesulfonamide (174 mg, 0.488 mmol) at room temperature. After stirring for 48 hours the resulting residue was washed with water, brine, dried over MgSO$_4$ and concentrated. The crude product was purified on silica gel with 1-50% EtOAc/Hexane to give a 63% yield of racemic 6-(sec-butyl)-2-(4-fluorophenyl)-3-(methylcarbamoyl)benzofuran-5-yl trifluoromethanesulfonate as a white solid.

$^1$H NMR (400 MHz, DMSO-d6) δ ppm 8.46-8.54 (m, 1H), 7.91-8.00 (m, 3H), 7.57 (s, 1H), 7.37-7.50 (m, 2H), 3.01 (m, 1H), 2.84 (d, J=4.77 Hz, 3H), 1.65-1.76 (m, 2H), 1.31 (d, J=7.03 Hz, 3H), 0.82 (t, J=7.28 Hz, 3H).

LCMS Rt=2.178 min., m/z 474.1 (M+H), 95% purity.

The LC/MS data was obtained on a Shimadzu analytical LCMS (ESI+) at 220 nm using the following set of conditions: Phenomenex Luna 3 μm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute.

General Procedure:

product solution was cooled to room temperature, filtered through celite and added to 50 mL of cold aq. 0.1M HCl. The resulting fine white solids were filtered to give 61-89% yield of the carboxylic acid product.

3-(2-(4-Fluorophenyl)-3-(methylcarbamoyl)-6-propylbenzofuran-5-yl)benzoic acid

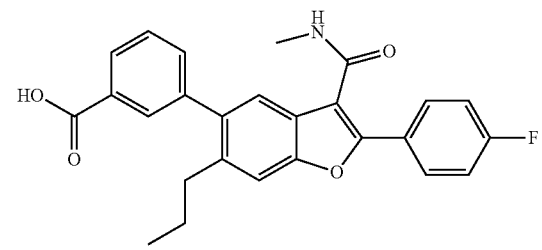 [SMILES: CCCc1cc2oc(-c3ccc(F)cc3)c(C(=O)NC)c2cc1-c1cccc(C(=O)O)c1]

89% yield of a white solid.

$^1$H NMR (400 MHz, DMSO-d$_6$) δ ppm 13.13 (br. s., 1H), 8.46 (m, 1H), 7.98-8.06 (m, 3H), 7.87-7.96 (m, 1H), 7.58-7.70 (m, 3H), 7.35-7.47 (m, 3H), 2.82 (d, J=4.77 Hz, 3H), 2.58-2.68 (m, 2H), 1.41-1.55 (m, 2H), 0.77 (t, J=7.28 Hz, 3H).

LCMS Rt=3.655 min., m/z 432.3 (M+H), 95% purity.

The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

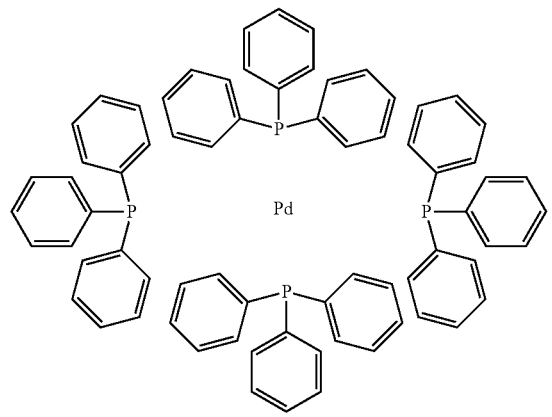

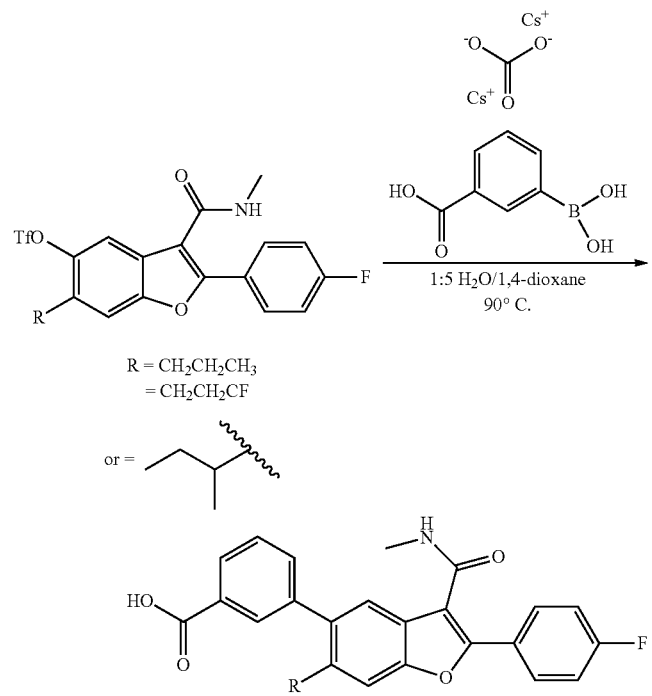

To a small sealed tube was added 2-(4-fluorophenyl)-3-(methylcarbamoyl)-6-(3,3,3-trifluoropropyl)benzofuran-5-yl trifluoromethanesulfonate (100 mg, 0.195 mmol), or 2-(4-fluorophenyl)-3-(methylcarbamoyl)-6-propylbenzofuran-5-yl trifluoromethanesulfonate (90 mg, 0.195 mmol), or 6-(sec-butyl)-2-(4-fluorophenyl)-3-(methylcarbamoyl)benzofuran-5-yl trifluoromethanesulfonate (92 mg, 0.195 mmol), dioxane (4 mL), water (800 μL), 2.5 eq. cesium carbonate (159 mg, 0.487 mmol), 1.3 eq. 3-carboxy-phenyl boronic acid (0.253 mmol) and 0.1 eq. palladium tetrakis (22.51 mg, 0.019 mmol). The mixture was de-gassed/flushed with nitrogen ×5 then heated for 5 hours at 90° C. The

73

3-(2-(4-Fluorophenyl)-3-(methylcarbamoyl)-6-(3,3,3-trifluoropropyl)benzofuran-5-yl)benzoic acid

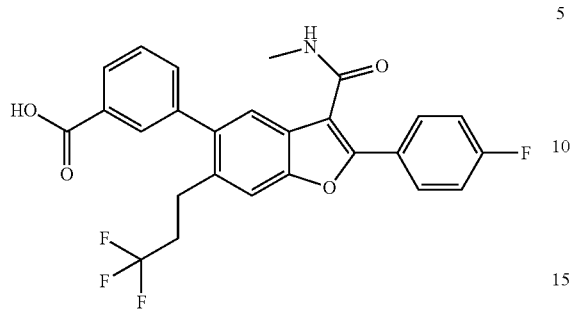

71% yield of a white solid.

$^1$H NMR (500 MHz, DMSO-d$_6$) δ ppm 13.14 (br. s., 1H), 8.45 (m, 1H), 7.97-8.04 (m, 3H), 7.91-7.94 (m, 1H), 7.81 (s, 1H), 7.61-7.66 (m, 2H), 7.47 (s, 1H), 7.37 (m, 2H), 2.86-2.91 (m, 2H), 2.83 (m, 3H), 2.37-2.49 (m, 2H).

LCMS Rt=3.285 min., m/z 486.3 (M+H), 99% purity.

The LC/MS data was obtained on a Shimadzu analytical LC/Micromass Platform LC (ESI+) at 220 nm using the following set of conditions:

Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

74

3-(6-(sec-Butyl)-2-(4-fluorophenyl)-3-(methylcarbamoyl)benzofuran-5-yl)benzoic acid

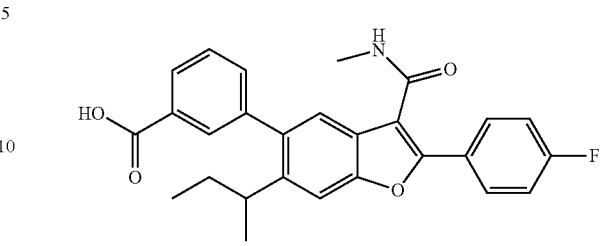

61% yield of a white solid.

$^1$H NMR (500 MHz, DMSO-d$_6$) δ ppm 13.05 (br. s., 1H), 8.43 (m, 1H), 7.96-8.05 (m, 3H), 7.87 (m, 1H), 7.71 (s, 1H), 7.59-7.65 (m, 1H), 7.54-7.59 (m, 1H), 7.35-7.44 (m, 3H), 2.80 (d, J=4.57 Hz, 3H), 2.69-2.76 (m, 1H), 1.51-1.69 (m, 2H), 1.18 (d, J=6.78 Hz, 3H), 0.66 (t, J=7.33 Hz, 3H).

LCMS Rt=3.555 min., m/z 446.3 (M+H), 100% purity.

The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

General Procedure

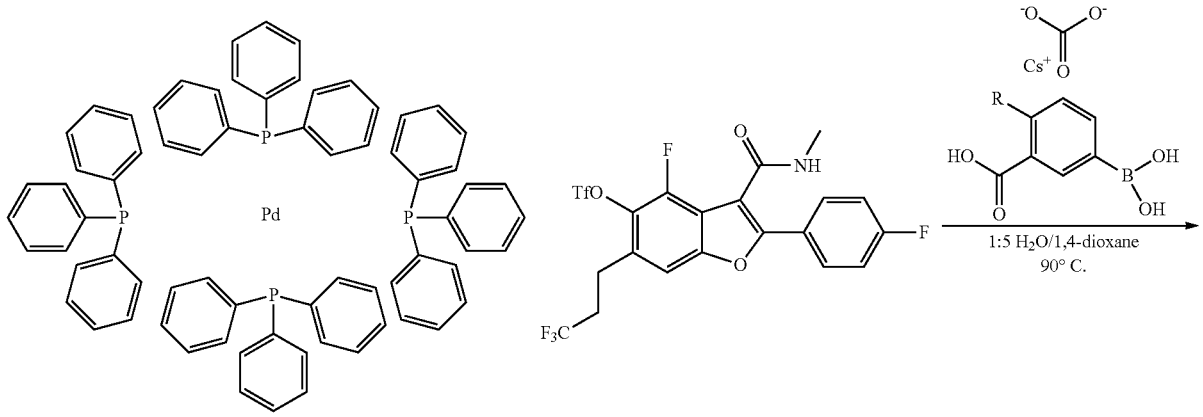

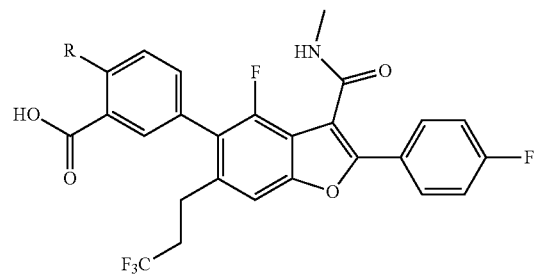

R = H, F

To a small sealed tube was added 4-fluoro-2-(4-fluorophenyl)-3-(methylcarbamoyl)-6-(3,3,3-trifluoropropyl)benzofuran-5-yl trifluoromethanesulfonate (103.6 mg, 0.195 mmol), dioxane (4 mL), water (800 µL), 2.5 eq. cesium carbonate (159 mg, 0.487 mmol), 1.3 eq. 3-carboxy-phenyl (or 3-carboxy-4-fluorophenyl) boronic acid (0.253 mmol) and 0.1 eq. palladium tetrakis (22.51 mg, 0.019 mmol). The mixture was de-gassed/flushed with nitrogen ×5 then heated for 5 hours at 90° C. The product solution was cooled to room temperature, filtered through celite and added to 50 mL of aq. 0.1M HCl. The resulting fine white solids were filtered then purified by prepHPLC (using a Shimadzu preparative HPLC employing acetonitrile/water/TFA where solvent A was 10% acetonitrile/90% water/0.1% trifluoroacetic acid and solvent B was 10% water/90% acetonitrile/ 0.1% trifluoroacetic acid with a XTERRA 5 u C18 30×100 mm column at a gradient of 30-100% B and a flow rate of 40 mL/min. over 12 minutes with a 10 minute hold) to give 45-59% yield of the carboxylic acid product.

3-(4-Fluoro-2-(4-fluorophenyl)-3-(methylcarbamoyl)-6-(3,3,3-trifluoropropyl)benzofuran-5-yl)benzoic acid

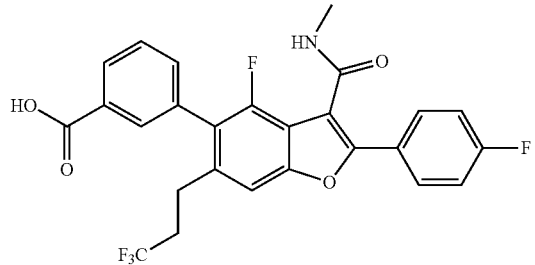 [SMILES: CNC(=O)c1c(-c2ccc(F)cc2)oc2cc(CCC(F)(F)F)c(-c3cccc(C(=O)O)c3)c(F)c12]

45% yield of a white solid.
$^1$H NMR (400 MHz, THF-d8) δ ppm 8.04-8.15 (m, 3H), 7.99 (s, 1H), 7.69 (m, 1H), 7.52-7.64 (m, 2H), 7.49 (s, 1H), 7.17-7.28 (m, 2H), 2.81-2.91 (m, 5H), 2.26-2.41 (m, 2H).
LCMS Rt=3.325 min., m/z 504.2 (M+H), 100% purity.

The LC/MS data was obtained on a Shimadzu analytical LC/Micromass Platform LC (ESI+) at 220 nm using the following set of conditions: Phenomenex Luna 3 µm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

2-Fluoro-5-(4-fluoro-2-(4-fluorophenyl)-3-(methylcarbamoyl)-6-(3,3,3-trifluoropropyl)benzofuran-5-yl)benzoic acid

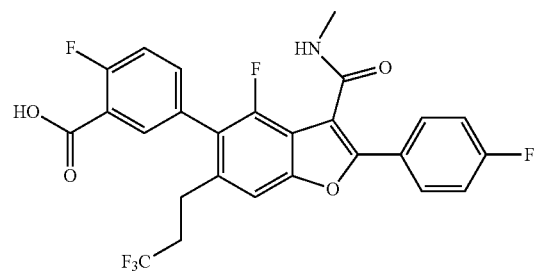 [SMILES: CNC(=O)c1c(-c2ccc(F)cc2)oc2cc(CCC(F)(F)F)c(-c3ccc(F)c(C(=O)O)c3)c(F)c12]

59% yield of a white solid.
$^1$H NMR (400 MHz, THF-d8) δ ppm 8.04-8.12 (m, 2H), 7.91 (dd, J=6.90, 2.38 Hz, 1H), 7.68 (m, 1H), 7.55 (m, 1H), 7.49 (s, 1H), 7.34 (dd, J=10.54, 8.53 Hz, 1H), 7.18-7.27 (m, 2H), 2.77-2.94 (m, 5H), 2.29-2.45 (m, 2H).
LCMS Rt=4.008 min., m/z 522.0 (M+H), 100% purity.
The LC/MS data was obtained on a Shimadzu analytical LC/Micromass Platform
LC (ESI+) at 220 nm using the following set of conditions:
Phenomenex Luna 3 µm C18, 2×50 mm column, with a gradient of 0-100% B (B=90% HPLC grade acetonitrile/ 0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.
General Procedure

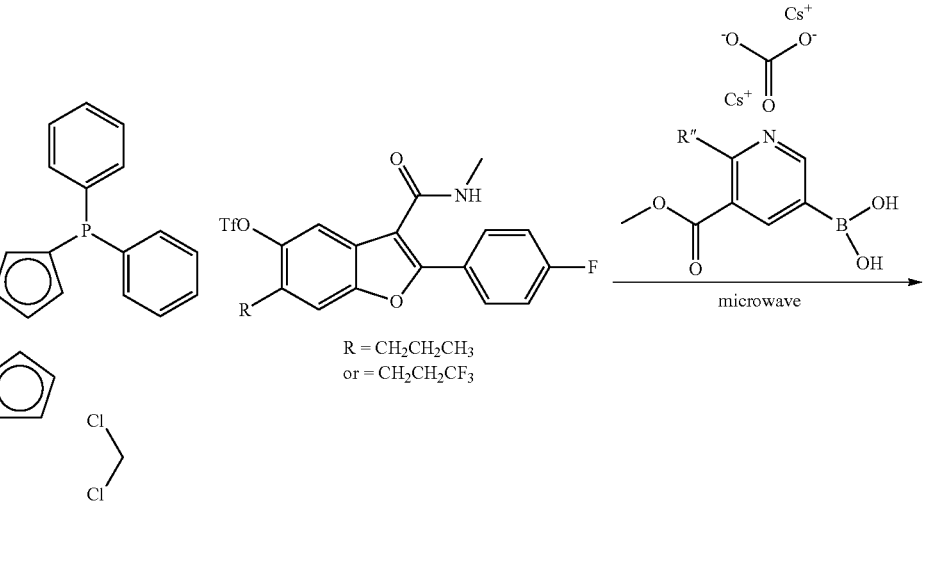

R = CH$_2$CH$_2$CH$_3$
or = CH$_2$CH$_2$CF$_3$

-continued

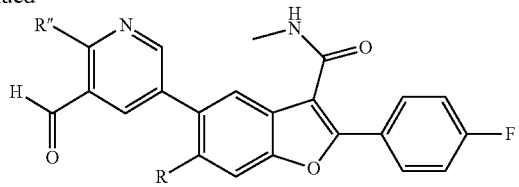

To a Biotage microwave tube was added 2-(4-fluorophenyl)-3-(methylcarbamoyl)-6-(3,3,3-trifluoropropyl)benzofuran-5-yl trifluoromethanesulfonate (84 mg, 0.163 mmol) or 2-(4-fluorophenyl)-3-(methylcarbamoyl)-6-propylbenzofuran-5-yl trifluoromethanesulfonate (75 mg, 0.163 mmol), dioxane (2 mL), 24 eq. 2M aq potassium carbonate (2 mL, 4.00 mmol), 1.7 eq. 2-substituted 5-borono-3-carboxynicotinate (0.205 mmol) and 0.1 eq. palladium dppf (12.0 mg, 0.012 mmol). The mixture was de-gassed/flushed with nitrogen ×5 then subjected to microwave heating in a Biotage Initiator microwave for 20 minutes at 150° C. The product mixture was cooled to room temperature, diluted with 5 mL of 0.1M HCl, added to the top of a pre-wet (water) 35 cc/6 g Waters Oasis HLB cartridge. One column volume of water was pulled through the cartridge to remove inorganics and the desired product was eluted with methanol. Concentration of the volatiles gave the desired carboxylic acid product.

5-(2-(4-Fluorophenyl)-3-(methylcarbamoyl)-6-propylbenzofuran-5-yl)-2-methoxynicotinic acid

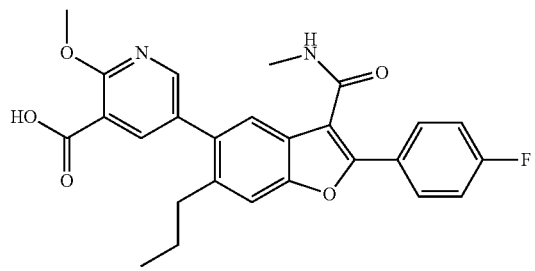 [SMILES: CCCc1cc2oc(-c3ccc(F)cc3)c(C(=O)NC)c2cc1-c1cnc(OC)c(C(=O)O)c1]

90% yield of a white solid.
$^1$H NMR (500 MHz, THF-d8) δ ppm 8.26 (d, J=2.52 Hz, 1H), 8.10-8.19 (m, 3H), 7.53 (s, 1H), 7.51 (s, 1H), 7.21 (t, J=8.83 Hz, 2H), 4.03 (s, 3H), 2.88 (d, J=4.73 Hz, 3H), 2.70-2.71 (m, 2H), 1.55 (m, 2H), 0.84 (t, J=7.41 Hz, 3H).
LCMS Rt=3.223 min., m/z 463.3 (M+H), 90% purity.
The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

5-(2-(4-Fluorophenyl)-3-(methylcarbamoyl)-6-(3,3,3-trifluoropropyl)benzofuran-5-yl)-2-methoxy nicotinic acid

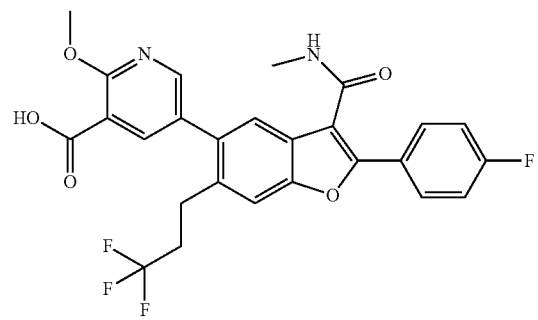 [SMILES: CNC(=O)c1c(-c2ccc(F)cc2)oc2cc(CCC(F)(F)F)c(-c3cnc(OC)c(C(=O)O)c3)cc12]

96% yield of a white solid.
$^1$H NMR (400 MHz, DMSO-d$_6$) δ ppm 8.49 (m, 1H), 7.99-8.07 (m, 2H), 7.95 (d, J=2.51 Hz, 1H), 7.79 (s, 1H), 7.48 (d, J=2.51 Hz, 1H), 7.36-7.45 (m, 3H), 3.85 (s, 3H), 2.87-2.96 (m, 2H), 2.80-2.86 (m, 3H), 2.46-2.60 (m, 2H).
LCMS Rt=3.096 min., m/z 517.2 (M+H), 89% purity.
The LC/MS data was obtained on a Shimadzu analytical LC/Micromass Platform LC (ESI+) at 220 nm using the following set of conditions:
Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

2-Fluoro-5-(2-(4-fluorophenyl)-3-(methylcarbamoyl)-6-propylbenzofuran-5-yl)nicotinic acid

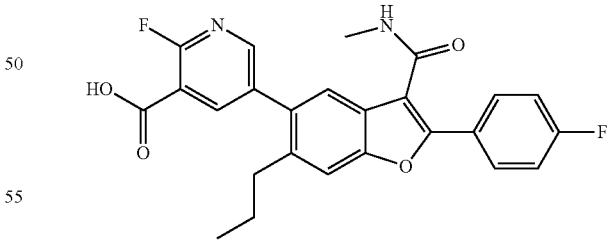

71% yield of a white solid.
$^1$H NMR (500 MHz, DMSO-d$_6$) δ ppm 13.21-13.55 (br. s., 1H), 8.43 (m, 1H), 8.00 (m, 2H), 7.79 (dd, J=7.01, 2.29 Hz, 1H), 7.65 (s, 1H), 7.56-7.62 (m, 1H), 7.39-7.42 (m, 3H), 2.79-2.82 (m, 3H), 2.57-2.65 (m, 2H), 1.42-1.52 (m, 2H), 0.78 (t, J=7.33 Hz, 3H).
LCMS Rt=3.566 min., m/z 451.3 (M+H), 85% purity.
The LC/MS data was obtained on a Shimadzu analytical LC/Micromass Platform LC (ESI+) at 220 nm using the following set of conditions:

Phenomenex Luna 3 μm C18, 2×50 mm column, with a gradient of 0-100% B (B=90% HPLC grade acetonitrile/ 0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

2-Fluoro-5-(2-(4-fluorophenyl)-3-(methylcarbamoyl)-6-(3,3,3-trifluoropropyl)benzofuran-5-yl)nicotinic acid

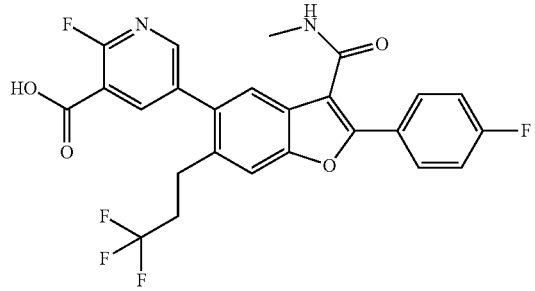

90% yield of a white solid.

$^1$H NMR (400 MHz, DMSO-d$_6$) δ ppm 13.77 (br.s., 1H), 8.52 (d, J=1.76 Hz, 1H), 8.47 (m, 1H), 8.39 (dd, J=9.03, 1.76 Hz, 1H), 8.02 (dd, J=8.66, 5.40 Hz, 2H), 7.86 (s, 1H), 7.57 (s, 1H), 7.42 (m, 2H), 2.86-2.93 (m, 2H), 2.83 (d, J=4.52 Hz, 3H), 2.55-2.62 (m, 2H).

LCMS Rt=3.095 min., m/z 505.2 (M+H), 89% purity.

The LC/MS data was obtained on a Shimadzu analytical LC/Micromass Platform LC (ESI+) at 220 nm using the following set of conditions:

Phenomenex Luna 3 μm C18, 2×50 mm column, with a gradient of 0-100% B (B=90% HPLC grade acetonitrile/ 0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

Final Submitted Compounds.

General Procedure:

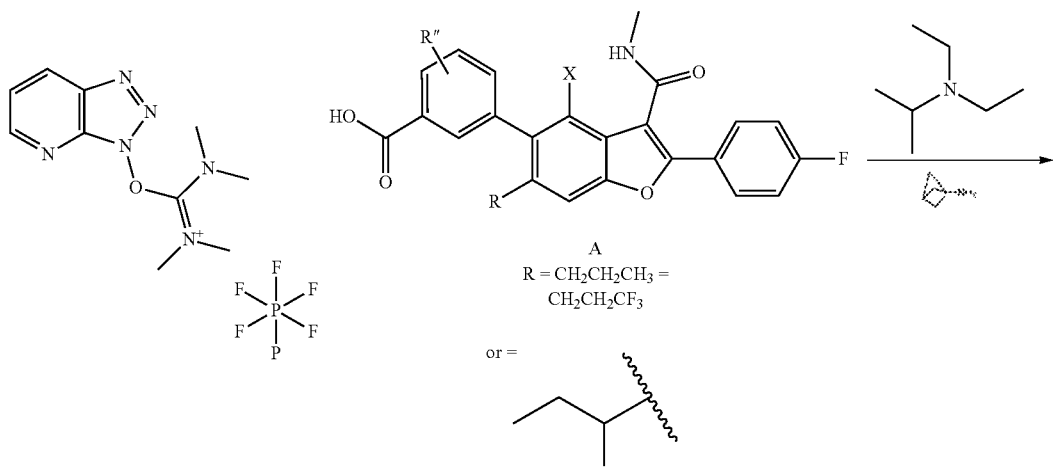

A
R = CH$_2$CH$_2$CH$_3$ =
CH$_2$CH$_2$CF$_3$ or =

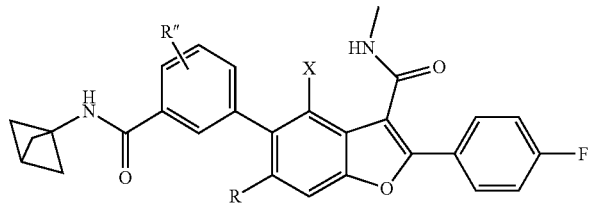

R$^2$ = H or F  X = H or F
or C5-phenyl was replaced by:

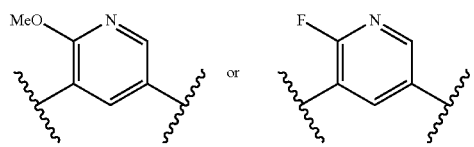

To a scintillation vial or small RBF was added the benzofuran-5-yl-benzoic acid (0.133 mmol) A, DMF (4 mL), 6.0 eq of N-ethyl-N,N-diisopropylpropan-2-amine (0.140 mL, 0.801 mmol), 2.5 eq of bicyclo[1.1.1]pentan-1-amine, HCl (39.9 mg, 0.334 mmol) and 3.0 eq of HATU (152 mg, 0.400 mmol). The vial or flask was sealed and the mixture stirred or shaken overnight at room temperature. The mixture was pushed through a syringe filter, concentrated, diluted to 2 mL with acetonitrile and purified by prepHPLC.

5-(3-(Bicyclo[1.1.1]pentan-1-ylcarbamoyl)phenyl)-2-(4-fluorophenyl)-N-methyl-6-(3,3,3-trifluoropropyl)benzofuran-3-carboxamide

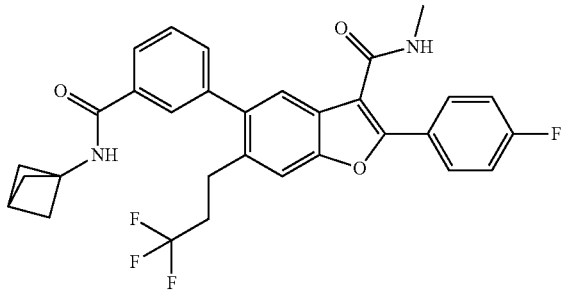 [SMILES: CNC(=O)c1c(-c2ccc(F)cc2)oc2cc(CCC(F)(F)F)c(-c3cccc(C(=O)NC45CC(C4)C5)c3)cc12]

The product was purified using a preparative LC/MS employing acetonitrile/water/20 mM ammonium acetate where solvent A was 100% water with 20 mM ammonium acetate and solvent B was 5% water with 20 mM ammonium acetate/95% acetonitrile with a Waters XBridge 5 μm C18, 19×200 mm column at a gradient of 55-95% B and a flow rate of 20 mL/min. over 20 minutes with a 4 minute hold. 62% Yield.

$^1$H NMR (500 MHz, DMSO-d$_6$) δ ppm 9.06 (s, 1H), 8.44 (m, 1H), 7.95 (dd, J=8.85, 5.49 Hz, 2H), 7.87 (d, J=7.32 Hz, 1H), 7.80 (s, 1H), 7.77 (s, 1H), 7.50-7.58 (m, 2H), 7.33-7.45 (m, 3H), 2.82-2.90 (m, 2H), 2.78 (d, J=4.88 Hz, 3H), 2.33-2.47 (m, 3H), 2.01-2.13 (m, 6H).

(MeOH) LCMS Rt=4.31 min, m/z 551.4 (M+H), m/z 549.4 (M−H), 95% purity.

(MeCN) LCMS Rt=3.29 min, m/z 551.5 (M+H), m/z 549.5 (M−H), 92% purity.

Two analytical LC/MS injections were used to determine the final purity. The LC/MS analytical data was obtained on a Waters Aquity analytical LCMS (ESI+/−) at 220 nm using the following set of conditions: Waters BEH 1.7 μm C18, 2×50 mm column at 40° C., with a gradient of 0-100% B (B=95:5 acetonitrile/water with 10 mM ammonium acetate), (A=5:95 acetonitrile/water with 10 mM ammonium acetate), in 4 minutes with a 0.5 minute hold at 1 mL/min. The purity was then confirmed with an orthogonal solvent system employing a gradient of 0-100% B (B=95:5 methanol/water with 10 mM ammonium acetate), (A=5:95 methanol/water with 10 mM ammonium acetate), in 4 minutes with a 0.5 minute hold at 1 mL/min.

5-(3-(Bicyclo[1.1.1]pentan-1-ylcarbamoyl)phenyl)-2-(4-fluorophenyl)-N-methyl-6-propyl benzofuran-3-carboxamide

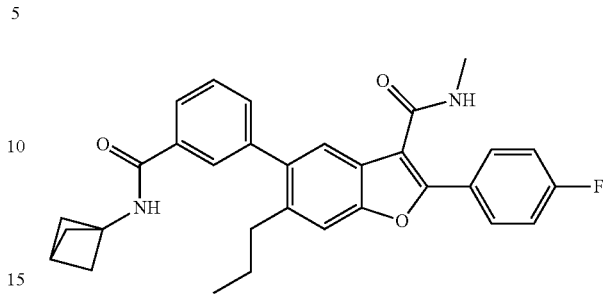

The product was purified using a preparative LC/MS employing acetonitrile/water/20 mM ammonium acetate where solvent A was 100% water with 20 mM ammonium acetate and solvent B was 5% water with 20 mM ammonium acetate/95% acetonitrile with a Waters XBridge 5 μm C18, 19×200 mm column at a gradient of 60-100% B and a flow rate of 20 mL/min. over 12 minutes with a 5 minute hold. 62% Yield.

$^1$H NMR (500 MHz, DMSO-d$_6$) δ ppm 9.04 (s, 1H), 8.42 (m, 1H), 7.97 (m, 2H), 7.86 (d, J=7.63 Hz, 1H), 7.81 (s, 1H), 7.63 (s, 1H), 7.46-7.56 (m, 2H), 7.32-7.43 (m, 3H), 2.79 (d, J=4.58 Hz, 3H), 2.60 (t, J=7.63 Hz, 2H), 2.45 (br. s, 1H), 2.08 (br. s, 6H), 1.36-1.48 (m, 2H), 0.73 (t, J=7.17 Hz, 3H).

(MeOH) LCMS Rt=4.45 min, m/z 497.3 (M+H), m/z 495.2 (M−H), 100% purity.

(MeCN) LCMS Rt=3.49 min, m/z 497.5 (M+H), m/z 495.1 (M−H), 100% purity.

Two analytical LC/MS injections were used to determine the final purity. The LC/MS analytical data was obtained on a Waters Aquity analytical LCMS (ESI+/−) at 220 nm using the following set of conditions: Waters BEH 1.7 μm C18, 2×50 mm column at 40° C., with a gradient of 0-100% B (B=95:5 acetonitrile/water with 10 mM ammonium acetate), (A=5:95 acetonitrile/water with 10 mM ammonium acetate), in 4 minutes with a 0.5 minute hold at 1 mL/min. The purity was then confirmed with an orthogonal solvent system employing a gradient of 0-100% B (B=95:5 methanol/water with 10 mM ammonium acetate), (A=5:95 methanol/water with 10 mM ammonium acetate), in 4 minutes with a 0.5 minute hold at 1 mL/min.

5-(3-(Bicyclo[1.1.1]pentan-1-ylcarbamoyl)phenyl)-6-(sec-butyl)-2-(4-fluorophenyl)-N-methyl benzofuran-3-carboxamide, racemic mixture

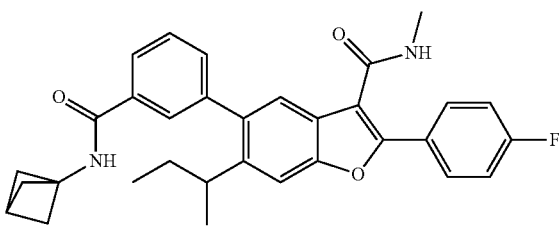 [SMILES: CCC(C)c1cc2oc(-c3ccc(F)cc3)c(C(=O)NC)c2cc1-c1cccc(C(=O)NC23CC(C2)C3)c1]

The product was purified using a preparative LC/MS employing acetonitrile/water/20 mM ammonium acetate where solvent A was 100% water with 20 mM ammonium acetate and solvent B was 5% water with 20 mM ammonium acetate/95% acetonitrile with a Waters XBridge 5 μm C18, 19×200 mm column at a gradient of 50-90% B and a flow rate of 20 mL/min. over 20 minutes with a 5 minute hold. 57% Yield.

$^1$H NMR (500 MHz, DMSO-d$_6$) δ ppm 9.04 (br. s., 1H), 8.42 (m, 1H), 7.92-8.01 (m, 2H), 7.86 (d, J=7.93 Hz, 1H), 7.77 (s, 1H), 7.67 (s, 1H), 7.53 (t, J=7.48 Hz, 1H), 7.34-7.46 (m, 4H), 2.79 (d, J=4.27 Hz, 3H), 2.70 (m, 1H), 2.45 (s, 1H), 2.08 (s, 6H), 1.45-1.67 (m, 2H), 1.16 (d, J=6.41 Hz, 3H), 0.63 (t, J=7.02 Hz, 3H).

(MeOH) LCMS Rt=4.45 min, m/z 511.5 (M+H), m/z 509.5 (M−H), 100% purity.

(MeCN) LCMS Rt=3.53 min, m/z 511.5 (M+H), m/z 509.5 (M−H), 100% purity.

Two analytical LC/MS injections were used to determine the final purity. The LC/MS analytical data was obtained on a Waters Aquity analytical LCMS (ESI+/−) at 220 nm using the following set of conditions: Waters BEH 1.7 μm C18, 2×50 mm column at 40° C., with a gradient of 0-100% B (B=95:5 acetonitrile/water with 10 mM ammonium acetate), (A=5:95 acetonitrile/water with 10 mM ammonium acetate), in 4 minutes with a 0.5 minute hold at 1 mL/min. The purity was then confirmed with an orthogonal solvent system employing a gradient of 0-100% B (B=95:5 methanol/water with 10 mM ammonium acetate), (A=5:95 methanol/water with 10 mM ammonium acetate), in 4 minutes with a 0.5 minute hold at 1 mL/min.

Twelve milligrams of the racemic mixture, 5-(3-(bicyclo[1.1.1]pentan-1-ylcarbamoyl)phenyl)-6-(sec-butyl)-2-(4-fluorophenyl)-N-methyl benzofuran-3-carboxamide underwent chiral preparative SFC using the following set of conditions to give enantiomers 1 and 2:

A Berger-Waters SFC with a Lux Cellulose-2, 21.2×250 mm, 5 μm column employing 20% methanol with 0.1% diethylamine/80% carbon dioxide at a flow rate of 60 mL/min, a pressure of 120 bar and 35° C., with a detector wavelength of 310 nm.

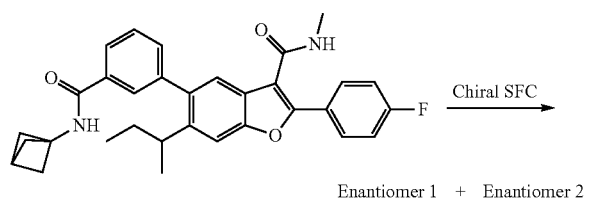

Enantiomer 1 + Enantiomer 2

Analytical chiral SFC was then run using 20% methanol with 0.1% diethylamine, 80% carbon dioxide, a Lux Cellulose-2, 4.6×250 mm column at 120 bar, and 3 mL/min at 35° C. and a wavelength of 310 and 210 nm.

Chiral LC Enantiomer 1 Rt=6.27 minutes $^1$H NMR (400 MHz, THF-d8) δ ppm 8.09-8.19 (m, 3H), 7.83 (m, 1H), 7.79 (s, 1H), 7.54 (s, 1H), 7.50 (s, 1H), 7.36-7.48 (m, 3H), 7.17-7.26 (m, 2H), 2.77-2.92 (m, 4H), 2.42 (s, 1H), 2.14 (s, 6H), 1.50-1.70 (m, 2H), 1.20 (d, J=6.78 Hz, 3H), 0.71 (t, J=7.28 Hz, 3H).

Chiral LC Enantiomer 2 Rt=7.90 minutes.

$^1$H NMR (400 MHz, THF-d8) δ ppm 8.09-8.18 (m, 3H), 7.83 (m, 1H), 7.79 (s, 1H), 7.53 (s, 1H), 7.50 (s, 1H), 7.37-7.49 (m, 3H), 7.17-7.26 (m, 2H), 2.79-2.90 (m, 4H), 2.42 (s, 1H), 2.14 (s, 6H), 1.50-1.70 (m, 2H), 1.20 (d, J=6.78 Hz, 3H), 0.71 (t, J=7.28 Hz, 3H).

N-(Bicyclo[1.1.1]pentan-1-yl)-5-(2-(4-fluorophenyl)-3-(methylcarbamoyl)-6-propylbenzofuran-5-yl)-2-methoxynicotinamide

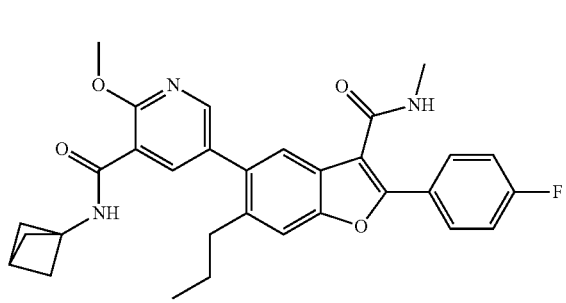 [SMILES: CCCc1cc2oc(-c3ccc(F)cc3)c(C(=O)NC)c2cc1-c1cnc(OC)c(C(=O)NC23CC(C2)C3)c1]

The product was purified using a preparative LC/MS employing acetonitrile/water/20 mM ammonium acetate where solvent A was 100% water with 20 mM ammonium acetate and solvent B was 5% water with 20 mM ammonium acetate/95% acetonitrile with a Waters XBridge 5 μm C18, 19×200 mm column at a gradient of 45-85% B and a flow rate of 20 mL/min. over 20 minutes with a 5 minute hold. 26% Yield.

$^1$H NMR (500 MHz, DMSO-d$_6$) δ ppm 8.68 (s, 1H), 8.42 (m, 1H), 8.27 (d, J=2.44 Hz, 1H), 7.94-8.04 (m, 3H), 7.64 (s, 1H), 7.33-7.43 (m, 3H), 4.02 (s, 3H), 2.80 (d, J=4.58 Hz, 3H), 2.60 (t, J=7.48 Hz, 2H), 2.46 (s, 1H), 2.09 (s, 6H), 1.41-1.51 (m, 2H), 0.77 (t, J=7.17 Hz, 3H).

(MeOH) LCMS Rt=4.13 min, m/z 528.3 (M+H), m/z 526.3 (M−H), 96% purity.

(MeCN) LCMS Rt=3.24 min, m/z 528.3 (M+H), m/z 526.2 (M−H), 96% purity.

Two analytical LC/MS injections were used to determine the final purity. The LC/MS analytical data was obtained on a Waters Aquity analytical LCMS (ESI+/−) at 220 nm using the following set of conditions: Waters BEH 1.7 μm C18, 2×50 mm column at 40° C., with a gradient of 0-100% B (B=95:5 acetonitrile/water with 10 mM ammonium acetate), (A=5:95 acetonitrile/water with 10 mM ammonium acetate), in 4 minutes with a 0.5 minute hold at 1 mL/min. The purity was then confirmed with an orthogonal solvent system employing a gradient of 0-100% B (B=95:5 methanol/water with 10 mM ammonium acetate), (A=5:95 methanol/water with 10 mM ammonium acetate), in 4 minutes with a 0.5 minute hold at 1 mL/min.

N-(Bicyclo[1.1.1]pentan-1-yl)-5-(2-(4-fluorophenyl)-3-(methylcarbamoyl)-6-(3,3,3-trifluoro propyl)benzofuran-5-yl)-2-methoxynicotinamide

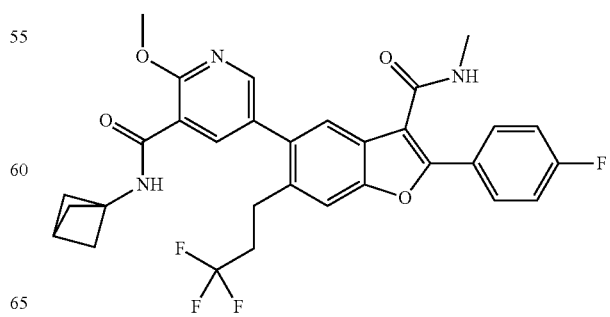

The product was purified using a preparative LC/MS employing acetonitrile/water/20 mM ammonium acetate where solvent A was 100% water with 20 mM ammonium acetate and solvent B was 5% water with 20 mM ammonium acetate/95% acetonitrile with a Waters XBridge 5 μm C18, 19×200 mm column at a gradient of 60-100% B and a flow rate of 20 mL/min. over 20 minutes with a 5 minute hold. 43% Yield.

$^1$H NMR (500 MHz, DMSO-d$_6$) δ ppm 8.69 (s, 1H), 8.45 (m, 1H), 8.33 (d, J=2.44 Hz, 1H), 7.95-8.07 (m, 3H), 7.81 (s, 1H), 7.46 (s, 1H), 7.40 (t, J=8.85 Hz, 2H), 4.03 (s, 3H), 2.85-2.92 (m, 2H), 2.81 (d, J=4.27 Hz, 3H), 2.54 (m, 1H), 2.47 (m, 2H), 2.11 (s, 6H).

(MeOH) LCMS Rt=4.40 min, m/z 582.5 (M+H), m/z 580.5 (M−H), 95% purity.

(MeCN) LCMS Rt=3.45 min, m/z 582.5 (M+H), m/z 580.6 (M−H), 98% purity.

Two analytical LC/MS injections were used to determine the final purity. The LC/MS analytical data was obtained on a Waters Aquity analytical LCMS (ESI+/−) at 220 nm using the following set of conditions: Waters BEH 1.7 μm C18, 2×50 mm column at 40° C., with a gradient of 0-100% B (B=95:5 acetonitrile/water with 10 mM ammonium acetate), (A=5:95 acetonitrile/water with 10 mM ammonium acetate), in 4 minutes with a 0.5 minute hold at 1 mL/min. The purity was then confirmed with an orthogonal solvent system employing a gradient of 0-100% B (B=95:5 methanol/water with 10 mM ammonium acetate), (A=5:95 methanol/water with 10 mM ammonium acetate), in 4 minutes with a 0.5 minute hold at 1 mL/min.

N-(Bicyclo[1.1.1]pentan-1-yl)-2-fluoro-5-(2-(4-fluorophenyl)-3-(methylcarbamoyl)-6-propyl benzofuran-5-yl)nicotinamide

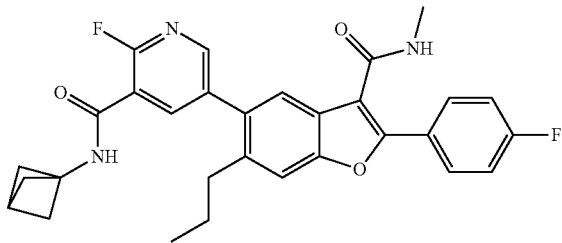 [SMILES: CCCc1cc2oc(-c3ccc(F)cc3)c(C(=O)NC)c2cc1-c1cnc(F)c(C(=O)NC23CC(C2)C3)c1]

The product was purified using a preparative LC/MS employing acetonitrile/water/20 mM ammonium acetate where solvent A was 100% water with 20 mM ammonium acetate and solvent B was 5% water with 20 mM ammonium acetate/95% acetonitrile with a Waters XBridge 5 μm C18, 19×200 mm column at a gradient of 30-100% B and a flow rate of 20 mL/min. over 20 minutes with a 5 minute hold. 30% Yield.

$^1$H NMR (500 MHz, DMSO-d$_6$) δ ppm 8.92 (br. s., 1H), 8.42 (m, 1H), 7.97 (m, 2H), 7.62 (s, 1H), 7.47 (m, 2H), 7.29-7.42 (m, 3H), 2.80 (m, 3H), 2.59 (m, 2H), 2.45 (s, 1H), 2.08 (br.s., 6H), 1.46 (m, 2H), 0.77 (t, J=7.17 Hz, 3H).

(MeOH) LCMS Rt=4.44 min, m/z 516.5 (M+H), m/z 514.6 (M−H), 100% purity.

(MeCN) LCMS Rt=3.51 min, m/z 516.4 (M+H), m/z 514.5 (M−H), 100% purity.

Two analytical LC/MS injections were used to determine the final purity. The LC/MS analytical data was obtained on a Waters Aquity analytical LCMS (ESI+/−) at 220 nm using the following set of conditions: Waters BEH 1.7 μm C18, 2×50 mm column at 40° C., with a gradient of 0-100% B (B=95:5 acetonitrile/water with 10 mM ammonium acetate), (A=5:95 acetonitrile/water with 10 mM ammonium acetate), in 4 minutes with a 0.5 minute hold at 1 mL/min. The purity was then confirmed with an orthogonal solvent system employing a gradient of 0-100% B (B=95:5 methanol/water with 10 mM ammonium acetate), (A=5:95 methanol/water with 10 mM ammonium acetate), in 4 minutes with a 0.5 minute hold at 1 mL/min.

N-(Bicyclo[1.1.1]pentan-1-yl)-2-fluoro-5-(2-(4-fluorophenyl)-3-(methylcarbamoyl)-6-(3,3,3-trifluoropropyl)benzofuran-5-yl)nicotinamide

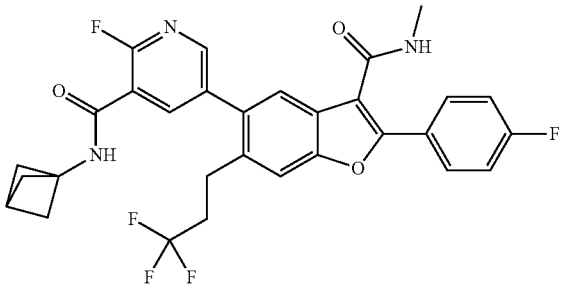 [SMILES: CNC(=O)c1c(-c2ccc(F)cc2)oc2cc(CCC(F)(F)F)c(-c3cnc(F)c(C(=O)NC45CC(C4)C5)c3)cc12]

The product was purified using a preparative LC/MS employing acetonitrile/water/20 mM ammonium acetate where solvent A was 100% water with 20 mM ammonium acetate and solvent B was 5% water with 20 mM ammonium acetate/95% acetonitrile with a Waters XBridge 5 μm C18, 19×200 mm column at a gradient of 30-95% B and a flow rate of 20 mL/min. over 20 minutes with a 14 minute hold. 37% Yield.

$^1$H NMR (500 MHz, DMSO-d$_6$) δ ppm 9.13 (br. s., 1H), 8.43 (m, 1H), 8.36 (br. s., 1H), 8.10 (d, J=7.02 Hz, 1H), 7.97 (m, 2H), 7.81 (s, 1H), 7.51 (s, 1H), 7.39 (t, J=8.39 Hz, 2H), 2.82-2.90 (m, 2H), 2.80 (d, J=4.27 Hz, 3H), 2.54 (m, 2H), 2.46 (s, 1H), 2.09 (br.s., 6H).

(MeOH) LCMS Rt=4.22 min, m/z 570.5 (M+H), m/z 568.5 (M−H), 96% purity.

(MeCN) LCMS Rt=3.22 min, m/z 570.4 (M+H), m/z 568.6 (M−H), 95% purity.

Two analytical LC/MS injections were used to determine the final purity. The LC/MS analytical data was obtained on a Waters Aquity analytical LCMS (ESI+/−) at 220 nm using the following set of conditions: Waters BEH 1.7 μm C18, 2×50 mm column at 40° C., with a gradient of 0-100% B (B=95:5 acetonitrile/water with 10 mM ammonium acetate), (A=5:95 acetonitrile/water with 10 mM ammonium acetate), in 4 minutes with a 0.5 minute hold at 1 mL/min. The purity was then confirmed with an orthogonal solvent system employing a gradient of 0-100% B (B=95:5 methanol/water with 10 mM ammonium acetate), (A=5:95 methanol/water with 10 mM ammonium acetate), in 4 minutes with a 0.5 minute hold at 1 mL/min.

87

5-(3-(Bicyclo[1.1.1]pentan-1-ylcarbamoyl)phenyl)-4-fluoro-2-(4-fluorophenyl)-N-methyl-6-(3,3,3-trifluoropropyl)benzofuran-3-carboxamide

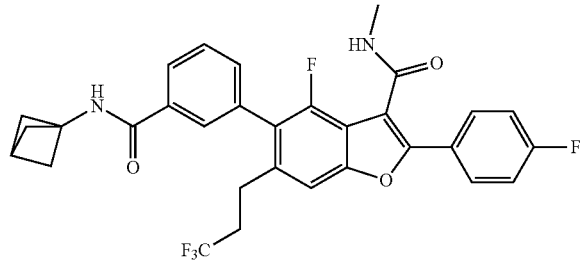 [SMILES: CNC(=O)c1c(-c2ccc(F)cc2)oc2cc(CCC(F)(F)F)c(-c3cccc(C(=O)NC45CC(C4)C5)c3)c(F)c12]

The product was purified using a preparative LC/MS employing acetonitrile/water/20 mM ammonium acetate where solvent A was 100% water with 20 mM ammonium acetate and solvent B was 5% water with 20 mM ammonium acetate/95% acetonitrile with a Waters XBridge 5 μm C18, 19×200 mm column at a gradient of 20-100% B and a flow rate of 20 mL/min. over 20 minutes with a 5 minute hold. 65% yield of a white solid.

$^1$H NMR (500 MHz, DMSO-$d_6$) δ ppm 9.06 (s, 1H), 8.69 (m, 1H), 7.88-7.97 (m, 3H), 7.81 (m, 1H), 7.70 (s, 1H), 7.57-7.64 (m, 1H), 7.52 (d, J=7.32 Hz, 1H), 7.42 (t, J=8.85 Hz, 2H), 2.78 (m, 5H), 2.37-2.48 (m, 3H), 2.09 (s, 6H).

(MeOH) LCMS Rt=4.22 min, m/z 569.5 (M+H), 567.6 (M−H), 96% purity.

(MeCN) LCMS Rt=3.25 min, m/z 569.5 (M+H), 567.6 (M−H), 99% purity.

Two analytical LC/MS injections were used to determine the final purity. The LC/MS analytical data was obtained on a Waters Aquity analytical LCMS (ESI+/−) at 220 nm using the following set of conditions: Waters BEH 1.7 μm C18, 2×50 mm column at 40° C., with a gradient of 0-100% B (B=95:5 acetonitrile/water with 10 mM ammonium acetate), (A=5:95 acetonitrile/water with 10 mM ammonium acetate), in 4 minutes with a 0.5 minute hold at 1 mL/min. The purity was then confirmed with an orthogonal solvent system employing a gradient of 0-100% B (B=95:5 methanol/water with 10 mM ammonium acetate), (A=5:95 methanol/water with 10 mM ammonium acetate), in 4 minutes with a 0.5 minute hold at 1 mL/min.

88

5-(3-(Bicyclo[1.1.1]pentan-1-ylcarbamoyl)-4-fluorophenyl)-4-fluoro-2-(4-fluorophenyl)-N-methyl-6-(3,3,3-trifluoropropyl)benzofuran-3-carboxamide

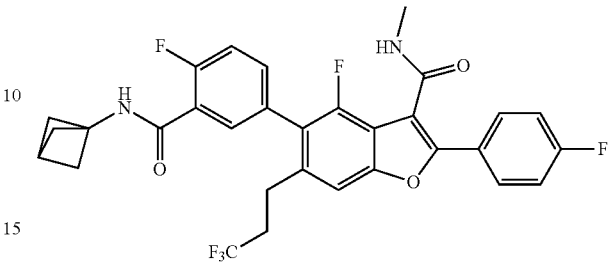

The product was purified using a preparative LC/MS employing acetonitrile/water/20 mM ammonium acetate where solvent A was 100% water with 20 mM ammonium acetate and solvent B was 5% water with 20 mM ammonium acetate/95% acetonitrile with a Waters XBridge 5 μm C18, 19×200 mm column at a gradient of 30-100% B and a flow rate of 20 mL/min. over 20 minutes with a 5 minute hold. 35% yield of a white solid.

$^1$H NMR (500 MHz, DMSO-$d_6$) δ ppm 8.94 (s, 1H), 8.68 (m, 1H), 7.86-7.96 (m, 2H), 7.66 (s, 1H), 7.48 (m, 2H), 7.35-7.44 (m, 3H), 2.76 (m, 5H), 2.44 (s, 3H), 2.07 (s, 6H).

(MeOH) LCMS Rt=4.23 min, m/z 587.5 (M+H), m/z 585.6 (M−H), 100% purity.

(MeCN) LCMS Rt=3.32 min, m/z 587.5 (M+H), 585.6 (M−H), 100% purity.

Two analytical LC/MS injections were used to determine the final purity. The LC/MS analytical data was obtained on a Waters Aquity analytical LCMS (ESI+) at 220 nm using the following set of conditions: Waters BEH 1.7 μm C18, 2×50 mm column at 40° C., with a gradient of 0-100% B (B=95:5 acetonitrile/water with 10 mM ammonium acetate), (A=5:95 acetonitrile/water with 10 mM ammonium acetate), in 4 minutes with a 0.5 minute hold at 1 mL/min. The purity was then confirmed with an orthogonal solvent system employing a gradient of 0-100% B (B=95:5 methanol/water with 10 mM ammonium acetate), (A=5:95 methanol/water with 10 mM ammonium acetate), in 4 minutes with a 0.5 minute hold at 1 mL/min.

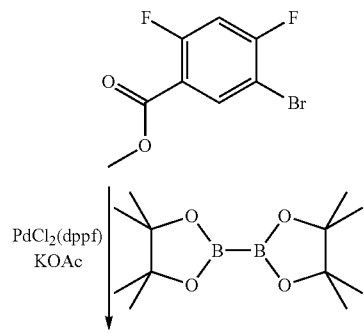

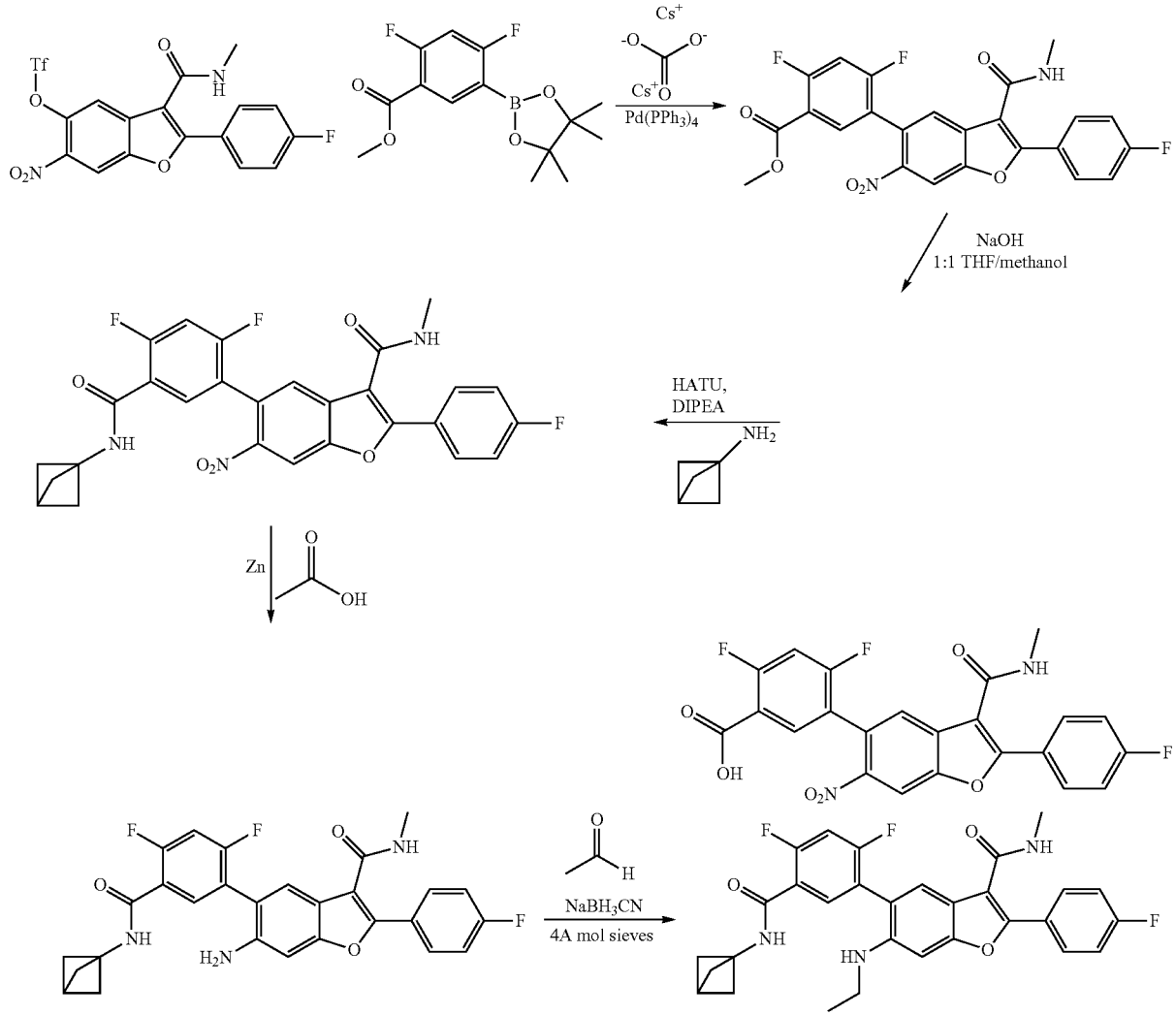

Methyl 2,4-difluoro-5-(4,4,5,5-tetramethyl-1,3,2-dioxaborolan-2-yl)benzoate

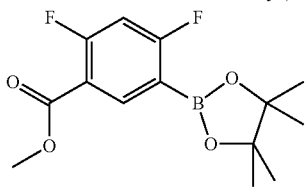

To a small RBF equipped with a reflux condenser was added methyl 5-bromo-2,4-difluorobenzoate (792.9 mg, 3.16 mmol), DMSO (21 mL), 1,1'-bis(diphenylphosphino)ferrocenepalladium(II) dichloride (78 mg, 0.095 mmol), potassium acetate (930 mg, 9.48 mmol) and 4,4,4',4',5,5,5',5'-octamethyl-2,2'-bi(1,3,2-dioxaborolane) (1.604 g, 6.32 mmol). The mixture was de-gassed, flushed with nitrogen ×3 and stirred at 80° C. for 4 hours. The mixture was cooled, diluted with ethyl acetate, washed with water, brine, pushed through a plug of 1:1 celite/sodium sulfate, and evaporated to a tan oil. The crude solid was purified on silica gel using 1-25% ethyl acetate/hexane to give a 46% yield (450 mgs) of a white solid.

$^1$H NMR (400 MHz, CDCl$_3$) δ ppm 8.39 (m, 1H), 6.84 (m, 1H), 3.93 (s, 3H), 1.33-1.40 (m, 6H), 1.24-1.31 (m, 6H).

LCMS Rt=1.652 min., m/z 299.06 (M+H), 93% purity.

The LC/MS data was obtained on a Shimadzu analytical LCMS (ESI+/−) at 220 nm using the following set of conditions: Phenomenex Luna 3 μm C18, 2×30 mm column, with a gradient of 0-100% B (B=95% HPLC grade methanol/10 mM ammonium acetate/5% HPLC grade water), (A=95% HPLC grade water/10 mM ammonium acetate/5% HPLC grade acetonitrile), in 2 minutes with a 1 minute hold at a rate of 1 mL/minute.

Methyl 2,4-difluoro-5-(2-(4-fluorophenyl)-3-(methylcarbamoyl)-6-nitrobenzofuran-5-yl)benzoate

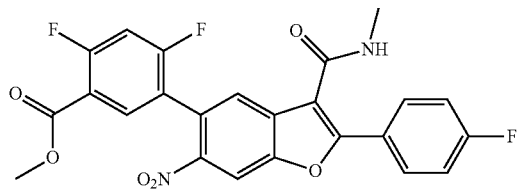 [SMILES: CNC(=O)c1c(-c2ccc(F)cc2)oc2cc([N+](=O)[O-])c(-c3cc(C(=O)OC)c(F)cc3F)cc12]

To a sealed tube was added 2-(4-fluorophenyl)-3-(methylcarbamoyl)-6-nitrobenzofuran-5-yltrifluoromethanesulfonate (100 mg, 0.216 mmol), 4 mL of a 5:1 solution of dioxane/water, methyl 2,4-difluoro-5-(4,4,5,5-tetramethyl-1,3,2-dioxaborolan-2-yl)benzoate (129 mg, 0.433 mmol), cesium carbonate (211 mg, 0.649 mmol), and tetrakis(triphenylphosphine)palladium (24.99 mg, 0.022 mmol). The solution was de-gassed and flushed with nitrogen ×3 and then heated for 5 hours at 90° C. The product mixture was cooled to room temperature, added to 50 mL of ice cold 0.1M aq HCl, filtered and dried to give 62% yield (72.3 mgs) of the product as a tan solid.

$^1$H NMR (400 MHz, DMSO-$d_6$) δ ppm 8.65 (s, 2H), 8.01-8.15 (m, 3H), 7.82 (s, 1H), 7.61 (t, J=10.42 Hz, 1H), 7.46 (t, J=8.66 Hz, 2H), 3.89 (s, 3H), 2.83 (d, J=4.52 Hz, 3H).

LCMS Rt=3.421 min., m/z 485.2 (M+H), 90% purity.

The LC/MS data was obtained on a Shimadzu analytical LCMS (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

2,4-Difluoro-5-(2-(4-fluorophenyl)-3-(methylcarbamoyl)-6-nitrobenzofuran-5-yl)benzoic acid

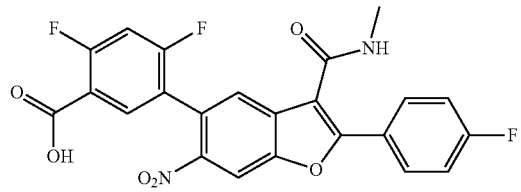

To a small RBF was added methyl 2,4-difluoro-5-(2-(4-fluorophenyl)-3-(methylcarbamoyl)-6-nitrobenzofuran-5-yl)benzoate (72.3 mg, 0.149 mmol), a 1:1 solution of methanol (2 mL)/THF (2 mL) and a 1 M solution of sodium hydroxide (0.597 mL, 0.597 mmol). The mixture was stirred at room temperature for eight hours. The reaction mixture was diluted with 50 mL of ethyl acetate and the pH adjusted to 7 with aq. 1M HCl. The product was extracted, washed with 20 mL of water, brine, dried over sodium sulfate and evaporated to give a tan solid (99% yield, 70 mgs).

LCMS Rt=3.095 min., m/z 471.2 (M+H), 90% purity.

The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

5-(5-(Bicyclo[1.1.1]pentan-1-ylcarbamoyl)-2,4-difluorophenyl)-2-(4-fluorophenyl)-N-methyl-6-nitrobenzofuran-3-carboxamide

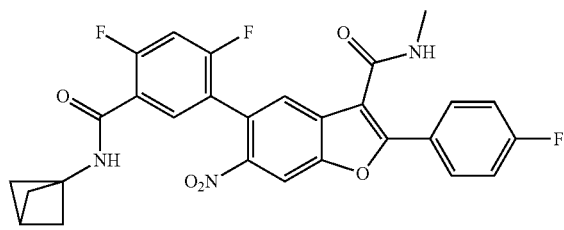 [SMILES: CNC(=O)c1c(-c2ccc(F)cc2)oc2cc([N+](=O)[O-])c(-c3cc(C(=O)NC45CC(C4)C5)c(F)cc3F)cc12]

To a vial was added 2,4-difluoro-5-(2-(4-fluorophenyl)-3-(methylcarbamoyl)-6-nitrobenzofuran-5-yl)benzoic acid (53 mg, 0.113 mmol) in DMF (6 mL) along with N,N-diisopropylpropylethylamine (0.118 mL, 0.676 mmol), and bicyclo[1.1.1]pentan-1-amine, HCl (33.7 mg, 0.282 mmol) followed by HATU (129 mg, 0.338 mmol). The vial was capped and the tan mixture shaken overnight at room temperature. The product mixture was diluted with 50 mL of DCM, washed with 0.1M aq HCl, water, brine, dried over sodium sulfate and evaporated to a tan oil. The crude product was purified using a Shimadzu preparative HPLC employing acetonitrile/water/trifluoroacetic acid where solvent A was 10% acetonitrile/90% water/0.1% trifluoroacetic acid and solvent B was 10% water/90% acetonitrile/0.1% trifluoroacetic acid with a XTERRA 5 g, C18 30×100 mm column at a gradient of 30-100% B and a flow rate of 40 mL/min. over 12 minutes with a 13 minute hold to give a 90% yield (65 mgs) of 5-(5-(bicyclo[1.1.1]pentan-1-ylcarbamoyl)-2,4-difluorophenyl)-2-(4-fluorophenyl)-N-methyl-6-nitrobenzofuran-3-carboxamide, trifluoroacetic acid as a tan solid.

$^1$H NMR (400 MHz, THF-d8) δ ppm 8.45 (s, 1H), 8.14-8.22 (m, 2H), 7.86-7.93 (m, 2H), 7.80 (s, 1H), 7.62 (m, 1H), 7.24-7.33 (m, 2H), 7.07-7.16 (m, 1H), 2.89 (m, 3H), 2.43 (m, 1H), 2.16 (s, 6H).

LCMS Rt=3.470 min., m/z 536.3 (M+H), 98% purity.

The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

6-Amino-5-(5-(bicyclo[1.1.1]pentan-1-ylcarbamoyl)-2,4-difluorophenyl)-2-(4-fluorophenyl)-N-methylbenzofuran-3-carboxamide

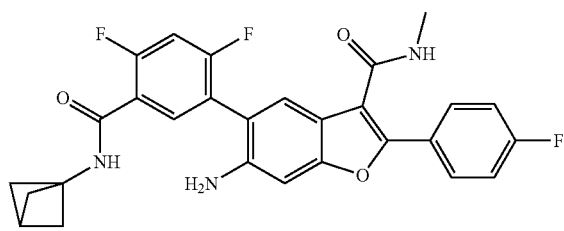 [SMILES: CNC(=O)c1c(-c2ccc(F)cc2)oc2cc(N)c(-c3cc(C(=O)NC45CC(C4)C5)c(F)cc3F)cc12]

To a small RBF was added 5-(5-(bicyclo[1.1.1]pentan-1-ylcarbamoyl)-2,4-difluorophenyl)-2-(4-fluorophenyl)-N-methyl-6-nitrobenzofuran-3-carboxamide, trifluoroacetic acid (65 mg, 0.108 mmol) in a 2:1 solution of DMF (3 mL) and methanol (1.5 mL), acetic acid (0.049 mL, 0.862 mmol) and zinc (116 mg, 0.647 mmol) powder. The mixture was heated to 55° C. with stirring for 2 hours. The reaction mixture was cooled, pushed through a plug of celite, diluted with 50 mL of DCM, washed 1M NaOH, water, brine, dried over sodium sulfate, filtered, and evaporated to give a 86% yield (43 mgs) of 6-amino-5-(5-(bicyclo[1.1.1]pentan-1-ylcarbamoyl)-2,4-difluorophenyl)-2-(4-fluorophenyl)-N-methyl benzofuran-3-carboxamidean as an orange solid.

$^1$H NMR (500 MHz, THF-d8) δ ppm 8.04-8.10 (m, 2H), 7.78-7.86 (m, 2H), 7.36 (m, 1H), 7.30 (s, 1H), 7.09-7.20 (m, 3H), 6.84 (s, 1H), 4.57 (br. s., 2H), 2.85 (d, J=4.73 Hz, 3H), 2.42 (s, 1H), 2.09-2.22 (m, 6H).

LCMS Rt=2.890 min., m/z 506.3 (M+H), 95% purity.

The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

5-(5-(Bicyclo[1.1.1]pentan-1-ylcarbamoyl)-2,4-difluorophenyl)-6-(ethylamino)-2-(4-fluorophenyl)-N-methylbenzofuran-3-carboxamide

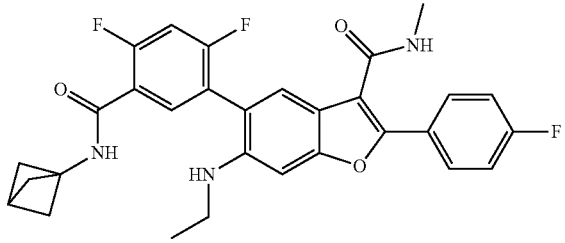 [SMILES: CCNc1cc2oc(-c3ccc(F)cc3)c(C(=O)NC)c2cc1-c1cc(C(=O)NC23CC(C2)C3)c(F)cc1F]

To a small RBF was added a small scoop of crushed 4 Å sieves, 6-amino-5-(5-(bicyclo[1.1.1]pentan-1-ylcarbamoyl)-2,4-difluorophenyl)-2-(4-fluorophenyl)-N-methylbenzofuran-3-carboxamide (28 mg, 0.055 mmol), a 2:1 mixture of THF (2 mL)/methanol (1 mL), acetaldehyde (0.037 mL, 0.665 mmol) and sodium cyanoborohydride (27.8 mg, 0.443 mmol). The mixture was stirred at room temperature for two days. The crude product was filtered and evaporated to an oil, and then purified using a preparative LC/MS employing acetonitrile/water/20 mM ammonium acetate where solvent A was 100% water with 20 mM ammonium acetate and solvent B was 5% water with 20 mM ammonium acetate/ 95% acetonitrile with a Waters XBridge 5 μm C18, 19×200 mm column at a gradient of 50-100% B and a flow rate of 20 mL/min. over 13 minutes with a 4 minute hold to give a 33% yield (10 mgs) of the desired product as a tan solid.

$^1$H NMR (500 MHz, DMSO-d$_6$) δ ppm 8.90 (s, 1H), 8.36 (m, 1H), 7.92 (dd, J=8.85, 5.49 Hz, 2H), 7.57 (t, J=8.24 Hz, 1H), 7.44 (t, J=9.92 Hz, 1H), 7.35 (t, J=8.85 Hz, 2H), 7.20 (s, 1H), 6.88 (s, 1H), 4.82 (t, J=5.65 Hz, 1H), 3.11-3.22 (m, 2H), 2.79 (d, J=4.58 Hz, 3H), 2.47 (s, 1H), 2.09 (s, 6H), 1.12 (t, J=7.02 Hz, 3H).

(MeOH) LCMS Rt=4.30 min, m/z 534.3 (M+H), 96% purity.

(ACN) LCMS Rt=3.30 min, m/z 534.3 (M+H), 93% purity.

Two analytical LC/MS injections were used to determine the final purity. The LC/MS analytical data was obtained on a Waters Aquity analytical LCMS (ESI+/−) at 220 nm using the following set of conditions: Waters BEH 1.7 μm C18, 2×50 mm column at 40° C., with a gradient of 0-100% B (B=95:5 acetonitrile/water with 10 mM ammonium acetate), (A=5:95 acetonitrile/water with 10 mM ammonium acetate), in 4 minutes with a 0.5 minute hold at 1 mL/min. The purity was then confirmed with an orthogonal solvent system employing a gradient of 0-100% B (B=95:5 methanol/water with 10 mM ammonium acetate), (A=5:95 methanol/water with 10 mM ammonium acetate), in 4 minutes with a 0.5 minute hold at 1 mL/min.

6-Amino-5-(3-(bicyclo[1.1.1]pentan-1-ylcarbamoyl)-4-methoxyphenyl)-2-(4-fluorophenyl)-N-methylbenzofuran-3-carboxamide was synthesized in a similar fashion as described above for 6-amino-5-(5-(bicyclo[1.1.1]pentan-1-ylcarbamoyl)-2,4-difluorophenyl)-2-(4-fluorophenyl)-N-methylbenzofuran-3-carboxamide.

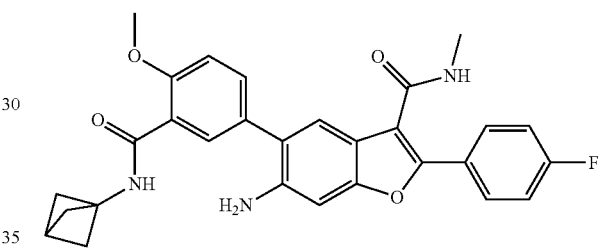

A sample was also recovered from the reductive amination described for the preparation of 5-(3-(bicyclo[1.1.1]pentan-1-ylcarbamoyl)-4-methoxyphenyl)-2-(4-fluorophenyl)-N-methyl-6-((2,2,2-trifluoroethyl)amino)benzofuran-3-carboxamide by using a preparative LC/MS employing acetonitrile/water/20 mM ammonium acetate where solvent A was 100% water with 20 mM ammonium acetate and solvent B was 5% water with 20 mM ammonium acetate/ 95% acetonitrile with a Waters XBridge 5 μm C18, 19×200 mm column at a gradient of 20-100% B and a flow rate of 20 mL/min. over 20 minutes with a 5 minute hold.

$^1$H NMR (500 MHz, DMSO-d$_6$) δ ppm 8.57 (m, 1H), 8.33 (m, 1H), 7.86-8.00 (m, 2H), 7.70 (m, 1H), 7.51 (m, 1H), 7.32 (m, 2H), 7.22 (m, 1H), 7.15 (s, 1H), 6.95 (s, 1H), 5.02 (br. s., 2H), 3.91 (s, 3H), 2.78 (d, J=4.58 Hz, 3H), 2.45 (s, 1H), 2.09 (s, 6H).

(MeOH) LCMS Rt=3.76 min, m/z 500.4 (M+H), 96.4% purity.

(MeCN) LCMS Rt=2.76 min, m/z 500.4 (M+H), 95.4% purity.

Two analytical LC/MS injections were used to determine the final purity. The LC/MS analytical data was obtained on a Waters Aquity analytical LCMS (ESI+/−) at 220 nm using the following set of conditions: Waters BEH 1.7 μm C18, 2×50 mm column at 40° C., with a gradient of 0-100% B (B=95:5 acetonitrile/water with 10 mM ammonium acetate), (A=5:95 acetonitrile/water with 10 mM ammonium acetate), in 4 minutes with a 0.5 minute hold at 1 mL/min. The purity was then confirmed with an orthogonal solvent system employing a gradient of 0-100% B (B=95:5 methanol/water 5-(3-(Bicyclo[1.1.1]pentan-1-ylcarbamoyl)-4-methoxyphenyl)-2-(4-fluorophenyl)-N-methyl-6-((2,2,2-trifluoroethyl)amino)benzofuran-3-carboxamide was synthesized in the following manner.

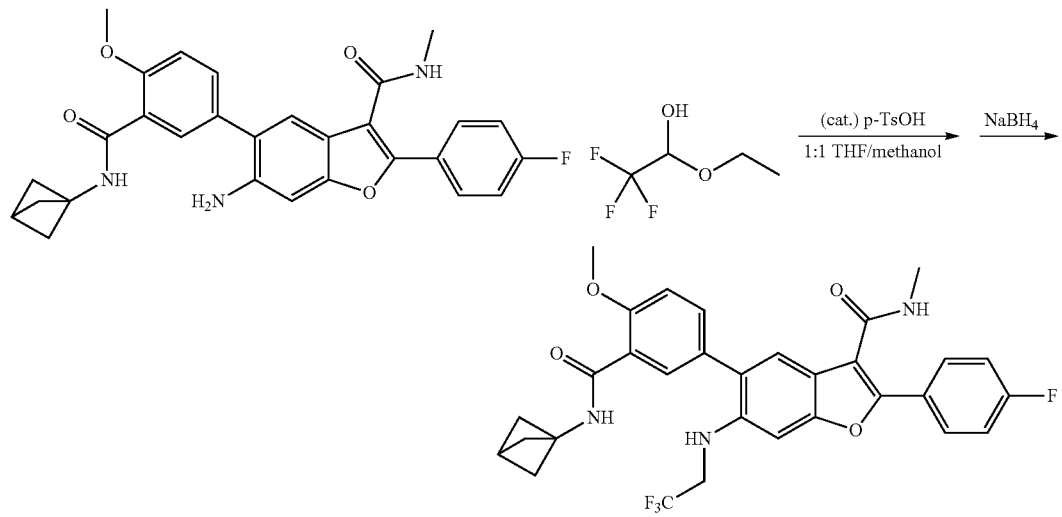

To a sealed tube was added 6-amino-5-(3-(bicyclo[1.1.1]pentan-1-ylcarbamoyl)-4-methoxyphenyl)-2-(4-fluorophenyl)-N-methylbenzofuran-3-carboxamide (68 mg, 0.136 mmol), a 1:1 mixture of tetrahydrofuran (2 mL)/methanol (2 mL), a catalytic amount of p-toluenesulfonic acid (0.104 mg, 0.545 μmol) and 1-ethoxy-2,2,2-trifluoroethanol (0.354 mL, 2.72 mmol). The vessel was sealed and the mixture heated overnight at 85° C. The mixture was cooled to room temperature and sodium borohydride was slowly added portion-wise (155 mg, 4.08 mmol) over 10 minutes. When effervescence ceased, the vessel was re-sealed and the mixture heated overnight at 85° C. The mixture was cooled and the crude product was diluted with 50 mL of DCM, washed with water, brine, dried over sodium sulfate, filtered and evaporated.

The product was purified using a preparative LC/MS employing acetonitrile/water/20 mM ammonium acetate where solvent A was 100% water with 20 mM ammonium acetate and solvent B was 5% water with 20 mM ammonium acetate/95% acetonitrile with a Waters XBridge 5 μm C18, 19×200 mm column at a gradient of 20-100% B and a flow rate of 20 mL/min. over 20 minutes with a 5 minute hold.

$^1$H NMR (500 MHz, DMSO-d6) δ ppm 8.54 (s, 1H), 8.35 (m, 1H), 7.86-7.97 (m, 2H), 7.67 (s, 1H), 7.47 (d, J=8.54 Hz, 1H), 7.34 (t, J=8.70 Hz, 2H), 7.25 (d, J=8.54 Hz, 1H), 7.18 (m, 2H), 5.25 (t, J=6.71 Hz, 1H), 3.97-4.09 (m, 2H), 3.92 (s, 3H), 2.78 (d, J=4.27 Hz, 3H), 2.45 (s, 1H), 2.08 (s, 6H).

(MeOH) LCMS Rt=4.20 min, m/z 582.4 (M+H), m/z 580.4 (M−H), 96% purity.

(MeCN) LCMS Rt=3.23 min, m/z 582.4 (M+H), m/z 580.5 (M−H), 96% purity.

Two analytical LC/MS injections were used to determine the final purity. The LC/MS analytical data was obtained on a Waters Acuity analytical LCMS (ESI+/−) at 220 nm using the following set of conditions: Waters BEH 1.7 μm C18, 2×50 mm column at 40° C., with a gradient of 0-100% B (B=95:5 acetonitrile/water with 10 mM ammonium acetate), (A=5:95 acetonitrile/water with 10 mM ammonium acetate), in 4 minutes with a 0.5 minute hold at 1 mL/min. The purity was then confirmed with an orthogonal solvent system employing a gradient of 0-100% B (B=95:5 methanol/water with 10 mM ammonium acetate), (A=5:95 methanol/water with 10 mM ammonium acetate), in 4 minutes with a 0.5 minute hold at 1 mL/min.

Additional Experimental Procedures

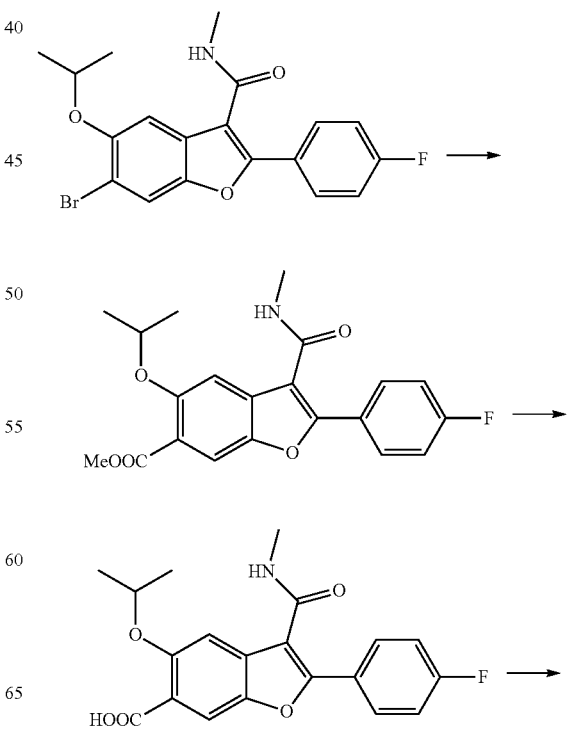

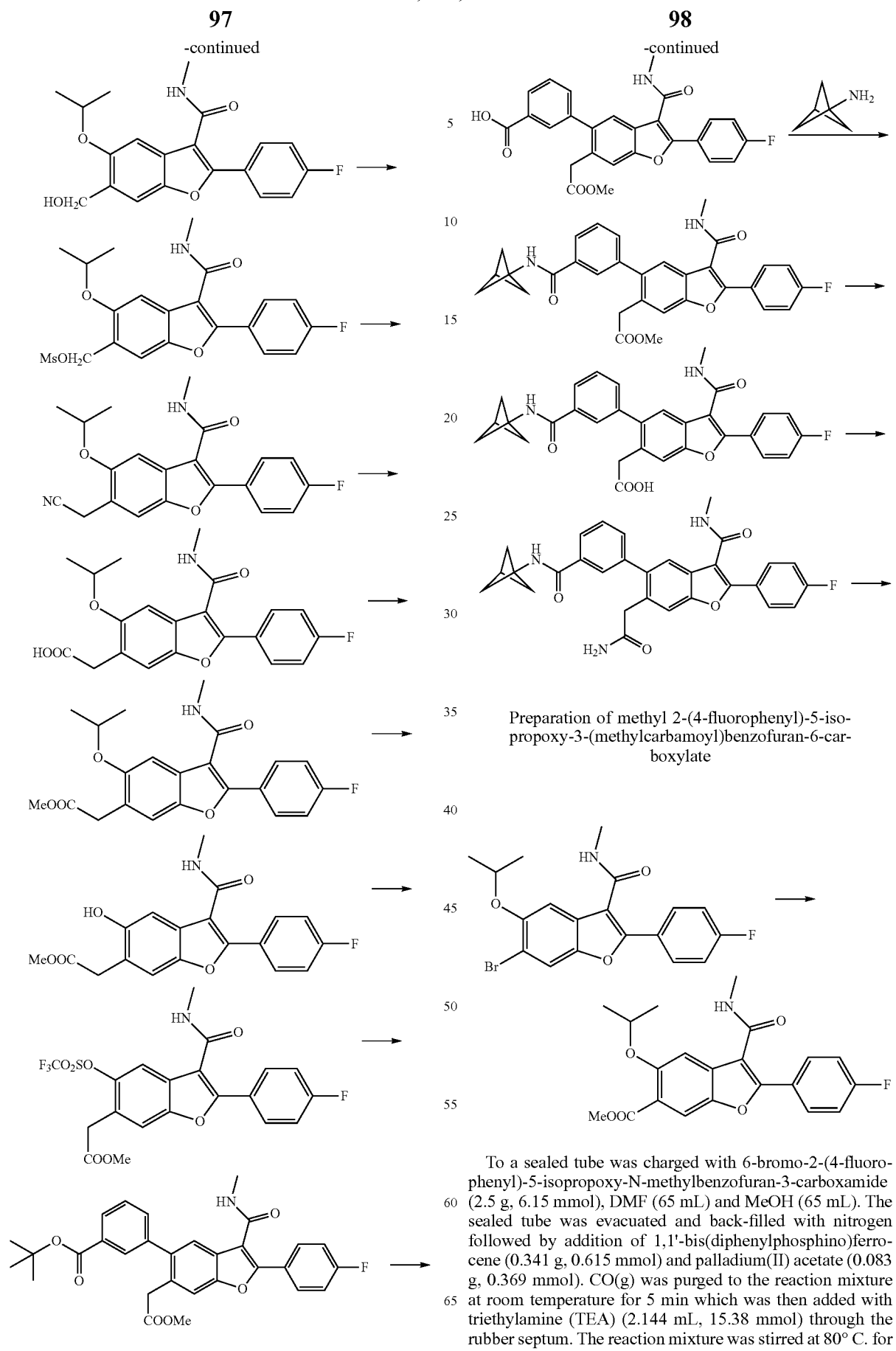

Preparation of methyl 2-(4-fluorophenyl)-5-isopropoxy-3-(methylcarbamoyl)benzofuran-6-carboxylate To a sealed tube was charged with 6-bromo-2-(4-fluorophenyl)-5-isopropoxy-N-methylbenzofuran-3-carboxamide (2.5 g, 6.15 mmol), DMF (65 mL) and MeOH (65 mL). The sealed tube was evacuated and back-filled with nitrogen followed by addition of 1,1'-bis(diphenylphosphino)ferrocene (0.341 g, 0.615 mmol) and palladium(II) acetate (0.083 g, 0.369 mmol). CO(g) was purged to the reaction mixture at room temperature for 5 min which was then added with triethylamine (TEA) (2.144 mL, 15.38 mmol) through the rubber septum. The reaction mixture was stirred at 80° C. for 5 hr in presence of a CO(g) balloon. After completion of the reaction (monitored by TLC), the mixture was cooled to room temperature and then partitioned between water (100 ml) and ethyl acetate (100 ml). The layers were separated and the aqueous layer was further extracted with ethyl acetate (100 ml×2). The combined ethyl acetate layers were washed with brine solution, dried over anhydrous $Na_2SO_4$ and concentrated under reduced pressure. The residue was purified by Combiflash over 40 g silica column using 20% EtOAc in petroleum (pet) ether as an eluent to obtain the desired compound as an off white solid. Yield: 1.9 g, (80%).

$^1$H NMR (400 MHz, $CDCl_3$) δ ppm 1.39 (d, J=6.0 Hz, 6H), 2.99 (d, J=4.7 Hz, 3H), 3.91 (s, 3H), 4.61 (dt, J=12.2, 6.05 Hz, 1H), 5.80 (br. s., 1H), 7.16-7.23 (m, 2H), 7.42 (s, 1H) 7.86-7.93 (m, 3H).

LCMS (ES+) m/z=386.30 (M+H).

Column—ACQUITY UPLC BEH C8 (50×2.1 mm; 1.7 μm)

M (Mobile) phase A: 5 mM Ammonium Acetate:MeCN (95:5)

M (Mobile) phase B: 5 mM Ammonium Acetate:MeCN (5:95)

Flow: 0.8 ml/Min

| Time | % A | % B |
|------|-----|-----|
| 0.0  | 95  | 5   |
| 1.1  | 5   | 95  |
| 1.7  | 5   | 95  |

Rt min: 1.04, wavelength: 220 nm

Preparation of 2-(4-fluorophenyl)-5-isopropoxy-3-(methylcarbamoyl)benzo-furan-6-carboxylic acid

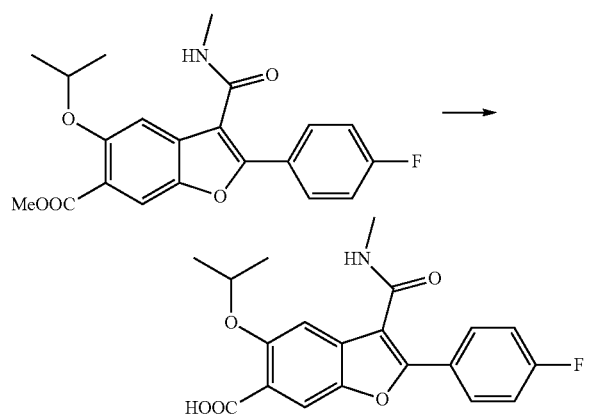

To a stirred solution of methyl 2-(4-fluorophenyl)-5-isopropoxy-3-(methylcarbamoyl)benzofuran-6-carboxylate (1.3 g, 3.37 mmol) in THF (60 mL) and MeOH (60 mL) was added sodium hydroxide (2.0M in water) (8.43 mL, 16.87 mmol) solution. The reaction mixture was stirred at room temperature for 16 hr. After completion of the reaction (monitored by TLC), the mixture was evaporated under reduced pressure. The residue was diluted with water (200 ml) and acidified by using 1.5N HCl slowly in cold condition till pH was acidic (pH ~3), and then stirred for 5 min. The precipitate was filtered, washed with water and dried under suction to afford the desired product as a white solid. Yield: 1.22 g, (98%).

$^1$H NMR (400 MHz, DMSO-$d_6$) δ ppm 1.31 (d, J=6.0 Hz, 6H), 2.84 (d, J=4.6 Hz, 3H), 4.65 (dt, J=12.1, 6.0 Hz, 1H), 7.36-7.43 (m, 2H), 7.88 (s, 1H), 7.92-7.99 (m, 2H), 8.44 (d, J=4.6 Hz, 1H), 12.66 (s, 1H).

LCMS (ES+) m/z=372.4 (M+H).

Column—ACQUITY UPLC BEH C8 (50×2.1 mm; 1.7 μm)

M phase A: 5 mM Ammonium Acetate:MeCN (95:5)

M phase B: 5 mM Ammonium Acetate:MeCN (5:95)

Flow: 0.8 ml/Min

| Time | % A | % B |
|------|-----|-----|
| 0.0  | 95  | 5   |
| 1.1  | 5   | 95  |
| 1.7  | 5   | 95  |

Rt min: 0.81, wavelength: 220 nm 2-(4-Fluorophenyl)-6-(hydroxymethyl)-5-isopropoxy-N-methylbenzofuran-3-carboxamide

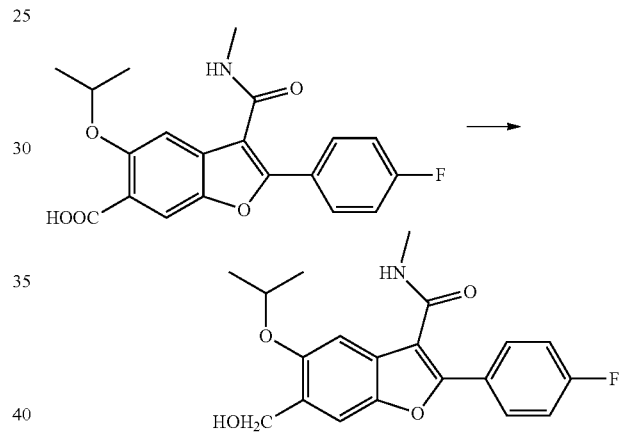

To a stirred solution of 2-(4-fluorophenyl)-5-isopropoxy-3-(methylcarbamoyl)benzofuran-6-carboxylic acid (1.2 g, 3.23 mmol) in THF (60 mL) at 0° C. under a $N_2$ atmosphere was added TEA (0.676 mL, 4.85 mmol) and isobutyl chloroformate (0.467 mL, 3.55 mmol) successively. The reaction mixture was stirred at the same temperature for 1 hr. The reaction mixture was filtered in cold condition and the solid was washed with cold THF (10 ml). To the filtrate at 0° C. was added sodium borohydride (0.367 g, 9.69 mmol) portionwise followed by MeOH (30 mL) slowly. The reaction mixture was allowed to come room temperature and stirred for overnight.

After completion of the reaction (monitored by TLC), the mixture was quenched with 1.0 N HCl slowly in cold condition, further diluted with water and extracted with EtOAc (50 ml×3). The combined organic layers were washed with 10%

$NaHCO_3$ (100 ml) solution, brine solution (100 ml), dried over anhydrous $Na_2SO_4$ and concentrated under reduced pressure. The residue was recrystalized using EtOAc and pet ether to obtain the product as a white solid.

Yield: 1.00 g, (87%).

$^1$H NMR (400 MHz, $CDCl_3$) δ ppm 1.40 (d, J=6.0 Hz, 6H), 2.54 (t, J=6.5 Hz, 1H), 2.98 (d, J=4.8 Hz, 3H), 4.65-4.77 (m, 3H), 5.75 (br. s., 1H), 7.18 (t, J=8.7 Hz, 2H), 7.35 (s, 1H), 7.42 (s, 1H), 7.82-7.88 (m, 2H).

LCMS (ES+) m/z=358.4 (M+H).

Column—ACQUITY UPLC BEH C8 (50×2.1 mm; 1.7 μm)

M phase A: 5 mM Ammonium Acetate:MeCN (95:5)

M phase B: 5 mM Ammonium Acetate:MeCN (5:95)

Flow: 0.8 ml/Min

| Time | % A | % B |
| --- | --- | --- |
| 0.0 | 95 | 5 |
| 1.1 | 5 | 95 |
| 1.7 | 5 | 95 |

Rt min: 0.90, wavelength: 220 nm

Preparation of (2-(4-fluorophenyl)-5-isopropoxy-3-(methylcarbamoyl) benzo-furan-6-yl)methyl methanesulfonate

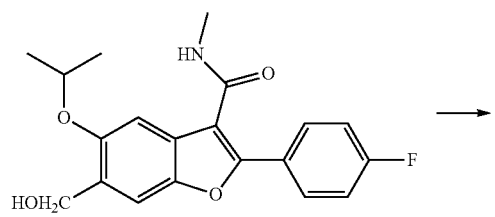

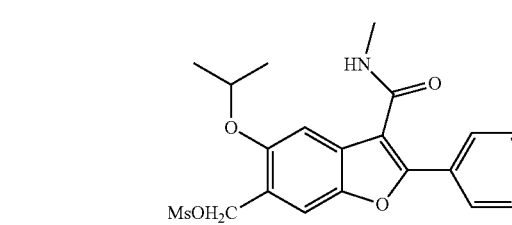

To a solution of 2-(4-fluorophenyl)-6-(hydroxymethyl)-5-isopropoxy-N-methylbenzofuran-3-carboxamide (800 mg, 2.239 mmol) in DCM (50 mL) at 0° C. under a N₂ atmosphere was added TEA (0.624 mL, 4.48 mmol) followed by DMAP (46.1 mg, 0.377 mmol) and then methanesulfonyl chloride (0.262 mL, 3.36 mmol). The reaction mixture was allowed to stir at room temperature for 16 hr. After completion of the reaction (monitored by TLC), the reaction mixture was diluted with water, the organic layer separated, and the aqueous layer subsequently extracted with DCM (100 ml×2). The combined DCM layers were washed with brine solution, dried over anhydrous Na₂SO₄ and concentrated under reduced pressure to afford the desired compound as a light yellow solid. Yield: 850 mg, (87%).

Preparation of 6-(cyanomethyl)-2-(4-fluorophenyl)-5-isopropoxy-N-methyl-benzofuran-3-carboxamide

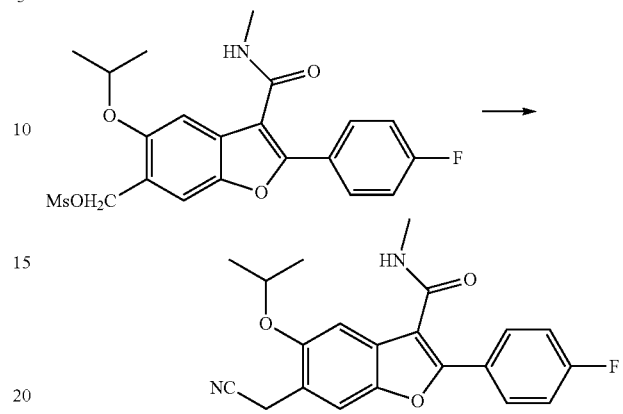

To a stirred solution of (2-(4-fluorophenyl)-5-isopropoxy-3-(methylcarbamoyl)benzofuran-6-yl)methyl methanesulfonate (800 mg, 1.837 mmol) in DMF (30 mL) at room temperature was added sodium cyanide (135 mg, 2.76 mmol). After being stirred at room temperature for overnight, the resulting mixture was diluted with water (200 ml), stirred for 15 min and filtered to obtain a solid, which was dried under suction to get the tile compound as a light yellow solid. Yield: 650 mg, (97%).

¹H NMR (400 MHz, CDCl₃) δ ppm 1.39 (d, J=6.0 Hz, 6H), 2.98 (d, J=4.8 Hz, 3H), 3.78 (s, 2H), 4.70 (dt, J=12.1, 6.0 Hz, 1H), 5.76 (bs, 1H), 7.20 (t, J=8.6 Hz, 2H), 7.37 (s, 1H), 7.53 (s, 1H), 7.84 (dd, J=8.9, 5.27 Hz, 2H).

LCMS (ES+) m/z=367.4 (M+H).

Column—ACQUITY UPLC BEH C8 (50×2.1 mm; 1.7 μm)

M phase A: 5 mM Ammonium Acetate:MeCN (95:5)

M phase B: 5 mM Ammonium Acetate:MeCN (5:95)

Flow: 0.8 ml/Min

| Time | % A | % B |
| --- | --- | --- |
| 0.0 | 95 | 5 |
| 1.1 | 5 | 95 |
| 1.7 | 5 | 95 |

Rt min: 1.01, wavelength: 220 nm

Alternative Preparation of 6-(cyanomethyl)-2-(4-fluorophenyl)-5-isopropoxy-N-methyl-benzofuran-3-carboxamide

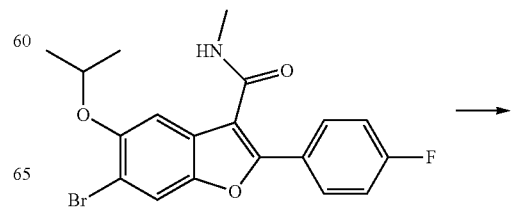

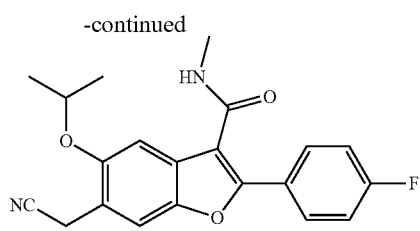

To a dried sealed tube was charged with 6-bromo-2-(4-fluorophenyl)-5-isopropoxy-N-methylbenzofuran-3-carboxamide (1.0 g, 2.462 mmol), sodium cyanoacetate (0.395 g, 3.69 mmol) and diglyme (40 mL). The reaction mixture was degassified and back-filled with nitrogen, followed by successive addition of 2-dicyclohexylphosphino-2',6'-dimethoxy-1,1'-biphenyl (0.061 g, 0.148 mmol), Pd$_2$(dba)$_3$ (0.045 g, 0.049 mmol) at room temperature. The reaction mixture was heated to 140° C. and stirred at same temperature for 5 hr. After completion, the mixture was cooled to room temperature, diluted with water, extracted with EtOAc (50 ml×3). The combined organic layers were washed with brine solution, dried over anhydrous Na$_2$SO$_4$ and concentrated under reduced pressure. The crude product was purified via Combiflash using 40 g silica column with 38% EtOAc in pet ether as an eluent to afford the product as a white solid. Yield: 650 mg, (72%).

Preparation of 2-(2-(4-fluorophenyl)-5-isopropoxy-3-(methylcarbamoyl) benzofuran-6-yl)acetic acid and 6-(2-amino-2-oxoethyl)-2-(4-fluorophenyl)-5-isopropoxy-N-methylbenzofuran-3-carboxamide

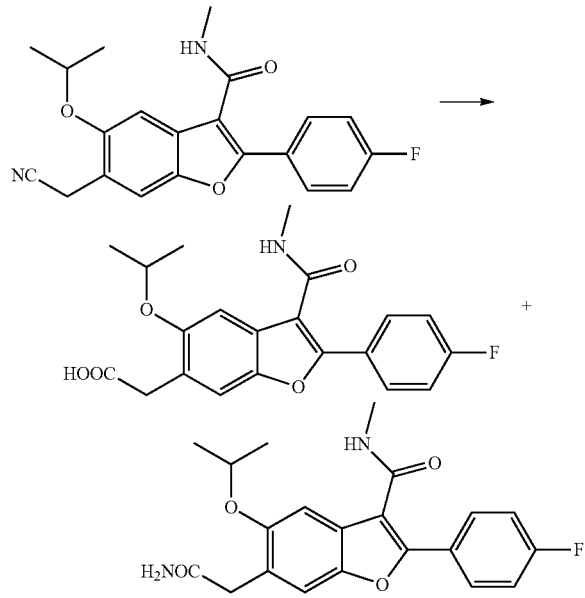

To a stirred solution of 6-(cyanomethyl)-2-(4-fluorophenyl)-5-isopropoxy-N-methylbenzofuran-3-carboxamide (600 mg, 1.638 mmol) in EtOH (60 mL) at room temperature in a sealed tube was added potassium hydroxide (1.0M in water) (4.91 mL, 4.91 mmol). The mixture was stirred at 80° C. for overnight. After completion (monitored by TLC), the reaction mixture was concentrated under reduced pressure to remove EtOH. The residue was diluted with water, acidified with con. HCl in cold condition using an ice bath, and stirred for 10 min. The solid obtained was filtered and dried under suction to afford a mixture of 2-(2-(4-fluorophenyl)-5-isopropoxy-3-(methylcarbamoyl)benzofuran-6-yl)acetic acid and 6-(2-amino-2-oxoethyl)-2-(4-fluorophenyl)-5-isopropoxy-N-methylbenzofuran-3-carboxamide.
The mixture of compounds was taken for the subsequent step. Yield: 550 mg.

LCMS (ES+) m/z=386.4 (M+H) of the acid, and 385.4 (M+H) of the amide.

Column—ACQUITY UPLC BEH C8 (50×2.1 mm; 1.7 µm)

M phase A: 5 mM Ammonium Acetate:MeCN (95:5)
M phase B: 5 mM Ammonium Acetate:MeCN (5:95)
Flow: 0.8 ml/Min

| Time | % A | % B |
|---|---|---|
| 0.0 | 95 | 5 |
| 1.1 | 5 | 95 |
| 1.7 | 5 | 95 |

Rt min: 0.84 and 0.81, wavelength: 220 nm

Preparation of methyl 2-(2-(4-fluorophenyl)-5-isopropoxy-3-(methylcarbamoyl) benzofuran-6-yl)acetate

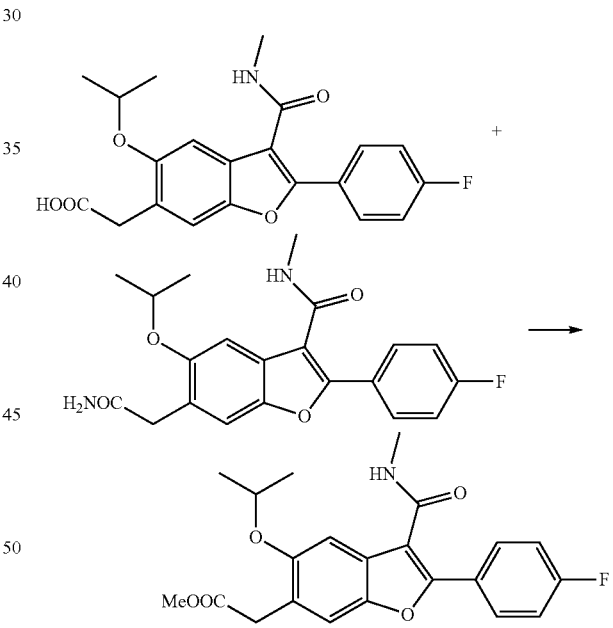

To a mixture of 2-(2-(4-fluorophenyl)-5-isopropoxy-3-(methylcarbamoyl)benzofuran-6-yl)acetic acid and 6-(2-amino-2-oxoethyl)-2-(4-fluorophenyl)-5-isopropoxy-N-methylbenzofuran-3-carboxamide in methanol (50 mL) at room temperature in a sealed tube was slowly added con. HCl (0.5 ml, 5.50 mmol) in cold condition. The mixture was stirred at 75° C. for 15 hr. After completion of the reaction (monitored by TLC), the mixture was cooled to room temperature, diluted with water, extracted with EtOAc (50 ml×3). The combined organic layers were washed with saturated brine solution, dried over Na$_2$SO$_4$ and concentrated in vacuum to give desired compound as a yellow solid. Yield: 500 mg, (88%).

LCMS (ES+) m/z=400.5 (M+H).
Column—ACQUITY UPLC BEH C8 (50×2.1 mm; 1.7 μm)
M phase A: 5 mM Ammonium Acetate:MeCN (95:5)
M phase B: 5 mM Ammonium Acetate:MeCN (5:95)
Flow: 0.8 ml/Min

| Time | % A | % B |
|---|---|---|
| 0.0 | 95 | 5 |
| 1.1 | 5 | 95 |
| 1.7 | 5 | 95 |

Rt min: 1.07, wavelength: 220 nm

Preparation of methyl 2-(2-(4-fluorophenyl)-5-hydroxy-3-(methylcarbamoyl) benzofuran-6-yl)acetate

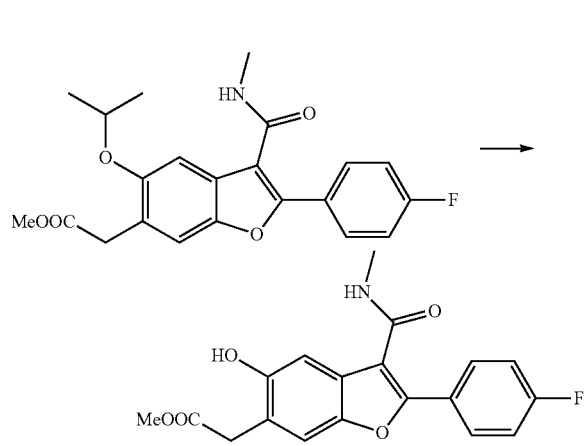

Trichloroborane (1.0M in toluene) (5.01 mL, 5.01 mmol) was added slowly to a solution of methyl 2-(2-(4-fluorophenyl)-5-isopropoxy-3-(methylcarbamoyl)benzofuran-6-yl)acetate (400 mg, 1.001 mmol) in DCM (25 mL) at −78° C. After being stirred at −78° C. to −20° C. for 2 hr, the reaction mixture was poured in to ice-water, stirred for 5 min and extracted with DCM (50 ml×3). The combined DCM layers were washed with saturated brine solution, dried over anhydrous Na$_2$SO$_4$ and concentrated under reduced pressure. The obtained crude product was recrystallized with pet ether and EtOAc to provide pure product as a yellow solid. Yield: 300 mg, (84%).

$^1$H NMR (400 MHz, CDCl$_3$) δ ppm 2.99 (s, 3H), 3.73-3.81 (m, 5H), 5.84 (br. s., 1H), 7.13-7.19 (m, 2H), 7.29 (s, 1H), 7.38 (s, 1H), 7.51 (d, J=3.5 Hz, 1H), 7.89-7.94 (m, 2H).

LCMS (ES+) m/z=358.4 (M+H).
Column—ACQUITY UPLC BEH C8 (50×2.1 mm; 1.7 μm)
M phase A: 5 mM Ammonium Acetate:MeCN (95:5)
M phase B: 5 mM Ammonium Acetate:MeCN (5:95)
Flow: 0.8 ml/Min

| Time | % A | % B |
|---|---|---|
| 0.0 | 95 | 5 |
| 1.1 | 5 | 95 |
| 1.7 | 5 | 95 |

Rt min: 0.88, wavelength: 220 nm

Preparation of methyl 2-(2-(4-fluorophenyl)-3-(methylcarbamoyl)-5-(((trifluoromethyl)sulfonyl)oxy)benzofuran-6-yl)acetate

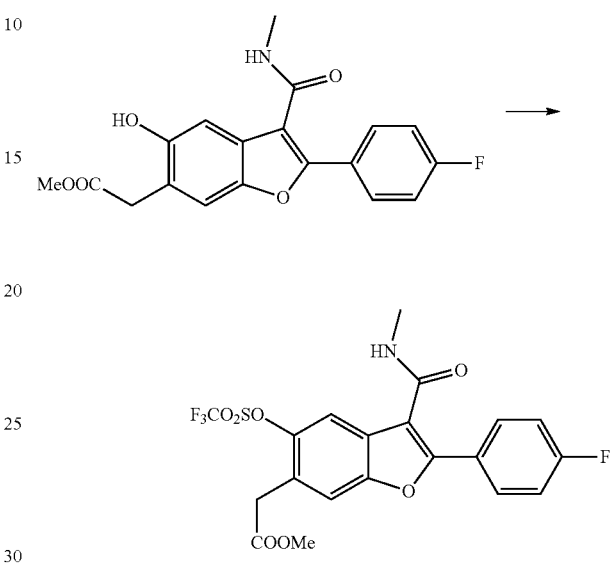

To a stirred solution of methyl 2-(2-(4-fluorophenyl)-5-hydroxy-3-(methylcarbamoyl)benzofuran-6-yl)acetate (250 mg, 0.700 mmol) in DMF (10 mL) at room temperature was successively added DMAP (128 mg, 1.049 mmol) and 1,1,1-trifluoro-N-phenyl-N-((trifluoromethyl)sulfonyl)methanesulfonamide (300 mg, 0.840 mmol). After being stirred at room temperature for overnight, the mixture was poured into water and extracted with EtOAc (75 ml×3). The combined organic layers were washed with saturated brine solution, dried over anhydrous Na$_2$SO$_4$ and concentrated under reduced pressure. The crude product was purified via Combiflash using 24 g silica column with 26% EtOAc in pet ether as eluent to get the desired product as a white solid. Yield: 275 mg, (80%).

$^1$H NMR (400 MHz, CDCl$_3$): δ 2.95-3.01 (m, 3H), 3.74 (s, 3H), 3.86 (s, 2H), 5.77 (br. s., 1H), 7.17-7.25 (m, 2H), 7.55 (s, 1H), 7.86-7.91 (m, 3H).

LCMS (ES+) m/z=490.4 (M+H).
Column—ACQUITY UPLC BEH C8 (50×2.1 mm; 1.7 μm)
M phase A: 5 mM Ammonium Acetate:MeCN (95:5)
M phase B: 5 mM Ammonium Acetate:MeCN (5:95)
Flow: 0.8 ml/Min

| Time | % A | % B |
|---|---|---|
| 0.0 | 95 | 5 |
| 1.1 | 5 | 95 |
| 1.7 | 5 | 95 |

Rt min: 1.09, wavelength: 220 nm

Preparation of tert-butyl 3-(2-(4-fluorophenyl)-6-(2-methoxy-2-oxoethyl)-3-(methylcarbamoyl)benzofuran-5-yl)benzoate

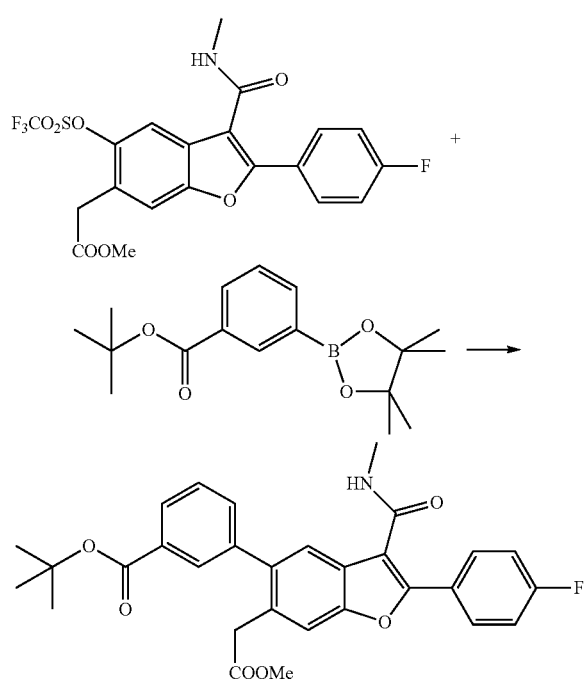

To a sealed tube was charged with methyl 2-(2-(4-fluorophenyl)-3-(methylcarbamoyl)-5-(((trifluoromethyl)sulfonyl)oxy)benzofuran-6-yl)acetate (300 mg, 0.613 mmol), tert-butyl 3-(4,4,5,5-tetramethyl-1,3,2-dioxaborolan-2-yl)benzoate (186 mg, 0.613 mmol), cesium carbonate (399 mg, 1.226 mmol), dioxane (45 mL) and water (4.5 mL). The reaction mixture was degasified and back-filled with $N_2$ followed by addition of $Pd(PPh_3)_4(0)$ (70.8 mg, 0.061 mmol) at room temperature. The teflon screw cap of the tube was tighten and the reaction mixture was stirred at 110° C. for overnight. After cooling the reaction mixture to room temperature, the mixture was filtered through a pad of celite, and the celite pad washed with EtOAc and the filtrate concentrated under reduced pressure. The residue obtained was purified via Combiflash using 24 g silica column with 28% EtOAc in pet ether as an eluent to afford the desired compound as a white solid. Yield: 280 mg, (88%).

$^1$H NMR (400 MHz, CDCl$_3$) δ 1.58 (s, 9H), 2.96 (d, J=4.64 Hz, 3H), 3.59-3.66 (m, 5H), 5.84 (bs, 1H), 7.14-7.22 (m, 2H), 7.43-7.50 (m, 2H), 7.67 (s, 1H), 7.93 (dt, J=2.0, 0.99 Hz, 1H), 7.96-8.06 (m, 4H).

Preparation of 3-(2-(4-fluorophenyl)-6-(2-methoxy-2-oxoethyl)-3-(methyl-carbamoyl)benzofuran-5-yl)benzoic acid

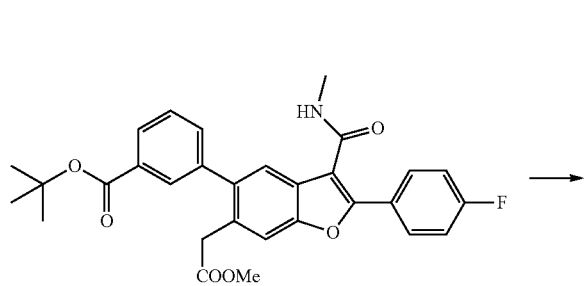

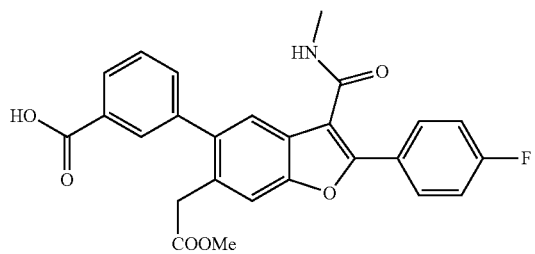

To a stirred solution of tert-butyl 3-(2-(4-fluorophenyl)-6-(2-methoxy-2-oxoethyl)-3-(methylcarbamoyl)benzofuran-5-yl)benzoate (75 mg, 0.145 mmol) in DCM (0.5 mL) at 0° C. was added TFA (0.223 mL, 2.90 mmol) slowly. The reaction mixture was allowed to stir at room temperature for 2 hr. After completion (monitored by TLC), the reaction mixture was concentrated under reduced pressure. To the residue was added ice-water, and then stirred for 10 min. The precipitate obtained was filtered, washed with water and dried under suction to afford the desired product as a white solid. Yield: 60 mg, (91%).

$^1$H NMR (400 MHz, DMSO-d$_6$): δ 2.78-2.86 (m, 3H), 3.50 (s, 3H), 3.72 (s, 2H), 7.40 (t, J=8.9 Hz, 2H), 7.48 (s, 1H), 7.54-7.65 (m, 2H), 7.73 (s, 1H), 7.81-7.88 (m, 1H), 7.91-8.07 (m, 3H), 8.47 (d, J=4.5 Hz, 1H), 13.05 (br. s., 1H).

LCMS (ES+) m/z=462.2 (M+H).

Column—ACQUITY UPLC BEH C18 (50×2.1 mm; 1.7 μm)

M phase A: 0.1% TFA in water

M phase B: Acetonitrile

Flow: 0.8 ml/Min

| Time | % A | % B |
|---|---|---|
| 0.0 | 98 | 2 |
| 1.0 | 2 | 98 |
| 1.7 | 2 | 98 |

Rt min: 0.89, wavelength: 220 nm

Preparation of methyl 2-(5-(3-(bicyclo[1.1.1]pentan-1-ylcarbamoyl)phenyl)-2-(4-fluorophenyl)-3-(methylcarbamoyl)benzofuran-6-yl)acetate

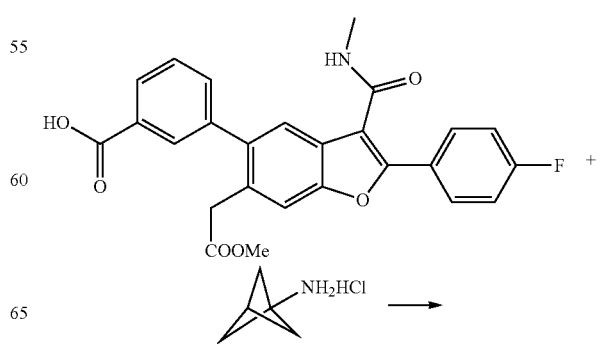

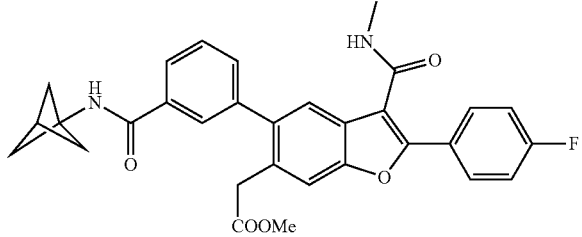

To a stirred solution of 3-(2-(4-fluorophenyl)-6-(2-methoxy-2-oxoethyl)-3-(methylcarbamoyl)benzofuran-5-yl)benzoic acid (15 mg, 0.033 mmol), bicyclo[1.1.1]pentan-1-amine hydrochloride (4.67 mg, 0.039 mmol) in DMF (1.0 mL) at room temperature under a $N_2$ atmosphere was added DIPEA (0.028 mL, 0.163 mmol). The mixture was cooled to 0° C. and added with 2-(7-aza-1H-benzotriazole-1-yl)-1,1,3,3-tetramethyluronium hexafluorophosphate (HATU) (18.54 mg, 0.049 mmol). The reaction mixture was allowed to stir at room temperature for overnight. After completion of the reaction (monitored by TLC), the mixture was diluted with water, stirred for 10 min, the precipitated solid filtered and dried under suction. The crude product was purified by Prep. (preparative) HPLC. Yield: 6 mg, 35%.

$^1$H NMR (400 MHz, $CDCl_3$): δ 2.21 (s, 6H), 2.51 (m, 1H), 2.99 (d, J=4.8 Hz, 3H), 3.63 (s, 2H), 3.65 (s, 3H), 5.84 (bs, 1H), 6.84 (s, 1H), 7.16-7.22 (m, 2H), 7.47-7.51 (m, 2H), 7.57 (s, 1H), 7.65-7.68 (m, 1H), 7.70 (s, 1H), 7.81-7.88 (m, 1H), 7.95-8.00 (m, 2H). $^{19}$F NMR (376.6 MHz, $CDCl_3$) δ: −109.50.

LCMS (ES+) m/z=527.2 (M+H).
Column—Ascentis Express C18 (50×2.1 mm-2.7 μm)
Mphase A: 10 mM $NH_4COOH$
Mphase B: MeCN
Flow=1 ML/MIN

| Time | % A | % B |
|---|---|---|
| 0.0 | 100 | 0 |
| 1.5 | 0 | 100 |
| 3.2 | 0 | 100 |

Rt min: 1.30, wavelength: 220 nm
Preparative HPLC Method
Column:
Inertsil ods (19*250)mm*5 u
Mobile Phase: 10 mM Ammonium acetate pH-4.5 with $CH_3COOH$
Mobile phase B: MeCN
Flow: 16 ml/min
Gradient:

| Time | % B |
|---|---|
| 0.0 | 30 |
| 8 | 70 |
| 15 | 100 |

Rt: 17.53 min
HPLC Method: COLUMN: Zorbax-SB-CN (150×4.6 MM) 5 microns
Mobile phase A: 10 mM ammonium acetate in water: MeCN (90:10)
Mobile phase B: 10 mM ammonium acetate in water: MeCN (10:90)
Flow: 1 ml/min

| Time | B % |
|---|---|
| 0 | 10 |
| 12 | 100 |
| 25 | 100 |

Wavelength: 254 nm, Rt min: 11.95
Wavelength: 220 nm, Rt min: 11.95
COLUMN: XBridge Phenyl (150×4.6 mm) 3.5 micron SC/749
Buffer: 0.05% TFA in water
Mobile Phase A: Buffer: MeCN (95:5)
Mobile Phase B: MeCN: Buffer (95:5)
Flow: 1 ml/min

| Time | B % |
|---|---|
| 0 | 10 |
| 25 | 100 |
| 30 | 100 |

Wavelength: 254 nm, Rt min: 16.47
Wavelength: 220 nm, Rt min: 16.65

Preparation of 2-(5-(3-(bicyclo[1.1.1]pentan-1-ylcarbamoyl)phenyl)-2-(4-fluorophenyl)-3-(methylcarbamoyl)benzofuran-6-yl)acetic acid

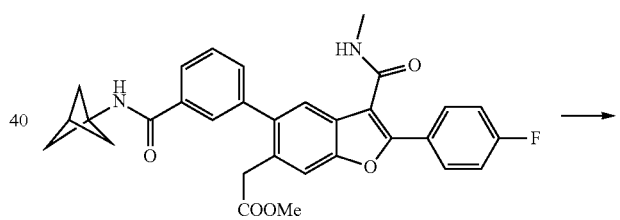

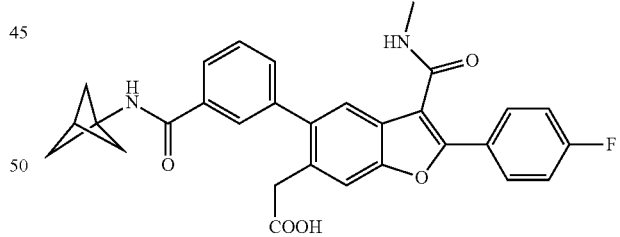

To a stirred solution of methyl 2-(5-(3-(bicyclo[1.1.1]pentan-1-ylcarbamoyl)phenyl)-2-(4-fluorophenyl)-3-(methylcarbamoyl)benzofuran-6-yl)acetate (120 mg, 0.228 mmol) in THF (5.0 mL) and MeOH (5.0 mL) was added sodium hydroxide (1.0M in water) (1.139 mL, 1.139 mmol). After being stirred at room temperature for overnight, the reaction mixture was concentrated under reduced pressure, and the reside diluted with water and acidified with 1.5N HCl to pH~3, and then stirred for 10 min. The precipitate was filtered, washed with water and dried under suction to afford the desired compound as a white solid. The crude solid obtained was purified by preparative HPLC. Yield: 110 mg, (95%).

¹H NMR (300 MHz, DMSO-d₆): δ 2.09 (s, 6H), 2.46 (s, 1H), 2.81 (d, J=4.6 Hz, 3H), 3.62 (s, 2H), 7.35-7.42 (m, 2H), 7.43-7.47 (m, 1H), 7.48-7.54 (m, 2H), 7.70 (s, 1H) 7.82 (s, 1H) 7.88 (s, 1H), 7.97-8.05 (m, 2H), 8.47 (s, 1H), 9.05 (s, 1H). ¹⁹F NMR (376.6 MHz, DMSO-d₆) δ: −109.50.

LCMS (ES+) m/z=513.2 (M+H).
Column—Ascentis Express C18 (50×2.1 mm-2.7 μm)
Mphase A: 10 mM NH₄COOH
Mphase B: MeCN
Flow=1 ML/MIN

| Time | % A | % B |
| --- | --- | --- |
| 0.0 | 100 | 0 |
| 1.5 | 0 | 100 |
| 3.2 | 0 | 100 |

Rt min: 2.16, wavelength: 220 nm
Preparative HPLC Method
Column: Inertsil ods (19*250)mm*5 u
Mobile Phase: 10 mM Ammonium acetate pH-4.5 with CH₃COOH
Mobile phase B: MeCN
Flow: 16 ml/min
Gradient:

| Time | % B |
| --- | --- |
| 0 | 20 |
| 10 | 70 |
| 15 | 100 |

Rt: 13.37 min
HPLC Method
COLUMN: SUNFIRE C18(150×4.6 mm) 3.5 micron
Buffer: 0.05% TFA in water
Mobile Phase A: Buffer: MeCN (95:5)
Mobile Phase B: MeCN: Buffer (95:5)
Flow: 1 ml/min

| Time | B % |
| --- | --- |
| 0 | 10 |
| 12 | 100 |
| 15 | 100 |

Wavelength: 254 nm, Rt min: 9.99
Wavelength: 220 nm, Rt min: 9.99
COLUMN: XBridge Phenyl (150×4.6 mm) 3.5 micron
Buffer: 0.05% TFA in water
Mobile Phase A: Buffer: MeCN (95:5)
Mobile Phase B: MeCN: Buffer (95:5)
Flow: 1 ml/min

| Time | B % |
| --- | --- |
| 0 | 10 |
| 12 | 100 |
| 15 | 100 |

Wavelength: 254 nm, Rt min: 9.26
Wavelength: 220 nm, Rt min: 9.26

Preparation of 6-(2-amino-2-oxoethyl)-5-(3-(bicyclo[1.1.1]pentan-1-ylcarbamoyl)phenyl)-2-(4-fluorophenyl)-N-methylbenzofuran-3-carboxamide

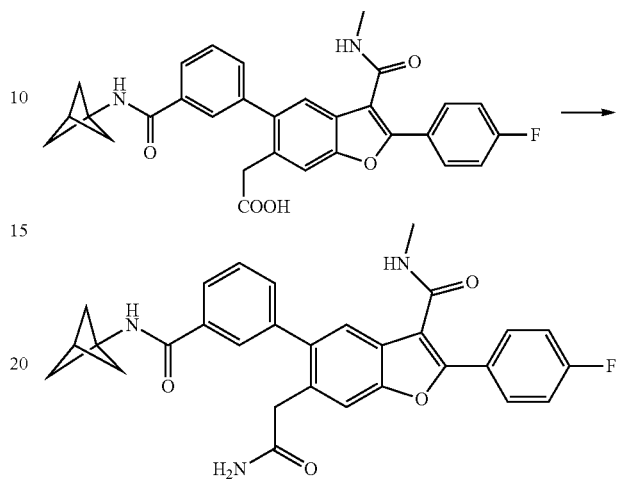

To a stirred solution of 2-(5-(3-(bicyclo[1.1.1]pentan-1-ylcarbamoyl)phenyl)-2-(4-fluorophenyl)-3-(methylcarbamoyl)benzofuran-6-yl)acetic acid (35 mg, 0.068 mmol) in DMF at room temperature (1.0 mL) was added ammonium chloride (4.38 mg, 0.082 mmol) and DIPEA (0.036 mL, 0.205 mmol) followed by HATU (38.9 mg, 0.102 mmol) at 0° C. The reaction mixture was allowed to stir at room temperature for overnight. After completion (monitored by TLC), the reaction mixture was diluted with water and the product extracted with EtOAc (20 ml×3). The combined organic layers were washed with saturated brine solution, dried over Na₂SO₄ and concentrated under reduced pressure. The crude product obtained was purified by preparative HPLC. Yield: 12 mg, (34%).

¹H NMR (400 MHz, DMSO-d₆): δ 2.13 (s, 6H) 2.47 (s, 1H), 2.82 (d, J=4.6 Hz, 3H) 3.46 (s, 2H), 6.88 (br. s., 1H), 7.28 (br. s., 1H), 7.40 (t, J=8.9 Hz, 2H), 7.45 (s, 1H) 7.50-7.56 (m, 2H), 7.67 (s, 1H) 7.79-7.89 (m, 2H), 7.98-8.05 (m, 2H), 8.45 (d, J=4.4 Hz, 1H), 9.01 (s, 1H). ¹⁹F NMR (376.6 MHz, DMSO-d₆) δ: −100.87.

LCMS (ES+) m/z=512.2 (M+H).
Column—Zorbax SB C18 (30×2.1 mm; 3.5 u)
Buffer: 10 mM Ammonium Formate in Water pH 4.5
Mphase A: Buffer+MeCN (98+2)
Mphase B: Buffer+MeCN (2+98)
Flow: 1.5 ml/min

| Time | % A | % B |
| --- | --- | --- |
| 0.0 | 94 | 6 |
| 1.5 | 0 | 100 |
| 2.2 | 0 | 100 |
| 2.6 | 94 | 6 |
| 3.0 | 94 | 6 |

Rt min: 1.30, wavelength: 220 nm
Preparative HPLC Method

Column:
SYMMETRY C8 (250×1,100
Mobile Phase: 10 mMm Ammonium acetate in water (A): MeCN (B)
Flow: 15 ml/min
Isocratic 0/30, 7/55, 21/100
Rt: 18.53 min
HPLC Method: SUNFIRE C18(150×4.6 mm) 3.5 micron
Buffer: 0.05% TFA in water pH 2.5
Mobile Phase A: Buffer: MeCN (95:5)
Mobile Phase B: MeCN:Buffer (95:5)
Flow: 1 ml/min

| Time | B % |
|---|---|
| 0 | 10 |
| 12 | 100 |
| 15 | 100 |

Wavelength: 254 nm, Rt min: 9.09
Wavelength: 220 nm, Rt min: 9.09
HPLC Method: XBridge Phenyl (150×4.6 mm) 3.5 micron SC/749
Buffer: 0.05% TFA in water pH 2.5
Mobile Phase A: Buffer: MeCN (95:5)
Mobile Phase B: MeCN: Buffer (95:5)
Flow: 1 ml/min

| Time | B % |
|---|---|
| 0 | 10 |
| 12 | 100 |
| 15 | 100 |

Wavelength: 254 nm, Rt min: 8.35
Wavelength: 220 nm, Rt min: 8.35

Synthesis of 5-(3-(bicyclo[1.1.1]pentan-1-ylcarbamoyl)phenyl)-2-(4-fluoro-phenyl)-N-methyl-6-(2-(methylamino)-2-oxoethyl)benzofuran-3-carboxamide

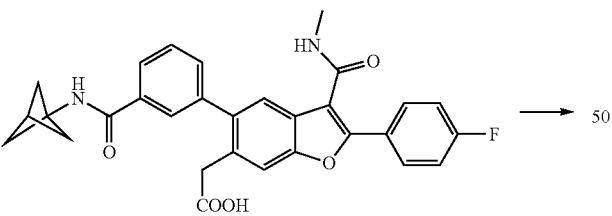

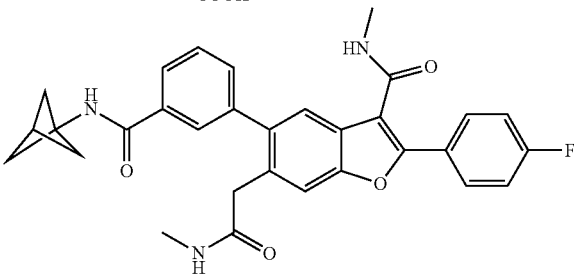

To a stirred solution of 2-(5-(3-(bicyclo[1.1.1]pentan-1-ylcarbamoyl)phenyl)-2-(4-fluorophenyl)-3-(methylcarbamoyl)benzofuran-6-yl)acetic acid (40 mg, 0.078 mmol) and methylamine hydrochloride (6.32 mg, 0.094 mmol) in DMF (2.5 mL) at room temperature under a $N_2$ atmosphere was added DIPEA (0.068 mL, 0.390 mmol). The mixture was cooled to 0° C. and added with HATU (44.5 mg, 0.117 mmol). The reaction mixture was allowed to stir at room temperature for overnight. After completion of the reaction (monitored by TLC), the mixture was diluted with water, extracted with EtOAc (20 ml×3). The combined organic layers were washed with saturated brine solution, dried over anhydrous $Na_2SO_4$ and concentrated under reduced pressure. The crude product obtained was purified by Prep. HPLC. Yield: 17 mg, (41%).

$^1$H NMR (400 MHz, CDCl$_3$): δ 2.22 (s, 6H), 2.51 (s, 1H), 2.78 (d, J=4.8 Hz, 3H), 3.00 (d, J=4.94 Hz, 3H), 3.53 (s, 2H), 5.51 (br. s., 1H), 5.84 (br. s., 1H), 7.01 (d, J=9.6 Hz, 1H), 7.17-7.24 (m, 2H), 7.42-7.53 (m, 2H), 7.55 (s, 2H), 7.76 (s, 1H), 7.79-7.85 (m, 1H), 7.90-8.03 (m, 2H). $^{19}$F NMR (376.6 MHz, CDCl$_3$) δ: −109.25.
LCMS (ES+) m/z=526.2 (M+H).
Column—Ascentis Express C18 (50×2.1 mm-2.7 μm)
Mphase A: 10 mM NH$_4$COOH
Mphase B: MeCN
Flow: 1 ml/min

| Time | % A | % B |
|---|---|---|
| 0.0 | 100 | 0 |
| 1.5 | 0 | 100 |
| 3.2 | 0 | 100 |

RT min: 2.46, wavelength: 220 nm
Preparative HPLC Method
Column:
Inertsil ods (19*250)mm*5 u
Mobile Phase: 10 mM Ammonium acetate pH 4.5 with CH$_3$COOH
Mobile phase B: MeCN
Flow: 16 ml/min
Gradient:

| Time | % B |
|---|---|
| 0 | 20 |
| 10 | 70 |
| 15 | 100 |

Rt: 13.38 min
HPLC Method
COLUMN: SUNFIRE C18(150×4.6 mm) 3.5 micron
Buffer: 0.05% TFA in water
Mobile Phase A: Buffer: MeCN (95:5)
Mobile Phase B: MeCN: Buffer (95:5)
Flow: 1 ml/min

| Time | B % |
|---|---|
| 0 | 10 |
| 12 | 100 |
| 15 | 100 |

Wavelength: 254 nm, Rt min: 9.43
Wavelength: 220 nm, Rt min: 9.43
COLUMN: XBridge Phenyl (150×4.6 mm) 3.5 micron
Buffer: 0.05% TFA in water
Mobile Phase A: Buffer: MeCN (95:5)
Mobile Phase B: MeCN: Buffer (95:5)
Flow: 1 ml/min

| Time | B % |
| --- | --- |
| 0 | 10 |
| 12 | 100 |
| 15 | 100 |

Wavelength: 254 nm, Rt min: 8.59
Wavelength: 220 nm, Rt min: 8.59

Preparation of 5-(3-(bicyclo[1.1.1]pentan-1-ylcarbamoyl)phenyl)-6-(2-(dimeth-ylamino)-2-oxoethyl)-2-(4-fluorophenyl)-N-methylbenzofuran-3-carboxamide

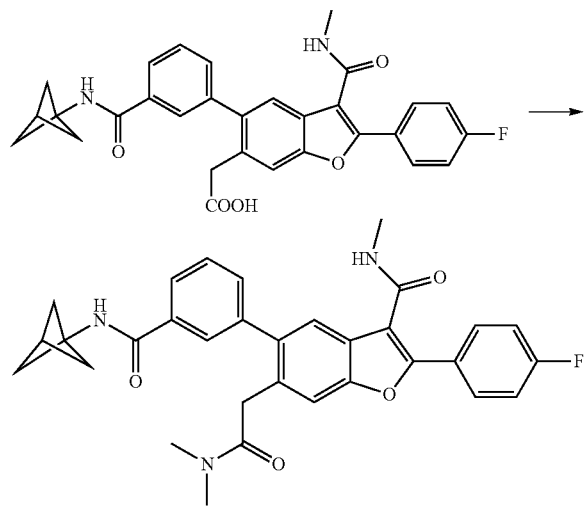

To a stirred solution of 2-(5-(3-(bicyclo[1.1.1]pentan-1-ylcarbamoyl)phenyl)-2-(4-fluorophenyl)-3-(methylcarbamoyl)benzofuran-6-yl)acetic acid (40 mg, 0.078 mmol), dimethylamine hydrochloride (7.64 mg, 0.094 mmol) in DMF (2.5 mL) at room temperature under a $N_2$ atmosphere was added DIPEA (0.068 mL, 0.390 mmol). The mixture was cooled to 0° C. and added with HATU (44.5 mg, 0.117 mmol). The reaction mixture after being stirred at room temperature for overnight, was poured into water and extracted with EtOAc (20 ml×3). The combined organic layers were washed with saturated brine solution, dried over anhydrous $Na_2SO_4$ and concentrated under reduced pressure. The crude product obtained was purified by Prep. HPLC.

Yield: 18.5 mg, (44%).

$^1$H NMR (400 MHz, CDCl$_3$): δ 2.20 (s, 6H), 2.51 (s, 1H), 2.74 (s, 3H), 2.92 (s, 3H), 2.98 (d, J=4.9 Hz, 3H), 3.63 (s, 2H), 5.84 (bs, 1H), 6.69 (bs, 1H), 7.14-7.22 (m, 2H), 7.40-7.53 (m, 3H), 7.61-7.70 (m, 2H), 7.81-7.87 (m, 1H), 7.91-8.02 (m, 2H). $^{19}$F NMR (376.6 MHz, CDCl$_3$) δ: −109.70.

LCMS (ES+) m/z=540.2 (M+H).

Column—Ascentis Express C18 (50×2.1 mm-2.7 μm)
Mphase A: 10 mM NH$_4$COOH
Mphase B: MeCN
Flow: 1 ml/min

| Time | % A | % B |
| --- | --- | --- |
| 0.0 | 100 | 0 |
| 1.5 | 0 | 100 |
| 3.2 | 0 | 100 |

Rt min: 2.52, wavelength: 220 nm
Preparative HPLC Method
Column: Atlantis DC18 (250 mm×19 mm ID, 10 u)
Mobile phase A=Buffer: 10 mM AA in water
Mobile phase B=Acetonitrile
Flow: 15 ml/min
Gradient:

| T | % B |
| --- | --- |
| 0 | 10 |
| 16 | 90 |
| 18 | 90 |
| 18.1 | 10 |
| 25 | 10 |

HPLC Method
COLUMN: SUNFIRE C18(150×4.6 mm) 3.5 micron
Buffer: 0.05% TFA in water
Mobile Phase A: Buffer: MeCN (95:5)
Mobile Phase B: MeCN: Buffer (95:5)
Flow: 1 ml/min

| Time | B % |
| --- | --- |
| 0 | 10 |
| 12 | 100 |
| 15 | 100 |

Wavelength: 254 nm, Rt min: 9.97
Wavelength: 220 nm, Rt min: 9.97
COLUMN: XBridge Phenyl (150×4.6 mm) 3.5 micron
Buffer: 0.05% TFA in water
Mobile Phase A: Buffer: MeCN (95:5)
Mobile Phase B: MeCN: Buffer (95:5)
Flow: 1 ml/min

| Time | B % |
| --- | --- |
| 0 | 10 |
| 12 | 100 |
| 15 | 100 |

Wavelength: 254 nm, Rt min: 9.10
Wavelength: 220 nm, Rt min: 9.10

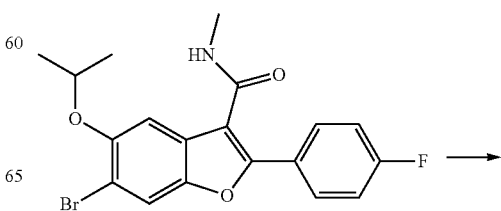

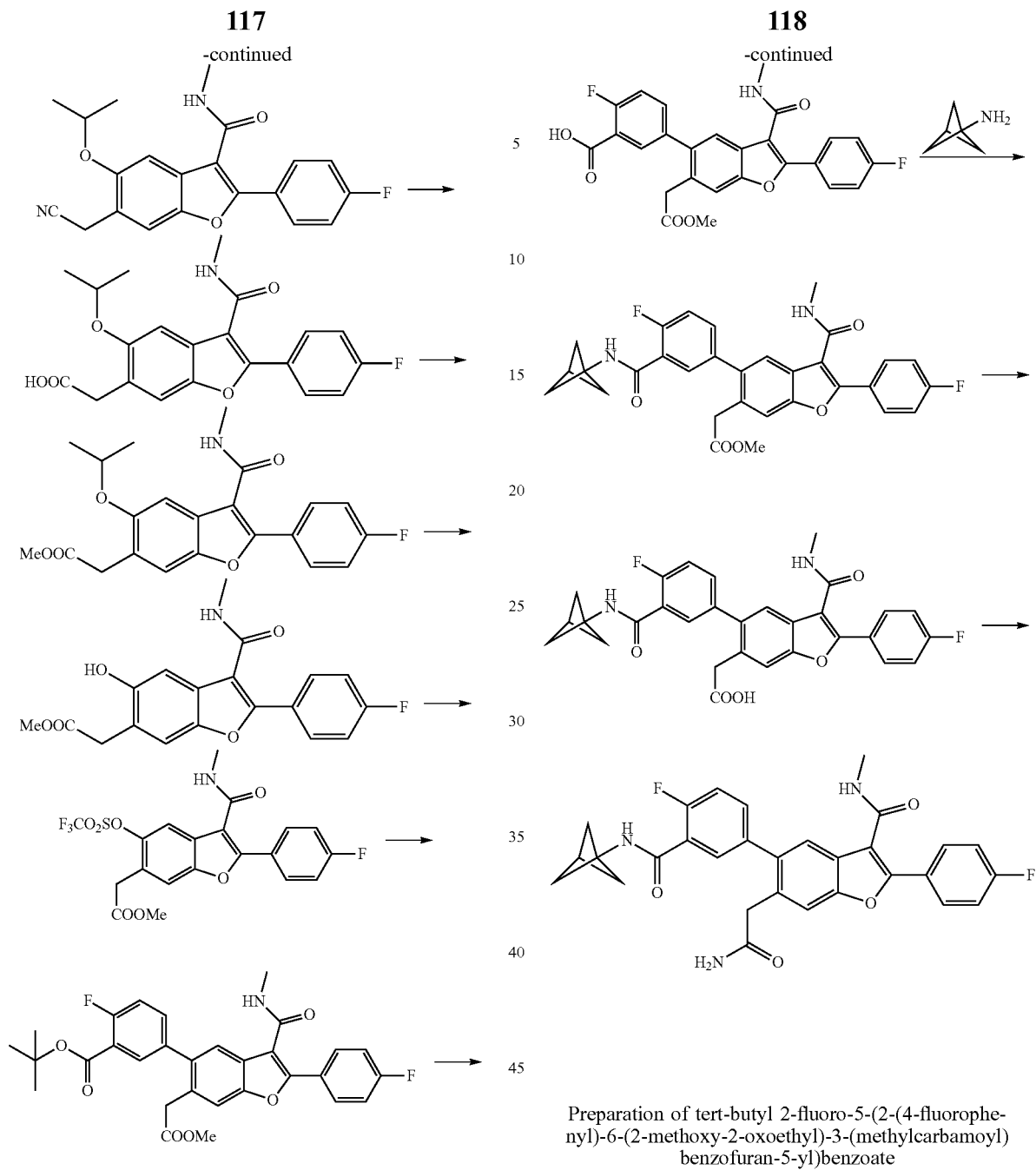
Preparation of tert-butyl 2-fluoro-5-(2-(4-fluorophenyl)-6-(2-methoxy-2-oxoethyl)-3-(methylcarbamoyl)benzofuran-5-yl)benzoate
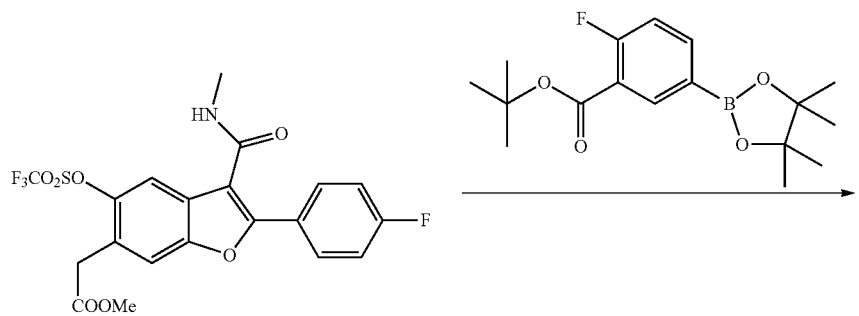

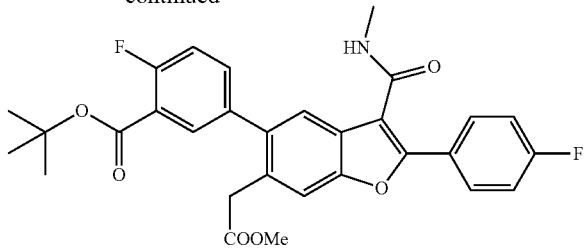

To a sealed tube was added methyl 2-(2-(4-fluorophenyl)-3-(methylcarbamoyl)-5-((((trifluoromethyl)sulfonyl)oxy)benzofuran-6-yl)acetate (250 mg, 0.511 mmol), tert-butyl 2-fluoro-5-(4,4,5,5-tetramethyl-1,3,2-dioxaborolan-2-yl)benzoate (197 mg, 0.613 mmol), potassium phosphate (217 mg, 1.022 mmol), dioxane (35 mL) and water (3.5 mL). The reaction mixture was degassed and back-filled with $N_2$, followed by addition of $PdCl_2(dppf)\text{-}CH_2Cl_2$ (41.7 mg, 0.051 mmol) at room temperature. The teflon screw cap of the tube was tighten and the reaction mixture was stirred at 110° C. for 16 hr. After completion (monitored by TLC), the reaction mixture was cooled to room temperature, diluted with water and extracted with EtOAc (75 mL×3). The combined organic layers were washed with saturated brine solution, dried over anhydrous $Na_2SO_4$ and concentrated in reduced pressure. The crude product obtained was purified via Combiflash using a 24 g silica column with 29% EtOAc in pet ether as an eluent to get the product as an off white solid. Yield: 240 mg (88%).

LCMS (ES+) m/z=536.2 (M+H).

Column—ACQUITY UPLC BEH C18 (50×2.1 mm; 1.7 μm)

M phase A: 0.1% TFA in water

M phase B: Acetonitrile

Flow: 0.8 ml/Min

| Time | % A | % B |
|------|-----|-----|
| 0    | 98  | 2   |
| 1.0  | 2   | 98  |
| 1.6  | 2   | 98  |

Rt min: 1.12, wavelength: 220 nm

Preparation of 2-fluoro-5-(2-(4-fluorophenyl)-6-(2-methoxy-2-oxoethyl)-3-(methylcarbamoyl)benzofuran-5-yl)benzoic acid

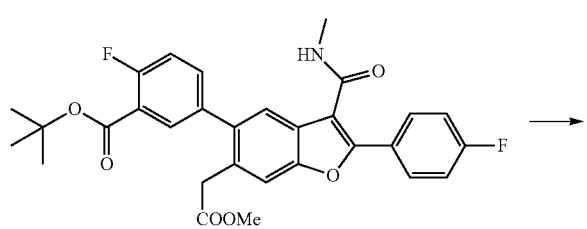

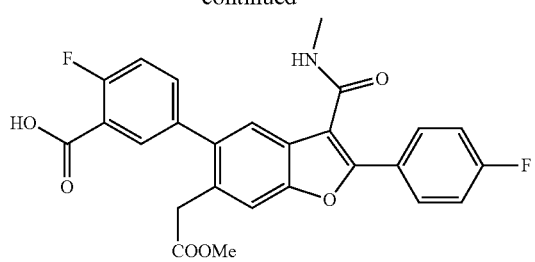

To a stirred solution of tert-butyl 2-fluoro-5-(2-(4-fluorophenyl)-6-(2-methoxy-2-oxoethyl)-3-(methylcarbamoyl)benzofuran-5-yl)benzoate (240 mg, 0.448 mmol) in DCM (5.0 mL) at 0° C. was added TFA (0.691 mL, 8.96 mmol) slowly. The reaction mixture was allowed the stir at room temperature for 2 hr. After completion (monitored by TLC), the reaction mixture was concentrated under reduced pressure, and the residue added with ice-water and then stirred for 10 min. The precipitate obtained was filtered, washed with water and dried under suction to give the desired compound as a white solid. Yield: 180 mg, 84%.

$^1$H NMR (400 MHz, DMSO-$d_6$): δ 2.81 (d, J=4.5 Hz, 3H), 3.51 (s, 3H), 3.73 (s, 2H), 7.33-7.44 (m, 3H), 7.48 (s, 1H), 7.53-7.61 (m, 1H), 7.71-7.77 (m, 2H), 7.98-8.05 (m, 2H), 8.46 (d, J=4.5 Hz, 1H), 13.34 (br. s., 1H).

LCMS (ES+) m/z=480.1 (M+H).

Column—ACQUITY UPLC BEH C18 (50×2.1 mm; 1.7 μm)

M phase A: 0.1% TFA in water

M phase B: Acetonitrile

Flow: 0.8 ml/Min

| Time | % A | % B |
|------|-----|-----|
| 0    | 98  | 2   |
| 1.0  | 2   | 98  |
| 1.6  | 2   | 98  |

Rt min: 0.88, wavelength: 220 nm

Preparation of methyl 2-(5-(3-(bicyclo[1.1.1]pentan-1-ylcarbamoyl)-4-fluoro-phenyl)-2-(4-fluorophenyl)-3-(methylcarbamoyl)benzofuran-6-yl)acetate

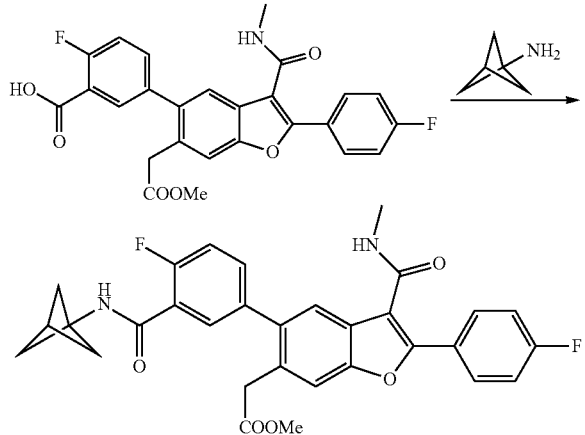

To a stirred solution of 2-fluoro-5-(2-(4-fluorophenyl)-6-(2-methoxy-2-oxoethyl)-3-(methylcarbamoyl)benzofuran-5-yl)benzoic acid (150 mg, 0.313 mmol), bicyclo[1.1.1]pentan-1-amine hydrochloride (44.9 mg, 0.375 mmol) in DMF (15 mL) at room temperature under a $N_2$ atmosphere was added DIPEA (0.273 mL, 1.564 mmol). The mixture was cooled to 0° C. and added with HATU (178 mg, 0.469 mmol). The reaction mixture was allowed to stir at room temperature for overnight. After completion, the reaction mixture was diluted with water, stirred for 10 min. The solid was filtered, washed with water and dried under suction. The crude product was purified by Prep. HPLC. Yield: 155 mg, (91%).

$^1$H NMR (400 MHz, CDCl3): δ 2.22 (s, 6H), 2.53 (s, 1H), 3.00 (d, J=4.8 Hz, 3H), 3.64 (s, 5H) 5.83 (bs, 1H), 7.05-7.15 (m, 1H), 7.16-7.22 (m, 3H), 7.43 (ddd, J=8.1, 4.9, 2.44 Hz, 1H), 7.51-7.55 (m, 1H,) 7.63 (s, 1H) 7.94-8.04 (m, 3H). $^{19}$F NMR (376.6 MHz, CDCl$_3$) δ: −109.65, −115.61.

LCMS (ES+) m/z=545.2 (M+H).
Column—Ascentis Express C18 (50×2.1 mm-2.7 μm)
Mphase A: 10 mM NH$_4$COOH
Mphase B: MeCN
Flow: 1 ml/min

| Time | % A | % B |
|---|---|---|
| 0.0 | 100 | 0 |
| 1.5 | 0 | 100 |
| 3.2 | 0 | 100 |

Rt min: 2.71, wavelength: 220 nm
Preparative HPLC Method
Column: Silca (250×19×50
M. Phase A: 0.2% DEA in Hexane
M, Phase B: Ethanol
Flow: 15 ml/min
Time (min)/% B: 0/30
Rt: 15.31 min
HPLC Method
COLUMN: Zorbax-SB-CN (150×4.6 MM) 5 microns
Mobile phase A: 10 mM ammonium acetate in water: MeCN (90:10)
Mobile phase B: 10 mM ammonium acetate in water: MeCN (10:90)
Flow: 1 ml/min

| Time | B % |
|---|---|
| 0 | 10 |
| 20 | 100 |
| 25 | 100 |

Wavelength: 254 nm, Rt min: 12.76
Wavelength: 220 nm, Rt min: 12.76
COLUMN: XBridge Phenyl (150×4.6 mm) 3.5 micron
Buffer: 0.05% TFA in water
Mobile Phase A: Buffer: MeCN (95:5)
Mobile Phase B: MeCN: Buffer (95:5)
Flow: 1 ml/min

| Time | B % |
|---|---|
| 0 | 10 |
| 25 | 100 |
| 30 | 100 |

Wavelength: 254 nm, Rt min: 16.60
Wavelength: 220 nm, Rt min: 16.60

Preparation of 2-(5-(3-(bicyclo[1.1.1]pentan-1-ylcarbamoyl)-4-fluorophenyl)-2-(4-fluorophenyl)-3-(methylcarbamoyl)benzofuran-6-yl)acetic acid

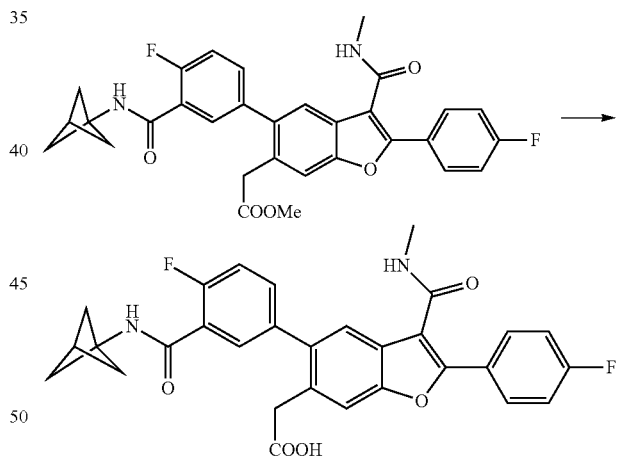

To a stirred solution of methyl 2-(5-(3-(bicyclo[1.1.1]pentan-1-ylcarbamoyl)-4-fluorophenyl)-2-(4-fluorophenyl)-3-(methylcarbamoyl)benzofuran-6-yl)acetate (140 mg, 0.257 mmol) in THF (7.5 mL) and MeOH (7.5 mL) was added sodium hydroxide (1.0M in water) (1.285 mL, 1.285 mmol). After being stirred at room temperature for 16 hr, the reaction mixture was concentrated under reduced pressure. The reside was diluted with water, acidified using 1.5N HCl to pH-3, and then stirred for 10 min. The precipitate formed was filtered, washed with water and dried under suction. The crude product obtained was purified by Prep HPLC. Yield: 130 mg, 96%.

$^1$H NMR (400 MHz, DMSO-d$_6$): δ 2.09 (s, 6H), 2.47 (s, 1H), 2.83 (s, 3H), 3.62 (s, 2H), 7.32-7.53 (m, 6H), 7.70 (s,

1H), 7.96-8.05 (m, 2H), 8.46 (d, J=4.5 Hz, 1H), 8.91 (s, 1H), 12.34 (br. s., 1H). $^{19}$F NMR (376.6 MHz, DMSO-d$_6$) δ: −110.77, −116.70.

LCMS (ES+) m/z=531.2 (M+H).
Column—Ascentis Express C18 (50×2.1 mm-2.7 μm)
Mphase A: 10 mM NH$_4$COOH
Mphase B: MeCN
Flow: 1 ml/min

| Time | % A | % B |
|---|---|---|
| 0.0 | 100 | 0 |
| 1.5 | 0 | 100 |
| 3.2 | 0 | 100 |

Rt min: 2.18, wavelength: 220 nm
Preparative HPLC Method
Column: Atlantis DC18 (250 mm×19 mm ID, 10 u)
Mobile phase A=Buffer: 10 mM Ammonium acetate in water
Mobile phase B=Acetonitrile
Flow: 15 ml/min
Gradient:

| Time | % B |
|---|---|
| 0 | 10 |
| 16 | 90 |
| 18 | 90 |
| 20 | 10 |

Rt: 13.38 min
HPLC Method
COLUMN: SUNFIRE C18(150×4.6 mm) 3.5 micron
Buffer: 0.05% TFA in water
Mobile Phase A: Buffer: MeCN (95:5)
Mobile Phase B: MeCN: Buffer (95:5)
Flow: 1 ml/min

| Time | B % |
|---|---|
| 0 | 10 |
| 25 | 100 |
| 30 | 100 |

Wavelength: 254 nm, Rt min: 16.62
Wavelength: 220 nm, Rt min: 16.62
COLUMN: XBridge Phenyl (150×4.6 mm) 3.5 micron
Buffer: 0.05% TFA in water
Mobile Phase A: Buffer: MeCN (95:5)
Mobile Phase B: MeCN: Buffer (95:5)
Flow: 1 ml/min

| Time | B % |
|---|---|
| 0 | 10 |
| 25 | 100 |
| 30 | 100 |

Wavelength: 254 nm, Rt min: 15.13
Wavelength: 220 nm, Rt min: 15.13

Preparation of 6-(2-amino-2-oxoethyl)-5-(3-(bicyclo[1.1.1]pentan-1-ylcarbamoyl)-4-fluorophenyl)-2-(4-fluorophenyl)-N-methylbenzofuran-3-carboxamide

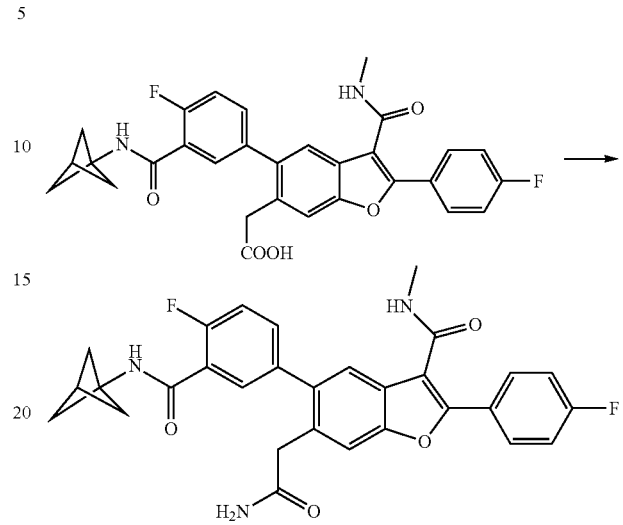

To a stirred solution of 2-(5-(3-(bicyclo[1.1.1]pentan-1-ylcarbamoyl)-4-fluorophenyl)-2-(4-fluorophenyl)-3-(methylcarbamoyl)benzofuran-6-yl)acetic acid (35 mg, 0.066 mmol) in DMF (1.0 mL) at room temperature was added ammonium chloride (4.23 mg, 0.079 mmol) and DIPEA (0.035 mL, 0.198 mmol). The mixture was cooled to 0° C. and added with HATU (37.6 mg, 0.099 mmol). The reaction mixture was allowed to stir at room temperature for 16 hr. After completion of the reaction, the mixture was diluted with water and extracted with EtOAc (25 ml×3). The combined organic layers were washed with saturated brine solution, dried over Na$_2$SO$_4$ and concentrated under reduced pressure. The crude product obtained was purified by Prep HPLC. Yield: 30 mg, (86%).

$^1$H NMR (400 MHz, CDCl$_3$): δ 2.21 (s, 6H), 2.53 (s, 1H), 2.99 (d, J=4.9 Hz, 3H), 3.58 (s, 2H), 5.20-5.41 (m, 2H), 5.82 (d, J=4.0 Hz, 1H), 7.11 (d, J=12.0 Hz, 1H), 7.15-7.23 (m, 3H), 7.45 (ddd, J=8.3, 4.8, 2.4 Hz, 1H), 7.57-7.61 (m, 1H), 7.68 (s, 1H), 7.93-8.09 (m, 3H). $^{19}$F NMR (376.6 MHz, CDCl$_3$): δ: −109.38, −115.39.

LCMS (ES+) m/z=530.2 (M+H).
Column—Ascentis Express C18 (50×2.1 mm-2.7 μm)
Mphase A: 10 mM NH$_4$COOH
Mphase B: MeCN
Flow: 1 ml/min

| Time | % A | % B |
|---|---|---|
| 0.0 | 100 | 0 |
| 1.5 | 0 | 100 |
| 3.2 | 0 | 100 |

Rt min: 2.44, wavelength: 220 nm
Preparative HPLC Method
Column:
Atlantis DC18 (250 mm×19 mm ID, 10 u)
Mobile phase A=Buffer: 10 mM Ammonium acetate in water
Mobile phase B=Acetonitrile
Flow: 15 ml/min Gradient:

| Time | % B |
| --- | --- |
| 0 | 30 |
| 16 | 90 |
| 18 | 90 |
| 18.1 | 30 |
| 20 | 30 |

HPLC Method
COLUMN: SUNFIRE C18(150×4.6 mm) 3.5 micron
Buffer: 0.05% TFA in water
Mobile Phase A: Buffer: MeCN (95:5)
Mobile Phase B: MeCN: Buffer (95:5)
Flow: 1 ml/min

| Time | B % |
| --- | --- |
| 0 | 10 |
| 25 | 100 |
| 30 | 100 |

Wavelength: 254 nm, Rt min: 14.36
Wavelength: 220 nm, Rt min: 14.36
COLUMN: XBridge Phenyl (150×4.6 mm) 3.5 micron
Buffer: 0.05% TFA in water
Mobile Phase A: Buffer: MeCN (95:5)
Mobile Phase B: MeCN: Buffer (95:5)
Flow: 1 ml/min

| Time | B % |
| --- | --- |
| 0 | 10 |
| 25 | 100 |
| 30 | 100 |

Wavelength: 254 nm, Rt min: 12.64
Wavelength: 220 nm, Rt min: 12.64

Preparation of 5-(3-(bicyclo[1.1.1]pentan-1-ylcarbamoyl)-4-fluorophenyl)-2-(4-fluorophenyl)-N-methyl-6-(2-(methylamino)-2-oxoethyl)benzofuran-3-carboxamide

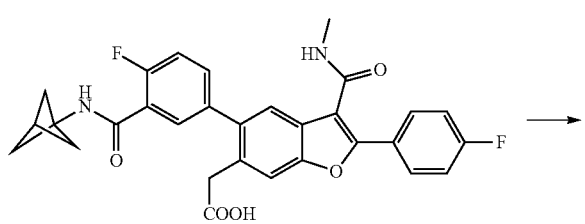

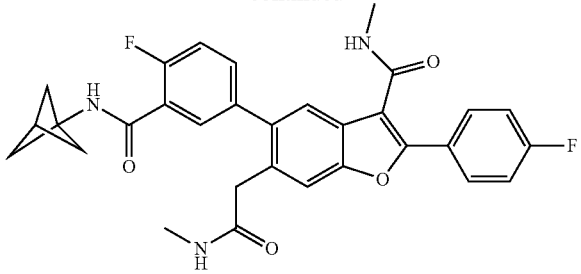

To a stirred solution of 2-(5-(3-(bicyclo[1.1.1]pentan-1-ylcarbamoyl)-4-fluorophenyl)-2-(4-fluorophenyl)-3-(methylcarbamoyl)benzofuran-6-yl)acetic acid (35 mg, 0.066 mmol), methylamine hydrochloride (5.35 mg, 0.079 mmol) in DMF (2.5 mL) at room temperature under a $N_2$ atmosphere was added DIPEA (0.058 mL, 0.330 mmol). The mixture was cooled to 0° C. and then added with HATU (37.6 mg, 0.099 mmol). The reaction mixture was allowed to stir at room temperature for 16 hr. After completion of the reaction (monitored by TLC), the mixture was diluted with water, extracted with EtOAc (25 ml×3). The combined organic layers were washed with saturated brine solution, dried over anhydrous $Na_2SO_4$ and concentrated under reduced pressure. The crude product was purified by Prep HPLC. Yield: 19 mg, (53)%.

$^1$H NMR (400 MHz, $CDCl_3$): δ 2.23 (s, 6H), 2.53 (s, 1H), 2.74 (d, J=4.8 Hz, 3H), 3.01 (d, J=4.9 Hz, 3H), 3.55 (s, 2H), 5.42 (bs, 1H) 5.8 (bs, 1H), 7.23 (d, J=1.0 Hz, 4H), 7.42 (ddd, J=8.4, 4.9, 2.4 Hz, 1H,) 7.57 (s, 1H), 7.68 (s, 1H), 7.94-7.99 (m, 3H). $^{19}$F NMR (376.6 MHz, $CDCl_3$): δ: −109.39, −115.51.

LCMS (ES+) m/z=544.2 (M+H).
Column—Ascentis Express C18 (50×2.1 mm-2.7 μm)
Mphase A: 10 mM $NH_4COOH$
Mphase B: MeCN
Flow: 1 ml/min

| Time | % A | % B |
| --- | --- | --- |
| 0.0 | 100 | 0 |
| 1.5 | 0 | 100 |
| 3.2 | 0 | 100 |

Rt min: 2.48, wavelength: 220 nm
Preparative HPLC Method
Column: ymc c-18(150*20)mm*5 u
Mobile phase A: 10 mM Ammonium acetate pH 4.5 with AcOH
Mobile phase B=Acetonitrile
Flow: 15 ml/min
Gradient:

| Time | % B |
| --- | --- |
| 0 | 20 |
| 12 | 70 |
| 15 | 100 |

Rt min: 11.66
HPLC Method
COLUMN: SUNFIRE C18(150×4.6 mm) 3.5 micron
Buffer: 0.05% TFA in water
Mobile Phase A: Buffer: MeCN (95:5)

Mobile Phase B: MeCN: Buffer (95:5)  
Flow: 1 ml/min

| Time | B % |
|---|---|
| 0 | 10 |
| 25 | 100 |
| 30 | 100 |

Wavelength: 254 nm, Rt min: 9.68  
Wavelength: 220 nm, Rt min: 9.68  
COLUMN: XBridge Phenyl (150×4.6 mm) 3.5 micron  
Buffer: 0.05% TFA in water  
Mobile Phase A: Buffer: MeCN (95:5)  
Mobile Phase B: MeCN: Buffer (95:5)  
Flow: 1 ml/min

| Time | B % |
|---|---|
| 0 | 10 |
| 25 | 100 |
| 30 | 100 |

Wavelength: 254 nm, Rt min: 8.80  
Wavelength: 220 nm, Rt min: 8.80

Preparation of 5-(3-(bicyclo[1.1.1]pentan-1-ylcarbamoyl)-4-fluorophenyl)-6-(2-(dimethylamino)-2-oxoethyl)-2-(4-fluorophenyl)-N-methylbenzofuran-3-carboxamide

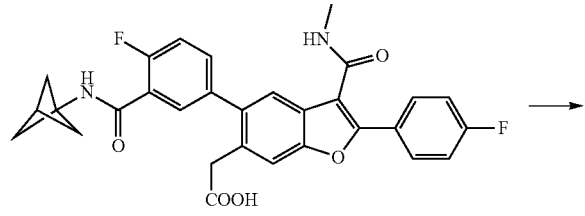

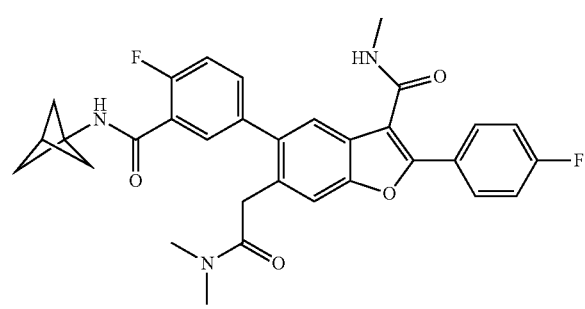

To a stirred solution of 2-(5-(3-(bicyclo[1.1.1]pentan-1-ylcarbamoyl)-4-fluorophenyl)-2-(4-fluorophenyl)-3-(methylcarbamoyl)benzofuran-6-yl)acetic acid (35 mg, 0.066 mmol), dimethylamine hydrochloride (6.46 mg, 0.079 mmol) in DMF (2.5 mL) at room temperature under a $N_2$ atmosphere was added DIPEA (0.058 mL, 0.330 mmol). The mixture was cooled to 0° C. and added with HATU (37.6 mg, 0.099 mmol). After being stirred at room temperature for 16 hr, the reaction mixture was diluted with water and then stirred for 10 min. The solid was filtered, washed with water and dried under suction. The crude product obtained was purified by Prep HPLC. Yield: 8 mg, 22%.

$^1$H NMR (400 MHz, CDCl$_3$): δ 2.22 (s, 6H), 2.53 (s, 1H), 2.75 (s, 3H), 2.92 (s, 3H), 3.00 (s, 3H), 3.65 (s, 2H), 5.84 (bs, 1H), 7.09 (d, J=12.5 Hz, 1H), 7.13-7.21 (m, 3H), 7.37-7.47 (m, 1H), 7.49 (s, 1H), 7.62 (s, 1H), 7.87-8.10 (m, 3H). $^{19}$F NMR (376.6 MHz, CDCl$_3$): δ: −109.79, −115.69.

LCMS (ES+) m/z=558.2 (M+H).  
Column—Ascentis Express C18 (50×2.1 mm-2.7 μm)  
Mphase A: 10 mM NH$_4$COOH  
Mphase B: MeCN  
Flow: 1 ml/min

| Time | % A | % B |
|---|---|---|
| 0.0 | 100 | 0 |
| 1.5 | 0 | 100 |
| 3.2 | 0 | 100 |

Rt min: 2.55, wavelength: 220 nm  
Preparative HPLC Method  
Column:  
sunfire c-18(150*19)mm*5 u  
Mobile phase A: 10 mM Ammonium acetate pH 4.5 with AcOH  
Mobile phase B=Acetonitrile  
Flow: 15 ml/min  
Gradient:

| Time | % B |
|---|---|
| 0 | 20 |
| 10 | 70 |
| 15 | 100 |

RT min: 12.40  
HPLC Method  
COLUMN: SUNFIRE C18(150×4.6 mm) 3.5 micron  
Buffer: 0.05% TFA in water  
Mobile Phase A: Buffer: MeCN (95:5)  
Mobile Phase B: MeCN: Buffer (95:5)  
Flow: 1 ml/min

| Time | B % |
|---|---|
| 0 | 10 |
| 12 | 100 |
| 15 | 100 |

Wavelength: 254 nm, Rt min: 10.28  
Wavelength: 220 nm, Rt min: 10.28  
COLUMN: XBridge Phenyl (150×4.6 mm) 3.5 micron  
Buffer: 0.05% TFA in water  
Mobile Phase A: Buffer: MeCN (95:5)  
Mobile Phase B: MeCN: Buffer (95:5)  
Flow: 1 ml/min

| Time | B % |
|---|---|
| 0 | 10 |
| 12 | 100 |
| 15 | 100 |

Wavelength: 254 nm, Rt min: 9.33  
Wavelength: 220 nm, Rt min: 9.33

129 130
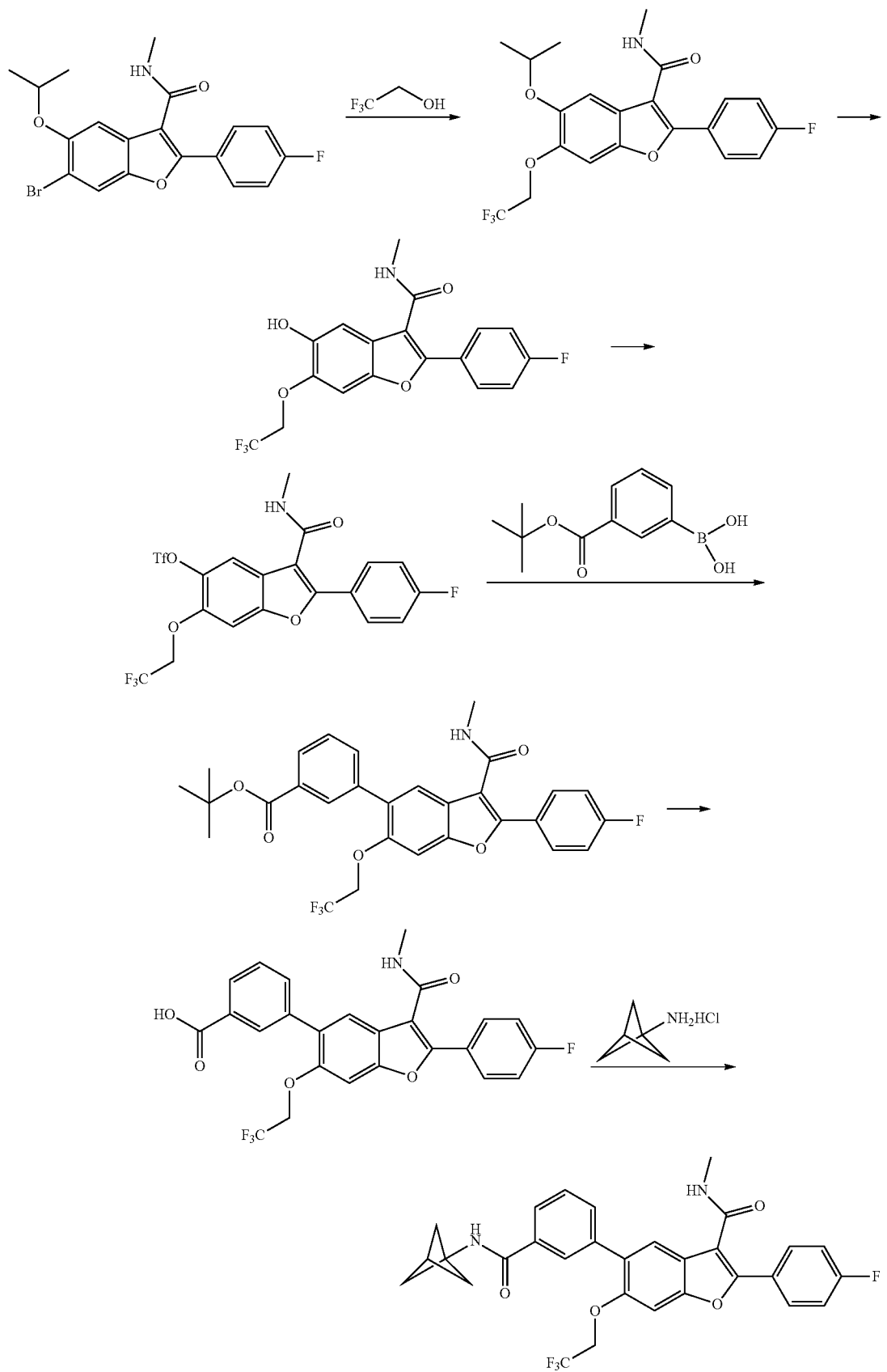

Preparation of 2-(4-fluorophenyl)-5-isopropoxy-N-methyl-6-(2,2,2-trifluoroethoxy) benzofuran-3-carboxamide

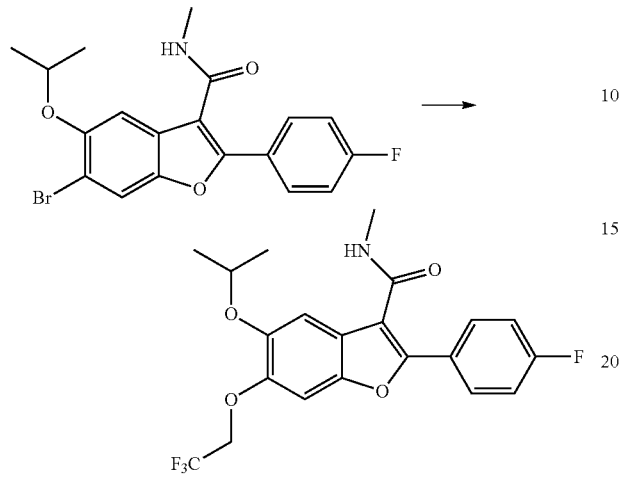

To a dried sealed tube was charged with 6-bromo-2-(4-fluorophenyl)-5-isopropoxy-N-methylbenzofuran-3-carboxamide (1.0 g, 2.462 mmol), sodium tert-butoxide (0.473 g, 4.92 mmol). 2,2,2-trifluoroethanol (0.884 mL, 12.31 mmol) and toluene (30 mL). The reaction mixture was degassed and back-filled with nitrogen followed by subsequent addition of 2-(dicyclohexylphosphino)-3,6-dimethoxy-2'-4'-6'-tri-propyl-1,1'biphenyl (0.132 g, 0.246 mmol) and Pd$_2$(dba)$_3$ (0.113 g, 0.123 mmol) at room temperature. The teflon screw cap was tighten and the reaction mixture was stirred at 110° C. for overnight. After completion of the reaction (monitored by TLC), the mixture was cooled to room temperature, filtered through a pad of celite and the celite pad washed with EtOAc (50 ml). After evaporation of the solvent under vacuum, the residue was purified via Combiflash using 40 g silica column with 17% EtOAc in pet ether as an eluent to give the desired compound as an off white solid. Yield: 170 mg, (16%).

$^1$H NMR (400 MHz, CDCl): δ 1.37 (d, J=6.0 Hz, 6H), 2.97 (d, J=4.8 Hz, 3H), 4.42 (q, J=8.4 Hz, 2H), 4.50-4.59 (m, 1H), 5.74 (bs, 1H), 7.13-7.21 (m, 3H), 7.41 (s, 1H), 7.83 (dd, J=9.04, 5.2 Hz, 2H).

LCMS (ES+) m/z=426.2 (M+H).

Column—Acquity BEH C18 (2.1×50 mm) 1.7 u

Buffer: 10 mM AmmoniumAcetate pH 5 adjusted with HCOOH

Mobile phase A: Buffer:MeCN (95:5)

Mobile phase B: Buffer:MeCN (5:95)

Flow: 0.8 ml/Min

| Time | % A | % B |
|------|-----|-----|
| 0.0  | 95  | 5   |
| 1.1  | 5   | 95  |
| 1.7  | 5   | 95  |

Rt min: 1.12, wavelength: 220 nm

Preparation of 2-(4-fluorophenyl)-5-hydroxy-N-methyl-6-(2,2,2-trifluoroethoxy)benzofuran-3-carboxamide

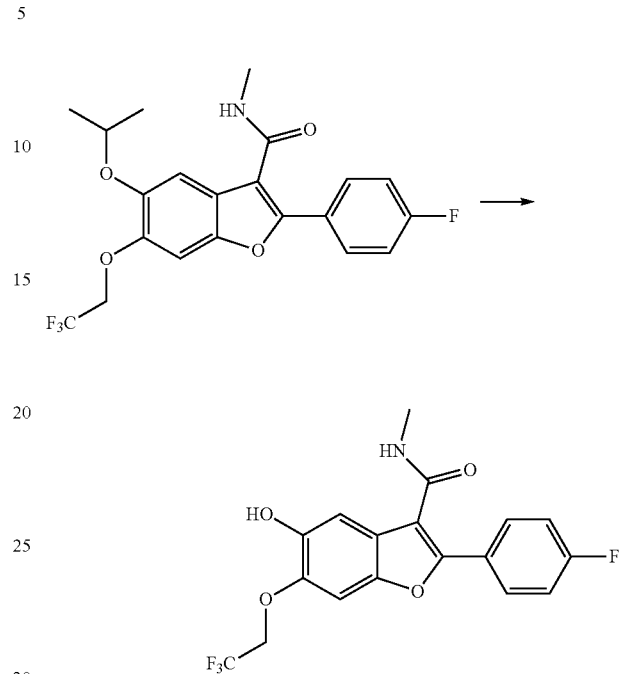

Trichloroborane (1.0M in toluene) (1.199 mL, 1.199 mmol) was added to a stirred solution of 2-(4-fluorophenyl)-5-isopropoxy-N-methyl-6-(2,2,2-trifluoroethoxy)benzofuran-3-carboxamide (170 mg, 0.400 mmol) in DCM (20 mL) at −78° C. The reaction mixture was allowed to stir at 0° C. for 15 min. After completion (monitored by TLC), the reaction mixture was poured into ice-water, stirred for 10 min and extracted with DCM (50 ml×3). The combined DCM layers were washed with brine solution, dried over anhydrous Na$_2$SO$_4$ and concentrated under reduced pressure. The residue was triturated with pet ether and filtered to obtain the product as an off white solid. Yield: 130 mg, (85%).

$^1$H NMR (300 MHz, CDCl$_3$): δ 3.03 (d, J=4.91 Hz, 3H) 4.51 (q, J=7.96 Hz, 2H) 5.61 (s, 1H), 5.83 (bs, 1H), 7.10 (s, 1H), 7.13-7.22 (m, 2H) 7.40 (s, 1H) 7.89-8.00 (m, 2H).

LCMS (ES+) m/z=384.1 (M+H).

Column—Acquity BEH C18 (2.1×50 mm) 1.7 u

Buffer: 10 mM AmmoniumAcetate pH 5 adjusted with HCOOH

Mobile phase A: Buffer:MeCN (95:5)

Mobile phase B: Buffer:MeCN (5:95)

Flow: 0.8 ml/Min

| Time | % A | % B |
|------|-----|-----|
| 0.0  | 95  | 5   |
| 1.1  | 5   | 95  |
| 1.7  | 5   | 95  |

Rt min: 0.95, wavelength: 220 nm

Preparation of 2-(4-fluorophenyl)-3-(methylcarbamoyl)-6-(2,2,2-trifluoro-ethoxy)benzofuran-5-yl trifluoromethanesulfonate

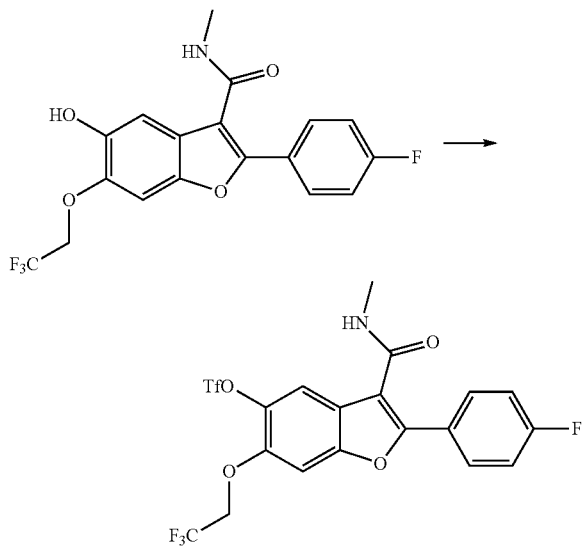

silica column with 26% EtOAc in pet ether as an eluent to afford the desired compound as an white solid. Yield: 135 mg, 84%.

$^1$H NMR (300 MHz, CDCl$_3$): δ 3.01 (d, J=4.9 Hz, 3H), 4.51 (q, J=7.8 Hz, 2H), 5.77 (bs, 1H), 7.20-7.28 (m, 3H), 7.82-7.92 (m, 3H).

LCMS (ES+) m/z=516.2 (M+H).
Column—Acquity BEH C18 (2.1×50 mm) 1.7 u
Buffer: 10 mM AmmoniumAcetate pH 5 adjusted with HCOOH
Mobile phase A: Buffer:MeCN (95:5)
Mobile phase B: Buffer:MeCN (5:95)
Flow: 0.8 ml/Min

| Time | % A | % B |
|---|---|---|
| 0.0 | 95 | 5 |
| 1.1 | 5 | 95 |
| 1.7 | 5 | 95 |

Rt min: 1.14, wavelength: 220 nm

Preparation of tert-butyl 3-(2-(4-fluorophenyl)-3-(methylcarbamoyl)-6-(2,2,2-trifluoroethoxy)benzofuran-5-yl)benzoate

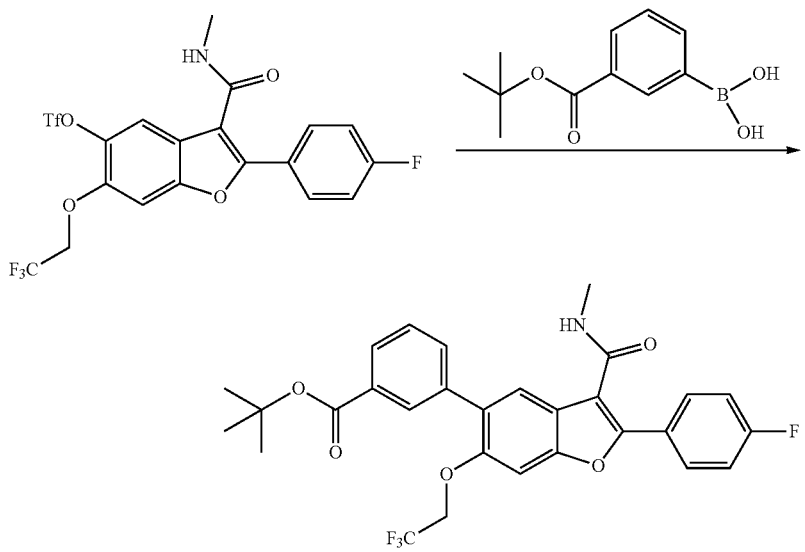

To a stirred solution of 2-(4-fluorophenyl)-5-hydroxy-N-methyl-6-(2,2,2-trifluoroethoxy)benzofuran-3-carboxamide (120 mg, 0.313 mmol) in DMF (7.5 mL) was added DMAP (38.2 mg, 0.313 mmol) followed by 1,1,1-trifluoro-N-phenyl-N-((trifluoromethyl)sulfonyl)methanesulfonamide (134 mg, 0.376 mmol).

After being stirred at room temperature for overnight, the resulting reaction mixture was poured into water and extracted with EtOAc (50 ml×3). The combined organic layers were washed with saturated brine solution, dried over anhydrous Na$_2$SO$_4$ and concentrated in reduced pressure. The crude product was purified via Combiflash using a 12 g 2-(4-Fluorophenyl)-3-(methylcarbamoyl)-6-(2,2,2-trifluoroethoxy)benzofuran-5-yltrifluoro-methanesulfonate (100 mg, 0.194 mmol), (3-(tert-butoxycarbonyl)phenyl)boronic acid (47.4 mg, 0.213 mmol), Cs$_2$CO$_3$ (126 mg, 0.388 mmol), dioxane (10 mL) and water (1.0 mL) were added into a sealed tube. The reaction mixture was degassed and back-filled with N$_2$ followed by addition of tetrakis(triphenylphosphine)palladium(0) (22.42 mg, 0.019 mmol) at room temperature. The teflon screw cap of the tube was tighten, and the reaction mixture heated to 110° C. and stir it for overnight. After completion of the reaction (monitored by TLC), the mixture was cooled to room temperature, filtered through a pad of celite and the celite pad washed with EtOA (50 ml). After evaporation of the solvent under vacuum, the residue was purified via Combiflash using a 40 g silica column with 28% EtOAc in pet ether as an eluent to give the desired compound as an white solid. Yield: 100 mg, (95%).

$^1$H NMR (400 MHz, CDCl$_3$): δ 1.61 (s, 9H), 3.01 (d, J=4.9 Hz, 3H), 4.31 (q, J=8.0 Hz, 2H), 5.83 (br. s., 1H), 7.14-7.21 (m, 3H), 7.48 (t, J=7.7 Hz, 1H), 7.63-7.71 (m, 1H), 7.78 (s, 1H) 7.89-7.96 (m, 2H), 7.98-8.04 (m, 1H), 8.14 (t, J=1.5 Hz, 1H).

LCMS (ES+) m/z=544.3 (M+H).

Column—Acquity BEH C18 (2.1×50 mm) 1.7 u

Buffer: 10 mM AmmoniumAcetate pH 5 adjusted with HCOOH

Mobile phase A: Buffer:MeCN (95:5)
Mobile phase B: Buffer:MeCN (5:95)
Flow: 0.8 ml/Min

| Time | % A | % B |
|---|---|---|
| 0.0 | 95 | 5 |
| 1.1 | 5 | 95 |
| 1.7 | 5 | 95 |

Rt min: 1.24, wavelength: 220 nm

Preparation of 3-(2-(4-fluorophenyl)-3-(methylcarbamoyl)-6-(2,2,2-trifluoroethoxy)benzofuran-5-yl)benzoic acid

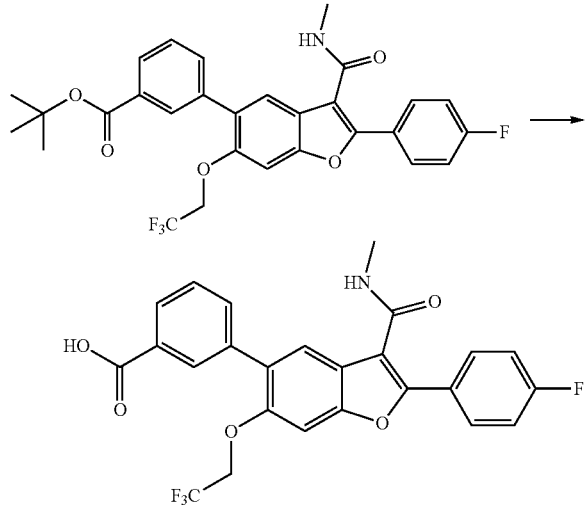

To a stirred solution of tert-butyl 3-(2-(4-fluorophenyl)-3-(methylcarbamoyl)-6-(2,2,2-trifluoroethoxy)benzofuran-5-yl)benzoate (80 mg, 0.147 mmol) in DCM (2.5 mL) at 0° C. was added TFA (0.227 mL, 2.94 mmol) slowly. The reaction mixture was allowed to stir at room temperature for 2 hr. After completion, the reaction mixture was concentrated under reduced pressure. The residue was triturated with pet ether to provide the product as a white solid.

Yield: 70 mg, 97%.

$^1$H NMR (300 MHz, DMSO-d$_6$): δ 2.83 (d, J=4.6 Hz, 3H), 4.89 (q, J=8.8 Hz, 2H), 7.33-7.44 (m, 2H) 7.54-7.62 (m, 2H), 7.68 (s, 1H), 7.73-7.80 (m, 1H), 7.92-8.02 (m, 3H), 8.12 (t, J=1.5 Hz, 1H), 8.48 (d, J=4.7 Hz, 1H), 13.12 (bs, 1H).

LCMS (ES+) m/z=488.3 (M+H).

Column—Acquity BEH C18 (2.1×50 mm) 1.7 u

Buffer: 10 mM AmmoniumAcetate pH 5 adjusted with HCOOH

Mobile phase A: Buffer:MeCN (95:5)
Mobile phase B: Buffer:MeCN (5:95)
Flow: 0.8 ml/Min

| Time | % A | % B |
|---|---|---|
| 0.0 | 95 | 5 |
| 1.1 | 5 | 95 |
| 1.7 | 5 | 95 |

Rt min: 0.82, wavelength: 220 nm

Preparation of 5-(3-(bicyclo[1.1.1]pentan-1-ylcarbamoyl)phenyl)-2-(4-fluoro-phenyl)-N-methyl-6-(2,2,2-trifluoroethoxy)benzofuran-3-carboxamide

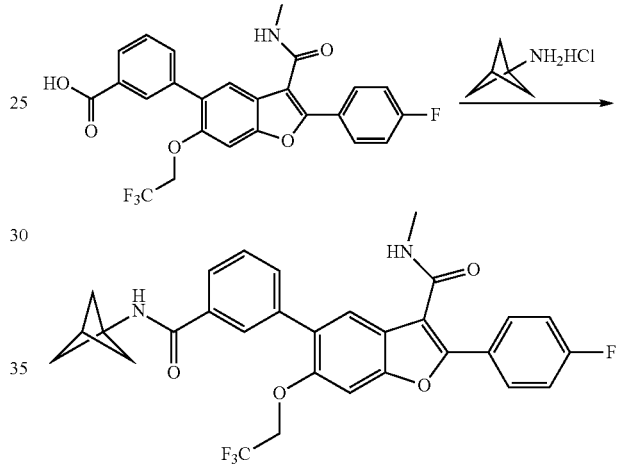

To a stirred solution of 3-(2-(4-fluorophenyl)-3-(methylcarbamoyl)-6-(2,2,2-trifluoroethoxy)benzofuran-5-yl)benzoic acid (25 mg, 0.051 mmol), bicyclo[1.1.1]pentan-1-amine hydrochloride (6.13 mg, 0.051 mmol) in DMF (2.5 mL) in DMF (2.5 mL) at room temperature under a N$_2$ atmosphere was added DIPEA (0.045 mL, 0.256 mmol). The mixture was cooled 0° C. and added with HATU (29.3 mg, 0.077 mmol). The reaction mixture was allowed to stir at room temperature for overnight. After completion of the reaction (monitored by TLC), the mixture was diluted with water and extracted with EtOAc (20 ml×3). The combined organic layers were washed with saturated bring solution, dried over Na$_2$SO$_4$ and concentrated. The crude product obtained was purified by Prep HPLC. Yield: 6.26 mg, 22%.

$^1$H NMR (400 MHz, CDCl$_3$): δ 2.22 (s, 6H), 2.52 (s, 1H), 3.01 (d, J=4.9 Hz, 3H), 4.32 (q, J=8.0 Hz, 2H), 5.83 (bs, 1H), 6.56 (bs, 1H), 7.11-7.23 (m, 3H), 7.45-7.53 (m, 1H), 7.67 (dt, J=7.94, 1.34 Hz, 1H), 7.77-7.83 (m, 2H), 7.86 (t, J=1.59 Hz, 1H), 7.89-7.95 (m, 2H). $^{19}$F NMR (376.6 MHz, CDCl$_3$): δ: −73.53, −109.59.

LCMS (ES+) m/z=553.2 (M+H).

Column—Kinetex C18 (50×2.1 mm-2.6 μm)
Mphase A: 2% MeCN—98% H$_2$O—10 mM NH$_4$COOH
Mphase B: 98% MeCN—2% H$_2$O—10 mM NH$_4$COOH
Flow: 1 ml/min

| Time | % A | % B |
|---|---|---|
| 0.0 | 100 | 0 |
| 1.5 | 0 | 100 |
| 3.2 | 0 | 100 |

Rt min: 2.35, wavelength: 220 nm
Preparative HPLC Method
Column:
X-BRIDGE C18(19*150)mm*5 u
Mobile phase A: 10 mM Ammonium acetate
Mobile phase B: MeCN
Flow: 15 ml/min
Gradient:

| Time | % B |
|---|---|
| 0 | 20 |
| 10 | 70 |
| 15 | 100 |

Rt min: 12.71
HPLC Method
COLUMN: SUNFIRE C18(150×4.6 mm) 3.5 micron
Buffer: 0.05% TFA in water
Mobile Phase A: Buffer: MeCN (95:5)
Mobile Phase B: MeCN: Buffer (95:5)
Flow: 1 ml/min

| Time | B % |
|---|---|
| 0 | 10 |
| 25 | 100 |
| 30 | 100 |

Wavelength: 254 nm, Rt min: 20.82
Wavelength: 220 nm, Rt min: 20.81
COLUMN: XBridge Phenyl (150×4.6 mm) 3.5 micron
Buffer: 0.05% TFA in water
Mobile Phase A: Buffer: MeCN (95:5)
Mobile Phase B: MeCN: Buffer (95:5)
Flow: 1 ml/min

| Time | B % |
|---|---|
| 0 | 10 |
| 25 | 100 |
| 30 | 100 |

Wavelength: 254 nm, Rt min: 20.00
Wavelength: 220 nm, Rt min: 20.00

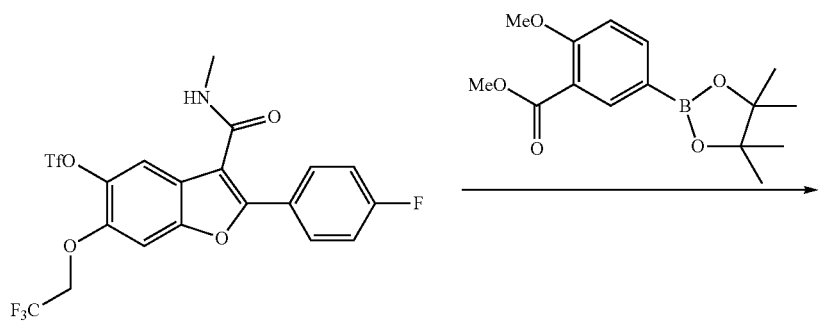

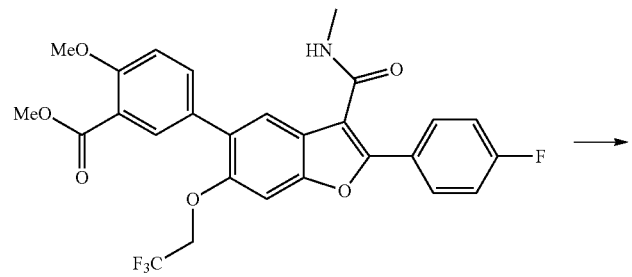

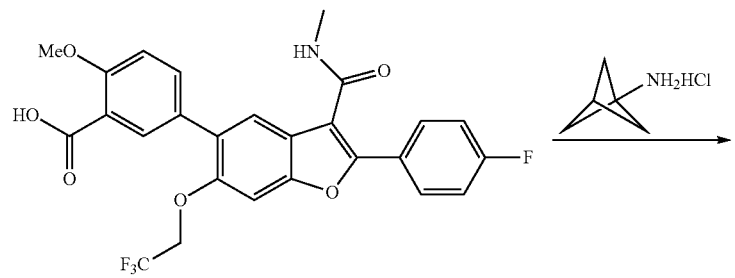

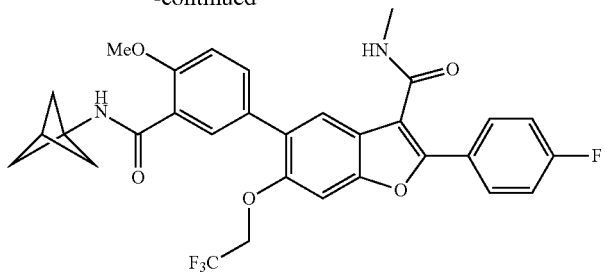

Preparation of methyl 5-(2-(4-fluorophenyl)-3-(methylcarbamoyl)-6-(2,2,2-trifluoroethoxy)benzofuran-5-yl)-2-methoxybenzoate

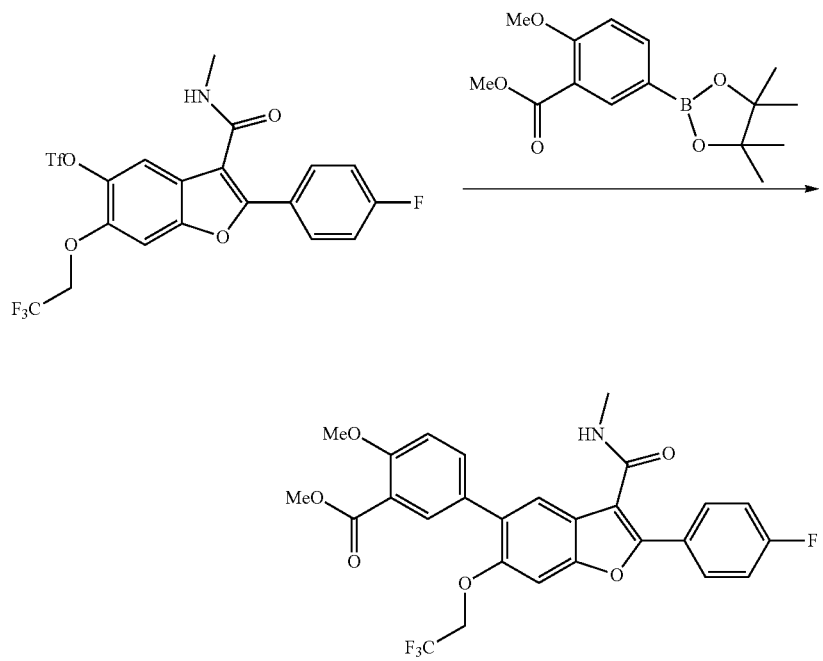

To a dried sealed tube was charged with 2-(4-fluorophenyl)-3-(methylcarbamoyl)-6-(2,2,2-trifluoroethoxy)benzofuran-5-yl trifluoromethanesulfonate (100 mg, 0.194 mmol), methyl 2-methoxy-5-(4,4,5,5-tetramethyl-1,3,2-dioxaborolan-2-yl)benzoate (62.4 mg, 0.213 mmol), K$_3$PO$_4$ (82 mg, 0.388 mmol), dioxane (2.0 mL) and water (0.2 mL) under a N$_2$ atmosphere. The reaction mixture was degassied and back-filled with N$_2$ followed by addition of PdCl$_2$(dppf)-CH$_2$Cl$_2$ (15.85 mg, 0.019 mmol) at room temperature. The teflon screw cap of the tube was tighten and the reaction mixture heated to stir at 110° C. for overnight. After completion of the reaction (monitored by TLC), the mixture was cooled to room temperature, filtered through a pad of celite and the celite pad washed with EtOAc (50 ml). After evaporation of the solvent under vacuum, the residue was purified via Combiflash using a 24 g silica column with 45% EtOAc in pet ether as an eluent to give the desired compound as a white solid. Yield: 98 mg, (95%).

$^1$H NMR (400 MHz, CDCl$_3$): δ 3.01 (d, J=4.9 Hz, 3H), 3.91 (s, 3H), 3.97 (s, 3H), 4.30 (q, J=8.1 Hz, 2H), 5.83 (bs, 1H), 7.05 (d, J=8.6 Hz, 1H) 7.14 (s, 1H), 7.21 (d, J=8.5 Hz, 2H), 7.67 (dd, J=8.6, 2.4 Hz, 1H), 7.77 (s, 1H), 7.92 (dd, J=9.0, 5.2 Hz, 2H), 8.00 (d, J=2.38 Hz, 1H). $^{19}$F NMR (376.6 MHz, CDCl$_3$): δ: −73.54, −109.71.

LCMS (ES+) m/z=532.1 (M+H).

Column—Acquity BEH C18 (2.1×50 mm) 1.7 u

Buffer: 10 mM AmmoniumAcetate pH 5 adjusted with HCOOH

Mobile phase A: Buffer:MeCN (95:5)

Mobile phase B: Buffer:MeCN (5:95)

Flow: 0.8 ml/Min

| Time | % A | % B |
|------|-----|-----|
| 0.0  | 95  | 5   |
| 1.1  | 5   | 95  |
| 1.7  | 5   | 95  |

Rt min: 1.09, wavelength: 220 nm

Preparation of 5-(2-(4-fluorophenyl)-3-(methylcarbamoyl)-6-(2,2,2-trifluoro-ethoxy)benzofuran-5-yl)-2-methoxybenzoic acid

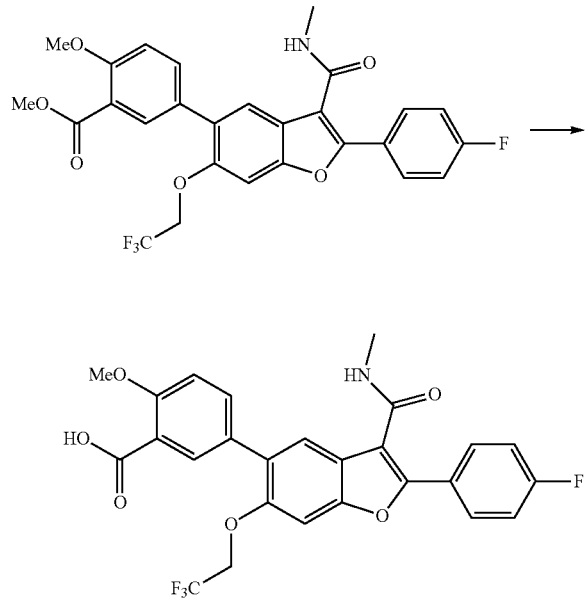

Sodium hydroxide (1.0M in water) (0.847 mL, 0.847 mmol) was added to a solution of methyl 5-(2-(4-fluorophenyl)-3-(methylcarbamoyl)-6-(2,2,2-trifluoroethoxy)benzofuran-5-yl)-2-methoxybenzoate (90 mg, 0.169 mmol) in MeOH (10 mL) and THF (10 mL) at room temperature. After being stirred at room temperature for overnight, the reaction mixture was concentrated under reduced pressure. The residue was diluted with water, acidified using 1.5N HCl to pH~3 and then stirred for 10 min. The solid was filtered, washed with water and dried under suction to provide the desired compound as a white solid. Yield: 73 mg, (83%).

$^1$H NMR (400 MHz, DMSO-$d_6$): δ 2.83 (d, J=4.6 Hz, 3H), 3.87 (s, 3H), 4.87 (q, J=8.8 Hz, 2H) 7.21 (d, J=8.78 Hz, 1H), 7.32-7.44 (m, 2H), 7.53 (s, 1H), 7.57-7.69 (m, 2H), 7.82 (d, J=2.4 Hz, 1H), 7.92-8.02 (m, 2H), 8.45 (d, J=4.6 Hz, 1H), 12.63 (bs, 1H).

LCMS (ES+) m/z=518.3 (M+H).

Column—Acquity BEH C18 (2.1×50 mm) 1.7 u

Buffer: 10 mM AmmoniumAcetate pH 5 adjusted with HCOOH

Mobile phase A: Buffer:MeCN (95:5)

Mobile phase B: Buffer:MeCN (5:95)

Flow: 0.8 ml/Min

| Time | % A | % B |
|---|---|---|
| 0.0 | 95 | 5 |
| 1.1 | 5 | 95 |
| 1.7 | 5 | 95 |

Rt min: 0.80, wavelength: 220 nm

Preparation of 5-(3-(bicyclo[1.1.1]pentan-1-ylcarbamoyl)-4-methoxyphenyl)-2-(4-fluorophenyl)-N-methyl-6-(2,2,2-trifluoroethoxy)benzofuran-3-carboxamide

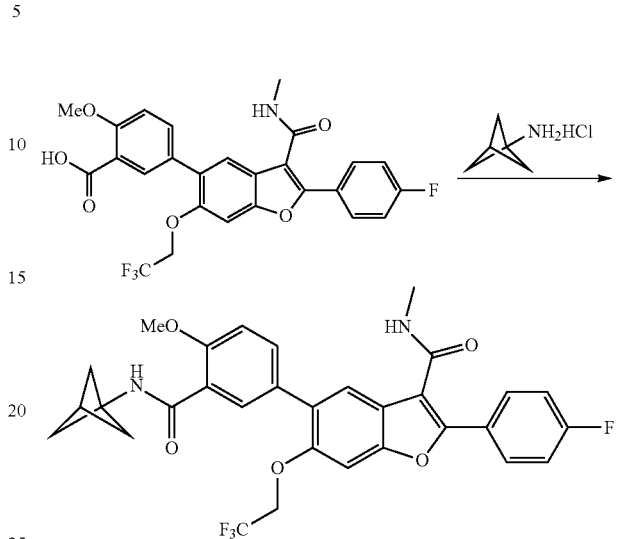

To a stirred solution of 5-(2-(4-fluorophenyl)-3-(methylcarbamoyl)-6-(2,2,2-trifluoroethoxy)benzofuran-5-yl)-2-methoxybenzoic acid (30 mg, 0.058 mmol), bicyclo[1.1.1]pentan-1-amine hydrochloride (6.93 mg, 0.058 mmol) in DMF (3.0 mL) at room temperature under a $N_2$ atmosphere was added DIPEA (0.051 mL, 0.290 mmol). The mixture was cooled to 0° C. and added with HATU (33.1 mg, 0.087 mmol). The reaction mixture was allowed to stir at room temperature for overnight. After completion of the reaction (monitored by TLC), the mixture was diluted with water and extracted with EtOAc (20 ml×3). The combined organic layers were washed with saturated brine solution, dried over $Na_2SO_4$ and concentrated. The crude product obtained was purified by Prep HPLC. Yield: 17 mg, 60%.

$^1$H NMR (400 MHz, CDCl$_3$): δ 2.21 (s, 6H), 2.51 (s, 1H), 3.03 (d, J=4.9 Hz, 3H), 4.03 (s, 3H) 4.20-4.32 (m, 2H), 5.88 (bs, 1H), 7.02 (d, J=8.6 Hz, 1H), 7.12-7.20 (m, 3H), 7.66 (dd, J=8.5, 2.4 Hz, 1H), 7.70 (s, 1H), 7.92-8.01 (m, 2H), 8.16-8.19 (m, 1H), 8.30 (d, J=2.4 Hz, 1H). $^{19}$F NMR (376.6 MHz, CDCl$_3$): δ: −73.63, −110.14.

LCMS (ES+) m/z=583.1 (M+H).

Column—Ascentis Express C18 (50×2.1 mm-2.7 μm)

Mphase A: 2% MeCN—98% H$_2$O—10 mM NH$_4$COOH

Mphase B: 98% MeCN—2% H$_2$O—10 mM NH$_4$COOH

Flow: 1 ml/min

| Time | % A | % B |
|---|---|---|
| 0.0 | 100 | 0 |
| 1.5 | 0 | 100 |
| 3.2 | 0 | 100 |

Rt min: 2.36, wavelength: 220 nm

Preparative HPLC Method

Column: X-BRIDGE C18(19*150)mm*5 u

Mobile phase A: 10 mM Ammonium acetate

Mobile phase B: MeCN

Flow: 16 ml/min

143

Gradient:

| Time | % B |
| --- | --- |
| 0 | 30 |
| 10 | 80 |

RT min: 10.18
HPLC Method
COLUMN: SUNFIRE C18(150×4.6 mm) 3.5 micron
Buffer: 0.05% TFA in water
Mobile Phase A: Buffer: MeCN (95:5)
Mobile Phase B: MeCN: Buffer (95:5)
Flow: 1 ml/min

| Time | B % |
| --- | --- |
| 0 | 40 |
| 25 | 100 |
| 30 | 100 |

144

Wavelength: 254 nm, Rt min: 15.36
Wavelength: 220 nm, Rt min: 15.36
COLUMN: XBridge Phenyl (150×4.6 mm) 3.5 micron
Buffer: 0.05% TFA in water
Mobile Phase A: Buffer: MeCN (95:5)
Mobile Phase B: MeCN: Buffer (95:5)
Flow: 1 ml/min

| Time | B % |
| --- | --- |
| 0 | 10 |
| 25 | 100 |
| 30 | 100 |

Wavelength: 254 nm, Rt min: 19.10
Wavelength: 220 nm, Rt min: 19.10

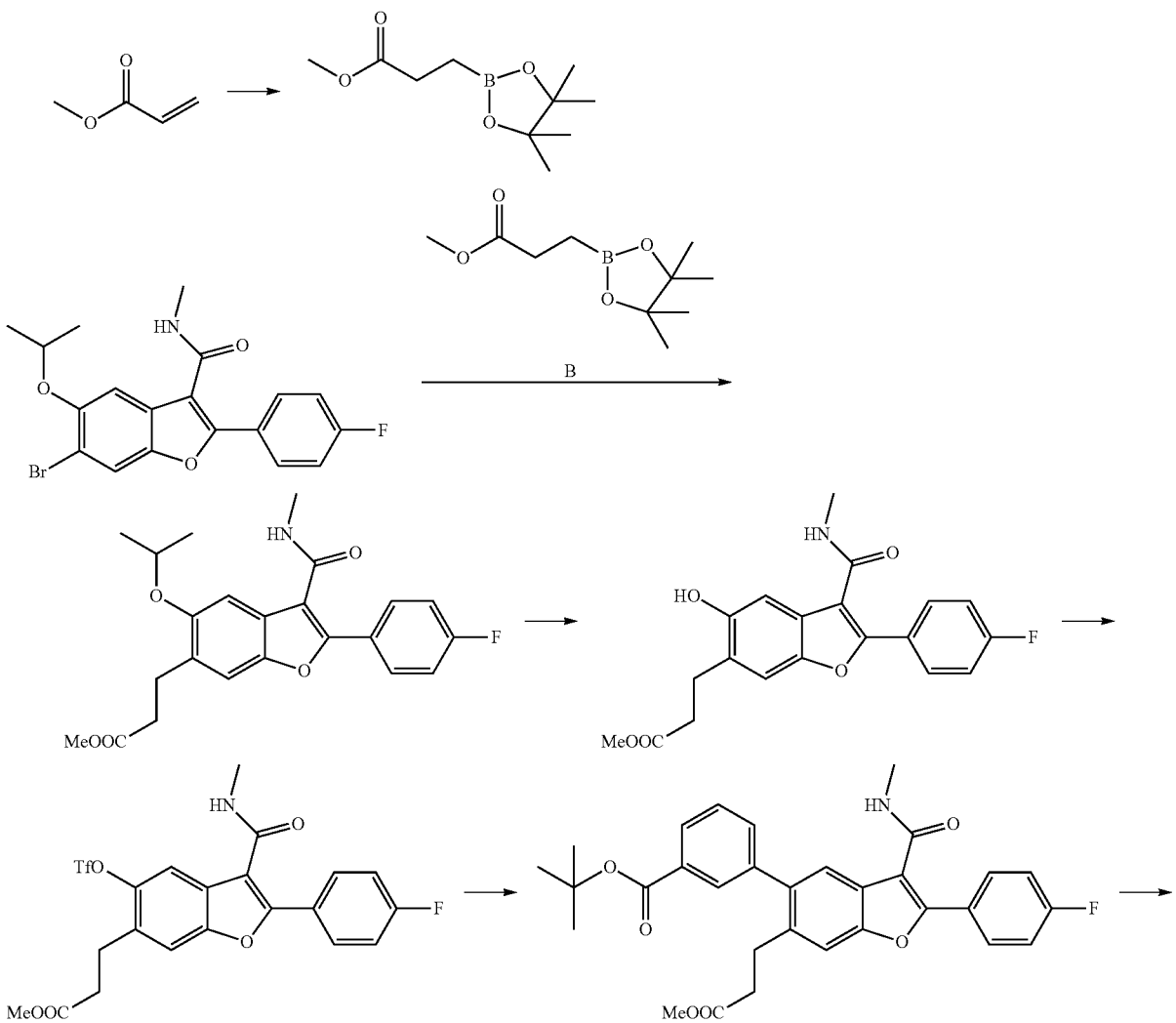

-continued
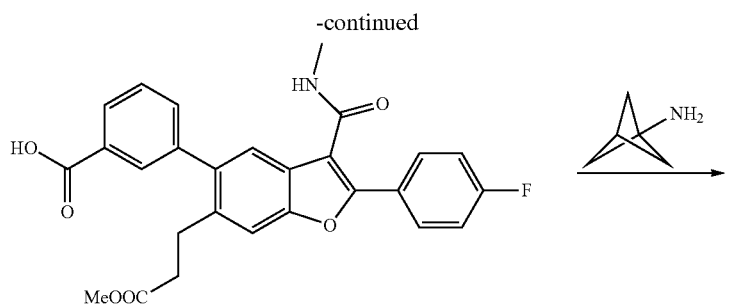
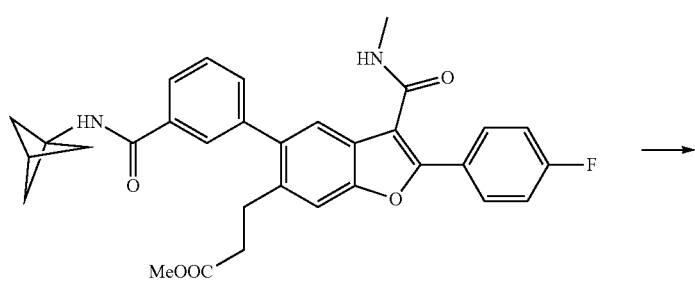
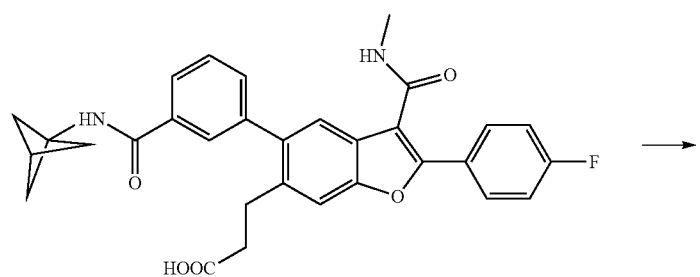
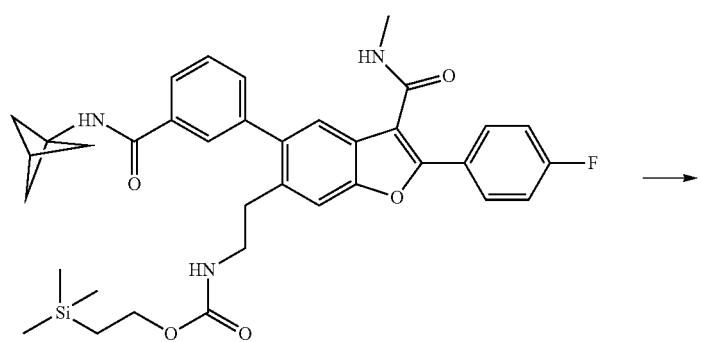
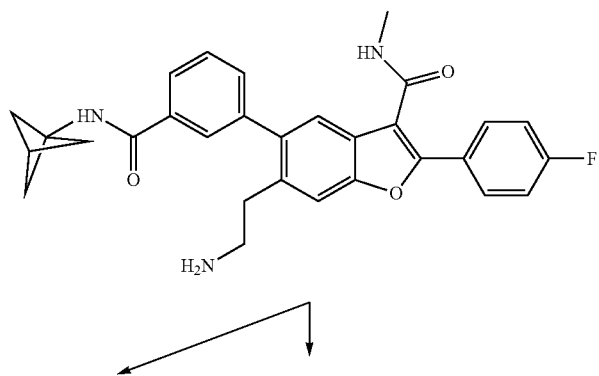

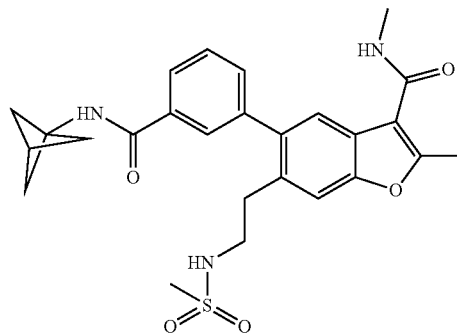

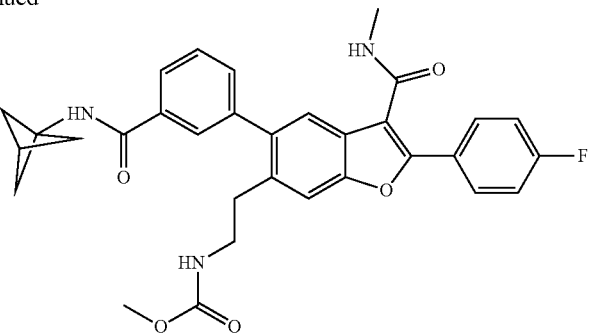

Preparation of methyl 3-(4,4,5,5-tetramethyl-1,3,2-dioxaborolan-2-yl)propanoate

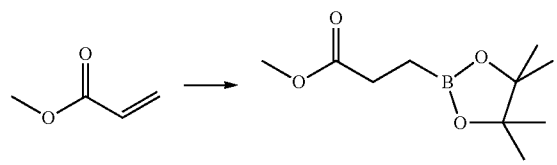

A mixture of copper(I) chloride (0.172 g, 1.742 mmol), sodium tert-butoxide (0.558 g, 5.81 mmol) and bis(2-diphenylphosphino)ferrocene (0.938 g, 1.742 mmol) in THF (8 ml) was purged with $N_2$ for 30 min and stirred at room temperature for 45 min. Bis(pinacolato)diboron (16.22 g, 63.9 mmol) in THF (17 ml) was added to the mixture via syringe, and the mixture stirred for another 30 min. The reaction flask was then cooled to 0° C. and methyl acrylate (5.0 g, 58.1 mmol) was added to the mixture by syringe followed immediately by methanol (9.40 mL, 232 mmol). The reaction was allowed to stir at room temperature overnight. The suspension was filtered through Celite and and n-hexane was added to the filtrate. A white suspension appeared which was removed by filtration and the filtrate was concentrated under vaccum. The residue was purified by Combiflash using pet ether and EtOAc (5%) as an eluant and a 40 g silica column. Yield: 5.2 g (42%).

$^1$H NMR (400 MHz, CHLOROFORM-d) δ ppm 3.66 (s, 3H) 2.43-2.48 (t, J=10 Hz, 2H) 1.25-1.27 (s, 12H) 1.01-1.06 (t, J=10 Hz, 2H).

Preparation of methyl 3-(2-(4-fluorophenyl)-5-isopropoxy-3-(methylcarbamoyl)benzofuran-6-yl)propanoate

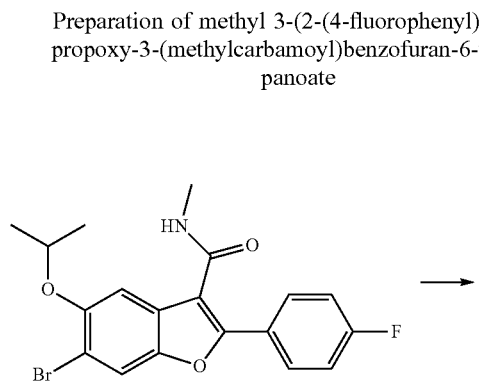

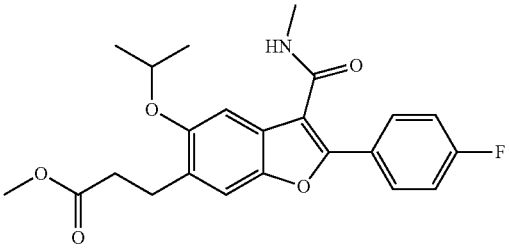

A mixture of 6-bromo-2-(4-fluorophenyl)-5-isopropoxy-N-methylbenzofuran-3-carboxamide (3.0 g, 7.38 mmol), methyl 3-(4,4,5,5-tetramethyl-1,3,2-dioxaborolan-2-yl)propanoate (1.897 g, 8.86 mmol) and cesium carbonate (7.22 g, 22.15 mmol) in toluene (40 mL) and water (2 mL) at room temperature was degassed for 10 min, added with $PdCl_2$ (dppf)-$CH_2Cl_2$ adduct (0.362 g, 0.443 mmol) and then degassed again for 5 min. The resulting reaction mixture was heated at 100° C. for overnight. The reaction mixture was filtered through celite, the celite bed washed with EtOAc and the filtrate concentrated. The residue was purified by Combiflash using a mixture of pet ether and EtOAc as an eluent and a 120 g silica gel column. The product was collected at 25% EtOAc in pet ether. Yield: 1.4 g (46%).

$^1$H NMR (400 MHz, CHLOROFORM-d) δ ppm 1.37 (d, J=6.02 Hz, 6H) 2.62-2.69 (m, 2H) 2.96-3.06 (m, 5H) 3.65-3.69 (m, 3H) 4.59-4.70 (m, 1H) 5.76 (br. s., 1H) 7.13-7.20 (m, 2H) 7.25-7.30 (m, 2H) 7.81-7.89 (m, 2H).

LCMS (ES+) m/z=414.1 (M+H).

Column—Acquity BEH C18 (2.1×50 mm) 1.7 u

M phase A: 0.1% TFA in water

M phase B: Acetonitrile

Flow: 0.8 ml/Min

| Time | % A | % B |
|------|-----|-----|
| 0.0  | 98  | 2   |
| 1.0  | 2   | 98  |
| 1.6  | 2   | 98  |

Rt min: 1.00, wavelength: 220 nm

Preparation of methyl 3-(2-(4-fluorophenyl)-5-hydroxy-3-(methylcarbamoyl)benzofuran-6-yl)propanoate

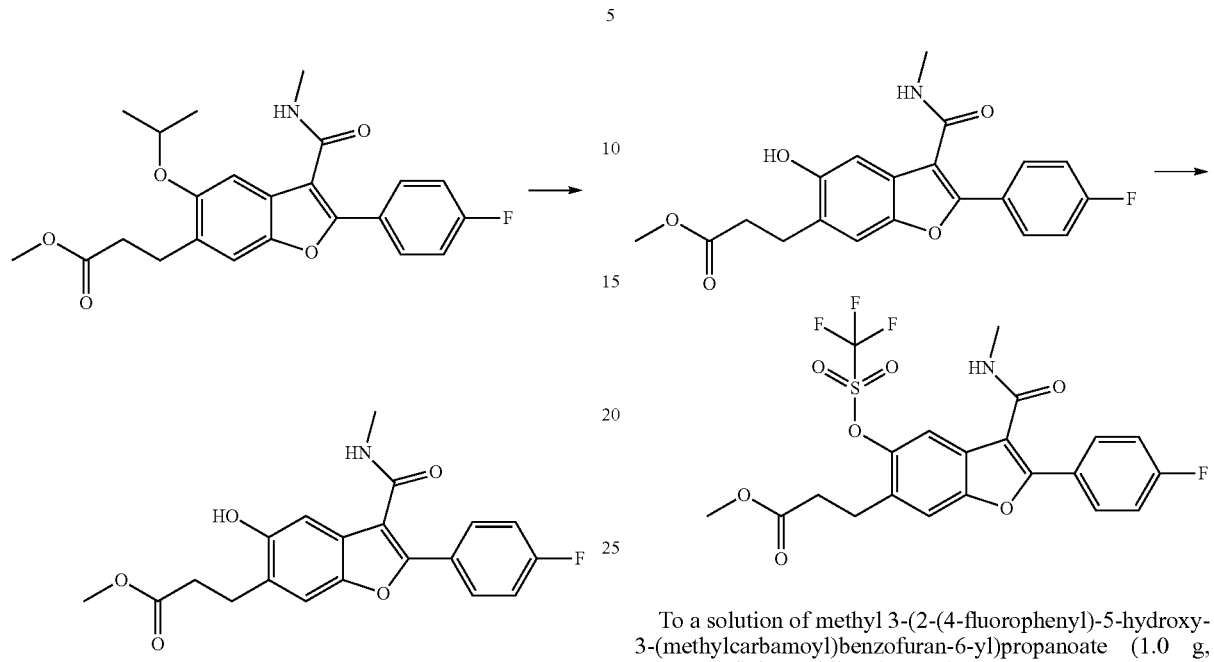

To a solution of methyl 3-(2-(4-fluorophenyl)-5-isopropoxy-3-(methylcarbamoyl)benzofuran-6-yl)propanoate (1.4 g, 3.39 mmol) in DCM (2 mL) at −50° C. was added boron trichloride (10.16 mL, 10.16 mmol) dropwise, and the reaction was then allowed to stir at room temperature for 4 hours. The reaction mixture was concentrated to remove the solvent, and ice-cold water was added to the residue. The solid was filtered and dried under suction to get the desired compound as a pale yellow solid. Yield: 1.25 g (99%).

$^1$H NMR (300 MHz, DMSO-$d_6$) δ ppm 2.58-2.67 (m, 2H), 2.82 (s, 3H) 2.90 (t, J=7.65 Hz, 2H) 3.73 (s, 3H), 7.14-7.26 (m, 1H) 7.31-7.41 (m, 3H) 7.87-7.95 (m, 2H) 8.37 (d, J=4.77 Hz, 1H).

LCMS (ES+) m/z=372.1 (M+H).

Column: Acentis Express C18 (50×2.1 mm; 2.7 u)

Buffer: 10 mM Ammonium Formate in Water pH 4.5

Mphase A: Buffer+MeCN (98+2)

Mphase B: Buffer+MeCN (2+98)

Flow: 1.0 ml/min

| Time(min): | % A | % B |
|---|---|---|
| 0.0 | 100 | 0 |
| 1.6 | 0 | 100 |
| 3.2 | 0 | 100 |
| 3.6 | 100 | 0 |

Rt min: 1.87, wavelength: 220 nm

Preparation of methyl 3-(2-(4-fluorophenyl)-3-(methylcarbamoyl)-5-(((trifluoromethyl)sulfonyl)oxy)benzofuran-6-yl)propanoate

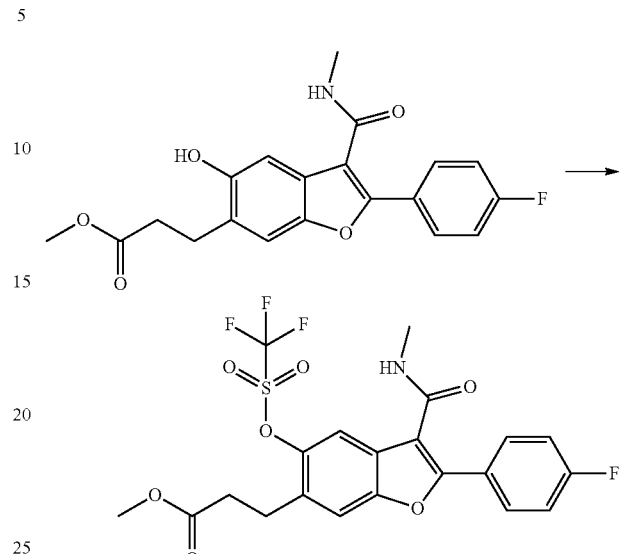

To a solution of methyl 3-(2-(4-fluorophenyl)-5-hydroxy-3-(methylcarbamoyl)benzofuran-6-yl)propanoate (1.0 g, 2.69 mmol) in pyridine (10 mL) at room temperature was added DMAP (0.033 g, 0.269 mmol). The mixture was cooled to 0° C. and added with triflic anhydride (1.137 mL, 6.73 mmol) dropwise. The reaction mixture was allowed to stir at room temperature for 3 hr. The reaction mixture was diluted with water and extracted with ethyl acetate (3×100) ml. The combined organic layers were dried and concentrated. The gummy compound obtained was triturated with 1:1 diethylether/n-hexane to get a pale yellow solid. Yield: 1.2 g (89%).

LCMS (ES+) m/z=504 (M+H).

Column—Acquity BEH C18 (2.1×50 mm) 1.7 u

M phase A: 0.1% TFA in water

M phase B: Acetonitrile

Flow: 0.8 ml/Min

| Time | % A | % B |
|---|---|---|
| 0.0 | 98 | 2 |
| 1.0 | 2 | 98 |
| 1.6 | 2 | 98 |

Rt min: 1.14, wavelength: 220 nm

Preparation of tert-butyl 3-(2-(4-fluorophenyl)-6-(3-methoxy-3-oxopropyl)-3-(methylcarbamoyl)benzofuran-5-yl)benzoate

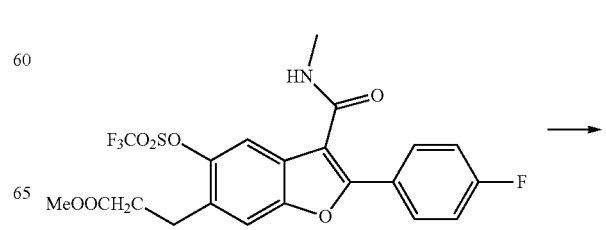

A mixture of methyl 3-(2-(4-fluorophenyl)-3-(methylcarbamoyl)-5-(((trifluoromethyl) sulfonyl)oxy)benzofuran-6-yl)propanoate (0.8 g, 1.589 mmol), tert-butyl 3-(4,4,5,5-tetramethyl-1,3,2-dioxaborolan-2-yl)benzoate (0.483 g, 1.589 mmol) and cesium carbonate (1.294 g, 3.97 mmol) in dioxane (15 mL) and water (1.0 mL) in a pressure tube was degassed for 5 min. The mixture was then added (PPh$_3$)$_4$Pd (0) (0.092 g, 0.079 mmol) and degassed again for 5 min. The resulting reaction mixture was heated at 90° C. for overnight. The reaction mixture was passed through celite and the celite bed washed with EtOAc (50 ml). The organic layer was dried over Na$_2$SO$_4$ and concentrated. The residue was purified by Combiflash using a mixture of pet ether and EtOAc as an eluent and a 40 g silica gel column. The desired compound was collected at 28% EtOAc in pet ether. Yield: 0.5 g (59%).

$^1$H NMR (400 MHz, CHLOROFORM-d) δ ppm 7.92-8.03 (m, 4H) 7.60 (s, 1H) 7.45-7.51 (m, 3H) 7.15-7.21 (m, 2H) 5.84 (d, J=4.58 Hz, 1H) 3.60 (s, 3H) 2.96-3.01 (m, 5H) 2.47 (t, J=7.75 Hz, 2H) 1.61 (s, 9H).

LCMS (ES+) m/z=532.2 (M+H).

Column: Acentis Express C8 (50×2.1 mm; 2.7 u)

Buffer: 10 mM Ammonium Formate in Water pH 4.5

Mphase A: Buffer+MeCN (98+2)

Mphase B: Buffer+MeCN (2+98)

Flow: 1.0 ml/min

| Time (min.): | % A | % B |
|---|---|---|
| 0.0 | 100 | 0 |
| 1.6 | 0 | 100 |
| 3.2 | 0 | 100 |
| 3.6 | 100 | 0 |

Rt min: 2.14, wavelength: 220 nm

Preparation of 3-(2-(4-fluorophenyl)-6-(3-methoxy-3-oxopropyl)-3-(methylcarbamoyl)benzofuran-5-yl)benzoic acid

A mixture of tert-butyl 3-(2-(4-fluorophenyl)-6-(3-methoxy-3-oxopropyl)-3-(methylcarbamoyl)benzofuran-5-yl)benzoate (0.5 g, 0.941 mmol) in TFA (1 mL) was stirred at room temperature for 2 hours. After completion of the reaction, the mixture was evaporated under vacuum. The residue was triturated in n-Hexane to obtain the desired compound. Yield: 0.43 g (96%).

$^1$H NMR (300 MHz, DMSO-d$_6$) δ ppm 8.44 (d, J=4.67 Hz, 1H) 7.95-8.04 (m, 4H) 7.57-7.67 (m, 3H) 7.34-7.44 (m, 3H) 3.51 (s, 3H) 2.87-2.95 (m, 2H) 2.80 (d, J=4.63 Hz, 3H) 2.53-2.57 (m, 2H).

LCMS (ES+) m/z=476.1 (M$^+$).

Column—Acquity BEH C18 (2.1×50 mm) 1.7 u

M phase A: 0.1% TFA in water

M phase B: Acetonitrile

Flow: 0.8 ml/Min

| Time | % A | % B |
|---|---|---|
| 0.0 | 98 | 2 |
| 1.0 | 2 | 98 |
| 1.6 | 2 | 98 |

Rt min: 0.92, wavelength: 220 nm

Preparation of methyl 3-(5-(3-(bicyclo[1.1.1]pentan-1-ylcarbamoyl)phenyl)-2-(4-fluorophenyl)-3-(methylcarbamoyl)benzofuran-6-yl)propanoate

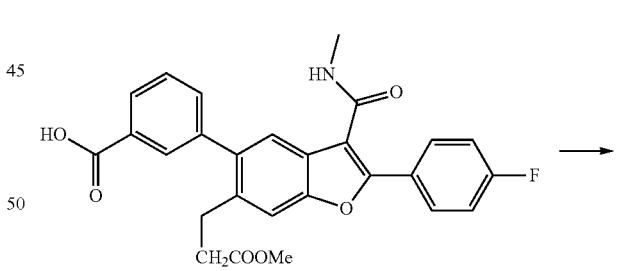

To a solution of 3-(2-(4-fluorophenyl)-6-(3-methoxy-3-oxopropyl)-3-(methyl carbamoyl)benzofuran-5-yl)benzoic acid (0.3 g, 0.631 mmol) and bicyclo[1.1.1]pentan-1-amine hydrochloride (0.091 g, 0.757 mmol) in DMF (2 mL) at 0°

C. was added DIPEA (0.331 mL, 1.893 mmol), followed by the addition of HATU (0.288 g, 0.757 mmol). The reaction was allowed to stir at room temperature for 2 hours. The reaction mixture was diluted with water, the solid filtered and dried under suction to obtain the desired compound as light yellow solid. Yield: 280 mg (82%).

$^1$H NMR (400 MHz, DMSO-$d_6$) δ ppm 9.03 (s, 1H) 8.42 (d, J=4.58 Hz, 1H) 7.95-8.02 (m, 2H) 7.80-7.91 (m, 2H) 7.68 (s, 1H) 7.49-7.58 (m, 2H) 7.32-7.43 (m, 3H) 3.52 (s, 3H) 2.88-2.95 (m, 3H) 2.77-2.83 (m, 2H), 2.46 (s, 1H), 2.06-2.13 (m, 8H).

LCMS (ES+) m/z=541.1 (M+H).

Column—Acquity BEH C18 (2.1×50 mm) 1.7 u
M phase A: 0.1% TFA in water
M phase B: Acetonitrile
Flow: 0.8 ml/Min

| Time | % A | % B |
|------|-----|-----|
| 0.0  | 98  | 2   |
| 1.0  | 2   | 98  |
| 1.6  | 2   | 98  |

Rt min: 1.01, wavelength: 220 nm

Preparation of 3-(5-(3-(bicyclo[1.1.1]pentan-1-ylcarbamoyl)phenyl)-2-(4-fluorophenyl)-3-(methylcarbamoyl)benzofuran-6-yl)propanoic acid

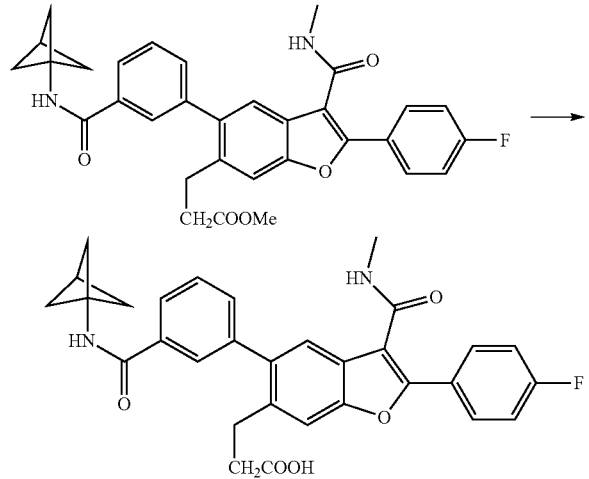

To a solution of methyl 3-(5-(3-(bicyclo[1.1.1]pentan-1-ylcarbamoyl)phenyl)-2-(4-fluorophenyl)-3-(methylcarbamoyl)benzofuran-6-yl)propanoate (0.28 g, 0.518 mmol) in THF (4 mL) was added NaOH (1.554 mL, 1.554 mmol, 1M aqueous). After stirring at room temperature for overnight, the reaction mixture was concentrated to remove the solvent. The residue was diluted with water, acidified by using 1.5 N HCl, filtered and the yellow solid dried under suction to give the desired compound. Yield: 240 mg (88%).

$^1$H NMR (400 MHz, DMSO-$d_6$) δ ppm 9.04 (s, 1H) 8.42 (d, J=4.83 Hz, 1H) 7.96-8.02 (m, 2H) 7.86-7.90 (m, 1H) 7.83 (s, 1H) 7.67 (s, 1H) 7.51-7.58 (m, 2H) 7.35-7.43 (m, 3H) 2.87 (t, J=7.69 Hz, 2H) 2.80 (d, J=4.58 Hz, 3H) 2.46 (s, 1H) 2.40 (t, J=7.69 Hz, 2H) 2.10 (s, 6H).

LCMS (ES+) m/z=527.1 (M+H).

Column—Acquity BEH C18 (2.1×50 mm) 1.7 u
M phase A: 0.1% TFA in water
M phase B: Acetonitrile
Flow: 0.8 ml/Min

| Time | % A | % B |
|------|-----|-----|
| 0.0  | 98  | 2   |
| 1.0  | 2   | 98  |
| 1.6  | 2   | 98  |

Rt min: 0.91, wavelength: 220 nm

Preparation of 2-(trimethylsilyl)ethyl (2-(5-(3-(bicyclo[1.1.1]pentan-1-ylcarbamoyl)phenyl)-2-(4-fluorophenyl)-3-(methylcarbamoyl)benzofuran-6-yl)ethyl) carbamate

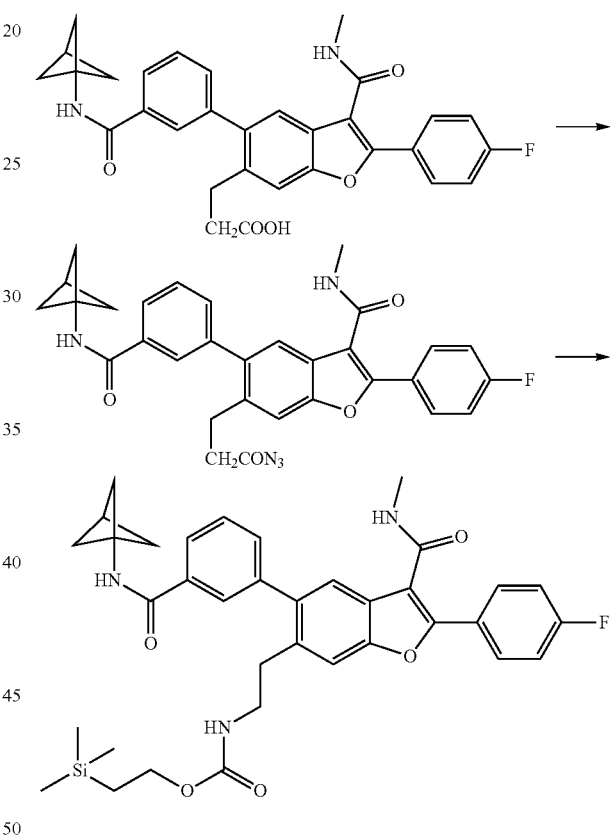

To a mixture of 3-(5-(3-(bicyclo[1.1.1]pentan-1-ylcarbamoyl)phenyl)-2-(4-fluorophenyl)-3-(methylcarbamoyl)benzofuran-6-yl)propanoic acid (0.05 g, 0.095 mmol) in acetone (2 mL) was added TEA (0.020 mL, 0.142 mmol) in one portion, and the reaction mixture stirred for 15 min at 0° C. Ethyl chloroformate (0.016 mL, 0.161 mmol) was added dropwise to the mixture. White emulsion was observed during addition. The reaction mixture was stirred at −10° C. for 2 hrs. Sodium azide (0.012 g, 0.190 mmol) in water (0.05 mL) was added dropwise to the mixture at −10° C., and the temperature was kept the same for another 2 h. The solvent was removed under under vacuum at low temperature, and the residue dissolved in ethylacetate and filtered. The filtrate was concentrated to obtain 3-(5-(3-(bicyclo[1.1.1]pentan-1-ylcarbamoyl)phenyl)-2-(4-fluorophenyl)-3-(methylcarbamoyl)benzofuran-6-yl)propanoyl azide, which was used immediately for the next step.

To a 10 ml sealed tube was charged with 3-(5-(3-(bicyclo[1.1.1]pentan-1-ylcarbamoyl)phenyl)-2-(4-fluorophenyl)-3-(methylcarbamoyl)benzofuran-6-yl)propanoyl azide (0.04 g, 0.058 mmol) and 2-(trimethylsilyl)ethanol (2 ml, 24.02 mmol). The reaction mixture was heated at 65° C. for overnight. The reaction mixture was diluted with water and extracted with DCM (3×50 ml). The organic layer was dried and concentrated. Yield: 40 mg (66%).

LCMS (ES+) m/z=642.5 (M+H).
Column: Acentis Express C8 (50×2.1 mm; 2.7 u)
Buffer: 10 mM Ammonium Acetate pH 5 adjusted with HCOOH
Mphase A: Buffer+MeCN (95+5)
Mphase B: Buffer+MeCN (5+95)
Flow: 1.0 ml/min

| Time (min.): | % A | % B |
|---|---|---|
| 0.0 | 100 | 5 |
| 1.1 | 5 | 95 |
| 1.7 | 5 | 95 |

Rt min: 1.21, wavelength: 220 nm

Preparation of 6-(2-aminoethyl)-5-(3-(bicyclo[1.1.1]pentan-1-yl-carbamoyl)phenyl)-2-(4-fluorophenyl)-N-methylbenzofuran-3-carboxamide

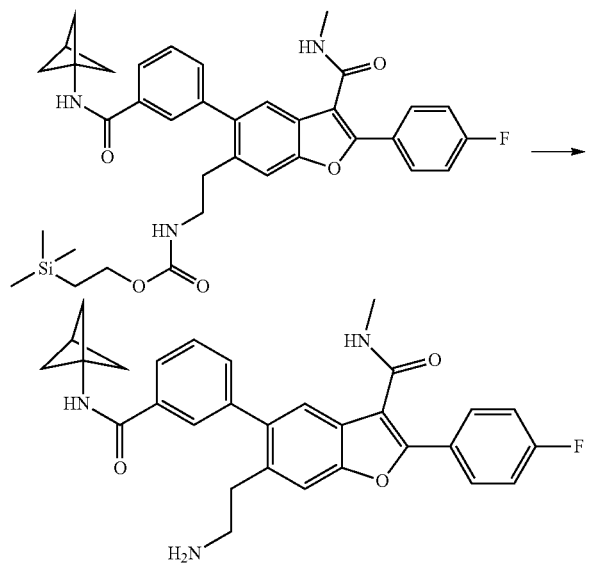

A solution of 2-(trimethylsilyl)ethyl (2-(5-(3-(bicyclo[1.1.1]pentan-1-ylcarbamoyl)phenyl)-2-(4-fluorophenyl)-3-(methylcarbamoyl)benzofuran-6-yl)ethyl)carbamate (0.04 g, 0.062 mmol) in TFA (0.5 ml, 6.49 mmol) was stirred at room temperature for 3 hr. The mixture was evaporated under vaccum. The residue was purified by Combiflash using a mixture of methanol and chloroform as an eluant and a 4 g silica gel column. The desired compound was collected at 16% methanol/chloroform. Yield: 30 mg (97%).

LCMS (ES+) m/z=498.1 (M+H).
Column—Acquity BEH C18 (2.1×50 mm) 1.7 u
M phase A: 0.1% TFA in water
M phase B: Acetonitrile
Flow: 0.8 ml/Min

| Time | % A | % B |
|---|---|---|
| 0.0 | 98 | 2 |
| 1.0 | 2 | 98 |
| 1.6 | 2 | 98 |

Rt min: 0.77, wavelength: 220 nm

Preparation of 5-(3-(bicyclo[1.1.1]pentan-1-ylcarbamoyl)phenyl)-2-(4-fluorophenyl)-N-methyl-6-(2-(methylsulfonamido)ethyl)benzofuran-3-carboxamide

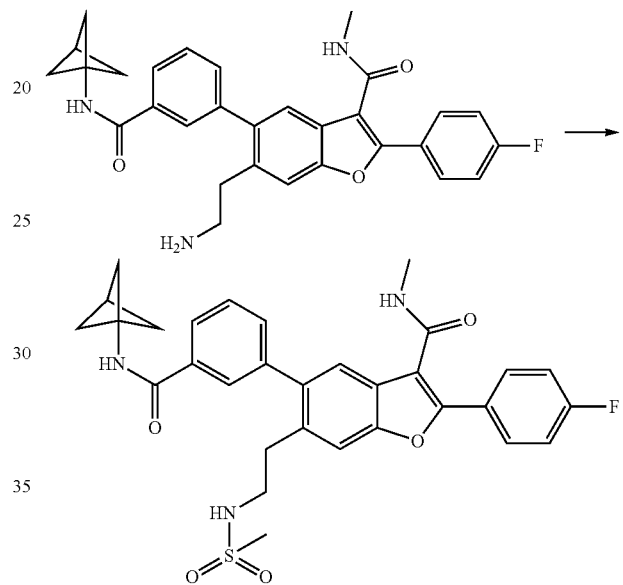

To a solution of 6-(2-aminoethyl)-5-(3-(bicyclo[1.1.1]pentan-1-ylcarbamoyl)phenyl)-2-(4-fluorophenyl)-N-methylbenzofuran-3-carboxamide (0.03 g, 0.060 mmol) in DCM (1 mL) was added DIPEA (0.032 mL, 0.181 mmol) and methanesulfonyl chloride (4.70 μl, 0.060 mmol) at 0° C. The treaction mixture was then allowed to stir at room temperature for 4 hr. After completion of reaction, the mixture was added with water and extracted with DCM (3×10 ml). The combined organic mixture were washed with brine, dried over $Na_2SO_4$ and concentrated. The residue was purified by Combiflash using a mixture of methanol and chloroform as an eluent and a 4 g silica gel column. The desired compound was collected at 5% methanol/chloroform. Yield: 6 mg (17%).

$^1$H NMR (400 MHz, Methanol-$d_4$) δ ppm 7.96-8.01 (m, 2H) 7.81-7.88 (m, 2H) 7.51-7.64 (m, 4H) 7.24-7.31 (m, 2H) 3.14-3.19 (m, 2H) 2.93-2.99 (m, 5H) 2.76 (s, 3H) 2.45 (s, 1H) 2.22 (s, 6H). $^{19}$F NMR (376.6 MHz, Methanol-$d_4$): δ–112.66.

LCMS (ES+) m/z=576.2 (M+H).
Column—Kinetex C18 (50×2.1 mm-2.6 μm)
M phase A: 2% MeCN—98% $H_2O$—10 mM $NH_4COOH$
M phase B: 98% MeCN—2% $H_2O$—10 mM $NH_4COOH$
Flow: 1 ml/Min

| Time | % A | % B |
| --- | --- | --- |
| 0.0 | 100 | 0 |
| 1.7 | 0 | 100 |
| 3.2 | 0 | 100 |

Rt min: 2.18, wavelength: 220 nm
HPLC Method: COLUMN: SUNFIRE C18(150×4.6 mm) 3.5 micron
Mobile Phase A: 0.05% TFA in Water:Acetonitrile (95:5)
Mobile Phase B: Acetonitrile: 0.05% TFA in Water (95:5)
Flow: 1.0 ml/min

| Time | B % |
| --- | --- |
| 0 | 10 |
| 12 | 100 |
| 15 | 100 |

Wavelength: 254 nm, Rt min: 10.59
Wavelength: 220 nm, Rt min: 10.59
HPLC Method: XBridge Phenyl (150×4.6 mm) 3.5 micron SC/749
Mobile Phase A: 0.05% TFA in water: Acetonitrile (95:5)
Mobile Phase B: Acetonitrile: 0.05% TFA in water (95:5)
Flow: 1.0 ml/min

| Time | B % |
| --- | --- |
| 0 | 10 |
| 12 | 100 |
| 15 | 100 |

Wavelength: 254 nm, Rt min: 9.55
Wavelength: 220 nm, Rt min: 9.55

Preparation of methyl (2-(5-(3-(bicyclo[1.1.1]pentan-1-ylcarbamoyl)phenyl)-2-(4-fluorophenyl)-3-(methylcarbamoyl)benzofuran-6-yl)ethyl)carbamate

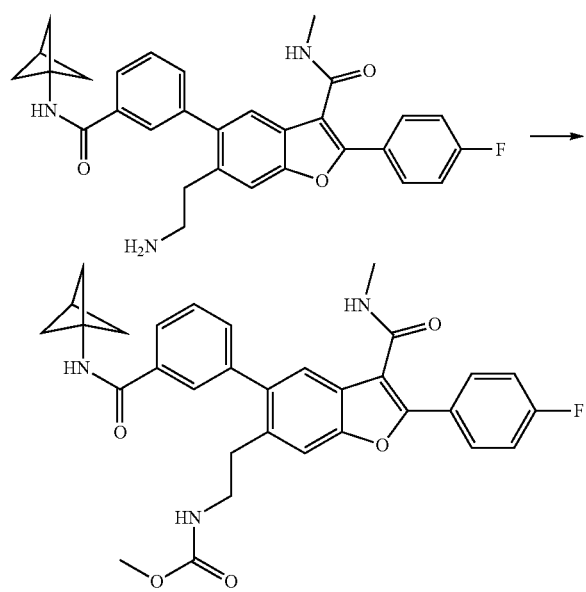

To a solution of 6-(2-aminoethyl)-5-(3-(bicyclo[1.1.1]pentan-1-ylcarbamoyl)phenyl)-2-(4-fluorophenyl)-N-methylbenzofuran-3-carboxamide (0.025 g, 0.050 mmol) in THF (2 mL) at 0° C. was added TEA (0.018 ml, 0.126 mmol) and methyl chloroformate (4.67 µl, 0.060 mmol). The reaction mixture was then allowed to stir at room temperature for 4 hours. The reaction mixture was diluted with water and extracted with EtOAc (3×10 ml). The combined organic extracts were washed with brine, dried over $Na_2SO_4$ and concentrated to obtain the compound as an off white solid. The crude product was purified by Prep HPLC. Yield: 8 mg (29%).

$^1$H NMR (400 MHz, Methanol-$d_4$) δ ppm 7.95-8.02 (m, 2H) 7.77-7.86 (m, 2H) 7.54-7.59 (m, 3H) 7.50 (s, 1H) 7.25-7.31 (m, 2H) 3.56 (s, 3H) 3.11-3.24 (m, 2H) 2.94 (s, 3H) 2.90 (t, J=7.34 Hz, 2H) 2.50 (s, 1H) 2.22 (s, 6H). $^{19}$F NMR (376.6 MHz, Methanol-$d_4$): δ−112.73.

LCMS (ES+) m/z=556.2 (M+H).
Column—Kinetex C18 (50×2.1 mm-2.6 µm)
M phase A: 2% MeCN—98% $H_2O$—10 mM $NH_4COOH$
M phase B: 98% MeCN—2% $H_2O$—10 mM $NH_4COOH$
Flow: 1 ml/Min

| Time | % A | % B |
| --- | --- | --- |
| 0.0 | 100 | 0 |
| 1.7 | 0 | 100 |
| 3.2 | 0 | 100 |

RT min: 2.25, wavelength: 220 nm
Preparative HPLC Method
Column:
X-BRIDGE C18(19×150)mm 5 u
Mobile phase A: 10 mM Ammonium acetate
Mobile phase B: MeCN
Flow: 16 ml/min
Gradient:

| Time | % B |
| --- | --- |
| 0 | 30 |
| 10 | 70 |
| 14 | 100 |

RT min: 9.41
HPLC Method: COLUMN: SUNFIRE C18(150×4.6 mm) 3.5 micron
Mobile Phase A: 0.05% TFA in Water:Acetonitrile (95:5)
Mobile Phase B: Acetonitrile: 0.05% TFA in Water (95:5)
Flow: 1.0 ml/min

| Time | B % |
| --- | --- |
| 0 | 10 |
| 12 | 100 |
| 15 | 100 |

Wavelength: 254 nm, Rt min: 11.11
Wavelength: 220 nm, Rt min: 11.11
HPLC Method: XBridge Phenyl (150×4.6 mm) 3.5 micron SC/749
Mobile Phase A: 0.05% TFA in water:Acetonitrile (95:5)
Mobile Phase B: Acetonitrile: 0.05% TFA in water (95:5)
Flow: 1.0 ml/min

| Time | B % |
| --- | --- |
| 0 | 10 |
| 12 | 100 |
| 15 | 100 |

Wavelength: 254 nm, Rt min: 9.86
Wavelength: 220 nm, Rt min: 9.86

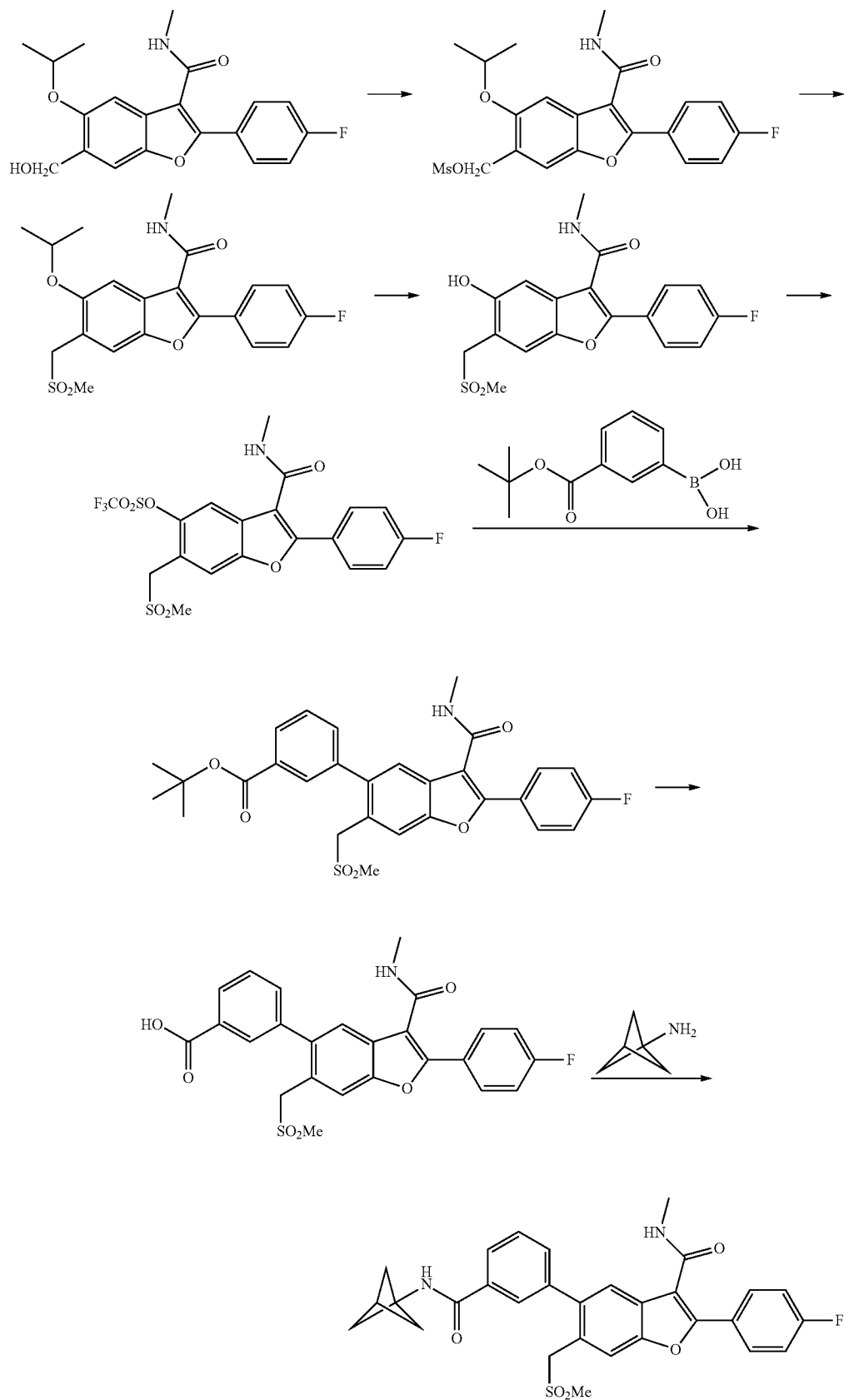

Preparation of 2-(4-fluorophenyl)-5-isopropoxy-N-methyl-6-((methylsulfonyl)methyl)benzofuran-3-carboxamide

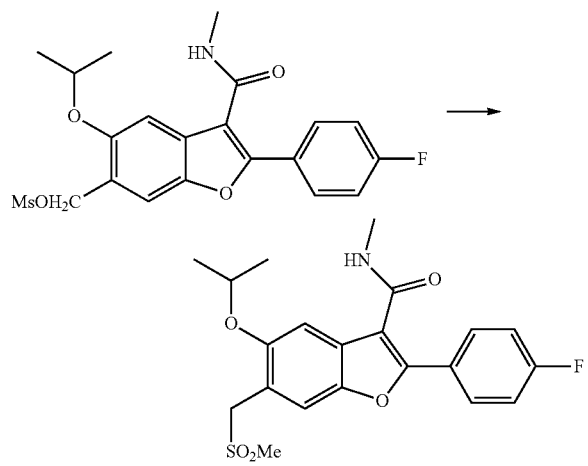

To a stirred solution of (2-(4-fluorophenyl)-5-isopropoxy-3-(methylcarbamoyl)benzofuran-6-yl)methyl methanesulfonate (270 mg, 0.620 mmol) in DMF (5 mL) was added sodium methanesulfinate (253 mg, 2.480 mmol), and the reaction mixture allowed to stir at 100° C. for 5 hr. Heating was stopped and the reaction mixture was poured into crushed ice, the solid precipitated out was filtered and dried under vacuum to obtain the compound. The crude product was used for the next step without any purification. Yield: 250 mg.

$^1$H NMR (400 MHz, Methanol-$d_4$) δ ppm 1.43 (d, J=6.02 Hz, 6H) 2.86 (s, 3H) 2.96 (s, 3H) 4.56 (s, 2H) 4.76-4.81 (m, 1H) 7.24-7.30 (m, 3H) 7.65 (s, 1H) 7.90-7.95 (m, 2H).

LCMS (ES+) m/z=420.2 (M+H).

Column—ACQUITY UPLC BEH C18 (50×2.1 mm; 1.7 μm)

M phase A: 0.1% TFA in water
M phase B: Acetonitrile
Flow: 0.8 ml/Min

| Time | % A | % B |
|---|---|---|
| 0.0 | 98 | 2 |
| 1.0 | 2 | 98 |
| 1.6 | 2 | 98 |

Rt min: 0.93, wavelength: 220 nm.

Preparation of 2-(4-fluorophenyl)-5-hydroxy-N-methyl-6-((methylsulfonyl)methyl)benzofuran-3-carboxamide

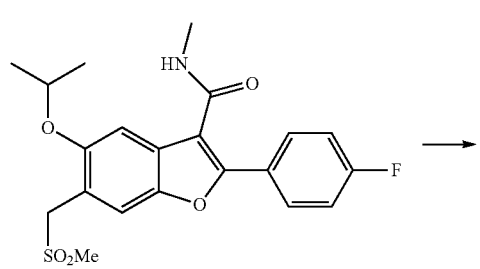

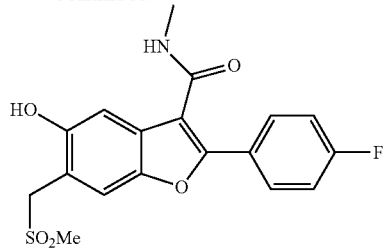

To a stirred solution of 2-(4-fluorophenyl)-5-isopropoxy-N-methyl-6-((methylsulfonyl)methyl)benzofuran-3-carboxamide (270 mg, 0.644 mmol) in DCM (10 mL) at −78° C. was added trichloroborane (1.0M in Toluene) (1.860 mL, 1.860 mmol), and the mixture allowed to come to room temperature and then stirred for overnight. Ice cold water was added to the mixture, and the resulting solid precipitated was filtered and dried. The crude product was purified by Combiflash using CHCl$_3$/MeOH (95:5%) as a mobile phase to obtain the desired compound. Yield: 250 mg.

$^1$H NMR (400 MHz, DMSO-$d_6$) δ ppm 2.83 (s, 3H) 2.90 (s, 3H) 4.52 (s, 2H) 7.10 (s, 1H) 7.33-7.45 (m, 2H) 7.59 (s, 1H) 7.89-7.99 (m, 2H) 8.43 (d, J=4.77 Hz, 1H) 10.01 (s, 1H).

LCMS (ES+) m/z=378.38 (M+H).

Column—ACQUITY UPLC BEH C18 (50×2.1 mm; 1.7 μm)

M phase A: 0.1% TFA in water
M phase B: Acetonitrile
Flow: 0.8 ml/Min

| Time | % A | % B |
|---|---|---|
| 0.0 | 98 | 2 |
| 1.0 | 2 | 98 |
| 1.6 | 2 | 98 |

Rt min: 0.83, wavelength: 220 nm.

Preparation of 2-(4-fluorophenyl)-3-(methylcarbamoyl)-6-((methylsulfonyl)-methyl)benzofuran-5-yl trifluoromethanesulfonate

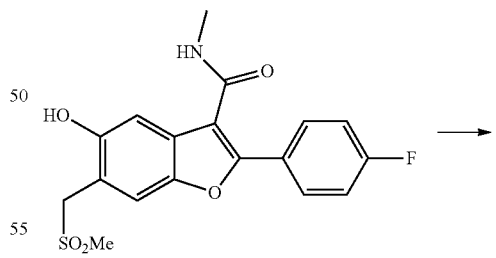

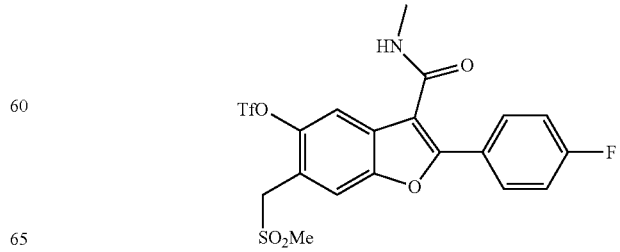

To a stirred solution of 2-(4-fluorophenyl)-5-hydroxy-N-methyl-6-((methylsulfonyl)methyl)benzofuran-3-carboxamide (50 mg, 0.132 mmol) in DCM (10 mL) was added DIPEA (0.070 mL, 0.381 mmol) and 1,1,1-trifluoro-N-phenyl-N-(trifluoromethyl)sulfonyl methanesulfonamide (54.5 mg, 0.153 mmol), and the mixture stirred at room temperature for overnight. After completion of reaction, ice-cold water was added to the mixture, and solid precipitated was filtered and dried to obtain a pale yellow solid. Yield: 50 mg (74%).

LCMS (ES+) m/z=510.2 (M+H).

Column—ACQUITY UPLC BEH C8 (50×2.1 mm; 1.7 μm)

M phase A: 5 mM Ammonium Acetate:MeCN (95:5)
M phase B: 5 mM Ammonium Acetate:MeCN (5:95)
Flow: 0.8 ml/Min

| Time | % A | % B |
|---|---|---|
| 0.0 | 95 | 5 |
| 1.1 | 5 | 95 |
| 1.7 | 5 | 95 |

Rt min: 0.95, wavelength: 220 nm

Preparation of tert-butyl 3-(2-(4-fluorophenyl)-3-(methylcarbamoyl)-6-((methylsulfonyl)-methyl)benzofuran-5-yl)benzoate

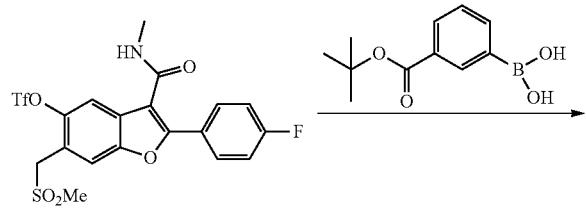

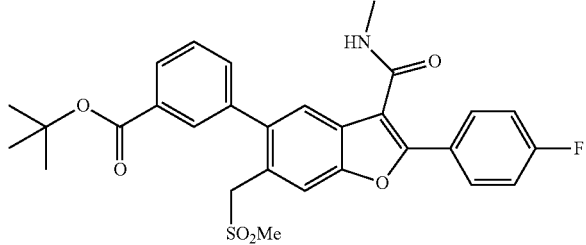

To a stirred solution of 2-(4-fluorophenyl)-3-(methylcarbamoyl)-6-((methylsulfonyl)-methyl)benzofuran-5-yl trifluoromethanesulfonate (50 mg, 0.098 mmol) in dioxane (2 mL) was added (3-(tert-butoxycarbonyl)phenyl)boronic acid (32.7 mg, 0.147 mmol) and Cs₂CO₃ (96 mg, 0.294 mmol). The mixture was degassed and then added with (PPh₃)₄Pd(0) (11.35 mg, 9.81 μmol) and water (0.2 ml). The mixture was purged with N₂ for 10 min and then stirred for overnight at 90° C. After completion of the reaction, the mixture was filtered through celite and solvent was evaporated. Ice-cold water was added to the crude reaction mixture, solid precipitated was filtered and dried to obtain the desired product. It was triturated in n-hexane and used for the next step without any purification. Yield: 50 mg.

LCMS (ES+) m/z=538.2 (M+H), 482 (M+H of the corresponding acid).

Column—ACQUITY UPLC BEH C18 (50×2.1 mm; 1.7 μm)

M phase A: 0.1% TFA in water
M phase B: Acetonitrile
Flow: 0.8 ml/Min

| Time | % A | % B |
|---|---|---|
| 0.0 | 98 | 2 |
| 1.0 | 2 | 98 |
| 1.6 | 2 | 98 |

Rt min: 1.19, wavelength: 220 nm.

Preparation of 3-(2-(4-fluorophenyl)-3-(methylcarbamoyl)-6-((methylsulfonyl)methyl)-benzofuran-5-yl)benzoic acid

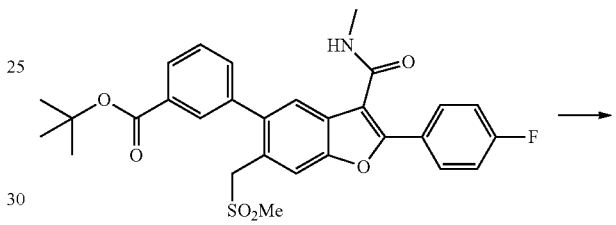

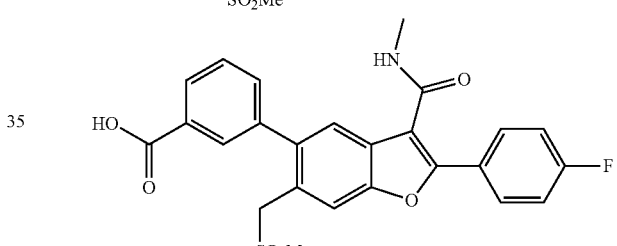

To a stirred solution of tert-butyl 3-(2-(4-fluorophenyl)-3-(methylcarbamoyl)-6-((methylsulfonyl)methyl)benzofuran-5-yl)benzoate (50 mg, 0.093 mmol) in DCM (5 mL) was added 2,2,2-trifluoroacetic acid (106 mg, 0.930 mmol), and the mixture stirred at room temperature for 2 hr. After completion of the reaction, the mixture was evaporated and ice-cold water was added. The solid precipitated was filtered and dried. The crude compound was taken for the next step without further treatment. Yield: 40 mg.

LCMS (ES+) m/z=482.2 (M+H).

Column—ACQUITY UPLC BEH C18 (50×2.1 mm; 1.7 μm)

M phase A: 0.1% TFA in water
M phase B: Acetonitrile
Flow: 0.8 ml/Min

| Time | % A | % B |
|---|---|---|
| 0.0 | 98 | 2 |
| 1.0 | 2 | 98 |
| 1.6 | 2 | 98 |

Rt min: 0.98, wavelength: 220 nm.

Preparation of 5-(3-(bicyclo[1.1.1]pentan-1-ylcarbamoyl)phenyl)-2-(4-fluorophenyl)-N-methyl-6-(methylsulfonylmethyl)benzofuran-3-carboxamide

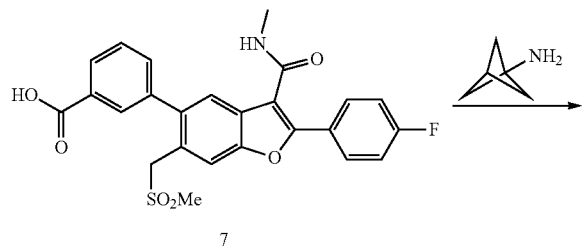

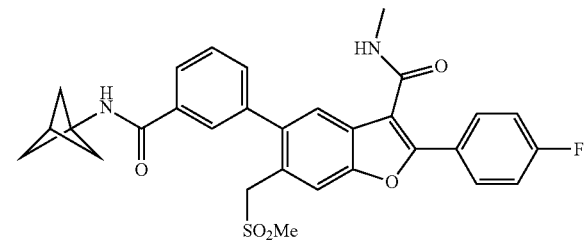

To a stirred solution of 3-(2-(4-fluorophenyl)-3-(methylcarbamoyl)-6-((methylsulfonyl)methyl)benzofuran-5-yl)benzoic acid (40 mg, 0.083 mmol) in DMF (2 mL) at 10° C. was added bicyclo[1.1.1]pentan-1-amine.HCl (11.92 mg, 0.100 mmol), TEA (0.035 mL, 0.249 mmol) and then (benzotriazol-1-yloxy)tris(dimethylamino)phosphonium hexafluorophosphate (BOP) (36.7 mg, 0.083 mmol). The reaction mixture was allowed to stir at room temperature for overnight. Ice-cold water was added to the reaction mixture, and the solid precipitated was filtered and dried. The crude compound was purified by Preparative HPLC. Yield: 4 mg (8.8%).

$^1$H NMR (400 MHz, Methanol-$d_4$) δ ppm 2.22 (s, 6H) 2.50 (s, 1H) 2.81 (s, 3H) 2.96 (s, 3H) 4.57 (s, 2H) 7.26-7.34 (m, 2H) 7.56-7.62 (m, 1H) 7.64-7.66 (m, 2H) 7.85-7.91 (m, 3H) 7.98-8.06 (m, 2H); $^{19}$F NMR (376.6 MHz, Methanol-$d_4$) δ −112.06

Preparative HPLC Method
Column:
ODS (250×20, 10μ)
Mobile Phase: 10 mM Ammonium acetate in water (A): MeCN (B)
Flow: 15 ml/min
Isocratic 0/60, 13/60, 14/100
RT: 12.49 min
LCMS (ES+) m/z=547.2 (M+H).
Column—Poroshell 120 (50×3.0 mm; 2.7 u)
Buffer: 10 mM Ammonium Acetate pH 5.0 adjusted with Formic acid
Mphase A: Buffer+MeCN (90+10)
Mphase B: Buffer+MeCN (10+90)
Flow: 1.5 ml/min

| Time | % A | % B |
| --- | --- | --- |
| 0.0 | 95 | 5 |
| 1.5 | 0 | 100 |
| 2.2 | 0 | 100 |
| 2.7 | 95 | 5 |
| 3.0 | 95 | 5 |

Rt min: 1.59, wavelength: 220 nm
HPLC Method: SUNFIRE C18(150×4.6 mm) 3.5 micron
Buffer: 0.05% TFA
Mobile Phase A: Buffer: MeCN (95:5)
Mobile Phase B: MeCN:Buffer (95:5)
Flow: 1 ml/min

| Time | B % |
| --- | --- |
| 0 | 10 |
| 12 | 100 |
| 15 | 100 |

Wavelength: 254 nm, Rt min: 10.11
Wavelength: 220 nm, Rt min: 10.11
HPLC Method: XBridge Phenyl (150×4.6 mm) 3.5 micron
Buffer: 0.05% TFA
Mobile Phase A: Buffer: MeCN (95:5)
Mobile Phase B: MeCN: Buffer (95:5)
Flow: 1 ml/min

| Time | B % |
| --- | --- |
| 0 | 10 |
| 12 | 100 |
| 15 | 100 |

Wavelength: 254 nm, Rt min: 9.80
Wavelength: 220 nm, Rt min: 9.80

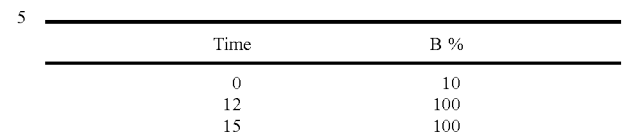

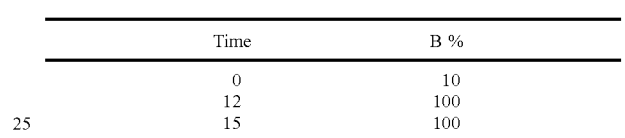

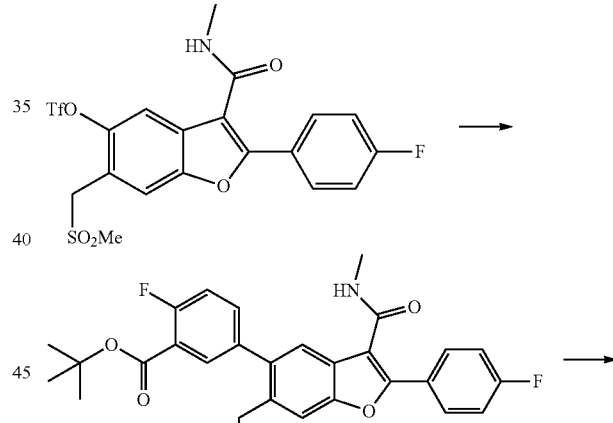

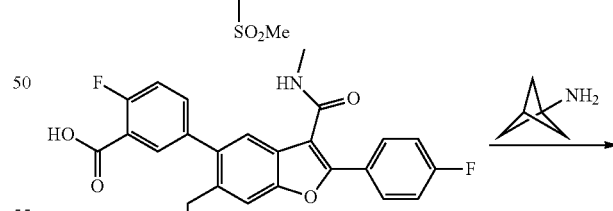

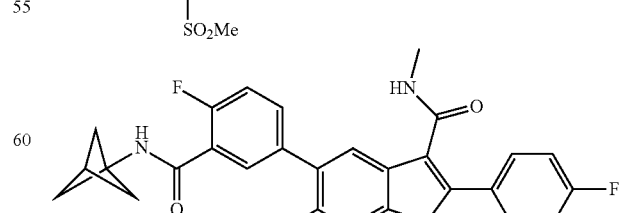

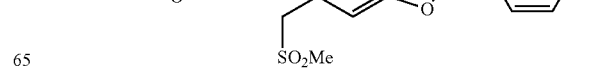

Preparation of tert-butyl 2-fluoro-5-(2-(4-fluorophenyl)-3-(methylcarbamoyl)-6-((methyl-sulfonyl)methyl)benzofuran-5-yl)benzoate

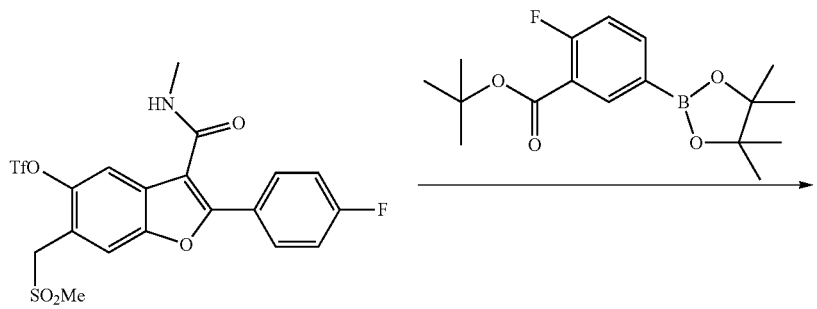

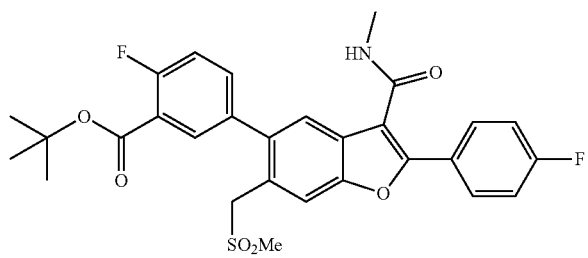

To a stirred solution of 2-(4-fluorophenyl)-3-(methylcarbamoyl)-6-((methylsulfonyl)methyl)benzofuran-5-yl trifluoromethanesulfonate (0.3 g, 0.589 mmol) in dioxan (10 mL) was added tert-butyl 2-fluoro-5-(4,4,5,5-tetramethyl-1,3,2-dioxaborolan-2-yl)benzoate (0.247 g, 0.766 mmol) and $K_3PO_4$ (0.376 g, 1.767 mmol). The mixture was degassed and then added with Pd(dppf)Cl$_2$ (0.048 g, 0.059 mmol) and water (1.0 ml). The mixture was purged with $N_2$ for 10 min and allowed to stir at 90° C. for overnight. The reaction mixture was filtered through celite and the solvent was evaporated. The crude compound was purified by Combiflash using 50% EtoAc/n-Hexane as a mobile phase to obtain the desired compound. Yield: 250 mg (76%).

LCMS (ES+) m/z=556.2 (M+H).

Column—ACQUITY UPLC BEH C18 (50×2.1 mm; 1.7 μm)

M phase A: 0.1% TFA in water

M phase B: Acetonitrile

Flow: 0.8 ml/Min

| Time | % A | % B |
|------|-----|-----|
| 0.0  | 98  | 2   |
| 1.0  | 2   | 98  |
| 1.6  | 2   | 98  |

Rt min: 1.54, wavelength: 220 nm.

Preparation of 2-fluoro-5-(2-(4-fluorophenyl)-3-(methylcarbamoyl)-6-((methylsulfonyl)-methyl)benzofuran-5-yl)benzoic acid

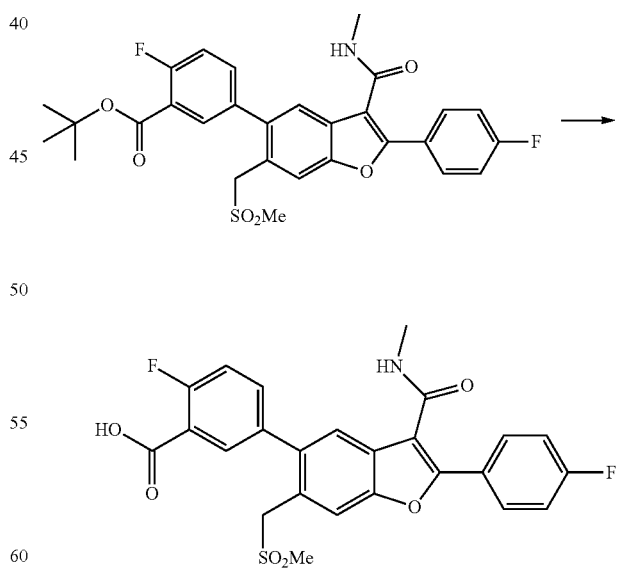

A solution of tert-butyl 2-fluoro-5-(2-(4-fluorophenyl)-3-(methylcarbamoyl)-6-((methyl-sulfonyl)methyl)benzofuran-5-yl)benzoate (200 mg, 0.360 mmol) in $CF_3COOH$ (5 mL, 0.360 mmol) was stirred overnight at room temperature. The mixture was evaporated and ice-cold water added to the crude reaction mixture. The solid separated was filtered and dried to obtain the compound. It was used for the next step without any purification. Yield: 80 mg.

LCMS (ES+) m/z=500.2 (M+H).

Column—ACQUITY UPLC BEH C8 (50×2.1 mm; 1.7 μm)

M phase A: 5 mM Ammonium Acetate:MeCN (95:5)
M phase B: 5 mM Ammonium Acetate:MeCN (5:95)
Flow: 0.8 ml/Min

| Time | % A | % B |
|---|---|---|
| 0.0 | 95 | 5 |
| 1.1 | 5 | 95 |
| 1.7 | 5 | 95 |

Rt min: 0.68, wavelength: 220 nm

Preparation of 5-(3-(bicyclo[1.1.1]pentan-1-ylcarbamoyl)-4-fluorophenyl-2-(4-fluorophenyl)-N-methyl-6-(methylsulfonylmethyl)benzofuran-3-carboxamide

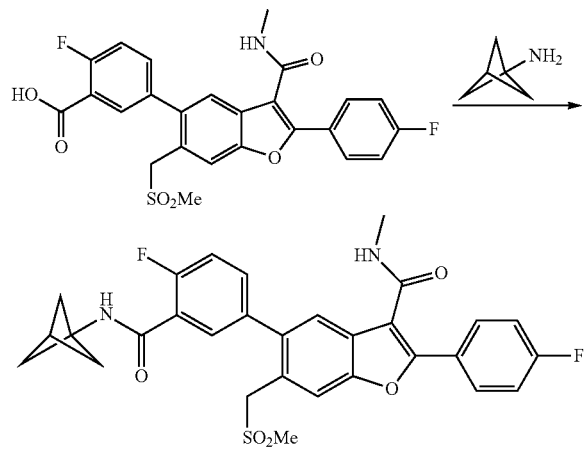

To a stirred solution of 2-fluoro-5-(2-(4-fluorophenyl)-3-(methylcarbamoyl)-6-((methylsulfonyl)methyl)benzofuran-5-yl)benzoic acid (80 mg, 0.160 mmol), bicyclo[1.1.1]pentan-1-amine.HCl (28.7 mg, 0.240 mmol) in DMF (2 mL) at 10° C. was added DIPEA (0.149 mL, 0.801 mmol) and HATU (91 mg, 0.240 mmol). The resulting reaction mixture was allowed to stir at room temperature for 5 hours. After completion of the reaction, ice-cold water was added to the reaction mixture. The solid separated was filtered and dried. It was then purified by preparative TLC using CHCl$_3$/MeOH (9:1) as a mobile phase to obtain the desired compound. Yield: 7.0 mg (8%).

$^1$H NMR (400 MHz, Methanol-d$_4$) δ ppm 2.22 (s, 6H) 2.51 (s, 1H) 2.86 (s, 3H) 2.96 (s, 3H) 4.56 (s, 2H) 7.26-7.36 (m, 3H) 7.61-7.65 (m, 2H) 7.70 (dd, J=6.84, 2.32 Hz, 1H) 7.89 (s, 1H) 7.96-8.04 (m, 2H); $^{19}$F NMR (376.6 MHz, Methanol-d$_4$) δ -112.06, -118.14.

LCMS (ES+) m/z=565.2 (M+H).
Column—Acentis Express C18 120 (50×2.1 mm; 2.7 u)
Buffer: 10 mM Ammonium Formate in water pH 4.5
Mphase A: Buffer+MeCN (98+2)
Mphase B: Buffer+MeCN (2+98)
Flow: 1.0 ml/min

| Time | % A | % B |
|---|---|---|
| 0.0 | 0 | 0 |
| 1.6 | 100 | 0 |
| 3.2 | 100 | 0 |
| 3.6 | 0 | 2 |

Rt min: 2.00, wavelength: 220 nm
HPLC Method: SUNFIRE C18(150×4.6 mm) 3.5 micron
Buffer: 0.05% TFA
Mobile Phase A: Buffer: MeCN (95:5)
Mobile Phase B: MeCN:Buffer (95:5)
Flow: 1 ml/min

| Time | B % |
|---|---|
| 0 | 10 |
| 25 | 100 |
| 30 | 100 |

Wavelength: 254 nm, Rt min: 15.83
Wavelength: 220 nm, Rt min: 15.83
HPLC Method: XBridge Phenyl (150×4.6 mm) 3.5 micron
Buffer: 0.05% TFA
Mobile Phase A: Buffer: MeCN (95:5)
Mobile Phase B: MeCN: Buffer (95:5)
Flow: 1 ml/min

| Time | B % |
|---|---|
| 0 | 10 |
| 25 | 100 |
| 30 | 100 |

Wavelength: 254 nm, Rt min: 14.78
Wavelength: 220 nm, Rt min: 14.78

Schemes for the preparation of analogs containing an aza benzofuran are shown below.

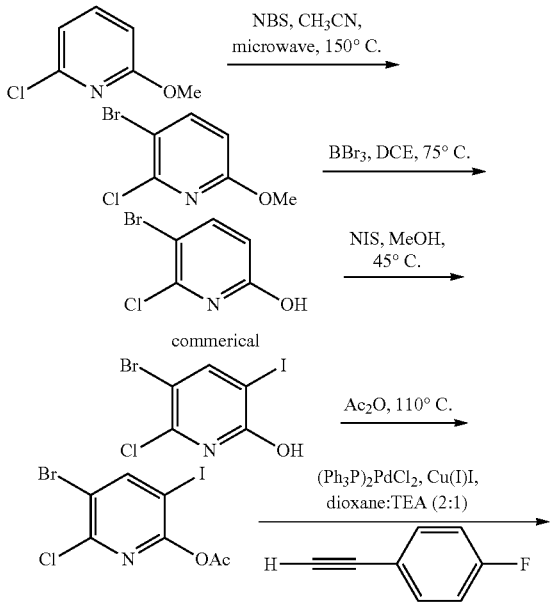

Azabenzofuran Scheme 1

171
-continued
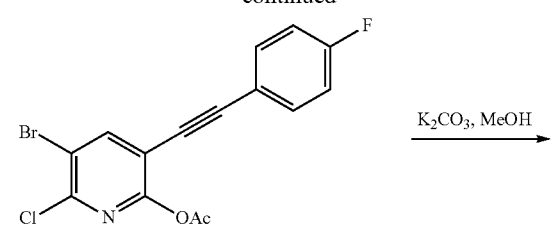
K₂CO₃, MeOH →
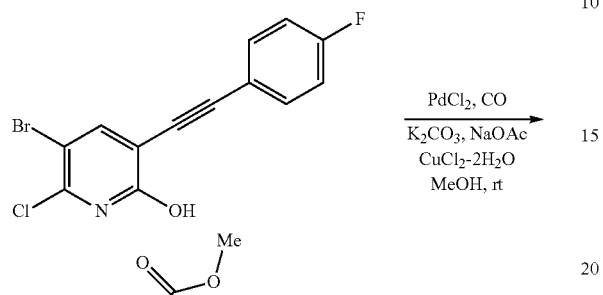
PdCl₂, CO
K₂CO₃, NaOAc
CuCl₂·2H₂O
MeOH, rt →
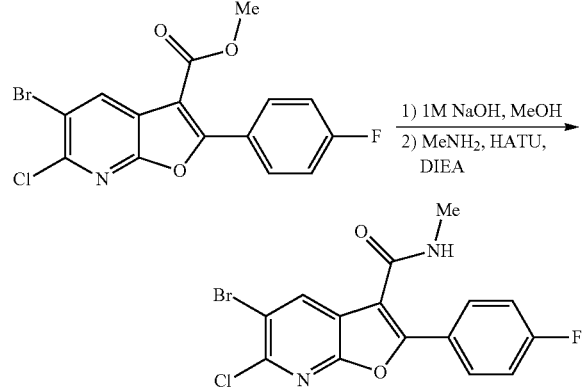
1) 1M NaOH, MeOH
2) MeNH₂, HATU, DIEA →
Azaindole Scheme 2
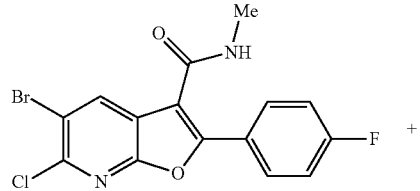 +
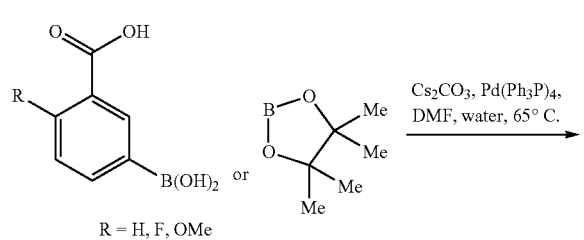
Cs₂CO₃, Pd(Ph₃P)₄, DMF, water, 65° C. →
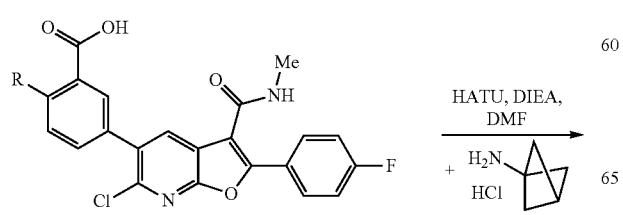
HATU, DIEA, DMF
+ H₂N—▲ · HCl →
172
-continued
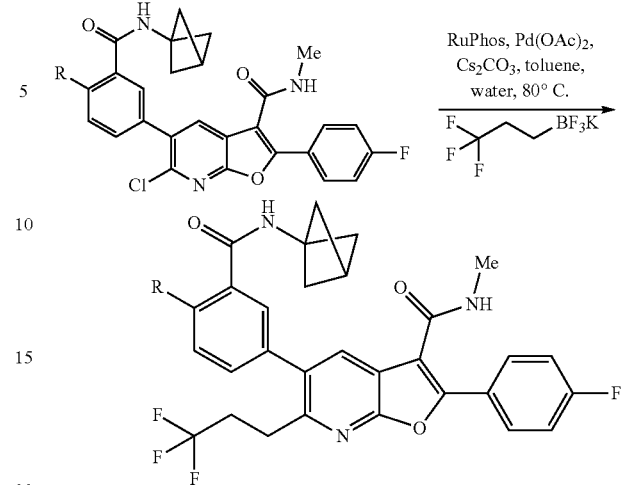
RuPhos, Pd(OAc)₂, Cs₂CO₃, toluene, water, 80° C.
F₃C–CH₂CH₂–BF₃K →
Azaindole Scheme 3
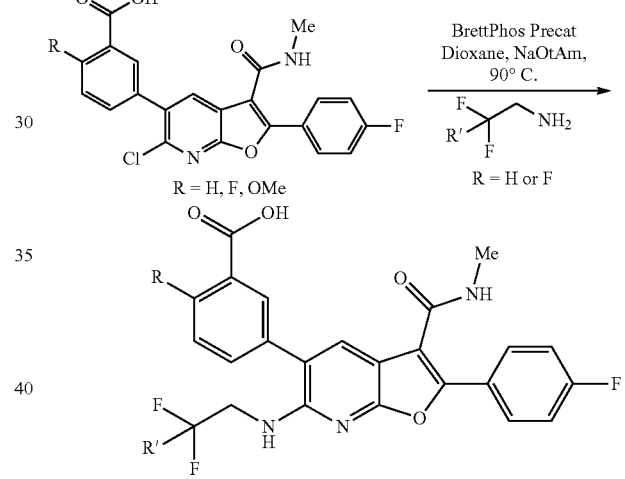
BrettPhos Precat
Dioxane, NaOtAm, 90° C.
CF₂R'–CH₂–NH₂
R = H or F →
Azaindole Scheme 4
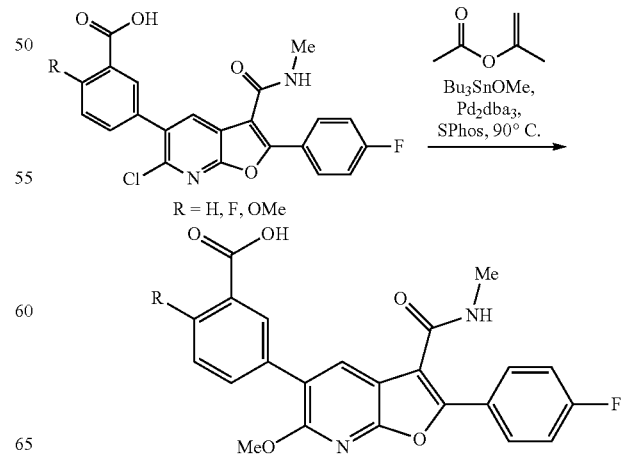
Bu₃SnOMe, Pd₂dba₃, SPhos, 90° C. →

173
Azaindole Scheme 5
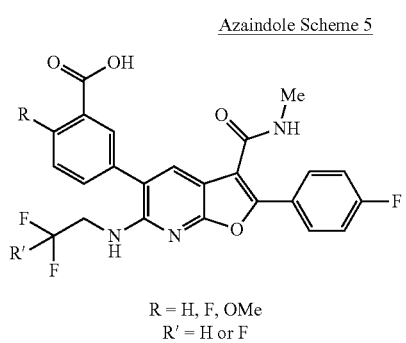
R = H, F, OMe
R' = H or F
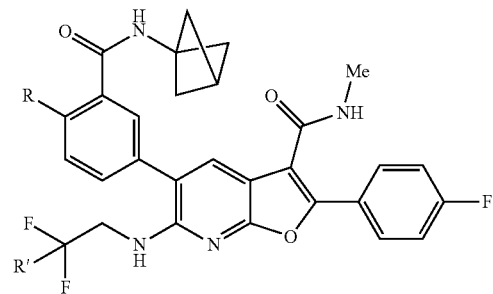
174
-continued
Azaindole Scheme 7
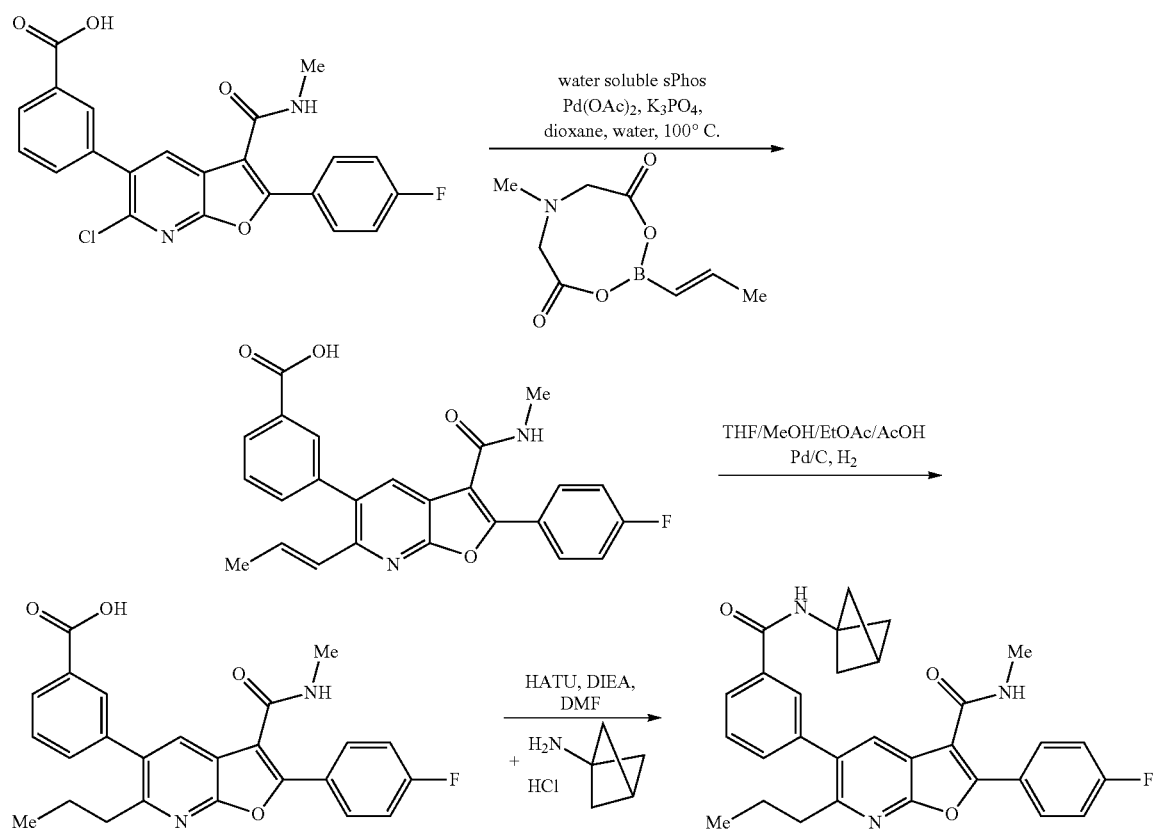
Azaindole Scheme 8
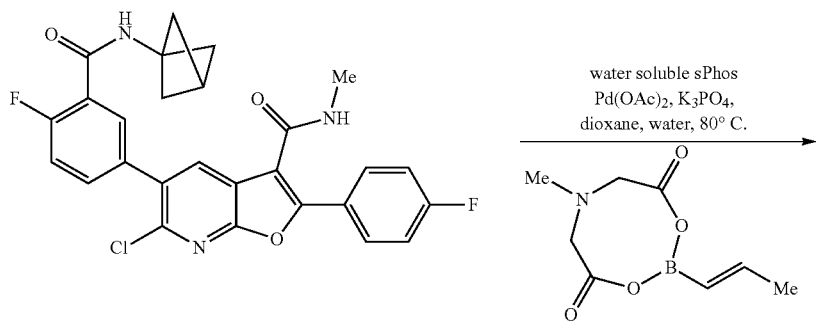

175
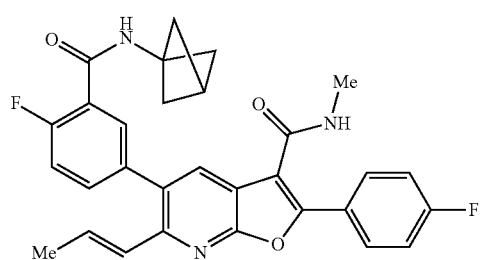
176
-continued
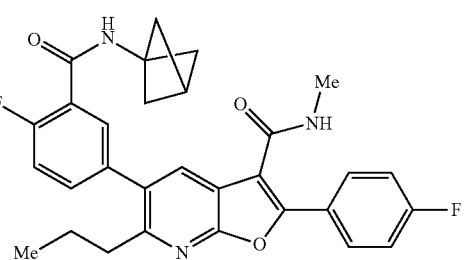
MeOH
Pd/C, H₂
-continued
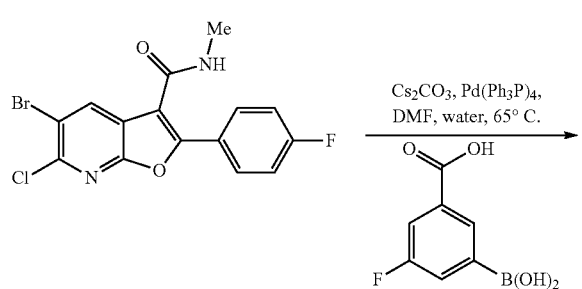
Cs₂CO₃, Pd(Ph₃P)₄,
DMF, water, 65° C.
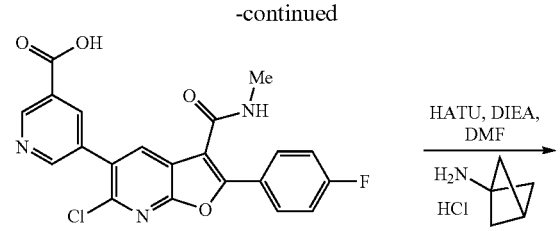
HATU, DIEA,
DMF
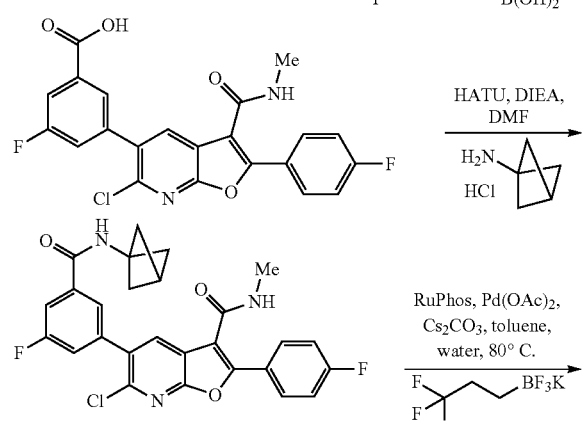
HATU, DIEA,
DMF
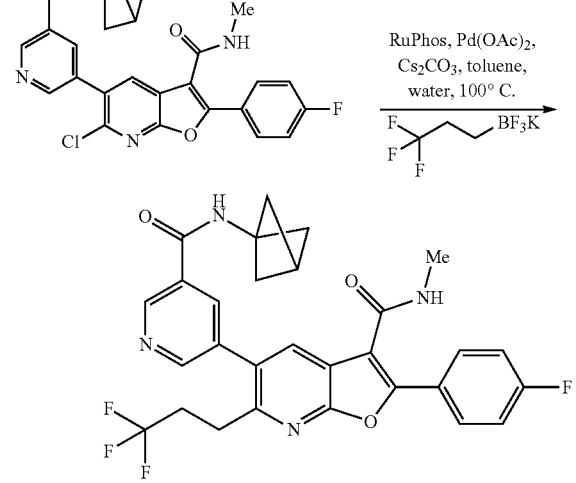
RuPhos, Pd(OAc)₂,
Cs₂CO₃, toluene,
water, 100° C.
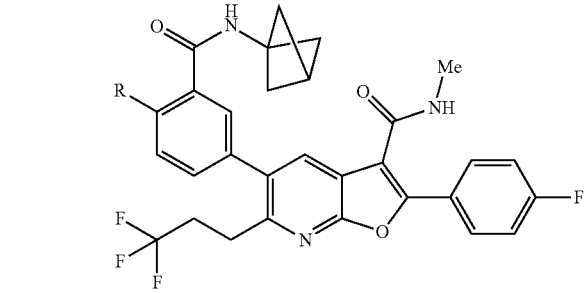
RuPhos, Pd(OAc)₂,
Cs₂CO₃, toluene,
water, 80° C.
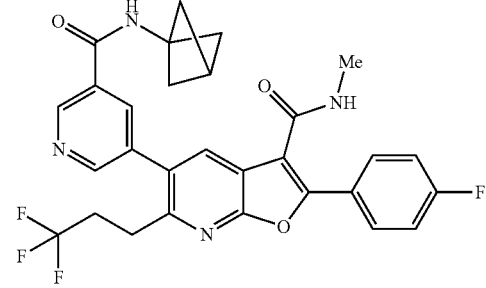
Azaindole Scheme 11
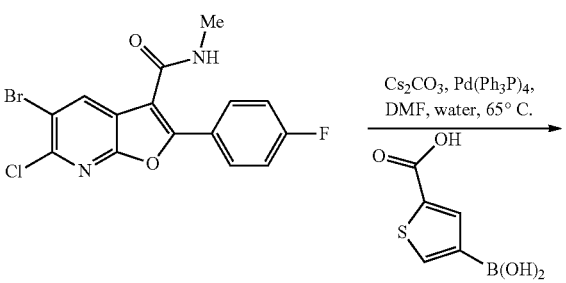
Cs₂CO₃, Pd(Ph₃P)₄,
DMF, water, 65° C.
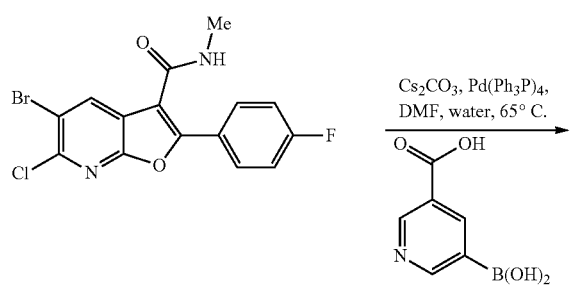
Azaindole Scheme 10
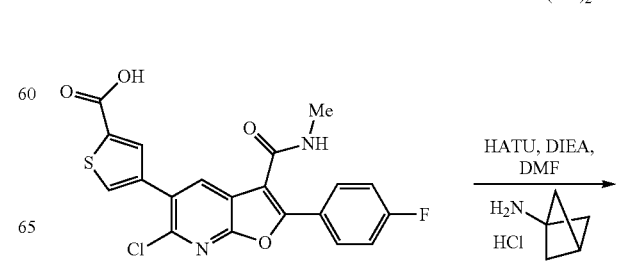
Cs₂CO₃, Pd(Ph₃P)₄,
DMF, water, 65° C.
HATU, DIEA,
DMF

177
-continued
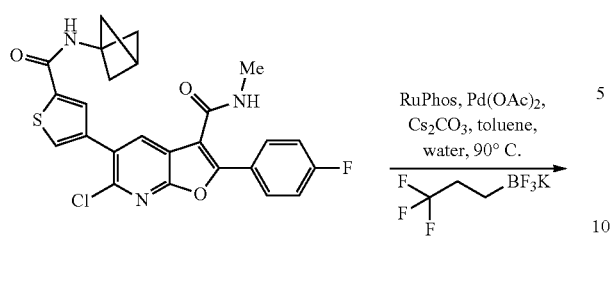
RuPhos, Pd(OAc)₂,
Cs₂CO₃, toluene,
water, 90° C.
→
178
-continued
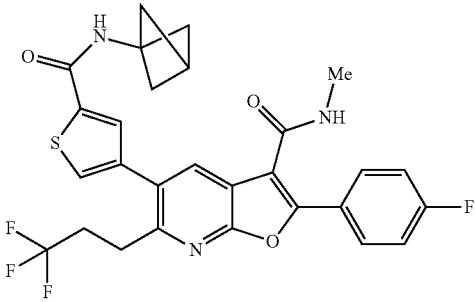
Azaindole Scheme 12
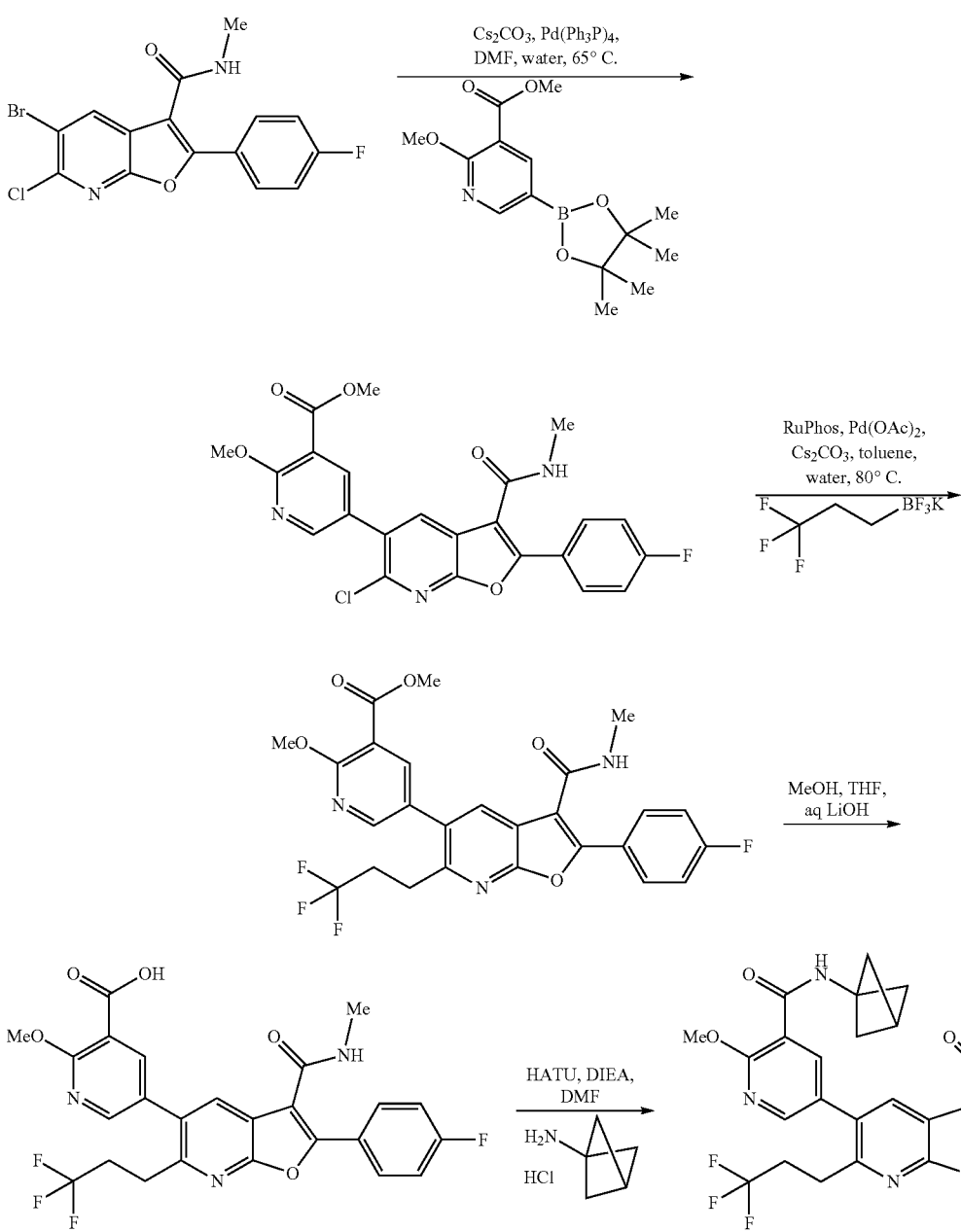

Azaindole 13
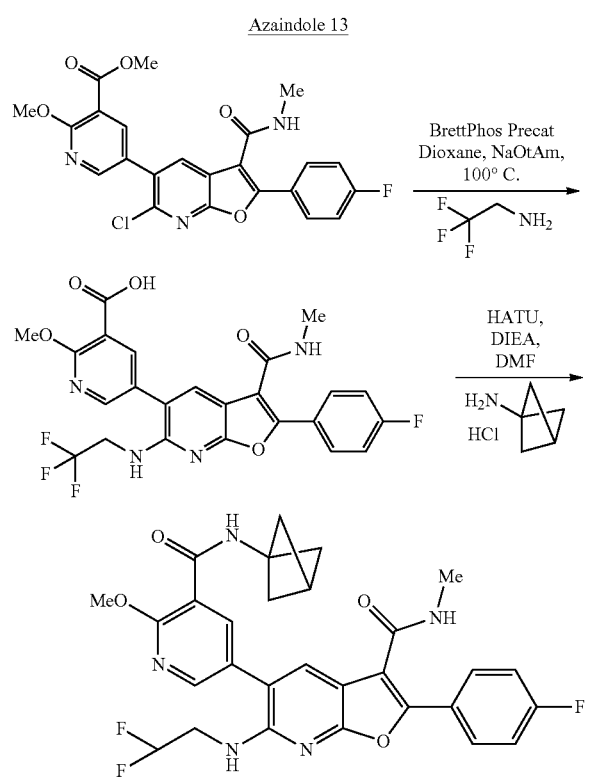 [SMILES: CNC(=O)c1c(-c2ccc(F)cc2)oc2nc(Cl)c(-c3cnc(OC)c(C(=O)OC)c3)cc12 ; NCC(F)(F)F ; CNC(=O)c1c(-c2ccc(F)cc2)oc2nc(NCC(F)(F)F)c(-c3cnc(OC)c(C(=O)O)c3)cc12 ; Cl ; NC12CC(C1)C2 ; CNC(=O)c1c(-c2ccc(F)cc2)oc2nc(NCC(F)F)c(-c3cnc(OC)c(C(=O)NC45CC(C4)C5)c3)cc12]
Azaindole Scheme 14
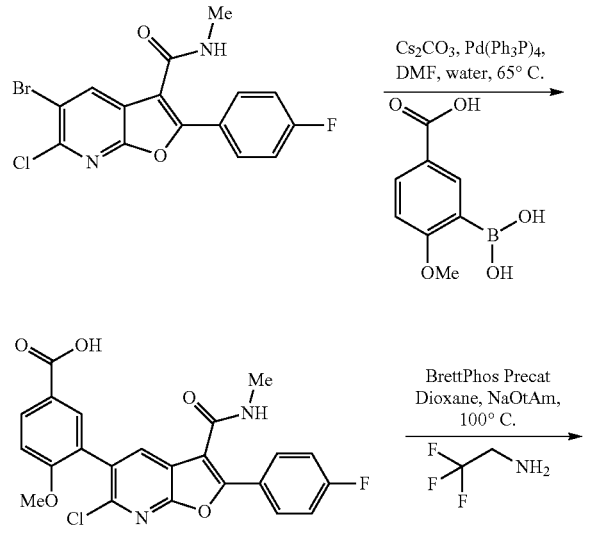
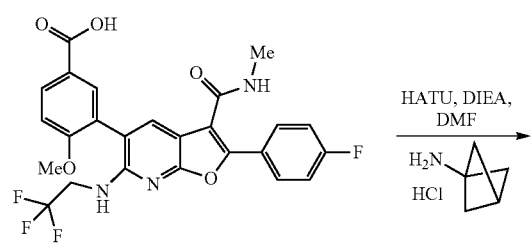
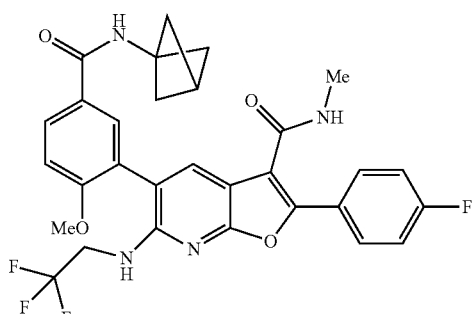
Azaindole Scheme 15
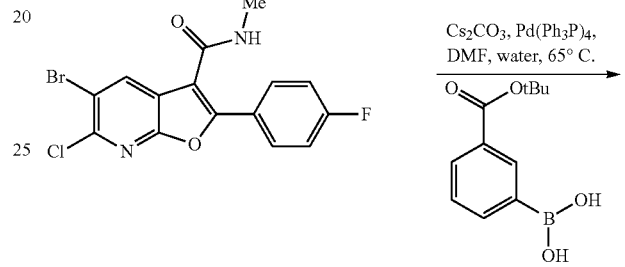
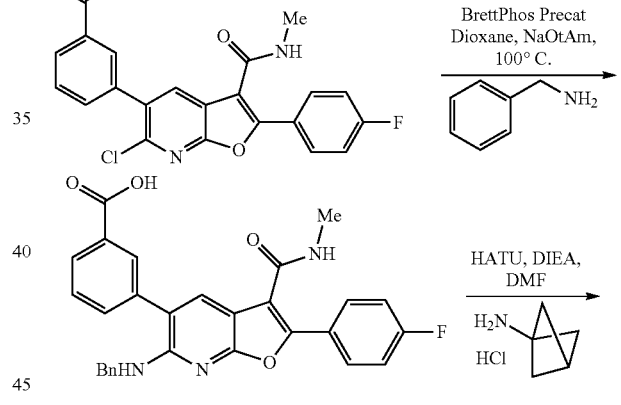
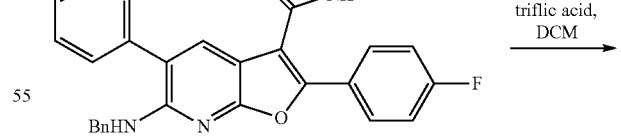
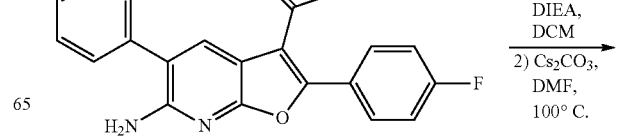

181
-continued

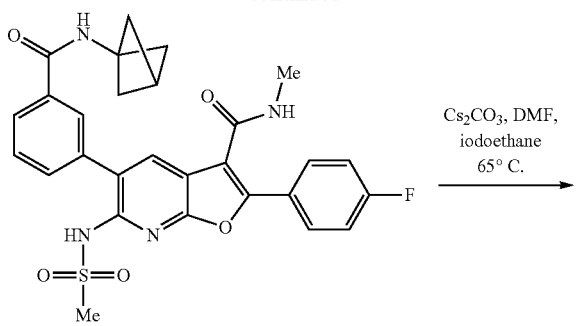

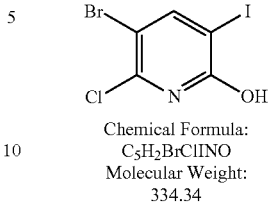

Cs₂CO₃, DMF,
iodoethane
65° C.

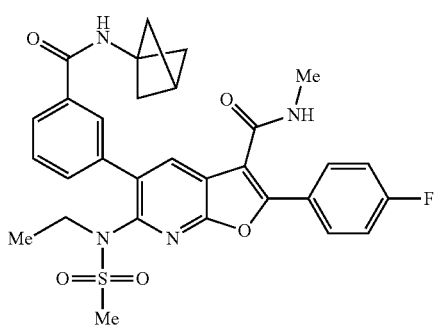

Azaindole Scheme 16

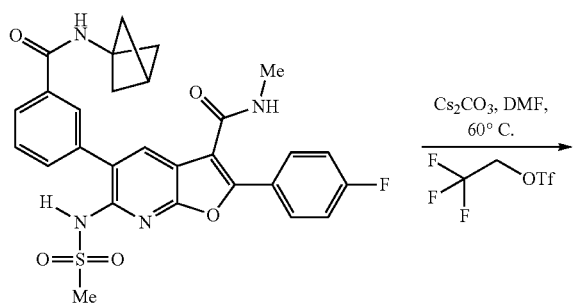

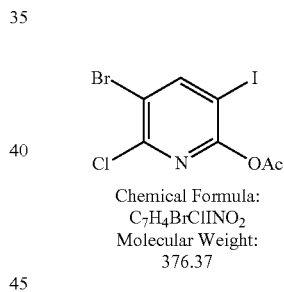

Cs₂CO₃, DMF,
60° C.

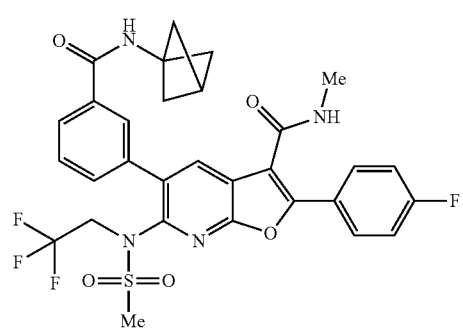

Experimental procedures for preparing azabenzofurans are below.

182

5-bromo-6-chloro-3-iodopyridin-2-ol

Br, I

Cl N OH

Chemical Formula:
C₅H₂BrClINO
Molecular Weight:
334.34

NIS (7.38 g, 32.8 mmol) was added to a stirring solution of commercially available 5-bromo-6-chloropyridin-2-ol (5.70 g, 27.3 mmol) in MeOH (50 ml) at 45° C. The reaction was allowed to stir at 45° C. for 1 h. The amber colored solution was cooled to rt and then concentrated in vacuo. The resulting yellow solids were diluted with 25 mL DCM, triturated for 30 min, then collected filtering with minimal DCM to give 5-bromo-6-chloro-3-iodopyridin-2-ol (7.60 g, 22.7 mmol, 83% yield) as a white solid consistent by LCMS and NMR.

LCMS: m/e 335 (M+H)⁺ LCMS retention time: 2.62 min. (Column: Phenomenex-Luna 50×2.0 mm 3 u. Solvent A=90% Water: 10% Methanol: 0.1% TFA. Solvent B=10% Water: 90% Methanol: 0.1% TFA. Start % B=0. Final % B=100. Gradient Time=4 min. Flow Rate=0.8 mL/min.).

$^1$H NMR (500 MHz, MeOD) ppm 8.26 (s, 1H).

5-bromo-6-chloro-3-iodopyridin-2-yl acetate

Br, I

Cl N OAc

Chemical Formula:
C₇H₄BrClINO₂
Molecular Weight:
376.37

5-bromo-6-chloro-3-iodopyridin-2-ol (12.9 g, 38.6 mmol) was suspended in acetic anhydride (40 mL, 420 mmol) and heated to 110° C. The mixture was heated at this temp for 1 h. After 1 h the reaction mixture appeared as a homogeneous solution. TLC (observed M+H mass in LCMS is primarily of des-OAc) indicated complete reaction. The solution was concentrated azeotroping with toluene (3×25 mL) to give 5-bromo-6-chloro-3-iodopyridin-2-yl acetate (14.5 g, 38.5 mmol, 100% yield) as a tan solid. The solid was taken onto the subsequent Sonogashira coupling without further purification.

Observed LCMS reveals mostly hydrolysis product (starting material), but desired mass is present. LCMS: m/e 377 (M+H)⁺ LCMS retention time: 2.71 min. (Column: Phenomenex-Luna 50×2.0 mm 3 u. Solvent A=90% Water: 10% Methanol: 0.1% TFA. Solvent B=10% Water: 90% Methanol: 0.1% TFA. Start % B=0. Final % B=100. Gradient Time=3 min. Flow Rate=0.8 mL/min.).

$^1$H NMR (500 MHz, CDCl3) ppm 8.37 (s, 1H), 2.38 (s, 3H).

5-bromo-6-chloro-3-((4-fluorophenyl)ethynyl)pyridin-2-yl acetate

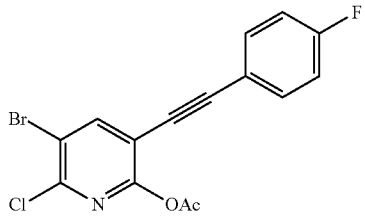

Chemical Formula: C₁₅H₈BrClFNO₂
Molecular Weight: 368.58

5-bromo-6-chloro-3-iodopyridin-2-yl acetate (14.5 g, 38.5 mmol) was dissolved in THF (50 mL) and cooled to 0° C. TEA (2.5 mL), Copper(I)Iodide (0.514 g, 2.70 mmol), and bistriphenylphosphine palladiumdichloride (0.270 g, 0.385 mmol) were added to the reaction mixture. The mixture was degassed and charged with N₂ (3×). Next, 1-ethynyl-4-fluorobenzene (5.55 g, 46.2 mmol) was added drop wise over the course of 1 h at 0° C. The reaction mixture was then allowed to slowly warm to rt and continue to stir for 18 h. LCMS and TLC show the reaction to be incomplete. An additional 2.5 mL of TEA was added. The mixture was then allowed to stir at rt over a long weekend (80 h). At this point, LCMS and TLC show no remaining starting material. The reaction mixture was concentrated to a dry solid. This solid was then taken up in DCM (50 mL) and washed with sat NH₄Cl. The aq layer was extracted with DCM (2×20 mL). The combined organic extracts were washed with water, brine, dried over Na₂SO₄, filtered and concentrated to >15 g of a brown solid. This solid was dissolved in DCM, adsorbed onto Celite and then flashed on silica gel eluting with a 10-100% DCM in hexanes gradient over 15 column volumes to give 5-bromo-6-chloro-3-((4-fluorophenyl)ethynyl)pyridin-2-yl acetate (11.7 g, 31.7 mmol, 82% yield) as a tan solid.

LCMS: m/e 369 (M+H)⁺ LCMS retention time: 3.74 min. (Column: Phenomenex-Luna 50×2.0 mm 3 u. Solvent A=90% Water: 10% Methanol: 0.1% TFA. Solvent B=10% Water: 90% Methanol: 0.1% TFA. Start % B=0. Final % B=100. Gradient Time=4 min. Flow Rate=0.8 mL/min.).

¹H NMR (500 MHz, CDCl3) ppm 8.13 (s, 1H), 7.48 (dd, J=8.7 Hz, 2H), 7.09 (dd, J=8.7 Hz, 2H), 2.39 (s, 3H).

5-bromo-6-chloro-3-((4-fluorophenyl)ethynyl)pyridin-2-ol

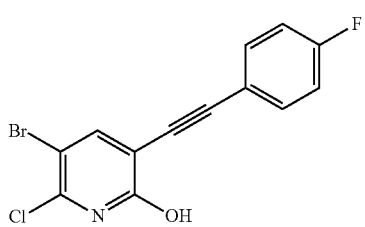

Chemical Formula: C₁₃H₆BrClFNO
Molecular Weight: 326.55

5-bromo-6-chloro-3-((4-fluorophenyl)ethynyl)pyridin-2-yl acetate (5.5 g, 15 mmol) was suspended in MeOH (75 ml) and K₂CO₃ (4.12 g, 29.8 mmol) was added. The mixture was stirred at rt for 1 h. At this point, LCMS and TLC show no remaining SM. The mixture was then sparged with a balloon of CO for ten minutes and carried onto the following step, carbonylative coupling, without isolation.

methyl 5-bromo-6-chloro-2-(4-fluorophenyl)furo[2,3-b]pyridine-3-carboxylate

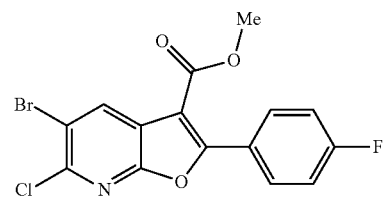

Chemical Formula: C₁₅H₈BrClFNO₃
Molecular Weight: 384.58

The entire reaction mixture from the previous step containing 5-bromo-6-chloro-3-((4-fluorophenyl)ethynyl)pyridin-2-ol (4.87 g, 14.9 mmol) was poured into a Parr Hydrogenation apparatus ("bomb") containing palladium(II) chloride (0.439 g, 2.48 mmol), sodium acetate (2.45 g, 29.8 mmol), copper(II) chloride dihydrate (7.63 g, 44.8 mmol). The reaction was charged with CO (350 PSI) minimizing the time the reaction is devoid of a blanket of CO. The reaction was stirred vigorously overnight at rt. LCMS shows both the desired product and the undesired C-3H adduct in a minor amount. The reaction mixture was concentrated to dryness and then partitioned between 75 mL 1M HCl and EtOAc (75 mL). The layers were separated and the aqueous layer was extracted with EtOAc (3×75 mL). The combined organic extracts were washed with brine, dried over Na₂SO₄, filtered and concentrated to give 5.04 g of a 4:1 ratio of the desired methyl 5-bromo-6-chloro-2-(4-fluorophenyl)furo[2,3-b]pyridine-3-carboxylate to the undesired 5-bromo-6-chloro-2-(4-fluorophenyl)furo[2,3-b]pyridine. The mixture was carried on crude to the hydrolysis after which the acid and the C-3 H adduct can be separated by acid base extraction or silica gel chromatography.

NOTE: The ratio of the desired product to the C-3 H adduct ranges from 2:1 to 9:1 depending on scale, with larger scale reactions giving less favorable results.

LCMS: m/e 386 (M+H)⁺ LCMS retention time: 3.97 min. (Column: Phenomenex-Luna 50×2.0 mm 3 u. Solvent A=90% Water: 10% Methanol: 0.1% TFA. Solvent B=10% Water: 90% Methanol: 0.1% TFA. Start % B=0. Final % B=100. Gradient Time=4 min. Flow Rate=0.8 mL/min.).

5-bromo-6-chloro-2-(4-fluorophenyl)furo[2,3-b]pyridine-3-carboxylic acid

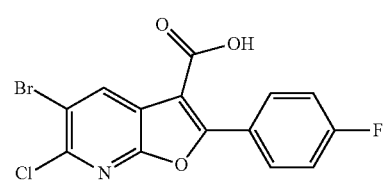

Chemical Formula: C₁₄H₆BrClFNO₃
Molecular Weight: 370.56

A 4:1 inseparable mixture of methyl 5-bromo-6-chloro-2-(4-fluorophenyl)furo[2,3-b]pyridine-3-carboxylate (2.38 g, 6.19 mmol) and 5-bromo-6-chloro-2-(4-fluorophenyl)furo[2,3-b]pyridine (0.265 g, 0.812 mmol) was taken up in a 1:1:1 mixture of MeOH (50 mL), THF (50 mL), 1M NaOH (50 mL). The entire mixture was heated in an oil bath to an internal temp of 65° C. This mixture was allowed to stir at this temp for 1 h. The solution was then concentrated to an aqueous mixture. This mixture was diluted with EtOAc and 1 M HCl (50 mL). The layers were separated and the aqueous layer was extracted with EtOAc (3×20 mL). The combined organic extracts were washed with water, brine, dried over $Na_2SO_4$, filtered and concentrated to give a white solid. This solid was adsorbed onto $SiO_2$ and flashed on silica gel eluting with a 0-10% MeOH in DCM solution containing 1% AcOH to give 5-bromo-6-chloro-2-(4-fluorophenyl)furo[2,3-b]pyridine-3-carboxylic acid (1.85 g, 4.99 mmol, 81% yield).

LCMS: m/e 371 (M+H)+ LCMS retention time: 3.30 min. (Column: Phenomenex-Luna 50×2.0 mm 3 u. Solvent A=90% Water: 10% Methanol: 0.1% TFA. Solvent B=10% Water: 90% Methanol: 0.1% TFA. Start % B=0. Final % B=100. Gradient Time=4 min. Flow Rate=0.8 mL/min.).

$^1$H NMR (500 MHz, MeOD) ppm 8.66 (s, 1H), 8.21 (dd, J=9.2 Hz, 2H), 7.27 (dd, J=8.9 Hz, 2H).

5-bromo-6-chloro-2-(4-fluorophenyl)-N-methylfuro[2,3-b]pyridine-3-carboxamide

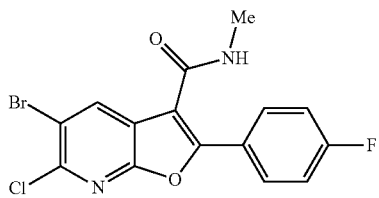

Chemical Formula: $C_{15}H_9BrClFN_2O_2$
Molecular Weight: 383.60

HATU (1.69 g, 4.45 mmol) was added to a stirring solution of 5-bromo-6-chloro-2-(4-fluorophenyl)furo[2,3-b]pyridine-3-carboxylic acid (1.1 g, 3.0 mmol), methylamine hydrochloride (1.00 g, 14.8 mmol), and DIEA (2.59 mL, 14.8 mmol) in a sealable tube in DMF (20 mL) at rt. The reaction tube was sealed and allowed to stir at rt for 2 hours. LCMS and TLC indicate complete conversion. The solution was then diluted with EtOAc (50 mL) and 1 M HCl (50 mL). The layers were separated and the aqueous layer was extracted with EtOAc (2×20 mL). The combined organic extracts were washed with water, brine, dried over $Na_2SO_4$, filtered and concentrated to give a tan solid. This solid was adsorbed onto $SiO_2$ and eluted on silica gel with a 0-5% MeOH in DCM gradient over 40 CV (very slow gradient) to give 5-bromo-6-chloro-2-(4-fluorophenyl)-N-methylfuro[2,3-b]pyridine-3-carboxamide (1.1 g, 2.7 mmol, 92% yield) as a white fluffy solid.

LCMS: m/e 385 (M+H)+ LCMS retention time: 3.04 min. (Column: Phenomenex-Luna 50×2.0 mm 3 u. Solvent A=90% Water: 10% Methanol: 0.1% TFA. Solvent B=10% Water: 90% Methanol: 0.1% TFA. Start % B=0. Final % B=100. Gradient Time=4 min. Flow Rate=0.8 mL/min.).

$^1$H NMR (500 MHz, CDCl3) ppm 8.50 (s, 1H), 7.89 (dd, J=9.0 Hz, 2H), 7.23 (dd, J=8.7 Hz, 2H), 5.85 (br s, 1H), 3.00 (d, J=4.8 Hz, 3H).

5-(6-chloro-2-(4-fluorophenyl)-3-(methylcarbamoyl)furo[2,3-b]pyridin-5-yl)-2-fluorobenzoic acid

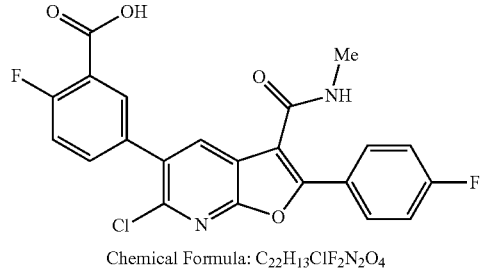

Chemical Formula: $C_{22}H_{13}ClF_2N_2O_4$
Molecular Weight: 442.80

A mixture of 5-bromo-6-chloro-2-(4-fluorophenyl)-N-methylfuro[2,3-b]pyridine-3-carboxamide (3.0 g, 7.8 mmol), 5-borono-2-fluorobenzoic acid (1.58 g, 8.60 mmol), $Pd(Ph_3P)_4$ (0.90 g, 0.78 mmol) and cesium carbonate (3.82 g, 11.7 mmol) was evacuated and charged with $N_2$ (3×) and then diluted with water (0.95 mL)/DMF (9.5 mL). The mixture was again evacuated and charged with $N_2$ (3×) and heated to 65° C. under $N_2$ atmosphere. The reaction was allowed to stir at 65° C. for 16 h. LCMS showed peak with the expected M+H. The mixture was diluted with EtOAc (30 mL) and washed with 1M HCl, and sat aq NaCl. The organic phase was dried over $Na_2SO_4$, filtered and concentrated to give solid which was triturated with DCM to give the expected product 5-(6-chloro-2-(4-fluorophenyl)-3-(methylcarbamoyl)furo[2,3-b]pyridin-5-yl)-2-fluorobenzoic acid (2.4 g, 5.4 mmol, 69% yield) consistent by LCMS and NMR.

LC-MS retention time: 2.64 min; m/z (MH+): 443. LC data was recorded on a Shimadzu LC-10AS liquid chromatograph equipped with a Phenomenex-Luna 3 u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 2 min, and an analysis time of 4 min where solvent A was 5% MeOH/95% $H_2O$/10 mM ammonium acetate and solvent B was 5% $H_2O$/95% MeOH/10 mM ammonium acetate. MS data was determined using a Micromass Platform for LC in electrospray mode.

$^1$H NMR (400 MHz, DMSO-$d_6$) δ 13.46 (br. s, 1H), 8.55 (d, J=4.8 Hz, 1H), 8.21 (s, 1H), 8.10-8.04 (m, 2H), 8.00 (dd, J=7.0, 2.5 Hz, 1H), 7.82 (ddd, J=8.5, 4.5, 2.5 Hz, 1H), 7.52-7.39 (m, 3H), 2.82 (d, J=4.8 Hz, 3H).

5-(3-(bicyclo[1.1.1]pentan-1-ylcarbamoyl)-4-fluorophenyl)-6-chloro-2-(4-fluorophenyl)-N-methylfuro[2,3-b]pyridine-3-carboxamide

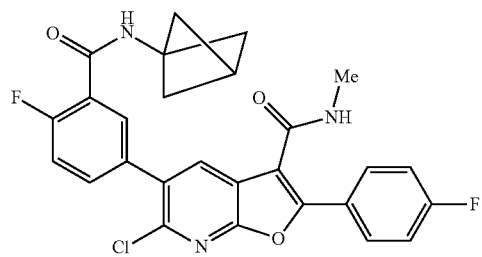

Chemical Formula: $C_{27}H_{20}ClF_2N_3O_3$
Molecular Weight: 507.92

5-(6-chloro-2-(4-fluorophenyl)-3-(methylcarbamoyl)furo[2,3-b]pyridin-5-yl)-2-fluorobenzoic acid (1.00 g, 2.26 mmol) was taken up in DMF (2.3 mL) and treated with N-ethyl-N-isopropylpropan-2-amine (2.63 mL, 13.6 mmol), bicyclo[1.1.1]pentan-1-amine hydrochloride (540 mg, 4.52 mmol) followed by 2-(3H-[1,2,3]triazolo[4,5-b]pyridin-3-yl)-1,1,3,3-tetramethylisouronium hexafluorophosphate(V) (1.29 g, 3.39 mmol). The reaction was allowed to stir for 16 h at rt. The reaction mixture was concentrated, absorbed onto Celite and then purified on silica gel (Biotage, 0-100% DCM in EtOAc gradient over 75 CV (slow gradient was not run to completion!), fraction collection at λ=254 nm and at approximately the 15$^{th}$ CV) to give the expected product 5-(3-(bicyclo[1.1.1]pentan-1-ylcarbamoyl)-4-fluorophenyl)-6-chloro-2-(4-fluorophenyl)-N-methylfuro[2,3-b]pyridine-3-carboxamide (745 mg, 1.47 mmol, 65% yield) consistent by LCMS and NMR.

LC-MS retention time: 3.08 min; m/z (MH+): 508. LC data was recorded on a Shimadzu LC-10AS liquid chromatograph equipped with a Phenomenex-Luna 3 u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 2 min, and an analysis time of 4 min where solvent A was 5% MeOH/95% H$_2$O/10 mM ammonium acetate and solvent B was 5% H$_2$O/95% MeOH/10 mM ammonium acetate. MS data was determined using a Micromass Platform for LC in electrospray mode.

$^1$H NMR (400 MHz, DMSO-d$_6$) δ 8.99 (s, 1H), 8.60-8.50 (m, 1H), 8.18 (s, 1H), 8.09-8.01 (m, 2H), 7.73-7.64 (m, 2H), 7.46-7.40 (m, 3H), 2.83 (d, J=4.5 Hz, 3H), 2.46 (s, 1H), 2.09 (s, 6H)

5-(3-(bicyclo[1.1.1]pentan-1-ylcarbamoyl)-4-fluorophenyl)-2-(4-fluorophenyl)-N-methyl-6-(3,3,3-trifluoropropyl)furo[2,3-b]pyridine-3-carboxamide

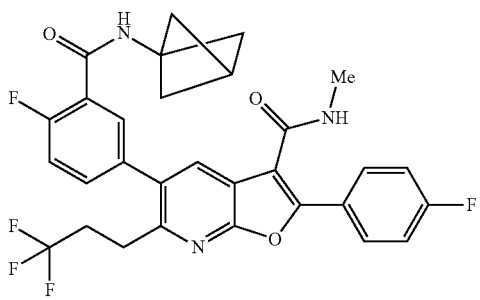

Chemical Formula: C$_{30}$H$_{24}$F$_5$N$_3$O$_3$
Molecular Weight: 569.52

A mixture of 5-(3-(bicyclo[1.1.1]pentan-1-ylcarbamoyl)-4-fluorophenyl)-6-(2,2-difluoroethyl)amino)-2-(4-fluorophenyl)-N-methylfuro[2,3-b]pyridine-3-carboxamide (300 mg, 0.591 mmol), 3,3,3-trifluoropropane-1-trifluoroborate (602 mg, 2.95 mmol), dicyclohexyl(2',6'-diisopropoxy-[1,1'-biphenyl]-2-yl)phosphine (110 mg, 0.236 mmol), PdOAc$_2$ (26.5 mg, 0.118 mmol), and cesium carbonate (577 mg, 1.77 mmol) were degassed and backfilled with N$_2$. The resultant nitrogen blanketed mixture was suspended in Toluene (20 mL) and Water (2.0 mL) at rt then heated to 80° C. with stirring. The reaction was allowed to stir at this temp for 16 h. LCMS indicated a major peak with the expected mass. The mixture was diluted with EtOAc (50 mL) and washed with 1M HCl (50 mL), and sat NaCl. The organic phase was concentrate, dissolved in DCM, adsorbed onto Celite and then was purified on silica gel (Biotage, 0-100% EtOAc in DCM gradient over 40 CV, fraction collection at λ=254 nm) to give 5-(3-(bicyclo[1.1.1]pentan-1-ylcarbamoyl)-4-fluorophenyl)-2-(4-fluorophenyl)-N-methyl-6-(3,3,3-trifluoropropyl)furo[2,3-b]pyridine-3-carboxamide (775 mg, 1.36 mmol, 73% yield) consistent by LCMS and NMR.

LC-MS retention time: 3.18 min; m/z (MH+): 570. LC data was recorded on a Shimadzu LC-10AS liquid chromatograph equipped with a Phenomenex-Luna 3 u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 2 min, and an analysis time of 4 min where solvent A was 5% MeOH/95% H$_2$O/10 mM ammonium acetate and solvent B was 5% H$_2$O/95% MeOH/10 mM ammonium acetate. MS data was determined using a Micromass Platform for LC in electrospray mode.

$^1$H NMR (400 MHz, DMSO-d6) δ 8.97 (s, 1H), 8.51 (d, J=4.8 Hz, 1H), 8.08-8.03 (m, 2H), 7.94 (s, 1H), 7.64-7.55 (m, 2H), 7.46-7.38 (m, 3H), 3.04-2.97 (m, 2H), 2.85-2.71 (m, 5H), 2.46 (s, 1H), 2.08 (s, 6H)

5-(3-(bicyclo[1.1.1]pentan-1-ylcarbamoyl)-4-fluorophenyl)-6-((2,2-difluoroethyl)amino)-2-(4-fluorophenyl)-N-methylfuro[2,3-b]pyridine-3-carboxamide

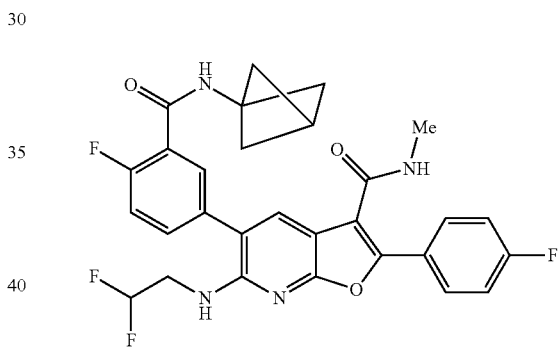

Chemical Formula: C$_{29}$H$_{24}$F$_4$N$_4$O$_3$
Molecular Weight: 552.52

Step 1: Preparation of 5-(6-(2,2-difluoroethyl)amino)-2-(4-fluorophenyl)-3-(methylcarbamoyl)furo[2,3-b]pyridin-5-yl)-2-fluorobenzoic acid

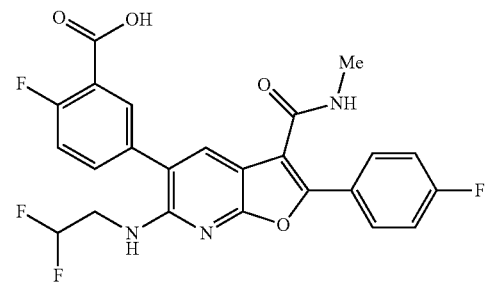

Chemical Formula: C$_{24}$H$_{17}$F$_4$N$_3$O$_4$
Molecular Weight: 487.40

Sodium 2-methylbutan-2-olate (808 mg, 7.34 mmol), 5-(6-chloro-2-(4-fluorophenyl)-3-(methylcarbamoyl)furo[2,3-b]pyridin-5-yl)-2-fluorobenzoic acid (650 mg, 1.468 mmol), 2,2-difluoroethanamine (595 mg, 7.34 mmol), Brett Phos precatalyst (117 mg, 0.147 mmol) were combined in dioxane (25 mL) at 90° C. in a sealable flask under inert atmosphere. LCMS shows a peak that contains the desired product mass and no sign of starting material after 30 min at 90° C. TLC remains unchanged. The mixture was concentrated to dryness, diluted with EtOAc (30 mL) and washed with sat aq $NH_4Cl$. The layers were separated and the aq layer was extracted with EtOAc (2×10 ml). The combined organic extracts were washed with brine, dried over $Na_2SO_4$, filtered and concentrated to give a yellow residue that was adsorbed onto $SiO_2$ and purified on silica gel eluting with a 0-10% MeOH in DCM gradient containing 1% AcOH over 15 CV to give 5-(6-((2,2-difluoroethyl)amino)-2-(4-fluorophenyl)-3-(methylcarbamoyl)furo[2,3-b]pyridin-5-yl)-2-fluorobenzoic acid (450 mg, 0.923 mmol, 63% yield) as a white fluffy solid.

LC-MS retention time: 2.89 min; m/z (MH+): 488. LC data was recorded on a Shimadzu LC-10AS liquid chromatograph equipped with a Phenomenex-Luna 3 u C18 2.0×30 mm column using a SPD-10AV UV-Vis detector at a detector wave length of 220 nM. The elution conditions employed a flow rate of 0.8 mL/min, a gradient of 100% solvent A/0% solvent B to 0% solvent A/100% solvent B, a gradient time of 4 min, a hold time of 1 min, and an analysis time of 5 min where solvent A was 10% acetonitrile/90% $H_2O$/0.1% trifluoroacetic acid and solvent B was 10% $H_2O$/90% acetonitrile/0.1% trifluoroacetic acid. MS data was determined using a Micromass Platform for LC in electrospray mode.

$^1$H NMR (400 MHz, METHANOL-$d_4$) 8.39 (d, J=3.5 Hz, 1H), 8.01-7.89 (m, 3H), 7.69-7.61 (m, 2H), 7.33 (dd, J=10.5, 8.5 Hz, 1H), 7.28-7.19 (m, 2H), 6.10 (tt, J=58.0, 4.4 Hz, 1H), 3.78 (td, J=14.2, 4.4 Hz, 2H), 2.97-2.88 (m, 3H)

Step 2: Preparation of Title Compound

N-ethyl-N-isopropylpropan-2-amine (0.057 mL, 0.33 mmol) was added to stirring solution of 5-(6-((2,2-difluoroethyl)amino)-2-(4-fluorophenyl)-3-(methylcarbamoyl)furo[2,3-b]pyridin-5-yl)-2-fluorobenzoic acid (40 mg, 0.082 mmol), 2-(3H-[1,2,3]triazolo[4,5-b]pyridin-3-yl)-1,1,3,3-tetramethylisouronium hexafluorophosphate(V) (47 mg, 0.12 mmol) and bicyclo[1.1.1]pentan-1-amine (14 mg, 0.17 mmol) in DMF (1 mL) at rt. The mixture was allowed to stir at rt for 30 min. LCMS shows the desired product. The mixture was then directly purified via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 40-100% B over 14 minutes, then a 4-minute hold at 100% B; Flow: 20 mL/min. Fractions containing the desired product were combined and dried via centrifugal evaporation to give 5-(3-(bicyclo[1.1.1]pentan-1-ylcarbamoyl)-4-fluorophenyl)-6-((2,2-difluoroethyl)amino)-2-(4-fluorophenyl)-N-methylfuro[2,3-b]pyridine-3-carboxamide (7.1 mg, 0.013 mmol, 16% yield) consistent by LCMS and NMR. The estimated purity by LCMS analysis was 100%.

LC-MS retention time: 4.17 min; m/z (MH+): 553. LC data was recorded on a Shimadzu LC-10AS liquid chromatograph equipped with a Phenomenex-Luna 3 u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 4 min, a hold time of 2 min, and an analysis time of 4 min where solvent A was 5% MeOH/95% $H_2O$/10 mM ammonium acetate and solvent B was 5% $H_2O$/95% MeOH/10 mM ammonium acetate. MS data was determined using a Micromass Platform for LC in electrospray mode.

$^1$H NMR (500 MHz, DMSO-$d_6$) δ 8.91 (s, 1H), 8.45-8.29 (m, 1H), 7.96 (dd, J=8.9, 5.5 Hz, 2H), 7.63 (s, 1H), 7.62-7.58 (m, 1H), 7.58-7.51 (m, 1H), 7.41 (dd, J=10.1, 8.5 Hz, 1H), 7.34 (t, J=8.9 Hz, 2H), 6.52 (t, J=5.8 Hz, 1H), 6.33-6.04 (m, 1H), 3.81-3.69 (m, 2H), 2.79 (d, J=4.6 Hz, 3H), 2.46 (s, 1H), 2.09 (s, 6H)

5-(3-(bicyclo[1.1.1]pentan-1-ylcarbamoyl)-4-fluorophenyl)-2-(4-fluorophenyl)-N-methyl-6-((2,2,2-trifluoroethyl)amino)furo[2,3-b]pyridine-3-carboxamide

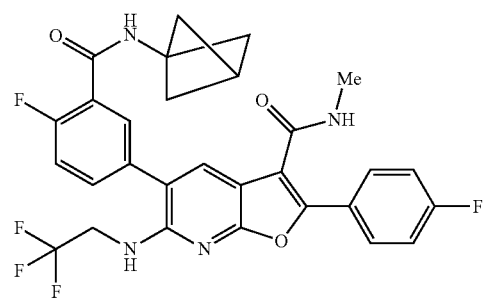

Chemical Formula: $C_{29}H_{23}F_5N_4O_3$
Molecular Weight: 570.51

Step 1: Preparation of 2-fluoro-5-(2-(4-fluorophenyl)-3-(methylcarbamoyl)-6-((2,2,2-trifluoroethyl)amino)furo[2,3-b]pyridin-5-yl)benzoic acid

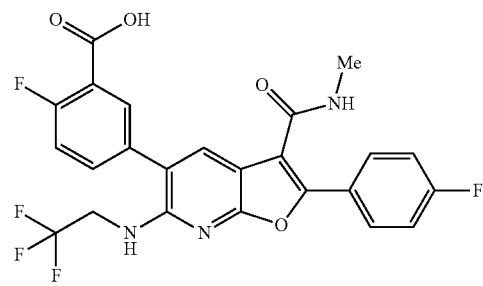

Chemical Formula: $C_{24}H_{16}F_5N_3O_4$
Molecular Weight: 505.39

Sodium 2-methylbutan-2-olate (121 mg, 1.10 mmol), 5-(6-chloro-2-(4-fluorophenyl)-3-(methylcarbamoyl)furo[2,3-b]pyridin-5-yl)-2-fluorobenzoic acid (97 mg, 0.22 mmol), 2,2,2-trifluoroethanamine (108 mg, 1.10 mmol), Brett Phos precatalyst (17.5 mg, 0.0220 mmol) were combined in dioxane (25 mL) at 90° C. in a sealable flask under inert ($N_2$) atmosphere. LCMS shows a peak that contains the desired product and no sign of SM after 30 min at 90° C. TLC remains unchanged. The mixture was concentrated to dryness, diluted with EtOAc (30 mL) and washed with sat aq NH₄Cl. The layers were separated and the aq layer was extracted with EtOAc (2×10 ml). The combined organic extracts were washed with brine, dried over Na₂SO₄, filtered and concentrated to give a yellow residue that was adsorbed onto SiO2 and flashed on silica eluting with a 0-10% MeOH in DCM gradient containing 1% AcOH over 15 CV to give 2-fluoro-5-(2-(4-fluorophenyl)-3-(methylcarbamoyl)-6-((2,2,2-trifluoroethyl)amino)furo[2,3-b]pyridin-5-yl)benzoic acid (77 mg, 0.15 mmol, 70% yield).

LC-MS retention time: 3.77 min; m/z (MH+): 506. LC data was recorded on a Shimadzu LC-10AS liquid chromatograph equipped with a Phenomenex-Luna 3 u C18 2.0×50 mm column using a SPD-10AV UV-Vis detector at a detector wave length of 220 nM. The elution conditions employed a flow rate of 0.8 mL/min, a gradient of 100% solvent A/0% solvent B to 0% solvent A/100% solvent B, a gradient time of 4 min, a hold time of 1 min, and an analysis time of 5 min where solvent A was 5% MeOH/95% H₂O/10 mM ammonium acetate and solvent B was 5% H₂O/95% MeOH/10 mM ammonium acetate. MS data was determined using a Micromass Platform for LC in electrospray mode.

¹H NMR (400 MHz, METHANOL-d₄) 7.98 (dd, J=6.9, 2.4 Hz, 1H), 7.95-7.87 (m, 2H), 7.69-7.61 (m, 2H), 7.32 (dd, J=11.1, 8.5 Hz, 1H), 7.29-7.17 (m, 3H), 4.17 (q, J=9.3 Hz, 2H), 2.92-2.87 (m, 3H)

Step 2: Preparation of Title Compound 2-fluoro-5-(2-(4-fluorophenyl)-3-(methylcarbamoyl)-6-((2,2,2-trifluoroethyl)amino)furo[2,3-b]pyridin-5-yl)benzoic acid (25 mg, 0.049 mmol) was taken up in DMF (500 μl) and treated with N-ethyl-N-isopropylpropan-2-amine (35 μl, 0.20 mmol), bicyclo[1.1.1]pentan-1-amine dihydrochloride (15 mg, 0.099 mmol) followed by 2-(3H-[1,2,3]triazolo[4,5-b]pyridin-3-yl)-1,1,3,3-tetramethylisouronium hexafluorophosphate(V) (28 mg, 0.074 mmol). The reaction was allowed to stir for 4 h. LCMS showed a peak with the expected M+H=571. The crude material was purified via preparative LC/MS with the following conditions: Column: Waters XBridge C18, 19×100 mm, 5-μm particles; Guard Column: Waters XBridge C18, 19×10 mm, 5-μm particles; Mobile Phase A: water; Mobile Phase B: acetonitrile; Buffer: 20-mM ammonium acetate; Gradient: 20-95% B over 10.9 minutes, then a 4.0 minute hold at 95% B; Flow: 25 mL/min. Fractions containing the desired product were combined and dried via centrifugal evaporation. The yield of the product was 9.6 mg, and its estimated purity by LCMS analysis was 95%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. LCMS retention time=3.18 Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. LCMS retention time=4.20. M+H=571. Proton NMR was acquired in deuterated DMSO.

¹H NMR (500 MHz, DMSO-d6) 8.89 (s, 1H), 8.41-8.34 (m, 1H), 7.97 (dd, J=8.7, 5.3 Hz, 2H), 7.67 (s, 1H), 7.61 (dd, J=6.7, 2.1 Hz, 1H), 7.58-7.53 (m, 1H), 7.45-7.39 (m, 1H), 7.34 (t, J=8.9 Hz, 2H), 6.68 (t, J=6.4 Hz, 1H), 4.23-4.13 (m, 2H), 2.80 (d, J=4.3 Hz, 3H), 2.46 (s, 1H), 2.09 (s, 6H)

5-(3-(bicyclo[1.1.1]pentan-1-ylcarbamoyl)-4-fluorophenyl)-2-(4-fluorophenyl)-6-methoxy-N-methylfuro[2,3-b]pyridine-3-carboxamide

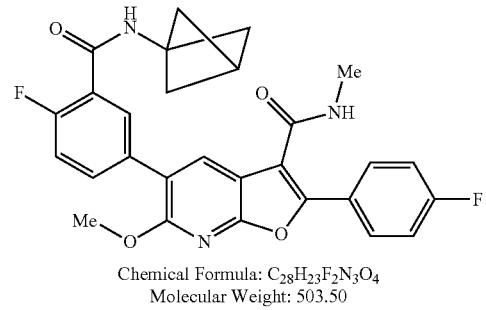 [SMILES: CNC(=O)c1c(-c2ccc(F)cc2)oc2nc(OC)c(-c3ccc(F)c(C(=O)NC45CC(C4)C5)c3)cc12]

Chemical Formula: C₂₈H₂₃F₂N₃O₄
Molecular Weight: 503.50

A solution of 5-(3-(bicyclo[1.1.1]pentan-1-ylcarbamoyl)-4-fluorophenyl)-6-chloro-2-(4-fluorophenyl)-N-methylfuro[2,3-b]pyridine-3-carboxamide (20 mg, 0.039 mmol) in anhydrous toluene was treated with Isopropenyl acetate (4.7 mg, 0.047 mmol), tributyltin methoxide (14 μl, 0.047 mmol), and Pd₂dba₃ (0.36 mg, 0.39 μmol). The resulting mixture was degassed and charged with N₂ (3×). The nitrogen blanketed mixture was then heated to 90° C. and allowed to stir at this temp overnight. With no progress overnight, it was realized that S-Phos was omitted from the reaction. Thus, 2-Dicyclohexylphosphino-2',6'-dimethoxy-1,1'-biphenyl (0.81 mg, 2.0 μmol) was added, the reaction mixture was degassed and charged with N₂ (3×) and the mixture was re-subjected to stirring at 90° C. and stirred for two hours. LCMS and TLC reveal no starting material remains. LCMS seems to suggest a product wherein OMe has replaced Cl. The mixture was concentrated, adsorbed onto SiO₂ and flashed on silica gel eluting with a 0-75% EtOAc in hexanes mixture to give 5-(3-(bicyclo[1.1.1]pentan-1-ylcarbamoyl)-4-fluorophenyl)-2-(4-fluorophenyl)-6-methoxy-N-methylfuro[2,3-b]pyridine-3-carboxamide (10 mg) as an impure white solid. The impure material was purified via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 30-100% B over 20 minutes, then a 4-minute hold at 100% B; Flow: 20 mL/min. Fractions containing the desired product were combined and dried via centrifugal evaporation. The yield of the product was 3.9 mg, 7.8 umol, 20% yield, and its estimated purity by LCMS analysis was 100%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.;

Gradient: 0.5 min hold at 0% B, 0-100% B over 4 minutes, then a 0.5-minute hold at 100% B; Flow: 0.5 mL/min.

LC-MS retention time: 3.41 min; m/z (MH+): 504. LC data was recorded on a Shimadzu LC-10AS liquid chromatograph equipped with a Phenomenex-Luna 3 u C18 2.0×30 mm column using a SPD-10AV UV-Vis detector at a detector wave length of 220 nM. The elution conditions employed a flow rate of 0.8 mL/min, a gradient of 100% solvent A/0% solvent B to 0% solvent A/100% solvent B, a gradient time of 4 min, a hold time of 1 min, and an analysis time of 5 min where solvent A was 10% acetonitrile/90% $H_2O$/0.1% trifluoroacetic acid and solvent B was 10% $H_2O$/90% acetonitrile/0.1% trifluoroacetic acid. MS data was determined using a Micromass Platform for LC in electrospray mode.

$^1$H NMR (500 MHz, DMSO-$d_6$) δ 8.95 (s, 1H), 8.48 (d, J=4.6 Hz, 1H), 8.05-7.99 (m, 3H), 7.74-7.69 (m, 2H), 7.41-7.35 (m, 3H), 3.96 (s, 3H), 2.83 (d, J=4.6 Hz, 3H), 2.46 (s, 1H), 2.09 (s, 6H).

3-(6-chloro-2-(4-fluorophenyl)-3-(methylcarbamoyl)furo[2,3-b]pyridin-5-yl)benzoic acid

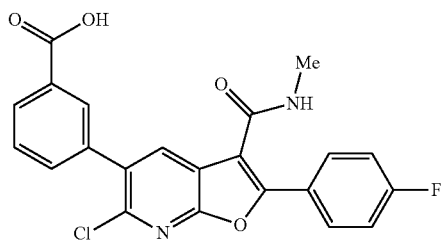

Chemical Formula: $C_{22}H_{14}ClFN_2O_4$
Molecular Weight: 424.81

A mixture of 3-(4,4,5,5-tetramethyl-1,3,2-dioxaborolan-2-yl)benzoic acid (241 mg, 0.972 mmol), Pd(Ph$_3$P)$_4$ (107 mg, 0.0930 mmol) and cesium carbonate (452 mg, 1.39 mmol) was degassed and diluted water (0.085 mL)/DMF (8.5 mL). The mixture was degassed and heated to 70° C. under N$_2$. The reaction was allowed to stir at 70° C. for 16 h. The mixture was diluted with EtOAc (25 mL) and 1M HCl (30 mL). The layers were separated and the aq layer was extracted with EtOAc (2×10 mL). The combined organic extracts were washed with water, brine, dried over Na$_2$SO$_4$ filtered and concentrated on SiO$_2$. The resultant adsorbed solids were flashed on silica gel eluting with 1:1 mixture of EtOAc and hexanes with 1% AcOH to give 3-(6-chloro-2-(4-fluorophenyl)-3-(methylcarbamoyl)furo[2,3-b]pyridin-5-yl)benzoic acid (0.276 g, 0.650 mmol, 70% yield) as a white solid.

LC-MS retention time: 2.62 min; m/z (MH+): 425. LC data was recorded on a Shimadzu LC-10AS liquid chromatograph equipped with a Phenomenex-Luna 3 u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 3 min, a hold time of 1 min, and an analysis time of 4 min where solvent A was 5% MeOH/95% $H_2O$/10 mM ammonium acetate and solvent B was 5% $H_2O$/95% MeOH/10 mM ammonium acetate. MS data was determined using a Micromass Platform for LC in electrospray mode.

$^1$H NMR (400 MHz, DMSO-$d_6$) 8.55 (d, J=4.8 Hz, 1H), 8.20 (s, 1H), 8.13-7.98 (m, 4H), 7.79 (d, J=7.8 Hz, 1H), 7.65 (t, J=7.8 Hz, 1H), 7.43 (t, J=8.9 Hz, 2H), 3.33 (br. s., 1H), 2.82 (d, J=4.8 Hz, 3H)

5-(3-(bicyclo[1.1.1]pentan-1-ylcarbamoyl)phenyl)-6-chloro-2-(4-fluorophenyl)-N-methylfuro[2,3-b]pyridine-3-carboxamide

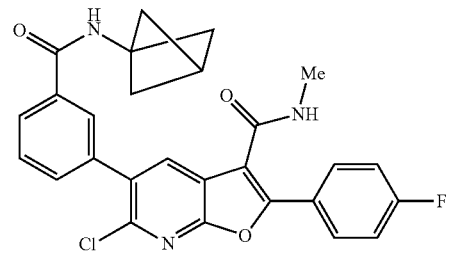

Chemical Formula: $C_{27}H_{21}ClFN_3O_3$
Molecular Weight: 489.93

N-ethyl-N-isopropylpropan-2-amine (0.395 mL, 2.26 mmol) was added to stirring solution of 3-(6-chloro-2-(4-fluorophenyl)-3-(methylcarbamoyl)furo[2,3-b]pyridin-5-yl)benzoic acid (120 mg, 0.282 mmol), 2-(3H-[1,2,3]triazolo[4,5-b]pyridin-3-yl)-1,1,3,3-tetramethylisouronium hexafluorophosphate(V) (161 mg, 0.424 mmol) and bicyclo[1.1.1]pentan-1-amine hydrochloride (33.8 mg, 0.282 mmol) in DMF (1 mL) at rt. The mixture was allowed to stir at rt for 16 h. The reaction mixture was then diluted with EtOAc (15 mL) and NH$_4$Cl. The layers were separated and the aq layer was extracted with EtOAc (2×10 mL). The combined organic extracts were washed with water, brine, dried over Na$_2$SO$_4$, filtered and concentrated to give a brown residue which was adsorbed on Celite and purified by flash column chromatography on silica gel eluting 0-100% EtOAc in hexanes gradient over 15 CV to give 5-(3-(bicyclo[1.1.1]pentan-1-ylcarbamoyl)phenyl)-6-chloro-2-(4-fluorophenyl)-N-methylfuro[2,3-b]pyridine-3-carboxamide (0.110 g, 0.225 mmol, 79% yield) as a white solid. LC-MS retention time: 3.09 min; m/z (MH+): 490. LC data was recorded on a Shimadzu LC-10AS liquid chromatograph equipped with a Phenomenex-Luna 3 u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 3 min, a hold time of 1 min, and an analysis time of 4 min where solvent A was 5% MeOH/95% $H_2O$/10 mM ammonium acetate and solvent B was 5% $H_2O$/95% MeOH/10 mM ammonium acetate. MS data was determined using a Micromass Platform for LC in electrospray mode.

$^1$H NMR (400 MHz, DMSO-$d_6$) 9.07 (s, 1H), 8.58-8.52 (m, 1H), 8.19 (s, 1H), 8.09-8.03 (m, 2H), 7.99-7.89 (m, 2H), 7.69 (dt, J=7.9, 1.3 Hz, 1H), 7.64-7.56 (m, 1H), 7.48-7.39 (m, 2H), 2.82 (d, J=4.5 Hz, 3H), 2.47 (s, 1H), 2.10 (s, 6H).

5-(3-(bicyclo[1.1.1]pentan-1-ylcarbamoyl)phenyl)-2-(4-fluorophenyl)-N-methyl-6-(3,3,3-trifluoropropyl)furo[2,3-b]pyridine-3-carboxamid

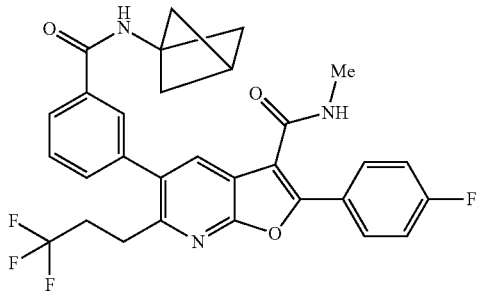

Chemical Formula: C30H25F4N3O3
Molecular Weight: 551.53

A flask containing a mixture of 5-(3-(bicyclo[1.1.1]pentan-1-ylcarbamoyl)phenyl)-6-chloro-2-(4-fluorophenyl)-N-methylfuro[2,3-b]pyridine-3-carboxamide (30 mg, 0.061 mmol), 3,3,3-trifluoropropane-1-trifluoroborate (62 mg, 0.31 mmol), dicyclohexyl(2',6'-diisopropoxy-[1,1'-biphenyl]-2-yl)phosphine (23 mg, 0.049 mmol), PdOAc₂ (5.5 mg, 0.024 mmol), cesium carbonate (60 mg, 0.18 mmol) was degassed and backfilled with N₂. The nitrogen blanketed solids were suspended in toluene (3.7 mL) and water (0.37 mL) at rt and then heated at 80° C. The reaction was allowed to stir at this temp for 16 h. The solution was the diluted with EtOAc (10 mL) and 1 M HCl (15 mL). The layers were separated and the aq layer was extracted with EtOAc (2×10 mL). The combined organic extracts were washed with water, brine, dried over Na₂SO₄, filtered and concentrated to give a brown residue. This residue was purified via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 55-95% B over 12 minutes, then a 5-minute hold at 100% B; Flow: 20 mL/min. Fractions containing the desired product were combined and dried via centrifugal evaporation to give 5-(3-(bicyclo[1.1.1]pentan-1-ylcarbamoyl)phenyl)-2-(4-fluorophenyl)-N-methyl-6-(3,3,3-trifluoropropyl)furo[2,3-b]pyridine-3-carboxamide as a white solid (18 mg, 0.032 mmol, 53% yield) consistent by LC/MS and ¹H NMR.

LCMS: m/e 552 (M+H)⁺ LCMS retention time: 3.55 min. (Column: Phenomenex-Luna 50×2.0 mm 3 u. Solvent A=90% Water: 10% Acetonitrile: 0.1% TFA. Solvent B=10% Water: 90% Acetonitrile: 0.1% TFA. Start % B=0. Final % B=100. Gradient Time=4 min. Hold time=1 min. Flow Rate=0.8 mL/min.).

¹H NMR (400 MHz, DMSO-d₆) 9.06 (s, 1H), 8.51 (q, J=4.1 Hz, 1H), 8.10-8.02 (m, 2H), 7.96 (s, 1H), 7.93 (s, 2H), 7.64-7.57 (m, 2H), 7.46-7.38 (m, 2H), 3.01 (dd, J=9.0, 6.5 Hz, 2H), 2.81 (d, J=4.5 Hz, 3H), 2.79-2.69 (m, 2H), 2.47 (s, 1H), 2.09 (s, 6H).

Preparation of 5-(3-(bicyclo[1.1.1]pentan-1-ylcarbamoyl)phenyl)-6-((2,2-difluoroethyl)amino)-2-(4-fluorophenyl)-N-methylfuro[2,3-b]pyridine-3-carboxamide

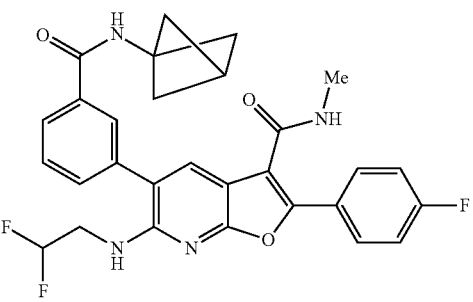

Chemical Formula: C29H25F3N4O3
Molecular Weight: 534.53

Sodium 2-methylbutan-2-olate (34 mg, 0.31 mmol), 5-(3-(bicyclo[1.1.1]pentan-1-ylcarbamoyl)phenyl)-6-chloro-2-(4-fluorophenyl)-N-methylfuro[2,3-b]pyridine-3-carboxamide (30 mg, 0.061 mmol), 2,2-difluoroethanamine (25 mg, 0.31 mmol), Chloro[2-(dicyclohexylphosphino)-3,6-dimethoxy-2',4',6'-triisopropyl-1,1'-biphenyl][2-(2-aminoethyl)phenyl]palladium(II) (5 mg, 6 μmol) were combined, degassed, and taken up in dioxane (1.2 ml) at rt and then was heated to 90° C. for 15 min. The reaction was then diluted with EtOAc and washed with 1M HCl aq, and sat NaCl aq. The organic phase was concentrated and the crude material was purified via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 20-100% B over 20 minutes, then a 4-minute hold at 100% B; Flow: 20 mL/min. Fractions containing the desired product were combined and dried via centrifugal evaporation. The yield of the product was 14.5 mg, and its estimated purity by LCMS analysis was 98%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Proton NMR was acquired in deuterated DMSO.

¹H NMR (500 MHz, DMSO-d6) 9.04 (s, 1H), 8.41-8.31 (m, 1H), 7.97-7.90 (m, 2H), 7.89-7.83 (m, 2H), 7.64-7.60 (m, 1H), 7.58 (d, J=1.8 Hz, 2H), 7.33 (t, J=8.9 Hz, 2H), 6.40 (t, J=6.0 Hz, 1H), 6.31-6.01 (m, 1H), 3.79-3.73 (m, 2H), 2.78 (d, J=4.6 Hz, 3H), 2.45 (s, 1H), 2.08 (s, 6H).

Preparation of 5-(3-(bicyclo[1.1.1]pentan-1-ylcarbamoyl)phenyl)-2-(4-fluorophenyl)-N-methyl-6-((2,2,2-trifluoroethyl)amino)furo[2,3-b]pyridine-3-carboxamide 5-(3-(bicyclo[1.1.1]pentan-1-ylcarbamoyl)-4-methoxyphenyl)-6-((2,2-difluoroethyl)amino)-2-(4-fluorophenyl)-N-methylfuro[2,3-b]pyridine-3-carboxamide

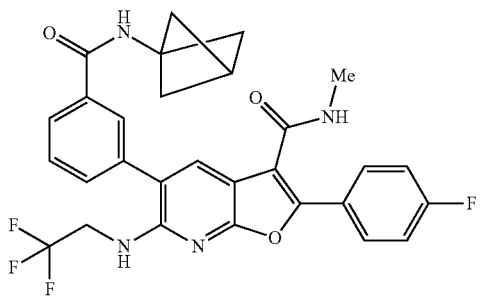

Chemical Formula: $C_{29}H_{24}F_4N_4O_3$
Molecular Weight: 552.52

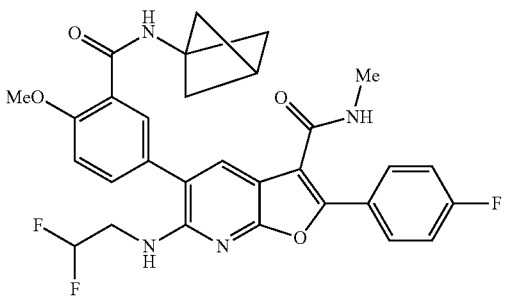

Chemical Formula: $C_{30}H_{27}F_3N_4O_4$
Molecular Weight: 564.55

Sodium 2-methylbutan-2-olate (34 mg, 0.31 mmol), 5-(3-(bicyclo[1.1.1]pentan-1-ylcarbamoyl)phenyl)-6-chloro-2-(4-fluorophenyl)-N-methylfuro[2,3-b]pyridine-3-carboxamide (30 mg, 0.061 mmol), 2,2,2-trifluoroethanamine (30 mg, 0.31 mmol), Chloro[2-(dicyclohexylphosphino)-3,6-dimethoxy-2',4',6'-triisopropyl-1,1'-biphenyl][2-(2-aminoethyl)phenyl]palladium(II) (5 mg, 6 μmol) were combined, degassed, and taken up in dioxane (1.2 ml) at rt and then was heated to 90° C. for 15 min. The reaction was then diluted with EtOAc and washed with 1M HCl aq, and sat NaCl aq. The organic phase was concentrated and the crude material was purified via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 50-90% B over 12 minutes, then a 5-minute hold at 100% B; Flow: 20 mL/min. Fractions containing the desired product were combined and dried via centrifugal evaporation. The yield of the product was 16.2 mg, and its estimated purity by LCMS analysis was 98%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Proton NMR was acquired in deuterated DMSO.

$^1$H NMR (500 MHz, DMSO-d6) 9.04 (s, 1H), 8.38 (d, J=4.6 Hz, 1H), 7.94 (dd, J=8.9, 5.5 Hz, 2H), 7.87 (m, 2H), 7.65 (s, 1H), 7.60-7.53 (m, 2H), 7.33 (t, J=8.9 Hz, 2H), 6.57 (t, J=6.3 Hz, 1H), 4.25-4.08 (m, 2H), 2.78 (d, J=4.6 Hz, 3H), 2.45 (s, 1H), 2.08 (s, 6H).

Step 1. Preparation of 5-(6-chloro-2-(4-fluorophenyl)-3-(methylcarbamoyl)furo[2,3-b]pyridin-5-yl)-2-methoxybenzoic acid

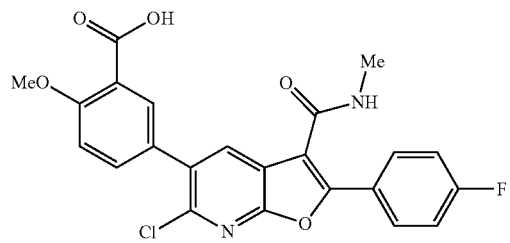

Chemical Formula: $C_{23}H_{16}ClFN_2O_5$
Molecular Weight: 454.83

A mixture of 5-bromo-6-chloro-2-(4-fluorophenyl)-N-methylfuro[2,3-b]pyridine-3-carboxamide (1.00 g, 2.61 mmol), 5-borono-2-methoxybenzoic acid (562 mg, 2.87 mmol), Pd(Ph₃P)₄ (301 mg, 0.261 mmol) and cesium carbonate (1.27 g, 3.91 mmol) was degassed and diluted with water (3.1 mL) and DMF (31 mL). The mixture was degassed and heated to 65° C. under N₂. The reaction was allowed to stir at 65° C. for 16 h. The mixture was diluted with EtOAc and washed with 1M HCl aq, and sat NaCl. The organic phase was dried over $Na_2SO_4$, filtered and concentrated. The residue was triturated with DCM to give the expected product 5-(6-chloro-2-(4-fluorophenyl)-3-(methylcarbamoyl)furo[2,3-b]pyridin-5-yl)-2-methoxybenzoic acid (890 mg, 1.96 mmol, 75% yield) consistent by LCMS and NMR.

LC-MS retention time: 2.46 min; m/z (MH+): 455. LC data was recorded on a Shimadzu LC-10AS liquid chromatograph equipped with a Phenomenex-Luna 3 u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 3 min, a hold time of 1 min, and an analysis time of 4 min where solvent A was 5% MeOH/95% H₂O/10 mM ammonium acetate and solvent B was 5% H₂O/95%

MeOH/10 mM ammonium acetate. MS data was determined using a Micromass Platform for LC in electrospray mode.

1H NMR (400 MHz, DMSO-d6) 12.82 (br. s., 1H), 8.58-8.50 (m, 1H), 8.14 (s, 1H), 8.10-8.02 (m, 2H), 7.79 (d, J=2.3 Hz, 1H), 7.69 (dd, J=8.5, 2.5 Hz, 1H), 7.47-7.38 (m, 2H), 7.28 (d, J=8.8 Hz, 1H), 3.90 (s, 3H), 2.83 (d, J=4.8 Hz, 3H)

Step 2. Preparation of 5-(6-((2,2-difluoroethyl)amino)-2-(4-fluorophenyl)-3-(methylcarbamoyl)furo[2,3-b]pyridin-5-yl)-2-methoxybenzoic acid

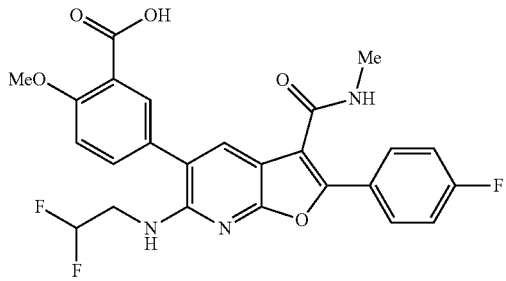

Chemical Formula: C$_{25}$H$_{20}$F$_3$N$_3$O$_5$
Molecular Weight: 499.44

Sodium 2-methylbutan-2-olate (242 mg, 2.20 mmol), 5-(6-chloro-2-(4-fluorophenyl)-3-(methylcarbamoyl)furo[2,3-b]pyridin-5-yl)-2-methoxybenzoic acid (200 mg, 0.440 mmol), 2,2-difluoroethanamine (178 mg, 2.20 mmol), Chloro[2-(dicyclohexylphosphino)-3,6-dimethoxy-2',4',6'-triisopropyl-1,1'-biphenyl][2-(2-aminoethyl)phenyl]palladium(II) (35 mg, 0.044 mmol) were combined in dioxane (9 mL) at 100° C. in a seal MW vial under inert atmosphere, N$_2$ (g). The reaction was allowed to stir for 2 hrs. LCMS showed major peak with expected M+H=500. The mixture was diluted with EtOAc and washed with 1M HCl (aq) followed by sat NaCl (aq). The organic phase was concentrated and purified on silica gel (Biotage, MeOH/DCM 1% AcOH gradient, fraction collection at λ=254 nm) to give the expected product 5-(6-((2,2-difluoroethyl)amino)-2-(4-fluorophenyl)-3-(methylcarbamoyl)furo[2,3-b]pyridin-5-yl)-2-methoxybenzoic acid (138 mg, 0.276 mmol, 63% yield) consistent by LCMS and NMR.

LC-MS retention time: 2.55 min; m/z (MH+): 500. LC data was recorded on a Shimadzu LC-10AS liquid chromatograph equipped with a Phenomenex-Luna 3 u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 3 min, a hold time of 1 min, and an analysis time of 4 min where solvent A was 5% MeOH/95% H$_2$O/10 mM ammonium acetate and solvent B was 5% H$_2$O/95% MeOH/10 mM ammonium acetate. MS data was determined using a Micromass Platform for LC in electrospray mode.

$_1$H NMR (400 MHz, DMSO-d6) 12.73 (br. s., 1H), 8.35 (q, J=4.4 Hz, 1H), 8.00-7.95 (m, 2H), 7.70 (d, J=2.3 Hz, 1H), 7.60-7.54 (m, 2H), 7.36-7.30 (m, 2H), 7.28 (d, J=8.8 Hz, 1H), 6.46 (t, J=5.9 Hz, 1H), 6.35-6.01 (m, 1H), 3.89 (s, 3H), 3.80-3.68 (m, 2H), 2.79 (d, J=4.8 Hz, 3H)

Step 3. Preparation of the Title Compound

HATU (23 mg, 0.060 mmol) was added to a stirring solution of 5-(6-((2,2-difluoroethyl)amino)-2-(4-fluorophenyl)-3-(methylcarbamoyl)furo[2,3-b]pyridin-5-yl)-2-methoxybenzoic acid (20 mg, 0.040 mmol), bicyclo[1.1.1]pentan-1-amine hydrochloride (14 mg, 0.12 mmol), DIEA (28 µl, 0.16 mmol) in DMF (801 µl) at rt. LCMS showed approximately 80% conversion after 1 hr. An additional 1.5 equiv of both amine and HATU was added and the reaction was allowed to stir for 1 hr. No change was observed by LCMS. The reaction mixture was directly purified via preparative LC/MS with the following conditions: Column: Waters XBridge C18, 19×150 mm, 5-µm particles; Guard Column: Waters XBridge C18, 19×10 mm, 5-µm particles; Mobile Phase A: water with 20-mM ammonium acetate; Mobile Phase B: 95:5 acetonitrile:water with 20-mM ammonium acetate; Gradient: 20-100% B over 19 minutes, then a 5-minute hold at 100% B; Flow: 20 mL/min. Fractions containing the desired product, M+H=565, were combined and dried via centrifugal evaporation. The yield of the product was 11 mg, and its estimated purity by LCMS analysis was 95%. Two analytical LC/MS injections were used to determine the final purity. Injection 1 conditions: Column: Waters BEH C18, 2.0×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. LC-MS retention time: 3.06 min. Injection 2 conditions: Column: Waters BEH C18, 2.0×50 mm, 1.7-µm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. LC-MS retention time: 4.09 min. Proton NMR was acquired in deuterated DMSO.

$^1$H NMR (500 MHz, DMSO-d6) 8.56 (s, 1H), 8.41-8.33 (m, 1H), 7.99-7.94 (m, 2H), 7.74-7.68 (m, 1H), 7.57 (s, 1H), 7.54-7.51 (m, 1H), 7.37-7.31 (m, 2H), 7.29-7.25 (m, 1H), 6.42-6.36 (m, 1H), 6.32-6.05 (m, 1H), 3.93 (s, 3H), 3.80-3.69 (m, 2H), 2.79 (d, J=4.6 Hz, 3H), 2.46 (s, 1H), 2.09 (s, 6H).

Preparation of 5-(3-(bicyclo[1.1.1]pentan-1-ylcarbamoyl)-4-methoxyphenyl)-2-(4-fluorophenyl)-N-methyl-6-(3,3,3-trifluoropropyl)furo[2,3-b]pyridine-3-carboxamide

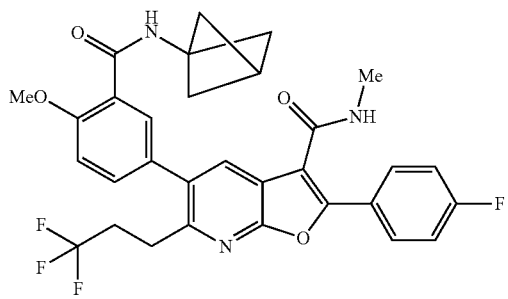

Chemical Formula: C$_{31}$H$_{27}$F$_4$N$_3$O$_4$
Molecular Weight: 581.56

Step 1: Preparation of 5-(3-(bicyclo[1.1.1]pentan-1-ylcarbamoyl)-4-methoxyphenyl)-6-chloro-2-(4-fluorophenyl)-N-methylfuro[2,3-b]pyridine-3-carboxamide

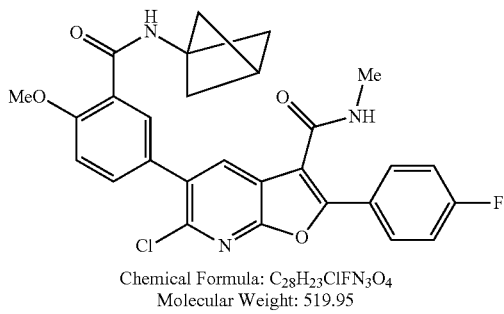 [SMILES: CNC(=O)c1c(-c2ccc(F)cc2)oc2nc(Cl)c(-c3ccc(OC)c(C(=O)NC45CC(C4)C5)c3)cc12]

Chemical Formula: $C_{28}H_{23}ClFN_3O_4$
Molecular Weight: 519.95

5-(6-chloro-2-(4-fluorophenyl)-3-(methylcarbamoyl)furo[2,3-b]pyridin-5-yl)-2-methoxybenzoic acid (60 mg, 0.13 mmol) was taken up in DMF (1.3 mL) and treated with N-ethyl-N-isopropylpropan-2-amine (92 µl, 0.53 mmol), bicyclo[1.1.1]pentan-1-amine dihydrochloride (41 mg, 0.26 mmol) followed by 2-(3H-[1,2,3]triazolo[4,5-b]pyridin-3-yl)-1,1,3,3-tetramethylisouronium hexafluorophosphate(V) (75 mg, 0.20 mmol). The reaction was allowed to stir for 4 h. The reaction was concentrated and was purified on silica gel (Biotage, EtOAc/hexanes gradient, fraction collection at λ=254 nm) to give the expected product 5-(3-(bicyclo[1.1.1]pentan-1-ylcarbamoyl)-4-methoxyphenyl)-6-chloro-2-(4-fluorophenyl)-N-methylfuro[2,3-b]pyridine-3-carboxamide (47 mg, 0.090 mmol, 69% yield) consistent by LCMS.

LC-MS retention time: 2.98 min; m/z (MH+): 520. LC data was recorded on a Shimadzu LC-10AS liquid chromatograph equipped with a Phenomenex-Luna 3 u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 3 min, a hold time of 1 min, and an analysis time of 4 min where solvent A was 5% MeOH/95% H₂O/10 mM ammonium acetate and solvent B was 5% H₂O/95% MeOH/10 mM ammonium acetate. MS data was determined using a Micromass Platform for LC in electrospray mode.

Step 2: Preparation of the Titled Compound 5-(3-(bicyclo[1.1.1]pentan-1-ylcarbamoyl)-4-methoxyphenyl)-6-chloro-2-(4-fluorophenyl)-N-methylfuro[2,3-b]pyridine-3-carboxamide (31 mg, 0.060 mmol), 3,3,3-trifluoropropane-1-trifluoroborate (61 mg, 0.30 mmol), dicyclohexyl(2',6'-diisopropoxy-[1,1'-biphenyl]-2-yl)phosphine (11 mg, 0.024 mmol), PdOAc₂ (2.7 mg, 0.012 mmol), cesium carbonate (58 mg, 0.18 mmol) were degassed and backfilled with N₂ then dissolved in toluene (5.4 mL) and water (540 µl) at rt then heated at 80° C. for 16 h. The mixture was diluted with EtOAc and washed with 1M HCl, and sat NaCl. The organic phase was concentrated, diluted with DMF/MeOH and then directly purified via preparative LC/MS with the following conditions: Column: Waters XBridge C18, 19×200 mm, 5-µm particles; Guard Column: Waters XBridge C18, 19×10 mm, 5-µm particles; Mobile Phase A: water with 20-mM ammonium acetate; Mobile Phase B: 95:5 acetonitrile:water with 20-mM ammonium acetate; Gradient: 60-100% B over 12 minutes, then a 5-minute hold at 100% B; Flow: 20 mL/min. Fractions containing the desired product were combined and dried via centrifugal evaporation. The yield of the product was 21 mg, and its estimated purity by LCMS analysis was 100%. Two analytical LC/MS injections were used to determine the final purity. Injection 1 conditions: Column: Waters BEH C18, 2.0×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Retention time=3.38. Injection 2 conditions: Column: Waters BEH C18, 2.0×50 mm, 1.7-µm particles; Mobile Phase A: 5:95 methanol:water with 10 mM ammonium acetate; MobilePhase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Retention time=4.38. M+H=582. Proton NMR was acquired in deuterated DMSO.

¹H NMR (500 MHz, DMSO-d6) δ 8.58 (s, 1H), 8.50 (q, J=4.3 Hz, 1H), 8.10-8.01 (m, 2H), 7.89 (s, 1H), 7.68 (d, J=2.4 Hz, 1H), 7.55 (dd, J=8.4, 2.3 Hz, 1H), 7.41 (t, J=8.9 Hz, 2H), 7.26 (d, J=8.9 Hz, 1H), 3.94 (s, 3H), 3.06-2.98 (m, 2H), 2.82 (d, J=4.6 Hz, 3H), 2.79-2.69 (m, 2H), 2.46 (s, 1H), 2.09 (s, 6H).

Preparation of 5-(3-(bicyclo[1.1.1]pentan-1-ylcarbamoyl)-4-methoxyphenyl)-2-(4-fluorophenyl)-N-methyl-6-((2,2,2-trifluoroethyl)amino)furo[2,3-b]pyridine-3-carboxamide

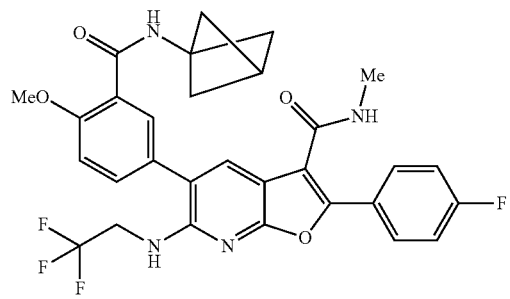

Chemical Formula: $C_{30}H_{26}F_4N_4O_4$
Molecular Weight: 582.55

Sodium 2-methylbutan-2-olate (16 mg, 0.14 mmol), 5-(3-(bicyclo[1.1.1]pentan-1-ylcarbamoyl)-4-methoxyphenyl)-6-chloro-2-(4-fluorophenyl)-N-methylfuro[2,3-b]pyridine-3-carboxamide (15 mg, 0.029 mmol), 2,2,2-trifluoroethanamine (14 mg, 0.14 mmol), and Chloro[2-(dicyclohexylphosphino)-3,6-dimethoxy-2',4',6'-triisopropyl-1,1'-biphenyl][2-(2-aminoethyl)phenyl]palladium(II) (2.3 mg, 2.9 µmol) were combined, degassed, charged with N₂, taken up in dioxane (600 µl) at rt and then heated to 90° C. LCMS at 15 min showed major peak with M+H matching that of the expected product. The reaction was diluted with EtOAc and washed with 1M HCl aq, and sat NaCl. The organic phase was concentrated and the crude material was purified via preparative LC/MS with the following conditions: Column: Waters XBridge C18, 19×200 mm, 5-µm particles; Guard Column: Waters XBridge C18, 19×10 mm, 5-µm particles; Mobile Phase A: water with 20-mM ammonium acetate; Mobile Phase B: 95:5 acetonitrile:water with 20-mM ammonium acetate; Gradient: 30-100% B over 20 minutes, then a 4-minute hold at 100% B; Flow: 20 mL/min. Fractions containing the desired product were combined and dried via centrifugal evaporation. The yield of the product was 8 mg, and its estimated purity by LCMS analysis was 100%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Retention time=3.23. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Retention time=4.18. M+H=583. Proton NMR was acquired in deuterated DMSO.

$^1$H NMR (500 MHz, DMSO-d6) 8.55 (s, 1H), 8.37 (q, J=4.5 Hz, 1H), 7.97 (dd, J=8.9, 5.5 Hz, 2H), 7.72 (d, J=2.4 Hz, 1H), 7.61 (s, 1H), 7.52 (dd, J=8.4, 2.3 Hz, 1H), 7.34 (t, J=9.0 Hz, 2H), 7.28 (d, J=8.9 Hz, 1H), 6.56 (t, J=6.4 Hz, 1H), 4.24-4.11 (m, 2H), 3.94 (s, 3H), 2.79 (d, J=4.6 Hz, 3H), 2.46 (s, 1H), 2.09 (s, 6H)

5-(3-(bicyclo[1.1.1]pentan-1-ylcarbamoyl)phenyl)-2-(4-fluorophenyl)-N-methyl-6-propylfuro[2,3-b]pyridine-3-carboxamide

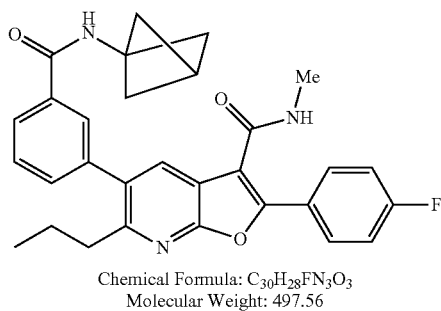 [SMILES: CCCc1nc2oc(-c3ccc(F)cc3)c(C(=O)NC)c2cc1-c1cccc(C(=O)NC23CC(C2)C3)c1]

Chemical Formula: $C_{30}H_{28}FN_3O_3$
Molecular Weight: 497.56

Step 1. (E)-3-(2-(4-fluorophenyl)-3-(methylcarbamoyl)-6-(prop-1-en-1-yl)furo[2,3-b]pyridin-5-yl)benzoic acid

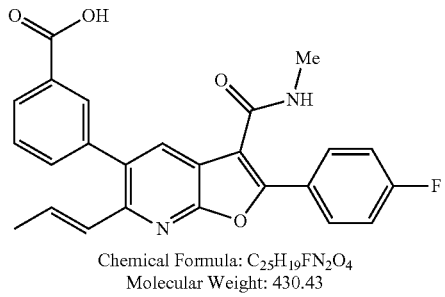 [SMILES: C/C=C/c1nc2oc(-c3ccc(F)cc3)c(C(=O)NC)c2cc1-c1cccc(C(=O)O)c1]

Chemical Formula: $C_{25}H_{19}FN_2O_4$
Molecular Weight: 430.43

3-(6-chloro-2-(4-fluorophenyl)-3-(methylcarbamoyl)furo[2,3-b]pyridin-5-yl)benzoic acid (100 mg, 0.235 mmol), K$_3$PO$_4$ (375 mg, 1.77 mmol), sodium 6-(dicyclohexylphosphino)-2',6'-dimethoxy-[1,1'-biphenyl]-3-sulfonate (24 mg, 0.047 mmol), diacetoxypalladium (5.3 mg, 0.024 mmol), (E)-6-methyl-2-(prop-1-en-1-yl)-1,3,6,2-dioxazaborocane-4,8-dione (93 mg, 0.47 mmol) were combined in a microwave vial, degassed and backfilled with N$_2$ then dissolved in dioxane (4 mL) and water (800 μl) at rt then heated to 100° C. for 2 h. LCMS showed a major peak with M+H of 431. The reaction was diluted with EtOAc and washed with 1M HCl aq, and sat NaCl. The organic phase was dried over Na$_2$SO$_4$, filtered, concentrated and triturated with DCM to give the expected product (E)-3-(2-(4-fluorophenyl)-3-(methylcarbamoyl)-6-(prop-1-en-1-yl)furo[2,3-b]pyridin-5-yl)benzoic acid (100 mg, 0.24 mmol, quant conversion) crude consistent by LCMS.

LC-MS retention time: 2.67 min; m/z (MH+): 431. LC data was recorded on a Shimadzu LC-10AS liquid chromatograph equipped with a Phenomenex-Luna 3 u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 3 min, a hold time of 1 min, and an analysis time of 4 min where solvent A was 5% MeOH/95% H$_2$O/10 mM ammonium acetate and solvent B was 5% H$_2$O/95% MeOH/10 mM ammonium acetate. MS data was determined using a Micromass Platform for LC in electrospray mode.

Step 2. Preparation of 3-(2-(4-fluorophenyl)-3-(methylcarbamoyl)-6-propylfuro[2,3-b]pyridin-5-yl)benzoic acid

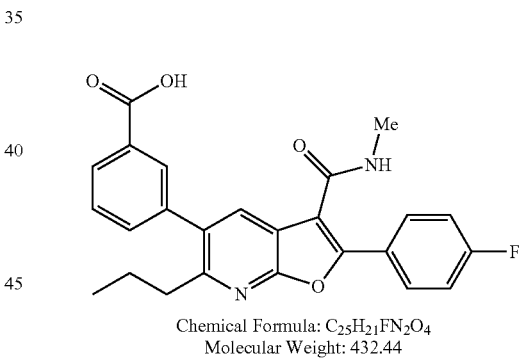

Chemical Formula: $C_{25}H_{21}FN_2O_4$
Molecular Weight: 432.44

10% Pd/C (155 mg, 0.145 mmol) was added to a stirring slurry of (E)-3-(2-(4-fluorophenyl)-3-(methylcarbamoyl)-6-(prop-1-en-1-yl)furo[2,3-b]pyridin-5-yl)benzoic acid (125 mg, 0.290 mmol) in 1:1:1:1 mixture of THF/MeOH/EtOAc/AcOH (20 mL) at rt. The reaction was placed in a Parr hydrogenation apparatus "bomb" and charged with 100 PSI of H$_2$ and allowed to stir overnight. LCMS showed the peak with M+H of 433. Celite was added to the reaction and it was filtered through a pad of Celite and washed successively with EtOAc/MeOH/DCM. The resultant filtrate was concentrated to give the expected product 3-(2-(4-fluorophenyl)-3-(methylcarbamoyl)-6-propylfuro[2,3-b]pyridin-5-yl)benzoic acid (120 mg, 0.277 mmol, 96% yield) consistent by LCMS and NMR.

LC-MS retention time: 2.61 min; m/z (MH+): 433. LC data was recorded on a Shimadzu LC-10AS liquid chromatograph equipped with a Phenomenex-Luna 3 u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 3 min, a hold time of 1 min, and an analysis time of 4 min where solvent A was 5% MeOH/95% H$_2$O/10 mM ammonium acetate and solvent B was 5% H$_2$O/95% MeOH/10 mM ammonium acetate. MS data was determined using a Micromass Platform for LC in electrospray mode.

$^1$H NMR (400 MHz, DMSO-d6) 13.18 (br. s, 1H), 8.54-8.46 (m, 1H), 8.09-8.03 (m, 2H), 8.02-7.98 (m, 1H), 7.94 (s, 1H), 7.90 (s, 1H), 7.67-7.56 (m, 2H), 7.45-7.36 (m, 2H), 2.81 (d, J=4.8 Hz, 3H), 2.76-2.69 (m, 2H), 1.71-1.63 (m, 2H), 0.80 (t, J=7.4 Hz, 3H).

Step 3. Preparation of the Title Compound

HATU (42 mg, 0.11 mmol) was added to a stirring solution of 3-(2-(4-fluorophenyl)-3-(methylcarbamoyl)-6-propylfuro[2,3-b]pyridin-5-yl)benzoic acid (32 mg, 0.074 mmol), bicyclo[1.1.1]pentan-1-amine hydrochloride (27 mg, 0.22 mmol), DIEA (52 µl, 0.30 mmol) in DMF (1 mL) at rt. The reaction was allowed to stir for 1 h. LCMS showed approximately 90% conversion. An additional 1.5 equiv of both amine and HATU was added and the reaction was allowed to stir for 1 h. No change was observed by LCMS. The crude material was purified via preparative LC/MS with the following conditions: Column: Waters XBridge C18, 19×200 mm, 5-µm particles; Guard Column: Waters XBridge C18, 19×10 mm, 5-µm particles; Mobile Phase A: water with 20-mM ammonium acetate; Mobile Phase B: 95:5 methanol:water with 20-mM ammonium acetate; Gradient: 55-95% B over 20 minutes, then a 5-minute hold at 100% B; Flow: 20 mL/min. Fractions containing the desired product were combined and dried via centrifugal evaporation. The yield of the product was 15 mg (42% yield), and its estimated purity by LCMS analysis was 92%. Two analytical LC/MS injections were used to determine the final purity. Injection 1 conditions: Column: Waters BEH C18, 2.0×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. LCMS retention time: 3.29. Injection 2 conditions: Column: Waters BEH C18, 2.0×50 mm, 1.7-µm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. LCMS retention time: 3.61. M+H=498. Proton NMR was acquired in deuterated DMSO.

$^1$H NMR (500 MHz, DMSO-d6) 9.06 (s, 1H), 8.50-8.45 (m, 1H), 8.08-8.02 (m, 2H), 7.92-7.88 (m, 2H), 7.87-7.85 (m, 1H), 7.60-7.54 (m, 2H), 7.44-7.38 (m, 2H), 2.83-2.78 (m, 3H), 2.75-2.71 (m, 2H), 2.46 (s, 1H), 2.09 (s, 6H), 1.70-1.61 (m, 2H), 0.82-0.76 (m, 3H).

Preparation of 5-(3-(bicyclo[1.1.1]pentan-1-ylcarbamoyl)-4-fluorophenyl)-2-(4-fluorophenyl)-N-methyl-6-propylfuro[2,3-b]pyridine-3-carboxamide

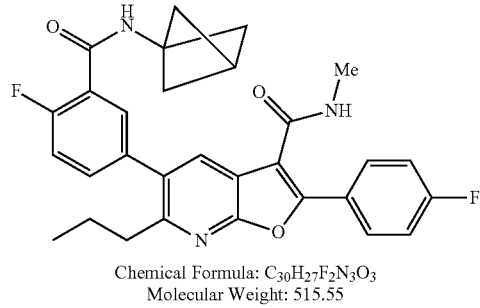 [SMILES: CCCc1nc2oc(-c3ccc(F)cc3)c(C(=O)NC)c2cc1-c1ccc(F)c(C(=O)NC23CC(C2)C3)c1]

Chemical Formula: C$_{30}$H$_{27}$F$_2$N$_3$O$_3$
Molecular Weight: 515.55

Step 1: Preparation of (E)-5-(3-(bicyclo[1.1.1]pentan-1-ylcarbamoyl)-4-fluorophenyl)-2-(4-fluorophenyl)-N-methyl-6-(prop-1-en-1-yl)furo[2,3-b]pyridine-3-carboxamide

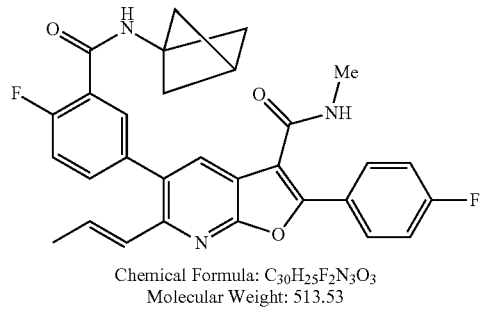 [SMILES: C/C=C/c1nc2oc(-c3ccc(F)cc3)c(C(=O)NC)c2cc1-c1ccc(F)c(C(=O)NC23CC(C2)C3)c1]

Chemical Formula: C$_{30}$H$_{25}$F$_2$N$_3$O$_3$
Molecular Weight: 513.53

5-(3-(bicyclo[1.1.1]pentan-1-ylcarbamoyl)-4-fluorophenyl)-6-chloro-2-(4-fluorophenyl)-N-methylfuro[2,3-b]pyridine-3-carboxamide (65 mg, 0.13 mmol), K$_3$PO$_4$ (204 mg, 0.960 mmol), sodium 6-(dicyclohexylphosphino)-2',6'-dimethoxy-[1,1'-biphenyl]-3-sulfonate (13 mg, 0.026 mmol), diacetoxypalladium (2.9 mg, 0.013 mmol), (E)-6-methyl-2-(prop-1-en-1-yl)-1,3,6,2-dioxazaborocane-4,8-dione (50 mg, 0.26 mmol) were combined in a microwave vial, degassed and backfilled with N$_2$ then dissolved in dioxane (2.1 mL) and water (0.43 mL) at rt then heated to 80° C. for 2 h. LCMS showed major peak with M+H of the expected product. The reaction was diluted with EtOAc and washed with 1M HCl aq, and sat NaCl. The organic phase was dried over Na$_2$SO$_4$, filtered and concentrated and was purified on silica gel (Biotage, EtOAc/hexanes gradient, fraction collection at λ=254 nm) to give the expected product (E)-5-(3-(bicyclo[1.1.1]pentan-1-ylcarbamoyl)-4-fluorophenyl)-2-(4-fluorophenyl)-N-methyl-6-(prop-1-en-1-yl)furo[2,3-b]pyridine-3-carboxamide (50 mg, 0.097 mmol, 76% yield) consistent by LCMS.

LC-MS retention time: 3.22 min; m/z (MH+): 514. LC data was recorded on a Shimadzu LC-10AS liquid chromatograph equipped with a Phenomenex-Luna 3 u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 3 min, a hold time of 1 min, and an analysis time of 4 min where solvent A was 5% MeOH/95% H$_2$O/10 mM ammonium acetate and solvent B was 5% H$_2$O/95% MeOH/10 mM ammonium acetate. MS data was determined using a Micromass Platform for LC in electrospray mode.

Step 2: Preparation of the Titled Compound

10% Pd/C (20 mg, 0.019 mmol) was added to a stirring solution of (E)-5-(3-(bicyclo[1.1.1]pentan-1-ylcarbamoyl)-4-fluorophenyl)-2-(4-fluorophenyl)-N-methyl-6-(prop-1-en-1-yl)furo[2,3-b]pyridine-3-carboxamide (50 mg, 0.097 mmol) in MeOH (1 mL) at rt under N$_2$. The reaction was allowed to stir 16 h under a balloon of H$_2$. LCMS showed a mixture of starting material and product. The atmosphere was replaced with N$_2$ and an additional amount of 10% Pd/C (20 mg, 0.019 mmol) was added and the reaction was allowed to stir 16 h under a balloon of H$_2$. LCMS showed the peak with M+H of 516. Celite was added to the reaction and the mixture was filtered through a pad of Celite and washed successively with EtOAc/DCM. The filtrate was concentrated. The crude material was purified via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 methanol:water with 20-mM ammonium acetate; Gradient: 60-100% B over 20 minutes, then a 5-minute hold at 100% B; Flow: 20 mL/min. Fractions containing the desired product were combined and dried via centrifugal evaporation. The yield of the product was 14 mg, and its estimated purity by LCMS analysis was 96%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Retention time=3.30. Injection 2 conditions: Column: Waters BEH C18, 2.0×50 mm, 1.7-μm particles; Mobile Phase A: 5:95 methanol:water with 10 mM ammonium acetate; MobilePhase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Retention time=4.19 min. M+H=516. Proton NMR was acquired in deuterated DMSO.

$^1$H NMR (500 MHz, DMSO-d6) 8.95 (s, 1H), 8.47 (d, J=4.6 Hz, 1H), 8.03 (dd, J=9.0, 5.3 Hz, 2H), 7.86 (s, 1H), 7.57-7.49 (m, 2H), 7.44-7.33 (m, 3H), 2.80 (d, J=4.6 Hz, 3H), 2.75-2.68 (m, 2H), 2.45 (s, 1H), 2.08 (s, 6H), 1.73-1.60 (m, 2H), 0.85-0.76 (m, 3H)

5-(3-(bicyclo[1.1.1]pentan-1-ylcarbamoyl)-5-fluorophenyl)-2-(4-fluorophenyl)-N-methyl-6-(3,3,3-trifluoropropyl)furo[2,3-b]pyridine-3-carboxamide

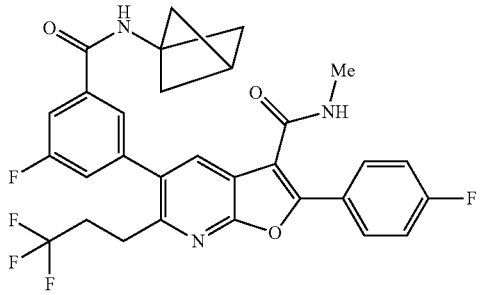

Chemical Formula: C$_{30}$H$_{24}$F$_5$N$_3$O$_3$
Molecular Weight: 569.52

Step 1: 3-(6-chloro-2-(4-fluorophenyl)-3-(methylcarbamoyl)furo[2,3-b]pyridin-5-yl)-5-fluorobenzoic acid

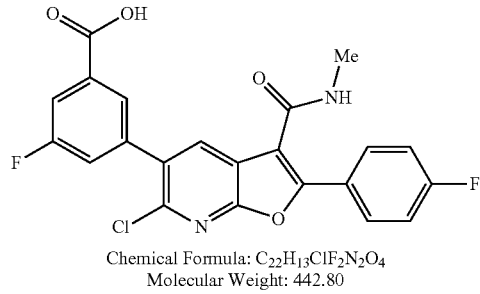 [SMILES: CNC(=O)c1c(-c2ccc(F)cc2)oc2nc(Cl)c(-c3cc(F)cc(C(=O)O)c3)cc12]

Chemical Formula: C$_{22}$H$_{13}$ClF$_2$N$_2$O$_4$
Molecular Weight: 442.80

A mixture of 5-bromo-6-chloro-2-(4-fluorophenyl)-N-methylfuro[2,3-b]pyridine-3-carboxamide (500 mg, 1.30 mmol), 3-borono-5-fluorobenzoic acid (264 mg, 1.43 mmol), Pd(Ph$_3$P)$_4$ (151 mg, 0.130 mmol) and cesium carbonate (637 mg, 1.96 mmol) was degassed and diluted with a water (1.6 mL)/DMF (16 mL) mixture. The mixture was degassed and heated to 65° C. under N$_2$. The reaction was allowed to stir at 65° C. for 16 h. LCMS showed starting material still remained. An additional 0.5 equiv of 3-borono-5-fluorobenzoic acid, Pd(Ph$_3$P)$_4$, and cesium carbonate was added and the reaction was allowed to stir for 3 h. LCMS indicated starting material was consumed. The mixture was diluted with EtOAc and washed with 1M HCl aq, and sat NaCl aq. The organic phase was dried over Na$_2$SO$_4$, filtered and concentrated and then triturated with DCM to give the expected product 3-(6-chloro-2-(4-fluorophenyl)-3-(methylcarbamoyl)furo[2,3-b]pyridin-5-yl)-5-fluorobenzoic acid (380 mg, 0.858 mmol, 66% yield) consistent by LCMS and NMR.

LC-MS retention time: 2.74 min; m/z (MH+): 442. LC data was recorded on a Shimadzu LC-10AS liquid chromatograph equipped with a Phenomenex-Luna 3 u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 3 min, a hold time of 1 min, and an analysis time of 4 min where solvent A was 5% MeOH/95% H$_2$O/10 mM ammonium acetate and solvent B was 5% H$_2$O/95% MeOH/10 mM ammonium acetate. MS data was determined using a Micromass Platform for LC in electrospray mode.

$^1$H NMR (400 MHz, DMSO-d6) δ 13.51 (br. s., 1H), 8.58-8.53 (m, 1H), 8.26 (s, 1H), 8.09-8.04 (m, 2H), 7.94 (t, J=1.5 Hz, 1H), 7.81-7.71 (m, 2H), 7.46-7.40 (m, 2H), 2.83 (d, J=4.8 Hz, 3H)

Step 2: Preparation of 5-(3-(bicyclo[1.1.1]pentan-1-ylcarbamoyl)-5-fluorophenyl)-6-chloro-2-(4-fluorophenyl)-N-methylfuro[2,3-b]pyridine-3-carboxamide

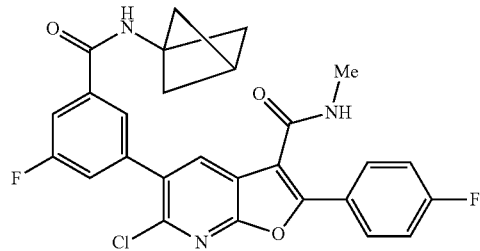

Chemical Formula: C$_{27}$H$_{20}$ClF$_2$N$_3$O$_3$
Molecular Weight: 507.92

3-(6-chloro-2-(4-fluorophenyl)-3-(methylcarbamoyl)furo [2,3-b]pyridin-5-yl)-5-fluorobenzoic acid (50 mg, 0.11 mmol) was taken up in DMF (1 mL) and treated with N-ethyl-N-isopropylpropan-2-amine (79 µl, 0.45 mmol), bicyclo[1.1.1]pentan-1-amine dihydrochloride (35 mg, 0.23 mmol) followed by 2-(3H-[1,2,3]triazolo[4,5-b]pyridin-3-yl)-1,1,3,3-tetramethylisouronium hexafluorophosphate(V) (64 mg, 0.17 mmol). The reaction was allowed to stir for 4 h. LCMS Showed a mixture of starting material and desired product. The reaction was concentrated and was purified on silica gel (Biotage, EtOAc/hexanes gradient, fraction collection at λ=254 nm) to give the expected product 5-(3-(bicyclo[1.1.1]pentan-1-ylcarbamoyl)-5-fluorophenyl)-6-chloro-2-(4-fluorophenyl)-N-methylfuro[2,3-b]pyridine-3-carboxamide (33 mg, 0.065 mmol, 58% yield) consistent by LCMS.

LC-MS retention time: 2.27 min; m/z (MH+): 508. LC data was recorded on a Shimadzu LC-10AS liquid chromatograph equipped with a Phenomenex-Luna 3 u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 3 min, a hold time of 1 min, and an analysis time of 4 min where solvent A was 5% MeOH/95% $H_2O$/10 mM ammonium acetate and solvent B was 5% $H_2O$/95% MeOH/10 mM ammonium acetate. MS data was determined using a Micromass Platform for LC in electrospray mode.

Step 3: Preparation of the Titled Compound 5-(3-(bicyclo[1.1.1]pentan-1-ylcarbamoyl)-5-fluorophenyl)-6-chloro-2-(4-fluorophenyl)-N-methylfuro[2,3-b]pyridine-3-carboxamide (33 mg, 0.065 mmol), 3,3,3-trifluoropropane-1-trifluoroborate (66 mg, 0.33 mmol), dicyclohexyl (2',6'-diisopropoxy-[1,1'-biphenyl]-2-yl)phosphine (12 mg, 0.026 mmol), $PdOAc_2$ (2.9 mg, 0.013 mmol), cesium carbonate (64 mg, 0.20 mmol) were combined, degassed and backfilled with $N_2$ (g) then dissolved in Toluene (4 mL) and water (400 µl) at rt then heated at 80° C. for 16 h. The mixture was then diluted with EtOAc and washed with 1M HCl, and sat NaCl. The organic phase was concentrated and the crude material was purified via preparative LC/MS with the following conditions: Column: Waters XBridge C18, 19×200 mm, 5-µm particles; Guard Column: Waters XBridge C18, 19×10 mm, 5-µm particles;
Mobile Phase A: water with 20-mM ammonium acetate; Mobile Phase B: 95:5 acetonitrile:water with 20-mM ammonium acetate; Gradient: 60-100% B over 12 minutes, then a 5-minute hold at100% B; Flow: 20 mL/min. Fractions containing the desired product were combined and dried via centrifugal evaporation. The yield of the product was 16 mg, and its estimated purity by LCMS analysis was 99%. Two analytical LC/MS injections were used to determine the final purity. Injection 1 conditions: Column: Waters BEH C18, 2.0×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Retention time=3.29. Injection 2 conditions: Column: Waters BEH C18, 2.0×50 mm, 1.7-µm particles; Mobile Phase A: 5:95 methanol:water with 10 mM ammonium acetate; MobilePhase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Retention time=4.29. M+H=570. Proton NMR was acquired in deuterated DMSO.

$^1$H NMR (500 MHz, DMSO-d6) δ 9.15 (s, 1H), 8.54-8.48 (m, 1H), 8.06 (dd, J=8.5, 5.5 Hz, 2H), 8.00 (s, 1H), 7.77-7.69 (m, 2H), 7.58 (d, J=9.5 Hz, 1H), 7.42 (t, J=8.9 Hz, 2H), 3.07-2.98 (m, 2H), 2.82 (d, J=4.6 Hz, 3H), 2.80-2.70 (m, 2H), 2.47 (s, 1H), 2.09 (s, 6H)

Preparation of 5-(5-(bicyclo[1.1.1]pentan-1-ylcarbamoyl)pyridin-3-yl)-2-(4-fluorophenyl)-N-methyl-6-(3,3,3-trifluoropropyl)furo[2,3-b]pyridine-3-carboxamide

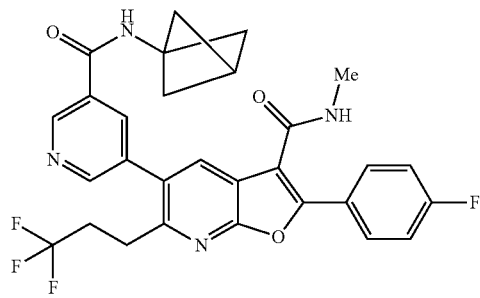

Chemical Formula: $C_{29}H_{24}F_4N_4O_3$
Molecular Weight: 552.52

Step 1: Preparation of 5-(6-chloro-2-(4-fluorophenyl)-3-(methylcarbamoyl)furo[2,3-b]pyridin-5-yl) nicotinic acid

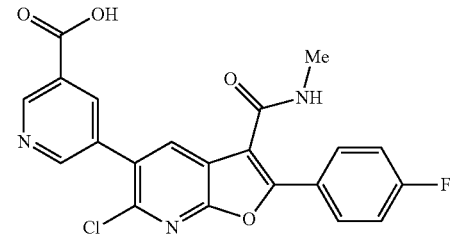

Chemical Formula: $C_{21}H_{13}ClFN_3O_4$
Molecular Weight: 425.80

A mixture of 5-bromo-6-chloro-2-(4-fluorophenyl)-N-methylfuro[2,3-b]pyridine-3-carboxamide (400 mg, 1.04 mmol), 5-borononicotinic acid (191 mg, 1.15 mmol), $Pd(Ph_3P)_4$ (120 mg, 0.104 mmol) and cesium carbonate (510 mg, 1.56 mmol) was degassed and diluted water (1.3 mL)/DMF (13 mL). The mixture was degassed, charges with $N_2$, and heated to 65° C. under $N_2$ atmosphere. The reaction mixture was allowed to stir at 65° C. for 16 h. LCMS showed starting material remained. An additional amount of 5-borononicotinic acid (191 mg, 1.147 mmol) as well as $Pd(Ph_3P)_4$ (60 mg, 0.052 mmol) was added and the reaction was stirred at 65° C. for 16 h. LCMS indicated starting material was consumed. The mixture was partitioned between EtOAc and a sat $NH_4Cl$/sat NaCl mixture. The entire mixture, which contained a ppt, was filtered and washed with $H_2O$. The collected solids were dried under high vacuum to give the expected product 5-(6-chloro-2-(4- fluorophenyl)-3-(methylcarbamoyl)furo[2,3-b]pyridin-5-yl) nicotinic acid (414 mg, 0.972 mmol, 93% yield) consistent by LCMS and NMR.

LC-MS retention time: 2.37 min; m/z (MH+): 426. LC data was recorded on a Shimadzu LC-10AS liquid chromatograph equipped with a Phenomenex-Luna 3 u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 3 min, a hold time of 1 min, and an analysis time of 4 min where solvent A was 5% MeOH/95% $H_2O$/10 mM ammonium acetate and solvent B was 5% $H_2O$/95% MeOH/10 mM ammonium acetate. MS data was determined using a Micromass Platform for LC in electrospray mode.

$^1$H NMR (400 MHz, DMSO-d6) 9.14 (s, 1H), 8.94 (s, 1H), 8.65-8.54 (m, 1H), 8.45-8.40 (m, 1H), 8.33 (s, 1H), 8.08 (dd, J=7.4, 5.4 Hz, 2H), 7.43 (t, J=8.8 Hz, 2H), 2.83 (d, J=4.3 Hz, 3H).

Step 2: Preparation of 5-(5-(bicyclo[1.1.1]pentan-1-ylcarbamoyl)pyridin-3-yl)-6-chloro-2-(4-fluorophenyl)-N-methylfuro[2,3-b]pyridine-3-carboxamide

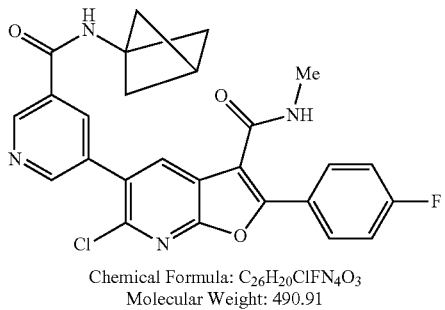 [SMILES: CNC(=O)c1c(-c2ccc(F)cc2)oc2nc(Cl)c(-c3cncc(C(=O)NC45CC(C4)C5)c3)cc12]

Chemical Formula: $C_{26}H_{20}ClFN_4O_3$
Molecular Weight: 490.91

5-(6-chloro-2-(4-fluorophenyl)-3-(methylcarbamoyl)furo[2,3-b]pyridin-5-yl)nicotinic acid (100 mg, 0.235 mmol) was taken up in DMF (2.4 mL) and treated with N-ethyl-N-isopropylpropan-2-amine (246 μl, 1.41 mmol), bicyclo[1.1.1]pentan-1-amine hydrochloride (84 mg, 0.71 mmol) followed by 2-(3H-[1,2,3]triazolo[4,5-b]pyridin-3-yl)-1,1,3,3-tetramethylisouronium hexafluorophosphate(V) (134 mg, 0.352 mmol). The reaction was allowed to stir for 16 h and was then was concentrated and subsequently purified on silica gel (Biotage, MeOH/DCM gradient, fraction collection at λ=254 nm) to give the expected product 5-(5-(bicyclo[1.1.1]pentan-1-ylcarbamoyl)pyridin-3-yl)-6-chloro-2-(4-fluorophenyl)-N-methylfuro[2,3-b]pyridine-3-carboxamide (76 mg, 0.16 mmol, 66% yield) consistent by LCMS.

LC-MS retention time: 3.09 min; m/z (MH+): 491. LC data was recorded on a Shimadzu LC-10AS liquid chromatograph equipped with a Phenomenex-Luna 3 u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 3 min, a hold time of 1 min, and an analysis time of 4 min where solvent A was 5% MeOH/95% $H_2O$/10 mM ammonium acetate and solvent B was 5% $H_2O$/95% MeOH/10 mM ammonium acetate. MS data was determined using a Micromass Platform for LC in electrospray mode.

Step 3: Preparation of the Titled Compound 5-(5-(bicyclo[1.1.1]pentan-1-ylcarbamoyl)pyridin-3-yl)-6-chloro-2-(4-fluorophenyl)-N-methylfuro[2,3-b]pyridine-3-carboxamide (40 mg, 0.081 mmol), 3,3,3-trifluoropropane-1-trifluoroborate (83 mg, 0.41 mmol), dicyclohexyl(2',6'-diisopropoxy-[1,1'-biphenyl]-2-yl)phosphine (15 mg, 0.033 mmol), PdOAc$_2$ (3.7 mg, 0.016 mmol), cesium carbonate (80 mg, 0.24 mmol) were degassed and backfilled with N$_2$ then dissolved in Toluene (5 mL) and water (500 μl) at rt then heated at 100° C. The reaction was allowed to stir 16 h. LCMS showed starting material remained. The reaction mixture was partitioned between water and EtOAc. The organic layer was dried over Na$_2$SO$_4$, filtered, concentrate to dryness and then re-subjected to the reaction conditions. The resulting mixture by LCMS showed a peak with the expected M+H. The mixture was diluted with EtOAc and washed with 1M HCl aq, and sat NaCl. The organic phase was concentrated the crude material was purified via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 30-100% B over 16 minutes, then a 4-minute hold at100% B; Flow: 20 mL/min. Fractions containing the desired product were combined and dried via centrifugal evaporation. The yield of the product was 2.9 mg, and its estimated purity by LCMS analysis was 98%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Retention time=2.95. Injection 2 conditions: Column: Waters BEH C18, 2.0×50 mm, 1.7-μm particles; Mobile Phase A: 5:95 methanol:water with 10 mM ammonium acetate; MobilePhase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Retention time=4.13. M+H=552. Proton NMR was acquired in deuterated DMSO.

$^1$H NMR (500 MHz, DMSO-d6) 9.25 (s, 1H), 9.05 (d, J=2.1 Hz, 1H), 8.82 (d, J=2.1 Hz, 1H), 8.50 (q, J=4.4 Hz, 1H), 8.25 (t, J=2.0 Hz, 1H), 8.10-8.04 (m, 3H), 7.42 (t, J=8.9 Hz, 2H), 3.01 (dd, J=9.0, 6.6 Hz, 2H), 2.82 (d, J=4.9 Hz, 3H), 2.80-2.70 (m, 2H), 2.49 (s, 1H), 2.12 (s, 6H).

Preparation of 5-(5-(bicyclo[1.1.1]pentan-1-ylcarbamoyl)thiophen-3-yl)-2-(4-fluorophenyl)-N-methyl-6-(3,3,3-trifluoropropyl)furo[2,3-b]pyridine-3-carboxamide

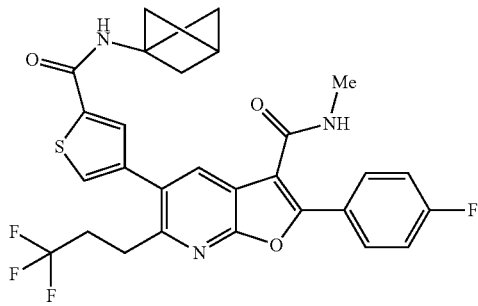

Chemical Formula: $C_{28}H_{23}F_4N_3O_3S$
Molecular Weight: 557.56

Step 1: Preparation of 4-(6-chloro-2-(4-fluorophenyl)-3-(methylcarbamoyl)furo[2,3-b]pyridin-5-yl)thiophene-2-carboxylic acid

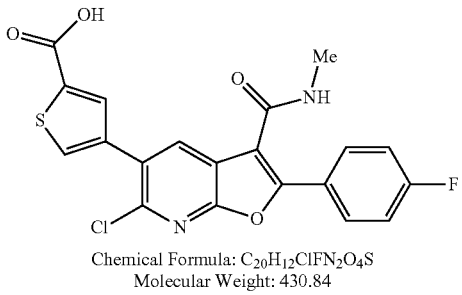 [SMILES: CNC(=O)c1c(-c2ccc(F)cc2)oc2nc(Cl)c(-c3csc(C(=O)O)c3)cc12]

Chemical Formula: $C_{20}H_{12}ClFN_2O_4S$
Molecular Weight: 430.84

A mixture of 5-bromo-6-chloro-2-(4-fluorophenyl)-N-methylfuro[2,3-b]pyridine-3-carboxamide (400 mg, 1.04 mmol), 4-boronothiophene-2-carboxylic acid (197 mg, 1.15 mmol), $Pd(Ph_3P)_4$ (120 mg, 0.104 mmol) and cesium carbonate (510 mg, 1.56 mmol) was degassed and diluted water (1.3 mL)/DMF (13 mL). The mixture was degassed and heated to 65° C. under $N_2$. The reaction was allowed to stir for 16 h. The mixture was diluted with EtOAc and washed with 1M HCl, and sat NaCl. The organic phase was dried over $Na_2SO_4$, filtered and concentrated and triturated with DCM to give 4-(6-chloro-2-(4-fluorophenyl)-3-(methylcarbamoyl)furo[2,3-b]pyridin-5-yl)thiophene-2-carboxylic acid (355 mg, 0.821 mmol, 79% yield) consistent by LCMS and NMR.

LC-MS retention time: 2.39 min; m/z (MH+): 431. LC data was recorded on a Shimadzu LC-10AS liquid chromatograph equipped with a Phenomenex-Luna 3 u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 3 min, a hold time of 1 min, and an analysis time of 4 min where solvent A was 5% MeOH/95% $H_2O$/10 mM ammonium acetate and solvent B was 5% $H_2O$/95% MeOH/10 mM ammonium acetate. MS data was determined using a Micromass Platform for LC in electrospray mode.

$^1$H NMR (400 MHz, DMSO-d6) δ 13.27 (br. s., 1H), 8.52-8.46 (m, 1H), 8.26 (s, 1H), 8.17 (d, J=1.8 Hz, 1H), 8.11-8.03 (m, 2H), 8.01 (d, J=1.5 Hz, 1H), 7.47-7.38 (m, 2H), 2.84 (d, J=4.5 Hz, 3H).

Step 2: Preparation of 5-(5-(bicyclo[1.1.1]pentan-1-ylcarbamoyl)thiophen-3-yl)-6-chloro-2-(4-fluorophenyl)-N-methylfuro[2,3-b]pyridine-3-carboxamide

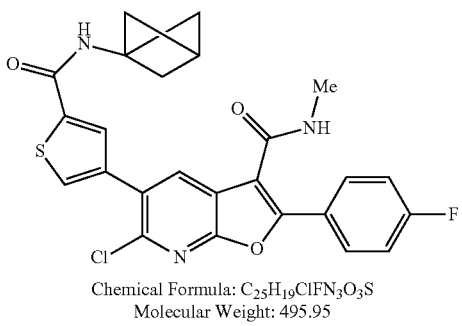 [SMILES: CNC(=O)c1c(-c2ccc(F)cc2)oc2nc(Cl)c(-c3csc(C(=O)NC45CC(C4)C5)c3)cc12]

Chemical Formula: $C_{25}H_{19}ClFN_3O_3S$
Molecular Weight: 495.95

4-(6-chloro-2-(4-fluorophenyl)-3-(methylcarbamoyl)furo[2,3-b]pyridin-5-yl)thiophene-2-carboxylic acid (100 mg, 0.232 mmol) was taken up in DMF (2.3 mL) and treated with N-ethyl-N-isopropylpropan-2-amine (122 μl, 0.696 mmol), bicyclo[1.1.1]pentan-1-amine hydrochloride (83 mg, 0.70 mmol) followed by 2-(3H-[1,2,3]triazolo[4,5-b]pyridin-3-yl)-1,1,3,3-tetramethylisouronium hexafluorophosphate(V) (132 mg, 0.348 mmol). The reaction was allowed to stir for 16 h. LCMS shows a major peak with the expected M+H=496. The reaction was concentrated and was purified on silica gel (Biotage, EtOAc/hexanes gradient, fraction collection at λ=254 nm) to give material that was triturated with DCM and washed with $Et_2O$ to give the expected product 5-(5-(bicyclo[1.1.1]pentan-1-ylcarbamoyl)thiophen-3-yl)-6-chloro-2-(4-fluorophenyl)-N-methylfuro[2,3-b]pyridine-3-carboxamide (100 mg, 0.202 mmol, 87% yield) consistent by LCMS.

LC-MS retention time: 2.96 min; m/z (MH+): 496. LC data was recorded on a Shimadzu LC-10AS liquid chromatograph equipped with a Phenomenex-Luna 3 u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 3 min, a hold time of 1 min, and an analysis time of 4 min where solvent A was 5% MeOH/95% $H_2O$/10 mM ammonium acetate and solvent B was 5% $H_2O$/95% MeOH/10 mM ammonium acetate. MS data was determined using a Micromass Platform for LC in electrospray mode.

Step 3: Preparation of the Titled Compound 5-(5-(bicyclo[1.1.1]pentan-1-ylcarbamoyl)thiophen-3-yl)-6-chloro-2-(4-fluorophenyl)-N-methylfuro[2,3-b]pyridine-3-carboxamide (40 mg, 0.081 mmol), 3,3,3-trifluoropropane-1-trifluoroborate (82 mg, 0.40 mmol), dicyclohexyl (2',6'-diisopropoxy-[1,1'-biphenyl]-2-yl)phosphine (15 mg, 0.032 mmol), $PdOAc_2$ (3.6 mg, 0.016 mmol), cesium carbonate (79 mg, 0.24 mmol) were degassed and backfilled with $N_2$ then suspended in Toluene (4.9 mL) and water (490 μl) at rt then heated at 90° C. for 16 h. The mixture was diluted with EtOAc and washed with 1M HCl aq, and sat NaCl. The organic phase was concentrated and the crude material was purified via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 55-95% B over 12 minutes, then a 5-minute hold at 100% B; Flow: 20 mL/min. Fractions containing the desired product were combined and dried via centrifugal evaporation. The yield of the product was 12 mg, and its estimated purity by LCMS analysis was 96%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Retention time=3.16. Injection 2 conditions: Column: Waters BEH C18, 2.0×50 mm, 1.7-μm particles; Mobile Phase A: 5:95 methanol:water with 10 mM ammonium acetate; MobilePhase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Retention time=4.20. M+H=558 Proton NMR was acquired in deuterated DMSO.

$^1$H NMR (500 MHz, DMSO-d6) 9.05 (s, 1H), 8.49 (q, J=4.3 Hz, 1H), 8.06-8.01 (m, 2H), 7.99 (s, 1H), 7.91 (d, J=4.3 Hz, 2H), 7.41 (t, J=9.0 Hz, 2H), 3.18-3.10 (m, 2H), 2.82 (d, J=4.6 Hz, 3H), 2.81-2.71 (m, 2H), 2.47 (s, 1H), 2.09 (s, 6H)

Preparation of 5-(5-(bicyclo[1.1.1]pentan-1-ylcarbamoyl)-6-methoxypyridin-3-yl)-2-(4-fluorophenyl)-N-methyl-6-(3,3,3-trifluoropropyl)furo[2,3-b]pyridine-3-carboxamide

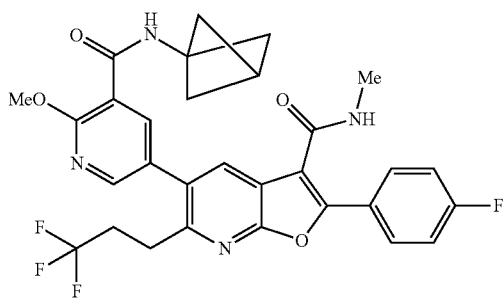

Chemical Formula: C$_{30}$H$_{26}$F$_4$N$_4$O$_4$
Molecular Weight: 582.55

Step 1: Preparation of methyl 5-(6-chloro-2-(4-fluorophenyl)-3-(methylcarbamoyl)furo[2,3-b]pyridin-5-yl)-2-methoxynicotinate

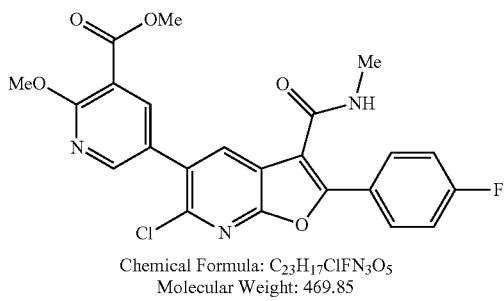 [SMILES: CNC(=O)c1c(-c2ccc(F)cc2)oc2nc(Cl)c(-c3cnc(OC)c(C(=O)OC)c3)cc12]

Chemical Formula: C$_{23}$H$_{17}$ClFN$_3$O$_5$
Molecular Weight: 469.85

A mixture of 5-bromo-6-chloro-2-(4-fluorophenyl)-N-methylfuro[2,3-b]pyridine-3-carboxamide (0.981 g, 2.56 mmol), methyl 2-methoxy-5-(4,4,5,5-tetramethyl-1,3,2-dioxaborolan-2-yl)nicotinate (1.05 g, 3.58 mmol), Pd(Ph$_3$P)$_4$ (0.444 g, 0.384 mmol) and cesium carbonate (1.67 g, 5.12 mmol) was degassed/charged with N$_2$ and diluted with water (0.5 ml)/DMF (5 mL). The resultant mixture was then degassed, charged with N$_2$, and heated in a 65° C. oil bath and allowed to stir under N$_2$ atmosphere for 4 h. LCMS shows desired product as well as some SM. The reaction was halted by cooling to rt and the reaction mixture was diluted with EtOAc and sat 1M HCl. The layers were separated and the aq layer was extracted with EtOAc (3×10 mL). The combined organic extracts were washed with water, brine, dried over Na$_2$SO$_4$ filtered and concentrated. The resultant solid was then purified on silica gel eluting with a 0-100% EtOAc in hexanes mixture over 12 CV and then held at 100% EtOAc for 8 CV to give methyl 5-(6-chloro-2-(4-fluorophenyl)-3-(methylcarbamoyl)furo[2,3-b]pyridin-5-yl)-2-methoxynicotinate (1.2 g, 2.6 mmol, 100% yield) as a brown solid.

LC-MS retention time: 2.08 min; m/z (MH+): 470. LC data was recorded on a Shimadzu LC-10AS liquid chromatograph equipped with a Phenomenex-Luna 3 u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 5% MeOH/95% H$_2$O/10 mM ammonium acetate and solvent B was 5% H$_2$O/95% MeOH/10 mM ammonium acetate. MS data was determined using a Micromass Platform for LC in electrospray mode.

$^1$H NMR (400 MHz, CHLOROFORM-d) 8.43 (d, J=2.5 Hz, 1H), 8.29 (d, J=2.5 Hz, 1H), 8.22 (s, 1H), 7.95-7.91 (m, 2H), 7.26-7.21 (m, 2H), 4.13 (s, 3H), 3.94 (s, 3H), 2.99 (d, J=5.0 Hz, 3H)

Step 2: Preparation of methyl 5-(2-(4-fluorophenyl)-3-(methylcarbamoyl)-6-(3,3,3-trifluoropropyl)furo[2,3-b]pyridin-5-yl)-2-methoxynicotinate

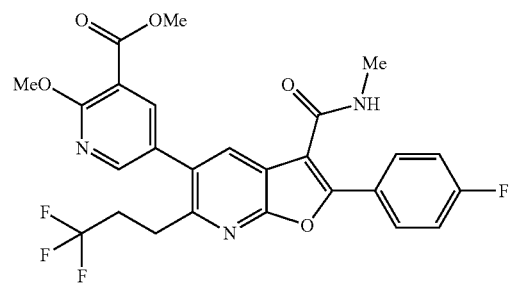

Chemical Formula: C$_{26}$H$_{21}$F$_4$N$_3$O$_5$
Molecular Weight: 531.46

Methyl 5-(6-chloro-2-(4-fluorophenyl)-3-(methylcarbamoyl)furo[2,3-b]pyridin-5-yl)-2-methoxynicotinate (600 mg, 1.28 mmol), 3,3,3-trifluoropropane-1-trifluoroborate (651 mg, 3.19 mmol), dicyclohexyl(2',6'-diisopropoxy-[1, 1'-biphenyl]-2-yl)phosphine (238 mg, 0.511 mmol), PdOAc$_2$ (57.3 mg, 0.255 mmol), cesium carbonate (1.25 g, 3.83 mmol) were degassed and backfilled with N$_2$ then dissolved in Toluene (2 mL) and water (0.2 mL) at rt then heated at 80° C. The reaction was allowed to stir at 80° C. for 16 h. LCMS indicated a major peak with the expected M+H. The reaction mixture was combined and the mixture was diluted with EtOAc (30 mL) and washed with 1M HCl (75 mL), and sat NaCl. The organic layer was dried over Na$_2$SO$_4$, filtered and concentrated to give a yellow solid. This solid was purified on silica gel (Biotage) eluting with a 0-100 EtOAc in hexanes gradient over 15 CV to give methyl 5-(2-(4-fluorophenyl)-3-(methylcarbamoyl)-6-(3,3,3-trifluoropropyl)furo[2,3-b]pyridin-5-yl)-2-methoxynicotinate (0.638 g, 1.20 mmol, 94% yield) as a white solid.

LC-MS retention time: 2.12 min; m/z (MH+): 532. LC data was recorded on a Shimadzu LC-10AS liquid chromatograph equipped with a Phenomenex-Luna 3 u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis Step 3: Preparation of 5-(2-(4-fluorophenyl)-3-(methylcarbamoyl)-6-(3,3,3-trifluoropropyl)furo[2,3-b]pyridin-5-yl)-2-methoxynicotinic acid

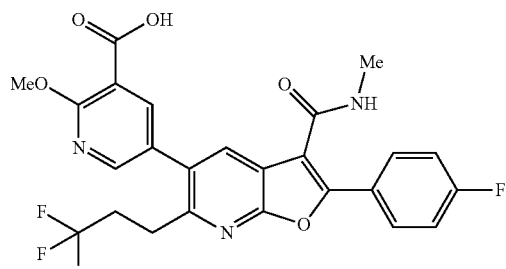

Chemical Formula: $C_{25}H_{19}F_4N_3O_5$
Molecular Weight: 517.43

A solution of LiOH (287 mg, 12.00 mmol) in water (1 mL) was added to a stirring solution of methyl 5-(2-(4-fluorophenyl)-3-(methylcarbamoyl)-6-(3,3,3-trifluoropropyl)furo[2,3-b]pyridin-5-yl)-2-methoxynicotinate (640 mg, 1.2 mmol) in a 1:1 mixture of MeOH (1 mL) and THF (1 mL). After 1 hour of stirring, LCMS shows complete conversion. The reaction mixture was concentrated to dryness and then partitioned between 1M HCl (80 mL) and EtOAc (50 mL). The layers were separated and then aq layer was then extracted with EtOAc (2×30 mL). The combined organic extracts were washed with water, brine dried over $Na_2SO_4$, filtered and concentrated to give 5-(2-(4-fluorophenyl)-3-(methylcarbamoyl)-6-(3,3,3-trifluoropropyl)furo[2,3-b]pyridin-5-yl)-2-methoxynicotinic acid (562 mg, 1.09 mmol, 91% yield) as a white residue. This material was carried on crude to amide coupling reactions.

LC-MS retention time: 1.72 min; m/z (MH+): 518. LC data was recorded on a Shimadzu LC-10AS liquid chromatograph equipped with a Phenomenex-Luna 3 u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 10% acetonitrile/90% $H_2O/0.1\%$ trifluoroacetic acid and solvent B was 10% $H_2O/90\%$ acetonitrile/0.1% trifluoroacetic acid. MS data was determined using a Micromass Platform for LC in electrospray mode.

$^1$H NMR (500 MHz, DMSO-$d_6$) 13.14 (br s, 1H), 8.48 (d, J=4.6 Hz, 1H), 8.45 (d, J=2.5 Hz, 1H), 8.18 (d, J=2.4 Hz, 1H), 8.10-8.04 (m, 2H), 8.02 (s, 1H), 7.45-7.38 (m, 2H), 4.00 (s, 3H), 3.03 (dd, J=9.0, 6.6 Hz, 2H), 2.82 (d, J=4.7 Hz, 3H), 2.81-2.72 (m, 2H)

Step 4: Preparation of Title Compound

N-ethyl-N-isopropylpropan-2-amine (27 μl, 0.16 mmol) was added to stirring solution of 5-(2-(4-fluorophenyl)-3-(methylcarbamoyl)-6-(3,3,3-trifluoropropyl)furo[2,3-b]pyridin-5-yl)-2-methoxynicotinic acid (10 mg, 0.019 mmol), 2-(3H-[1,2,3]triazolo[4,5-b]pyridin-3-yl)-1,1,3,3-tetramethylisouronium hexafluorophosphate(V) (11 mg, 0.029 mmol) and bicyclo[1.1.1]pentan-1-amine hydrochloride (2.3 mg, 0.019 mmol) in DMF (1) at rt. The mixture was allowed to stir at rt for 1 h. LCMS shows complete reaction. The DMF solution was filtered and immediately purified via preparative LC/MS with the following conditions: Column: Waters XBridge C18, 19×200 mm, 5-μm particles; Mobile Phase A: water with 20-mM ammonium acetate; Mobile Phase B: 95:5 acetonitrile:water with 20-mM ammonium acetate; Gradient: 40-80% B over 20 minutes, then a 5-minute hold at 100% B; Flow: 20 mL/min. Fractions containing the desired product were combined and dried via centrifugal evaporation. The yield of the product was 8.6 mg, and its estimated purity by LCMS analysis was 100%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Proton NMR was acquired in deuterated DMSO.

LC-MS retention time: 2.05 min; m/z (MH+): 583. LC data was recorded on a Shimadzu LC-10AS liquid chromatograph equipped with a Phenomenex-Luna 3 u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 10% acetonitrile/90% $H_2O/0.1\%$ trifluoroacetic acid and solvent B was 10% $H_2O/90\%$ acetonitrile/0.1% trifluoroacetic acid. MS data was determined using a Micromass Platform for LC in electrospray mode.

$^1$H NMR (500 MHz, DMSO-$d_6$) δ 8.69 (s, 1H), 8.48 (d, J=4.6 Hz, 1H), 8.38 (d, J=2.4 Hz, 1H), 8.10 (d, J=2.4 Hz, 1H), 8.08-8.02 (m, 2H), 7.41 (t, J=9.0 Hz, 2H), 4.03 (s, 3H), 3.06-3.00 (m, 2H), 2.82 (d, J=4.6 Hz, 3H), 2.80-2.72 (m, 2H), 2.47 (s, 1H), 2.10 (s, 6H)

Preparation of 5-(5-(bicyclo[1.1.1]pentan-1-ylcarbamoyl)-6-methoxypyridin-3-yl)-2-(4-fluorophenyl)-N-methyl-6-((2,2,2-trifluoroethyl)amino)furo[2,3-b]pyridine-3-carboxamide

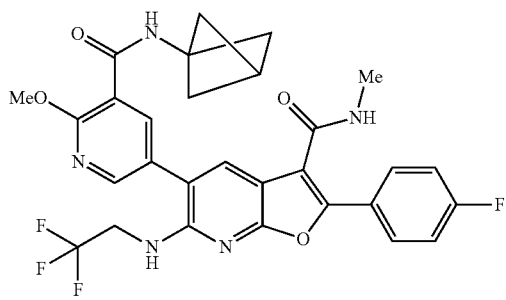

Chemical Formula: $C_{29}H_{25}F_4N_5O_4$
Molecular Weight: 583.53 time of 3 min where solvent A was 5% MeOH/95% $H_2O$/10 mM ammonium acetate and solvent B was 5% $H_2O$/95% MeOH/10 mM ammonium acetate. MS data was determined using a Micromass Platform for LC in electrospray mode.

Step 1: Preparation of 5-(2-(4-fluorophenyl)-3-(methylcarbamoyl)-6-((2,2,2-trifluoroethyl)amino)furo[2,3-b]pyridin-5-yl)-2-methoxynicotinic acid

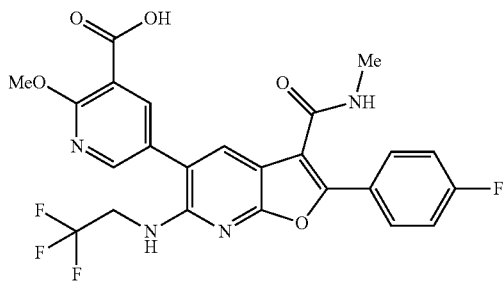

Chemical Formula: $C_{24}H_{18}F_4N_4O_5$
Molecular Weight: 518.42

Sodium 2-methylbutan-2-olate (1.40 g, 12.8 mmol) was added to a stirring solution of methyl 5-(6-chloro-2-(4-fluorophenyl)-3-(methylcarbamoyl)furo[2,3-b]pyridin-5-yl)-2-methoxynicotinate (600 mg, 1.28 mmol), 2,2,2-trifluoroethanamine (1.27 g, 12.8 mmol), Brett Phos precatalyst (102 mg, 0.128 mmol), in dioxane (12 mL) at 100° C. Immediately, the reaction mixture turned to a dark amber color. LCMS after 1 hour shows complete conversion to the desired Buchwald coupled product with simultaneous deprotection of the methyl ester. The reaction mixture was cooled to rt and concentrated to a dry solid. The resultant solid was then taken up in EtOAc and diluted with 1 M HCl. The layers were separated and the aq layer was extracted with EtOAc (2×15 mL). The layers were washed with water, brine, dried over $Na_2SO_4$, filtered and concentrated to give a yellow solid. This solid was then triturated with DCM (25 mL) for 3 hours. The solids were filtered to give the desired 5-(2-(4-fluorophenyl)-3-(methylcarbamoyl)-6-((2,2,2-trifluoroethyl)amino)furo[2,3-b]pyridin-5-yl)-2-methoxynicotinic acid (375 mg, 0.723 mmol, 57% yield) as a yellow solid.

LC-MS retention time: 1.92 min; m/z (MH+): 519. LC data was recorded on a Shimadzu LC-10AS liquid chromatograph equipped with a Phenomenex-Luna 3 u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 5% MeOH/95% $H_2O$/10 mM ammonium acetate and solvent B was 5% $H_2O$/95% MeOH/10 mM ammonium acetate. MS data was determined using a Micromass Platform for LC in electrospray mode.

$^1$H NMR (500 MHz, DMSO-$d_6$) 12.52 (br s, 1H), 8.36-8.30 (m, 2H), 8.04 (d, J=2.2 Hz, 1H), 8.01-7.94 (m, 2H), 7.37-7.31 (m, 2H), 6.86 (t, J=6.3 Hz, 1H), 4.15 (dd, J=9.3, 6.6 Hz, 2H), 3.98 (s, 3H), 2.80 (d, J=4.6 Hz, 3H)

Step 2: Preparation of Title Compound

N-ethyl-N-isopropylpropan-2-amine (27.0 µl, 0.154 mmol) was added to stirring solution of 5-(2-(4-fluorophenyl)-3-(methylcarbamoyl)-6-(2,2,2-trifluoroethyl)amino)furo[2,3-b]pyridin-5-yl)-2-methoxynicotinic acid (10 mg, 0.019 mmol), 2-(3H-[1,2,3]triazolo[4,5-b]pyridin-3-yl)-1,1,3,3-tetramethylisouronium hexafluorophosphate(V) (11 mg, 0.029 mmol) and bicyclo[1.1.1]pentan-1-amine hydrochloride (2.3 mg, 0.019 mmol) in DMF (1 mL) at rt. The mixture was allowed to stir at rt for 1 h. LCMS shows complete reaction. The DMF solution was filtered and immediately purified via preparative LC/MS with the following conditions: Column: Waters XBridge C18, 19×200 mm, 5-µm particles; Mobile Phase A: water with 20-mM ammonium acetate; Mobile Phase B: 95:5 acetonitrile:water with 20-mM ammonium acetate; Gradient: 40-80% B over 20 minutes, then a 5-minute hold at 100% B; Flow: 20 mL/min. Fractions containing the desired product were combined and dried via centrifugal evaporation. The yield of the product was 3.7 mg, and its estimated purity by LCMS analysis was 92%. Two analytical LC/MS injections were used to determine the final purity. Injection 1 conditions: Column: Waters BEH C18, 2.0×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7-µm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Proton NMR was acquired in deuterated DMSO.

LC-MS retention time: 1.96 min; m/z (MH+): 584. LC data was recorded on a Shimadzu LC-10AS liquid chromatograph equipped with a Phenomenex-Luna 3 u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 10% acetonitrile/90% $H_2O$/0.1% trifluoroacetic acid and solvent B was 10% $H_2O$/90% acetonitrile/0.1% trifluoroacetic acid. MS data was determined using a Micromass Platform for LC in electrospray mode.

$^1$H NMR (500 MHz, DMSO-$d_6$) δ 8.63 (s, 1H), 8.37-8.30 (m, 2H), 8.09 (d, J=2.4 Hz, 1H), 7.98 (dd, J=8.9, 5.5 Hz, 2H), 7.34 (t, J=8.9 Hz, 2H), 6.82 (t, J=6.3 Hz, 1H), 4.22-4.11 (m, 2H), 4.04 (s, 3H), 2.80 (d, J=4.6 Hz, 3H), 2.47 (s, 1H), 2.11 (s, 6H)

Preparation of 5-(5-(bicyclo[1.1.1]pentan-1-ylcarbamoyl)-2-methoxyphenyl)-2-(4-fluorophenyl)-N-methyl-6-((2,2,2-trifluoroethyl)amino)furo[2,3-b]pyridine-3-carboxamide

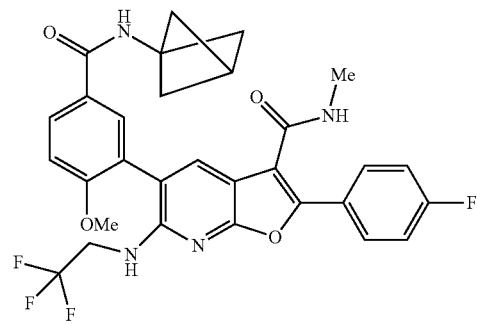

Chemical Formula: $C_{30}H_{26}F_4N_4O_4$
Molecular Weight: 582.55

Step 1: Preparation of 3-(6-chloro-2-(4-fluorophenyl)-3-(methylcarbamoyl)furo[2,3-b]pyridin-5-yl)-4-methoxybenzoic acid

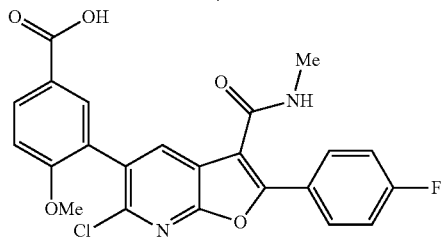

Chemical Formula: C₂₃H₁₆ClFN₂O₅
Molecular Weight: 454.83

A mixture of 5-bromo-6-chloro-2-(4-fluorophenyl)-N-methylfuro[2,3-b]pyridine-3-carboxamide (1.0 g, 2.6 mmol), 3-borono-4-methoxybenzoic acid (511 mg, 2.61 mmol), PdCl₂(dppf) (191 mg, 0.261 mmol) and cesium carbonate (1.3 g, 3.9 mmol) was degassed and diluted water (3.2 ml)/DMF (32 ml). The mixture was degassed and heated to 60° C. under N₂. The reaction was allowed to stir at 60° C. for 16 h. The mixture was diluted with EtOAc and washed with 1M HCl aq, and sat NaCl aq. The organic phase was dried over Na₂SO₄, filtered and concentrated. The crude residue was triturated with DCM to give the expected product 3-(6-chloro-2-(4-fluorophenyl)-3-(methylcarbamoyl)furo[2,3-b]pyridin-5-yl)-4-methoxybenzoic acid (1.1 g, 2.4 mmol, 93% yield) consistent by LCMS and NMR.

LC-MS retention time: 1.64 min; m/z (MH+): 455. LC data was recorded on a Shimadzu LC-10AS liquid chromatograph equipped with a Phenomenex-Luna 3 u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 10% acetonitrile/90% H₂O/0.1% trifluoroacetic acid and solvent B was 10% H₂O/90% acetonitrile/0.1% trifluoroacetic acid. MS data was determined using a Micromass Platform for LC in electrospray mode.

¹H NMR (400 MHz, DMSO-d₆) 12.32 (br. s., 1H), 8.57-8.50 (m, 1H), 8.12 (s, 1H), 8.09-8.02 (m, 2H), 7.84 (d, J=2.3 Hz, 1H), 7.48-7.39 (m, 2H), 7.27 (d, J=8.8 Hz, 1H), 6.51 (s, 1H), 3.83 (s, 3H), 2.83-2.78 (m, 3H).

Step 2: Preparation of 3-(2-(4-fluorophenyl)-3-(methylcarbamoyl)-6-((2,2,2-trifluoroethyl)amino)furo[2,3-b]pyridin-5-yl)-4-methoxybenzoic acid

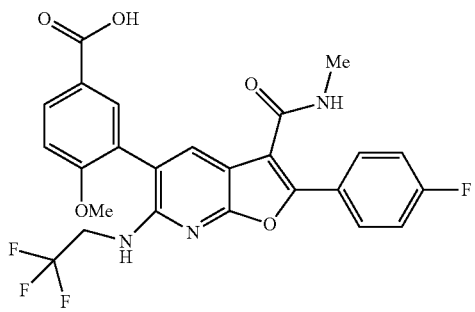

Chemical Formula: C₂₅H₁₉F₄N₃O₅
Molecular Weight: 517.43

Sodium 2-methylbutan-2-olate (121 mg, 1.10 mmol), 3-(6-chloro-2-(4-fluorophenyl)-3-(methylcarbamoyl)furo[2,3-b]pyridin-5-yl)-4-methoxybenzoic acid (100 mg, 0.220 mmol), 2,2,2-trifluoroethanamine (109 mg, 1.10 mmol), Chloro[2-(dicyclohexylphosphino)-3,6-dimethoxy-2',4',6'-triisopropyl-1,1'-biphenyl][2-(2-aminoethyl)phenyl]palladium(II) (18 mg, 0.022 mmol) was combined, degassed, and taken up in dioxane (4.4 ml) at rt and then was heated to 90° C. for 1 h. The mixture was diluted with EtOAc and washed with 1M HCl aq, and sat NaCl aq. The organic phase was dried over Na₂SO₄, filtered and concentrated and the residue was purified by preparative reverse phase HPLC on a C18 column using a suitably buffered H₂O/CH₃CN gradient, and concentrated to give the expected product 3-(2-(4-fluorophenyl)-3-(methylcarbamoyl)-6-((2,2,2-trifluoroethyl)amino)furo[2,3-b]pyridin-5-yl)-4-methoxybenzoic acid (30 mg, 0.058 mmol, 26% yield) consistent by LCMS.

LC-MS retention time: 1.84 min; m/z (MH+): 518. LC data was recorded on a Shimadzu LC-10AS liquid chromatograph equipped with a Phenomenex-Luna 3 u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 5% MeOH/95% H₂O/10 mM ammonium acetate and solvent B was 5% H₂O/95% MeOH/10 mM ammonium acetate. MS data was determined using a Micromass Platform for LC in electrospray mode.

Step 3: Preparation of the Title Compound 2-(3H-[1,2,3]triazolo[4,5-b]pyridin-3-yl)-1,1,3,3-tetramethylisouronium hexafluorophosphate(V) (12 mg, 0.032 mmol) was added to stirring solution of 3-(2-(4-fluorophenyl)-3-(methylcarbamoyl)-6-((2,2,2-trifluoroethyl)amino)furo[2,3-b]pyridin-5-yl)-4-methoxybenzoic acid (11 mg, 0.021 mmol), N-ethyl-N-isopropylpropan-2-amine (0.011 mL, 0.064 mmol) and bicyclo[1.1.1]pentan-1-amine hydrochloride (4 mg, 0.03 mmol) in DMF (1 mL) at rt. The mixture was allowed to stir at rt for 30 min. The crude material was purified via preparative LC/MS with the following conditions: Column: Waters XBridge C18, 19×200 mm, 5-μm particles; Mobile Phase A: water with 20-mM ammonium acetate; Mobile Phase B: 95:5 acetonitrile:water with 20-mM ammonium acetate; Gradient: 20-100% B over 20 minutes, then a 5-minute hold at 100% B; Flow: 20 mL/min. Fractions containing the desired product were combined and dried via centrifugal evaporation. The yield of the product was 6.1 mg, and its estimated purity by LCMS analysis was 97%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Proton NMR was acquired in deuterated DMSO.

¹H NMR (500 MHz, DMSO-d₆) 8.87 (s, 1H), 8.36 (d, J=4.6 Hz, 1H), 8.00-7.91 (m, 3H), 7.77 (d, J=2.1 Hz, 1H), 7.58 (s, 1H), 7.34 (t, J=8.9 Hz, 2H), 7.21 (d, J=8.9 Hz, 1H), 6.31-6.23 (m, 1H), 4.34-4.22 (m, 1H), 4.07-3.94 (m, 1H), 3.77 (s, 3H), 2.78 (d, J=4.6 Hz, 3H), 2.44 (s, 1H), 2.07 (s, 6H).

Preparation of 5-(3-(bicyclo[1.1.1]pentan-1-ylcarbamoyl)phenyl)-6-(N-ethylmethylsulfonamido)-2-(4-fluorophenyl)-N-methylfuro[2,3-b]pyridine-3-carboxamide

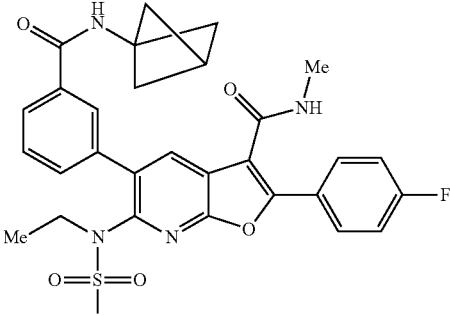

Chemical Formula: $C_{30}H_{29}FN_4O_5S$
Molecular Weight: 576.64

Step 1: Preparation of tert-butyl 3-(6-chloro-2-(4-fluorophenyl)-3-(methylcarbamoyl)furo[2,3-b]pyridin-5-yl)benzoate

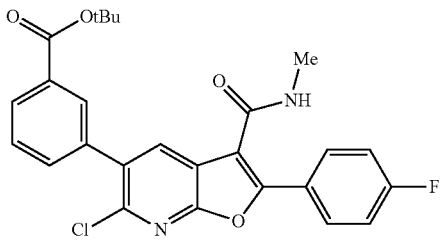

Chemical Formula: $C_{26}H_{22}ClFN_2O_4$
Molecular Weight: 480.92

A mixture of 5-bromo-6-chloro-2-(4-fluorophenyl)-N-methylfuro[2,3-b]pyridine-3-carboxamide (5.0 g, 13 mmol), (3-(tert-butoxycarbonyl)phenyl)boronic acid (2.75 g, 12.4 mmol). Pd(Ph$_3$P)$_4$ (2.26 g, 1.96 mmol) and cesium carbonate (8.49 g, 26.1 mmol) was degassed/charged with N$_2$ and diluted with water (22 ml)/DMF (220 ml). The resultant mixture was then degassed, charged with N$_2$, heated to an internal temperature of 65° C. and allowed to stir under N$_2$ atmosphere for 16 h. The reaction mixture was cooled to rt then diluted with EtOAc and sat. 1M HCl. The layers were separated and the aq layer was extracted with EtOAc (3×10 mL). The combined organic extracts were washed with water, brine, dried over Na$_2$SO$_4$ filtered and concentrated. The resultant solid was then flashed on SiO$_2$ eluting with a 0-100% EtOAc in hexanes gradient over 16 CV to give tert-butyl 3-(6-chloro-2-(4-fluorophenyl)-3-(methylcarbamoyl)furo[2,3-b]pyridin-5-yl)benzoate (5.2 g, 11 mmol, 83% yield) as a slightly yellow solid contaminated with the bis-coupled product di-tert-butyl 3,3'-(2-(4-fluorophenyl)-3-(methylcarbamoyl)furo[2,3-b]pyridine-5,6-diyl)dibenzoate.

$^1$H NMR (500 MHz, CHLOROFORM-d) δ 8.18 (s, 1H), 8.08-8.02 (m, 2H), 7.95-7.89 (m, 2H), 7.63 (dt, J=7.6, 1.5 Hz, 1H), 7.52 (t, J=7.6 Hz, 1H), 7.24-7.18 (m, 2H), 6.03 (d, J=4.3 Hz, 1H), 2.99 (d, J=4.9 Hz, 3H), 1.62 (s, 9H)

Step 2: Preparation of 3-(6-(benzylamino)-2-(4-fluorophenyl)-3-(methylcarbamoyl)furo[2,3-b]pyridin-5-yl)benzoic acid

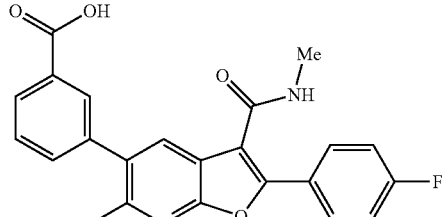

Chemical Formula: $C_{29}H_{22}FN_3O_4$
Molecular Weight: 495.50

Sodium 2-methylbutan-2-olate (2.29 g, 20.8 mmol) was added to a stirring solution of tert-butyl 3-(6-chloro-2-(4-fluorophenyl)-3-(methylcarbamoyl)furo[2,3-b]pyridin-5-yl)benzoate (1.0 g, 2.1 mmol), phenylmethanamine (4.54 ml, 41.6 mmol), Brett Phos precatalyst (0.166 g, 0.208 mmol), in dioxane (21 ml) at 100° C. Immediately, the reaction mixture turned to a dark amber color. LCMS after 1 h shows complete conversion to the desired Suzuki product with simultaneous deprotection of the tBu ester. The reaction mixture was first concentrated to near dryness and then diluted with 1 M HCl (50 ml) and EtOAc (50 mL). The layers were separated and the aq layer was extracted with EtOAc (2×20 mL). The combined organic extracts were washed with water, brine dried over Na$_2$SO$_4$, filtered and concentrated to give a orange solid. This solid was then triturated with DCM for 3 h to give 3-(6-(benzylamino)-2-(4-fluorophenyl)-3-(methylcarbamoyl)furo[2,3-b]pyridin-5-yl)benzoic acid (0.88 g, 1.8 mmol, 85% yield) as a yellow solid.

LC-MS retention time: 1.96 min; m/z (MH+): 496. LC data was recorded on a Shimadzu LC-10AS liquid chromatograph equipped with a Phenomenex-Luna 3 u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 5% MeOH/95% H$_2$O/10 mM ammonium acetate and solvent B was 5% H$_2$O/95% MeOH/10 mM ammonium acetate. MS data was determined using a Micromass Platform for LC in electrospray mode.

Step 3: Preparation of 6-(benzylamino)-5-(3-(bicyclo[1.1.1]pentan-1-ylcarbamoyl)phenyl)-2-(4-fluorophenyl)-N-methylfuro[2,3-b]pyridine-3-carboxamide

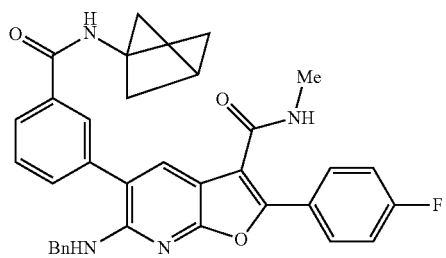

Chemical Formula: $C_{34}H_{29}FN_4O_3$
Molecular Weight: 560.62

N-ethyl-N-isopropylpropan-2-amine (2.48 mL, 14.2 mmol) was added to stirring solution of 3-(6-(benzylamino)-2-(4-fluorophenyl)-3-(methylcarbamoyl)furo[2,3-b]pyridin-5-yl)benzoic acid (0.88 g, 1.8 mmol), 2-(3H-[1,2,3]triazolo[4,5-b]pyridin-3-yl)-1,1,3,3-tetramethylisouronium hexafluorophosphate(V) (1.01 g, 2.66 mmol) and 1,1,1-amine HCl (0.255 g, 2.13 mmol) in DMF (10 mL) at rt. The mixture was allowed to stir at rt for 1 h. LCMS shows complete reaction. The mixture was diluted with EtOAc (25 mL) and 1 M HCl (20 mL). The layers were separated and the aq layer was extracted with EtOAc (2×20 mL). The combined organic extracts were washed with water, brine dried over Na$_2$SO$_4$, filtered and concentrated to give a white solid. This solid was purified on silica gel eluting with 0-100% EtOAc over 15 CV to give the desired product 6-(benzylamino)-5-(3-(bicyclo[1.1.1]pentan-1-ylcarbamoyl)phenyl)-2-(4-fluorophenyl)-N-methylfuro[2,3-b]pyridine-3-carboxamide (0.60 g, 1.1 mmol, 60% yield) as a white solid.

LC-MS retention time: 2.24 min; m/z (MH+): 561. LC data was recorded on a Shimadzu LC-10AS liquid chromatograph equipped with a Phenomenex-Luna 3 u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 5% MeOH/95% H$_2$O/10 mM ammonium acetate and solvent B was 5% H$_2$O/95% MeOH/10 mM ammonium acetate. MS data was determined using a Micromass Platform for LC in electrospray mode.

Step 4: Preparation of 6-amino-5-(3-(bicyclo[1.1.1]pentan-1-ylcarbamoyl)phenyl)-2-(4-fluorophenyl)-N-methylfuro[2,3-b]pyridine-3-carboxamide

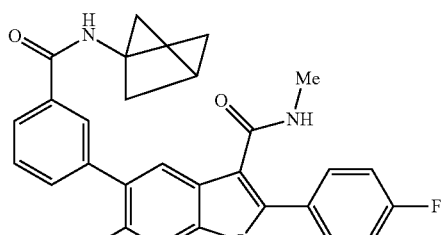

Chemical Formula: C$_{27}$H$_{23}$FN$_4$O$_3$
Molecular Weight: 470.49

Triflic acid (182 µl, 2.06 mmol) was added to a stirring solution of 6-(benzylamino)-5-(3-(bicyclo[1.1.1]pentan-1-ylcarbamoyl)phenyl)-2-(4-fluorophenyl)-N-methylfuro[2,3-b]pyridine-3-carboxamide (96 mg, 0.17 mmol) in DCM (6.8 mL) at rt. After 1 h, the reaction was concentrated and loaded onto a silica column and was purified on silica gel (Biotage, MeOH/DCM gradient, fraction collection at λ=254 nm) to give the desired product still in crude form, which was subsequently purified by preparative reverse phase HPLC on a C18 column using a suitably buffered H$_2$O/CH$_3$CN gradient, and concentrated to give the expected product 6-amino-5-(3-(bicyclo[1.1.1]pentan-1-ylcarbamoyl)phenyl)-2-(4-fluorophenyl)-N-methylfuro[2,3-b]pyridine-3-carboxamide (40 mg, 0.085 mmol, 50% yield) consistent by LCMS and NMR.

LC-MS retention time: 1.65 min; m/z (MH+): 471. LC data was recorded on a Shimadzu LC-10AS liquid chromatograph equipped with a Phenomenex-Luna 3 u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 10% acetonitrile/90% H$_2$O/0.1% trifluoroacetic acid and solvent B was 10% H$_2$O/90% acetonitrile/0.1% trifluoroacetic acid. MS data was determined using a Micromass Platform for LC in electrospray mode.

Step 5: Preparation of 5-(3-(bicyclo[1.1.1]pentan-1-ylcarbamoyl)phenyl)-2-(4-fluorophenyl)-N-methyl-6-(N-(methylsulfonyl)methylsulfonamido)furo[2,3-b]pyridine-3-carboxamide

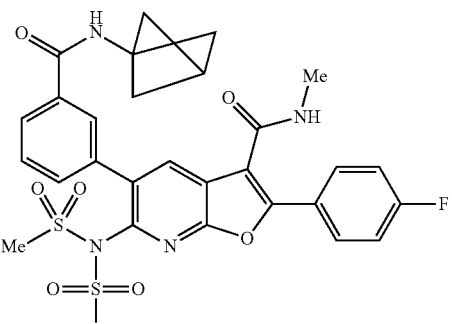

Chemical Formula: C$_{29}$H$_{27}$FN$_4$O$_7$S$_2$
Molecular Weight: 626.68

Mesyl-Cl (199 µl, 2.55 mmol) was added to a stirring solution of DIEA (835 µl, 4.78 mmol) 6-amino-5-(3-(bicyclo[1.1.1]pentan-1-ylcarbamoyl)phenyl)-2-(4-fluorophenyl)-N-methylfuro[2,3-b]pyridine-3-carboxamide (150 mg, 0.319 mmol) in DCM (6.4 mL) at rt. The reaction was allowed to stir for 2 h. The expected product 1 M+H was observed by LCMS. The mixture was diluted with sat NH$_4$Cl and DCM. The layers were separated and the aq layer was extracted with DCM (2×10 mL). The combined organic extracts were washed with water, brine, dried over Na$_2$SO$_4$, filtered and concentrated to give the desired 5-(3-(bicyclo[1.1.1]pentan-1-ylcarbamoyl)phenyl)-2-(4-fluorophenyl)-N-methyl-6-(N-(methylsulfonyl)methylsulfonamido)furo[2,3-b]pyridine-3-carboxamide (200 mg, 0.319 mmol, 100% crude yield) as a greenish solid.

LC-MS retention time: 1.77 min; m/z (MH+): 627. LC data was recorded on a Shimadzu LC-10AS liquid chromatograph equipped with a Phenomenex-Luna 3 u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 10% acetonitrile/90% H$_2$O/0.1% trifluoroacetic acid and solvent B was 10% H$_2$O/90% acetonitrile/0.1% trifluoroacetic acid. MS data was determined using a Micromass Platform for LC in electrospray mode.

Step 6: Preparation of 5-(3-(bicyclo[1.1.1]pentan-1-ylcarbamoyl)phenyl)-2-(4-fluorophenyl)-N-methyl-6-(methylsulfonamido)furo[2,3-b]pyridine-3-carboxamide

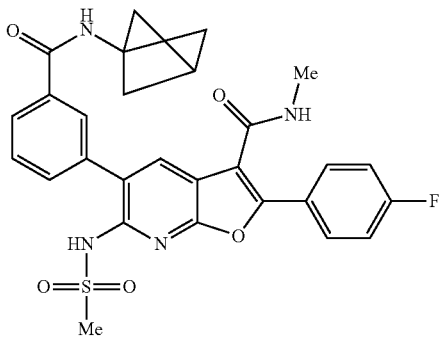

Chemical Formula: C₂₈H₂₅FN₄O₅S
Molecular Weight: 548.59

The concentrated reaction mixture from above (containing 5-(3-(bicyclo[1.1.1]pentan-1-ylcarbamoyl)phenyl)-2-(4-fluorophenyl)-N-methyl-6-(N-(methylsulfonyl)methylsulfonamido)furo[2,3-b]pyridine-3-carboxamide) was taken up in DMF (10 mL) and Cs₂CO₃ (520 mg, 1.59 mmol) was added. The mixture was heated to 100° C. and allowed to stir at this temp for 2 h. The reaction was diluted with 1 M HCl and EtOAc. The layers were separated and the aq layer was extracted with EtOAc (2×10 mL). The combined organic extracts were washed with water, brine, dried over Na₂SO₄ filtered and concentrated to give 5-(3-(bicyclo[1.1.1]pentan-1-ylcarbamoyl)phenyl)-2-(4-fluorophenyl)-N-methyl-6-(methylsulfonamido)furo[2,3-b]pyridine-3-carboxamide (125 mg, 0.228 mmol, 71% crude yield).

LC-MS retention time: 1.61 min; m/z (MH+): 549. LC data was recorded on a Shimadzu LC-10AS liquid chromatograph equipped with a Phenomenex-Luna 3 u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 10% acetonitrile/90% H₂O/0.1% trifluoroacetic acid and solvent B was 10% H₂O/90% acetonitrile/0.1% trifluoroacetic acid. MS data was determined using a Micromass Platform for LC in electrospray mode.

Step 7: Preparation of Title Compound

One third of the reaction mixture from above (containing -(3-(bicyclo[1.1.1]pentan-1-ylcarbamoyl)phenyl)-2-(4-fluorophenyl)-N-methyl-6-(methylsulfonamido)furo[2,3-b]pyridine-3-carboxamide) was transferred to a microwave vial (25 mL). Iodoethane (9.45 µl, 0.117 mmol) was added and the orange mixture was heated to 65° C. The mixture was allowed to stir at this temperature overnight. The reaction mixture was then filtered and immediately purified via preparative LC/MS with the following conditions: Column: Waters XBridge C18, 19×200 mm, 5-µm particles; Mobile Phase A: water with 20-mM ammonium acetate; Mobile Phase B: 95:5 acetonitrile:water with 20-mM ammonium acetate; Gradient: 30-100% B over 30 minutes, then a 5-minute hold at 100% B; Flow: 20 mL/min. Fractions containing the desired product were combined and dried via centrifugal evaporation. The yield of the product was 10.3 mg, and its estimated purity by LCMS analysis was 100%. Two analytical LC/MS injections were used to determine the final purity. Injection 1 conditions: Column: Waters BEH C18, 2.0×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7-µm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Proton NMR was acquired in deuterated DMSO.

LC-MS retention time: 1.74 min; m/z (MH+): 577. LC data was recorded on a Shimadzu LC-10AS liquid chromatograph equipped with a Phenomenex-Luna 3 u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 10% acetonitrile/90% H₂O/0.1% trifluoroacetic acid and solvent B was 10% H₂O/90% acetonitrile/0.1% trifluoroacetic acid. MS data was determined using a Micromass Platform for LC in electrospray mode.

¹H NMR (500 MHz, DMSO-d₆) 9.03 (s, 1H), 8.60 (d, J=4.3 Hz, 1H), 8.19 (s, 1H), 8.12-8.05 (m, 2H), 7.98 (s, 1H), 7.89 (d, J=7.0 Hz, 1H), 7.79 (d, J=7.3 Hz, 1H), 7.57 (t, J=7.8 Hz, 1H), 7.43 (t, J=8.9 Hz, 2H), 3.23 (s, 3H), 2.84 (d, J=4.3 Hz, 3H), 2.47 (s, 1H), 2.11 (s, 6H), 0.84 (t, J=7.2 Hz, 3H) Note: The missing ethyl sulfonamide methylene proton signal (expected quartet integrating for 2 protons) is presumed to be obscured by a large water peak at 3.37 ppm. See following example for very close analogue.

Preparation of 5-(3-(bicyclo[1.1.1]pentan-1-ylcarbamoyl)phenyl)-2-(4-fluorophenyl)-N-methyl-6-(N-(2,2,2-trifluoroethyl)methylsulfonamido)furo[2,3-b]pyridine-3-carboxamide

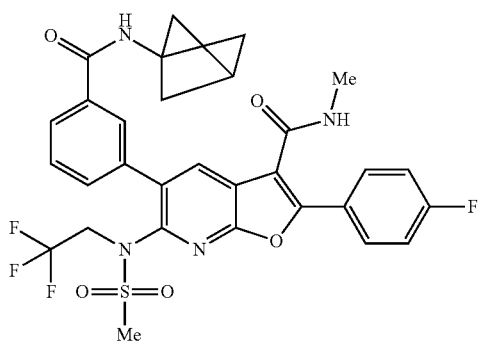

Chemical Formula: C₃₀H₂₆F₄N₄O₅S
Molecular Weight: 630.61

2,2,2-trifluoroethyl trifluoromethanesulfonate (40 µl, 0.27 mmol) was added to a stirring solution of cesium carbonate (71 mg, 0.22 mmol) and 5-(3-(bicyclo[1.1.1]pentan-1-ylcarbamoyl)phenyl)-2-(4-fluorophenyl)-N-methyl-6-(methylsulfonamido)furo[2,3-b]pyridine-3-carboxamide (30 mg, 0.055 mmol) in DMF (0.5 ml) at rt. The reaction was heated to 60° C. for 36 h. The crude material was purified via preparative LC/MS with the following conditions: Column: Waters XBridge C18, 19×200 mm, 5-µm particles; Mobile Phase A: water with 20-mM ammonium acetate; Mobile Phase B: 95:5 acetonitrile:water with 20-mM ammonium acetate; Gradient: 40-80% B over 20 minutes, then a 5-minute hold at 100% B; Flow: 20 mL/min. Fractions containing the desired product were combined and dried via centrifugal evaporation. The yield of the product was 3.1 mg, and its estimated purity by LCMS analysis was 92%. Two analytical LC/MS injections were used to determine the final purity. Injection 1 conditions: Column: Waters BEH C18, 2.0×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7-µm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Proton NMR was acquired in deuterated DMSO.

$^1$H NMR (500 MHz, DMSO-d$_6$) 9.00 (s, 1H), 8.63-8.57 (m, 1H), 8.20 (s, 1H), 8.11-8.05 (m, 2H), 7.98 (s, 1H), 7.90 (d, J=7.9 Hz, 1H), 7.74 (d, J=7.9 Hz, 1H), 7.57 (t, J=7.8 Hz, 1H), 7.43 (t, J=9.0 Hz, 2H), 4.41-4.20 (m, 2H), 3.22 (s, 3H), 2.83 (d, J=4.6 Hz, 3H), 2.47 (s, 1H), 2.11 (s, 6H)

Biological Methods

HCV NS5B RdRp Cloning, Expression, and Purification.

The cDNA encoding NS5B proteins of HCV genotype 1b (Con1), a genotype 1b variant with amino acid 316 mutated from cysteine to asparagine, and genotype 2a (JFH-1), were cloned into the pET21a expression vector. Each untagged protein was expressed with an 18 amino acid C-terminal truncation to enhance the solubility. The E. coli competent cell line BL21(DE3) was used for expression of the protein. Cultures were grown at 37° C. for ~4 hours until the cultures reached an optical density of 2.0 at 600 nm. The cultures were cooled to 20° C. and induced with 1 mM IPTG. Fresh ampicillin was added to a final concentration of 50 µg/mL and the cells were grown overnight at 20° C.

Cell pellets (3 L) were lysed for purification to yield 15-24 mgs of purified NS5B. The lysis buffer consisted of 20 mM Tris-HCl, pH 7.4, 500 mM NaCl, 0.5% triton X-100, 1 mM DTT, 1 mM EDTA, 20% glycerol, 0.5 mg/mL lysozyme, 10 mM MgCl$_2$, 15 ug/mL deoxyribonuclease I, and Complete™ protease inhibitor tablets (Roche). After addition of the lysis buffer, frozen cell pellets were resuspended using a tissue homogenizer. To reduce the viscosity of the sample, aliquots of the lysate were sonicated on ice using a microtip attached to a Branson sonicator. The sonicated lysate was centrifuged at 100,000×g for 30 minutes at 4° C. and filtered through a 0.2 µm filter unit (Corning).

The protein was purified using two sequential chromatography steps: Heparin sepharose CL-6B and polyU sepharose 4B. The chromatography buffers were identical to the lysis buffer but contained no lysozyme, deoxyribonuclease I, MgCl$_2$ or protease inhibitor and the NaCl concentration of the buffer was adjusted according to the requirements for charging the protein onto the column. Each column was eluted with a NaCl gradient which varied in length from 5-50 column volumes depending on the column type. After the final chromatography step, the resulting purity of the enzyme is >90% based on SDS-PAGE analysis. The enzyme was aliquoted and stored at −80° C.

HCV NS5B RdRp Enzyme Assay.

An on-bead solid phase homogeneous assay was used in a 384-well format to assess NS5B inhibitors (WangY-K, Rigat K, Roberts S, and Gao M (2006) Anal Biochem, 359: 106-111). The biotinylated oligo dT$_{12}$ primer was captured on streptavidin-coupled imaging beads (GE, RPNQ0261) by mixing primer and beads in 1× buffer and incubating at room temperature for three hours. Unbound primer was removed after centrifugation. The primer-bound beads were resuspended in 3× reaction mix (20 mM Hepes buffer, pH 7.5, dT primer coupled beads, poly A template, $^3$H-UTP, and RNAse inhibitor (Promega N2515)). Compounds were serially diluted 1:3 in DMSO and aliquoted into assay plates. Equal volumes (5 µL) of water, 3× reaction mix, and enzyme in 3× assay buffer (60 mM Hepes buffer, pH 7.5, 7.5 mM MgCl$_2$, 7.5 mM KCl, 3 mM DTT, 0.03 mg/mL BSA, 6% glycerol) were added to the diluted compound on the assay plate. Final concentration of components in 384-well assay: 0.36 nM template, 15 nM primer, 0.29 µM $^3$H-UTP (0.3 µCi, 1.6 U/µL RNAse inhibitor, 7 nM NS5B enzyme, 0.01 mg/mL BSA, 1 mM DTT, and 0.33 µg/µL beads, 20 mM Hepes buffer, pH 7.5, 2.5 mM MgCl$_2$, 2.5 mM KCl, and 0.1% DMSO.

Reactions were allowed to proceed for 24 hours at 30° C. and terminated by the addition of 50 mM EDTA (5 µL). After incubating for at least 15 minutes, plates were read on an Amersham LEADseeker multimodality imaging system.

IC$_{50}$ values for compounds were determined using ten different [I]. IC$_{50}$ values were calculated from the inhibition using the four-parameter logistic formula y=A+((B−A)/(1+((C/x)^D))), where A and B denote minimal and maximal % inhibition, respectively, C is the IC$_{50}$, D is hill slope and x represents compound concentration.

Cell Lines.

The cell lines used to evaluate compounds consist of a human hepatocyte derived cell line (Huh-7) that constitutively expresses a genotype 1b (Con-1) HCV replicon or a genotype 1b (Con-1) HCV replicon with an asparagine replacing the cysteine at amino acid 316, or a genotype 2a (JFH-1) replicon, containing a Renilla luciferase reporter gene. These cells were maintained in Dulbecco's modified Eagle medium (DMEM) containing 10% FBS, 100 U/mL penicillin/streptomycin and 1.0 mg/mL G418.

HCV Replicon Luciferase Assay.

To evaluate compound efficacy, titrated compounds were transferred to sterile 384-well tissue culture treated plates, and the plates were seeded with HCV replicon cells (50 µt at a density of 2.4×10$^3$ cells/well) in DMEM containing 4% FBS (final DMSO concentration at 0.5%). After 3 days incubation at 37° C., cells were analyzed for Renilla Luciferase activity using the EnduRen substrate (Promega cat #E6485) according to the manufacturer's directions. Briefly, the EnduRen substrate was diluted in DMEM and then added to the plates to a final concentration of 7.5 µM. The plates were incubated for at least 1 h at 37° C. then read on a Viewlux Imager (PerkinElmer) using a luminescence program. The 50% effective concentration (EC$_{50}$) was calculated using using the four-parameter logistic formula noted above.

To assess cytotoxicity of compounds, Cell Titer-Blue (Promega) was added to the EnduRen-containing plates and incubated for at least 4 h at 37° C. The fluorescence signal from each well was read using a Viewlux Imager. All $CC_{50}$ values were calculated using the four-parameter logistic formula.

1b replicon and enzyme data for compound I is reported in Table 2.

TABLE 2

| Structure | $IC_{50}$ (µM) | *$EC_{50}$ (µM) |
|---|---|---|
| 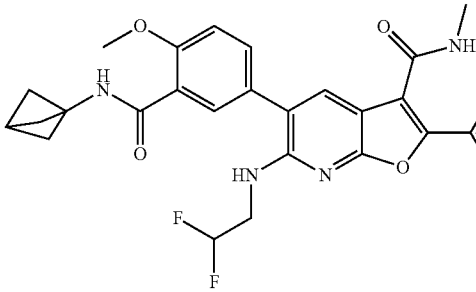 | 8.87E−03 | 6.23E−03 |
| 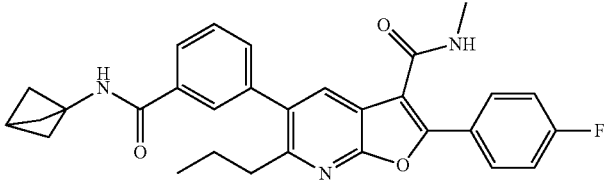 [SMILES: CCCc1nc2oc(-c3ccc(F)cc3)c(C(=O)NC)c2cc1-c1cccc(C(=O)NC23CC(C2)C3)c1] | 7.73E−03 | 5.26E−03 |
| 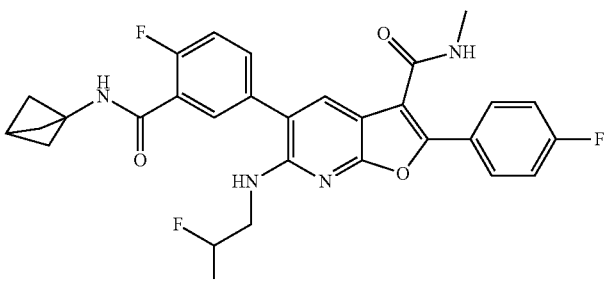 | 6.13E−03 | 2.13E−03 |
| 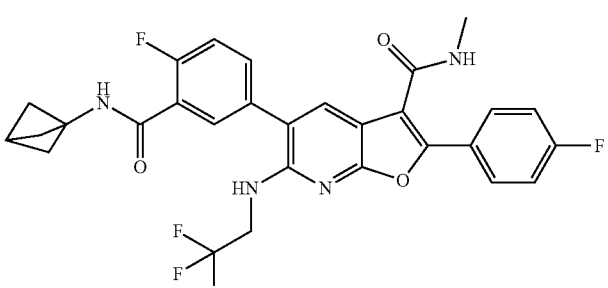 | 9.08E−03 | 4.34E−03 |
| 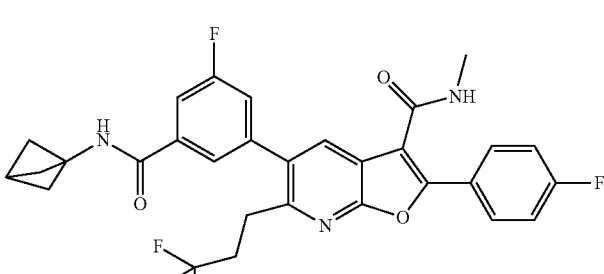 | 0.03 | 0.01 |

TABLE 2-continued
| Structure | IC$_{50}$ (μM) | *EC$_{50}$ (μM) |
|---|---|---|
| 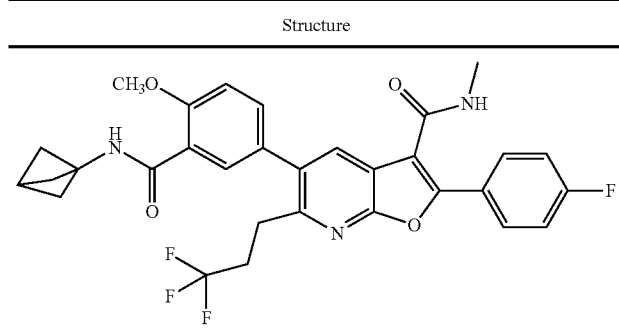 | 0.01 | 9.23E−03 |
| 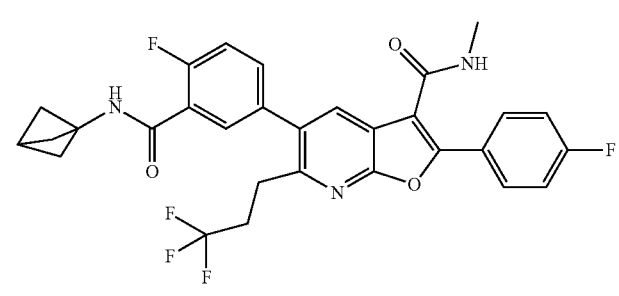 [SMILES: CNC(=O)c1c(-c2ccc(F)cc2)oc2nc(CCC(F)(F)F)c(-c3ccc(F)c(C(=O)NC45CC(C4)C5)c3)cc12] | 9.40E−03 | 5.05E−03 |
| 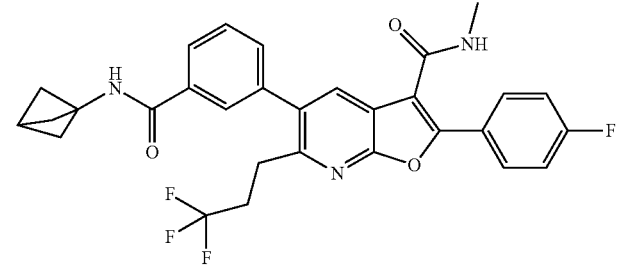 [SMILES: CNC(=O)c1c(-c2ccc(F)cc2)oc2nc(CCC(F)(F)F)c(-c3cccc(C(=O)NC45CC(C4)C5)c3)cc12] | 5.85E−03 | 4.07E−03 |
| 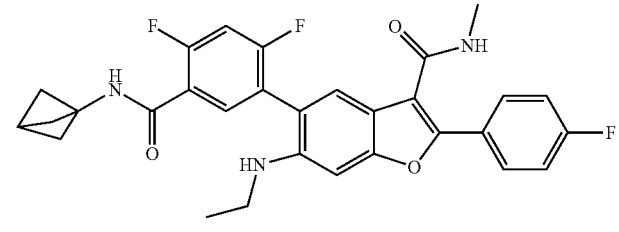 [SMILES: CCNc1cc2oc(-c3ccc(F)cc3)c(C(=O)NC)c2cc1-c1cc(C(=O)NC23CC(C2)C3)c(F)cc1F] | 0.02 | 0.01 |
| 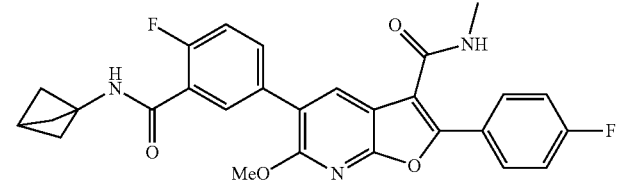 [SMILES: CNC(=O)c1c(-c2ccc(F)cc2)oc2nc(OC)c(-c3ccc(F)c(C(=O)NC45CC(C4)C5)c3)cc12] | 0.09 | 0.02 |
| 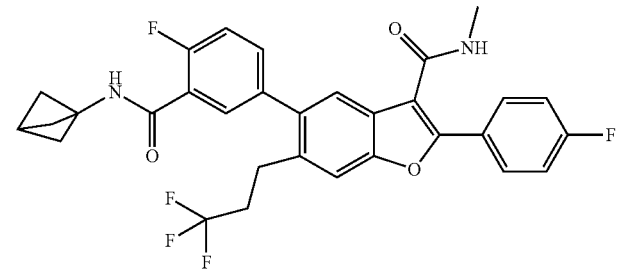 [SMILES: CNC(=O)c1c(-c2ccc(F)cc2)oc2cc(CCC(F)(F)F)c(-c3ccc(F)c(C(=O)NC45CC(C4)C5)c3)cc12] | 0.03 | 0.01 |

TABLE 2-continued

| Structure | IC$_{50}$ (μM) | *EC$_{50}$ (μM) |
|---|---|---|
| | 0.02 | |
| | 0.02 | 3.30E−03 |
| 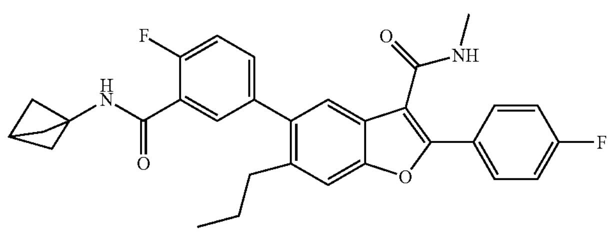 [SMILES: CCCc1cc2oc(-c3ccc(F)cc3)c(C(=O)NC)c2cc1-c1ccc(F)c(C(=O)NC23CC(C2)C3)c1] | 0.01 | 8.79E−03 |
| | 0.02 | 3.72E−03 |
| 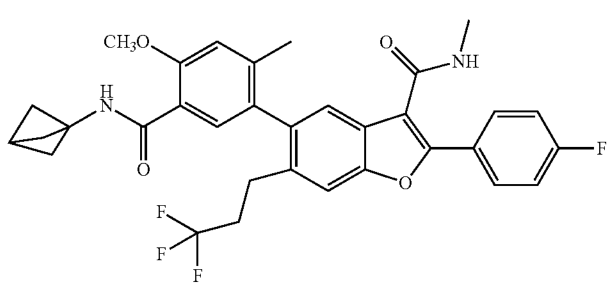 | 0.05 | 0.04 |

TABLE 2-continued
| Structure | IC$_{50}$ (μM) | *EC$_{50}$ (μM) |
|---|---|---|
| 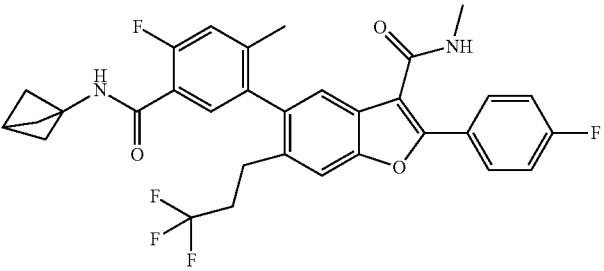 [SMILES: CNC(=O)c1c(-c2ccc(F)cc2)oc2cc(CCC(F)(F)F)c(-c3cc(C(=O)NC45CC(C4)C5)c(F)cc3C)cc12] | 0.02 | 0.02 |
| 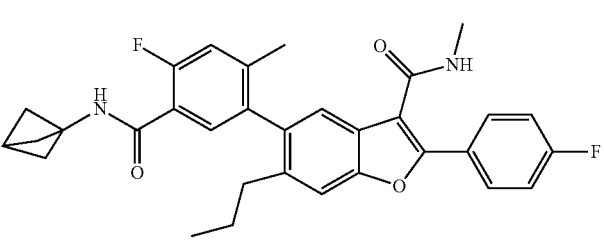 [SMILES: CCCc1cc2oc(-c3ccc(F)cc3)c(C(=O)NC)c2cc1-c1cc(C(=O)NC23CC(C2)C3)c(F)cc1C] | 0.02 | 0.03 |
| 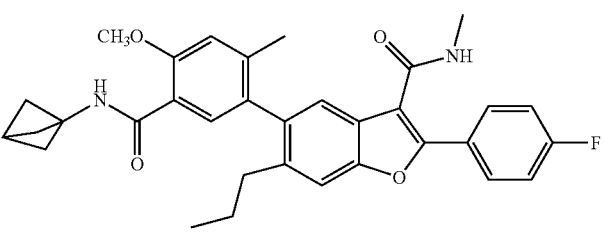 | 0.03 | 0.03 |
| 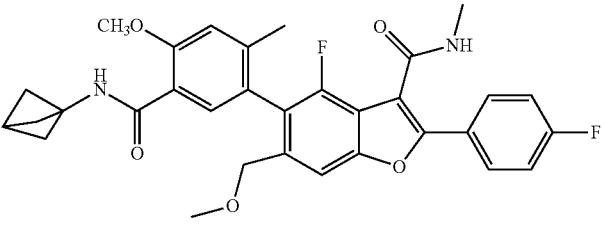 | 0.03 | 0.03 |
| 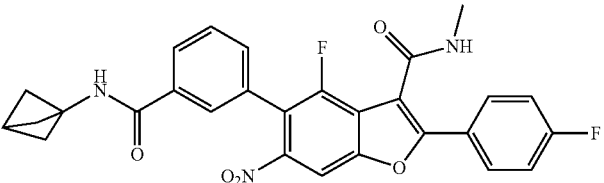 | 0.68 | 0.17 |
| 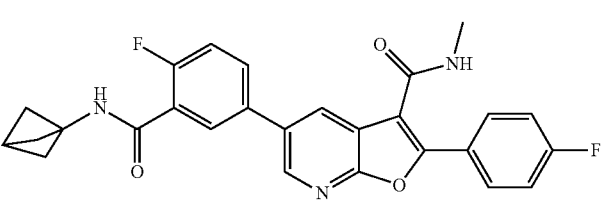 [SMILES: CNC(=O)c1c(-c2ccc(F)cc2)oc2ncc(-c3ccc(F)c(C(=O)NC45CC(C4)C5)c3)cc12] | 0.22 | 0.05 |
| 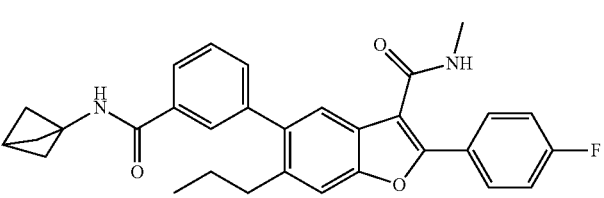 [SMILES: CCCc1cc2oc(-c3ccc(F)cc3)c(C(=O)NC)c2cc1-c1cccc(C(=O)NC23CC(C2)C3)c1] | 0.02 | 5.82E−03 |

TABLE 2-continued

| Structure | IC$_{50}$ (μM) | *EC$_{50}$ (μM) |
|---|---|---|
| 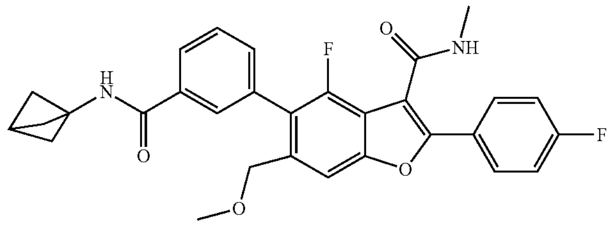 [SMILES: CNC(=O)c1c(-c2ccc(F)cc2)oc2cc(COC)c(-c3cccc(C(=O)NC45CC(C4)C5)c3)c(F)c12] | 0.21 | 7.88E−03 |
| 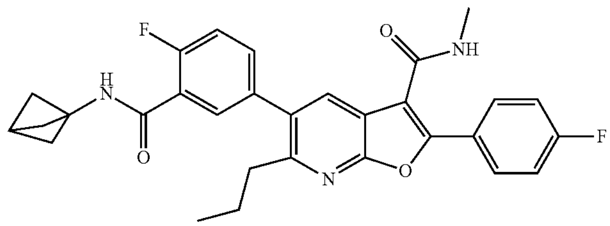 | 5.65E−03 | 5.16E−03 |
| 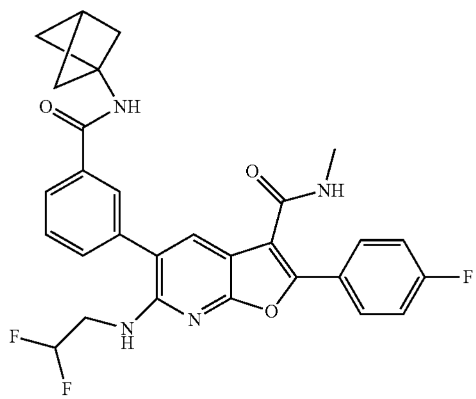 [SMILES: CNC(=O)c1c(-c2ccc(F)cc2)oc2nc(NCC(F)F)c(-c3cccc(C(=O)NC45CC(C4)C5)c3)cc12] | 8.63E−03 | 4.30E−03 |
| 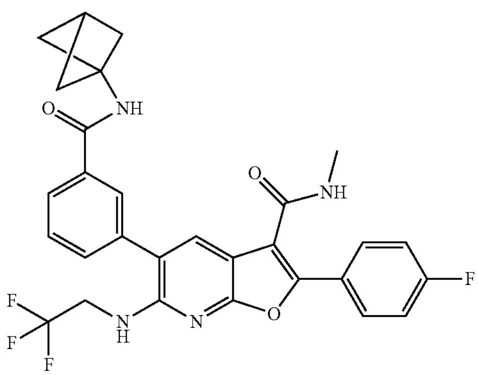 [SMILES: CNC(=O)c1c(-c2ccc(F)cc2)oc2nc(NCC(F)(F)F)c(-c3cccc(C(=O)NC45CC(C4)C5)c3)cc12] | 7.11E−03 | 3.58E−03 |
| 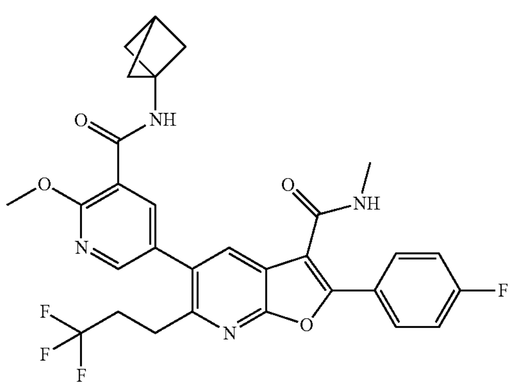 [SMILES: CNC(=O)c1c(-c2ccc(F)cc2)oc2nc(CCC(F)(F)F)c(-c3cnc(OC)c(C(=O)NC45CC(C4)C5)c3)cc12] | 3.65E−03 | 6.48E−03 |

TABLE 2-continued
| Structure | IC$_{50}$ (µM) | *EC$_{50}$ (µM) |
|---|---|---|
| 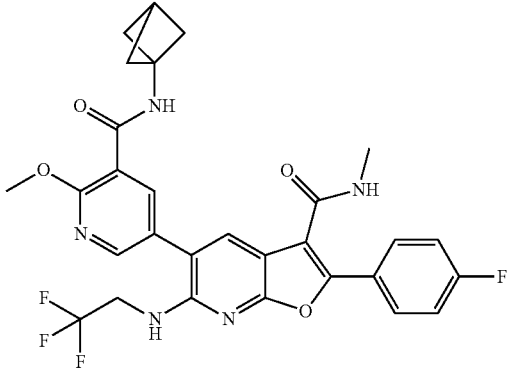 [SMILES: CNC(=O)c1c(-c2ccc(F)cc2)oc2nc(NCC(F)(F)F)c(-c3cnc(OC)c(C(=O)NC45CC(C4)C5)c3)cc12] | 6.54E−03 | 5.79E−03 |
| 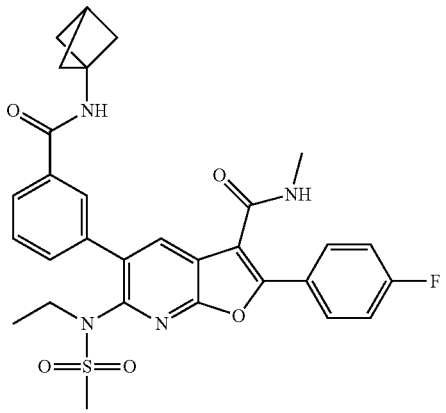 [SMILES: CCN(c1nc2oc(-c3ccc(F)cc3)c(C(=O)NC)c2cc1-c1cccc(C(=O)NC23CC(C2)C3)c1)S(C)(=O)=O] | 6.80E−03 | 2.85E−03 |
| 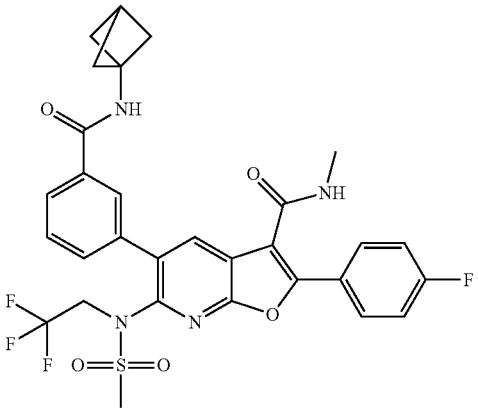 [SMILES: CNC(=O)c1c(-c2ccc(F)cc2)oc2nc(N(CC(F)(F)F)S(C)(=O)=O)c(-c3cccc(C(=O)NC45CC(C4)C5)c3)cc12] | 0.02 | |
| 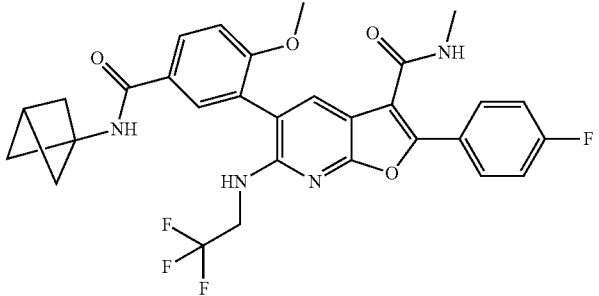 [SMILES: CNC(=O)c1c(-c2ccc(F)cc2)oc2nc(NCC(F)(F)F)c(-c3cc(C(=O)NC45CC(C4)C5)ccc3OC)cc12] | 9.14E−03 | |

TABLE 2-continued
| Structure | IC$_{50}$ (μM) | *EC$_{50}$ (μM) |
|---|---|---|
| 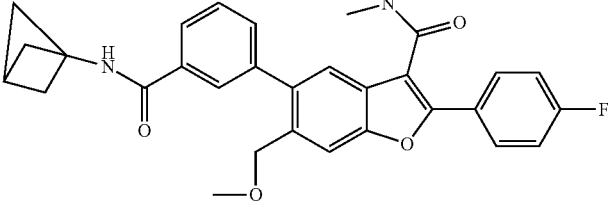 | | 6.21E−03 |
| 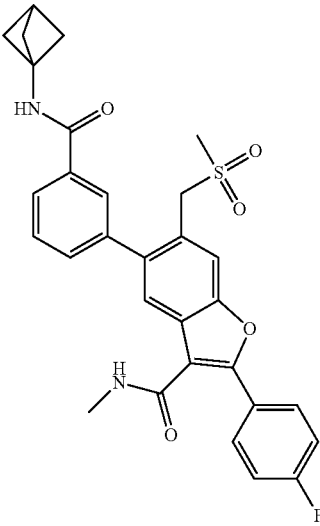 [SMILES: CNC(=O)c1c(-c2ccc(F)cc2)oc2cc(CS(C)(=O)=O)c(-c3cccc(C(=O)NC45CC(C4)C5)c3)cc12] | | 0.07 |
| 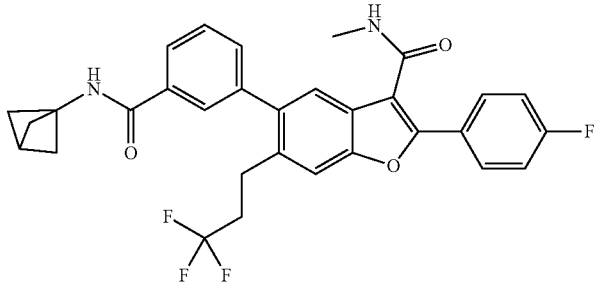 [SMILES: CNC(=O)c1c(-c2ccc(F)cc2)oc2cc(CCC(F)(F)F)c(-c3cccc(C(=O)NC45CC(C4)C5)c3)cc12] | | 0.03 |
| 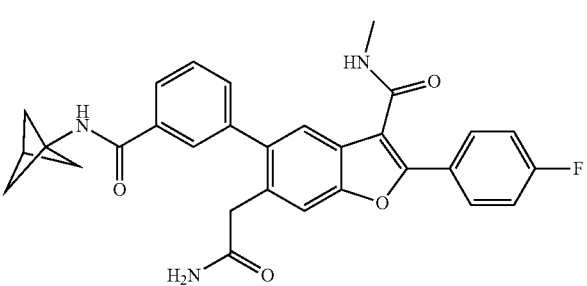 [SMILES: CNC(=O)c1c(-c2ccc(F)cc2)oc2cc(CC(N)=O)c(-c3cccc(C(=O)NC45CC(C4)C5)c3)cc12] | 0.04 | 0.02 |

TABLE 2-continued
| Structure | IC$_{50}$ (μM) | *EC$_{50}$ (μM) |
|---|---|---|
| 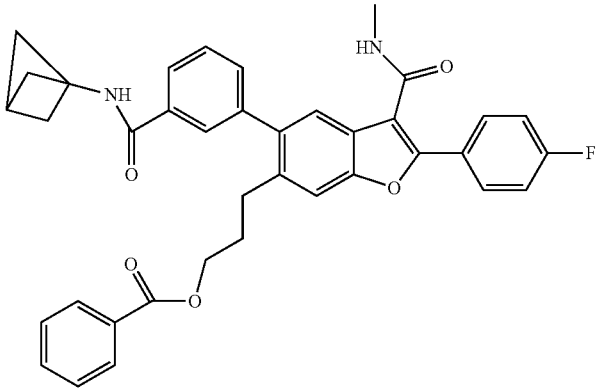 [SMILES: CNC(=O)c1c(-c2ccc(F)cc2)oc2cc(CCCOC(=O)c3ccccc3)c(-c3cccc(C(=O)NC45CC(C4)C5)c3)cc12] | | 0.14 |
| 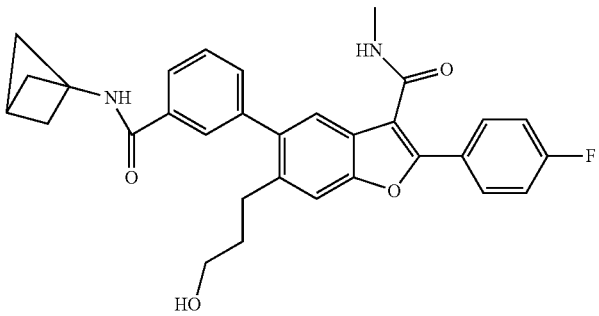 [SMILES: CNC(=O)c1c(-c2ccc(F)cc2)oc2cc(CCCF)c(-c3cccc(C(=O)NC45CC(C4)C5)c3)cc12] | 9.56E−03 | 3.86E−03 |
| 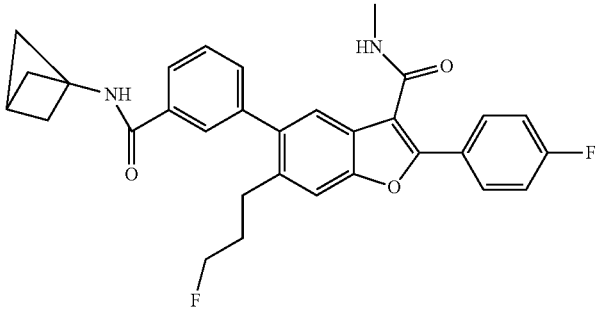 | 3.29E−03 | 3.33E−03 |
| 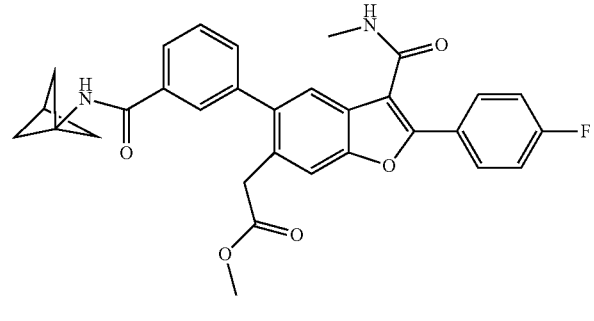 | 8.01E−03 | 8.19E−03 |
| 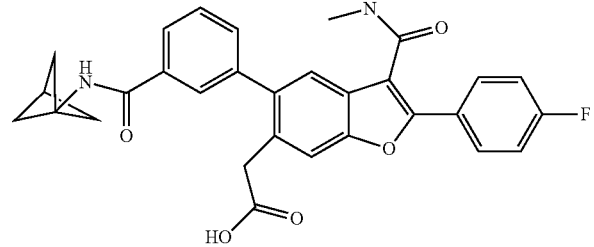 | | >10.00 |

TABLE 2-continued

| Structure | IC$_{50}$ (μM) | *EC$_{50}$ (μM) |
|---|---|---|
| | | 8.09 |
| 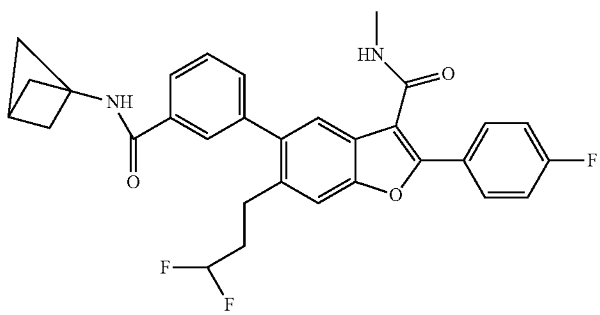 [SMILES: CNC(=O)c1c(-c2ccc(F)cc2)oc2cc(CCC(F)F)c(-c3cccc(C(=O)NC45CC(C4)C5)c3)cc12] | 7.19E-03 | 3.89E-03 |
| 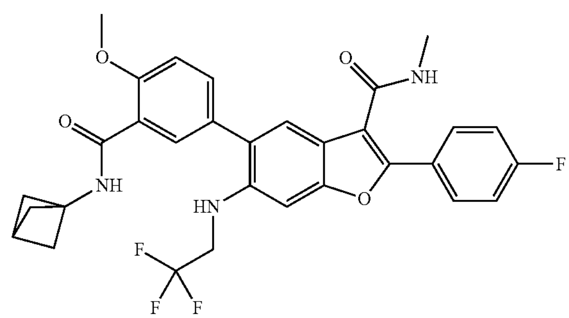 [SMILES: CNC(=O)c1c(-c2ccc(F)cc2)oc2cc(NCC(F)(F)F)c(-c3ccc(OC)c(C(=O)NC45CC(C4)C5)c3)cc12] | 7.17E-03 | 5.08E-03 |
| | | 0.01 |
| 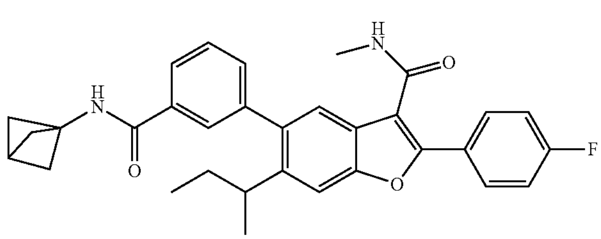 [SMILES: CCC(C)c1cc2oc(-c3ccc(F)cc3)c(C(=O)NC)c2cc1-c1cccc(C(=O)NC23CC(C2)C3)c1] | 0.01 | 0.01 |

TABLE 2-continued
| Structure | IC$_{50}$ (μM) | *EC$_{50}$ (μM) |
|---|---|---|
| 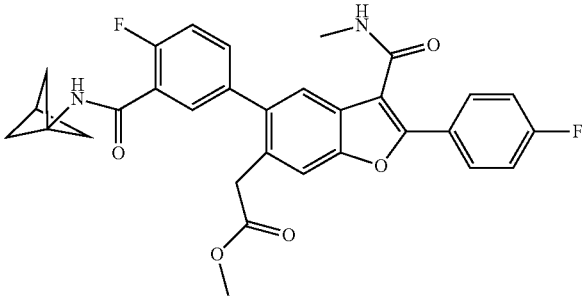 [SMILES: CNC(=O)Cc1cc2oc(-c3ccc(F)cc3)c(C(=O)NC)c2cc1-c1cccc(C(=O)NC23CC(C2)C3)c1] | | 0.02 |
| 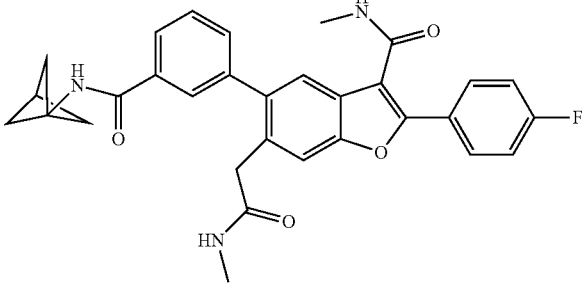 | | 0.05 |
| 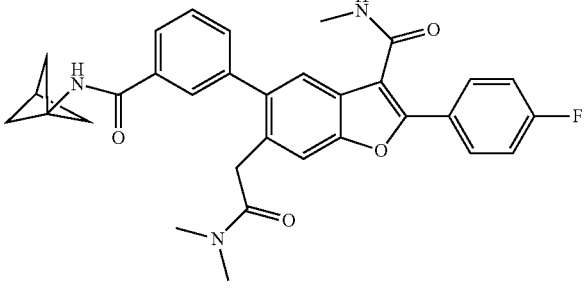 | | 0.31 |
| 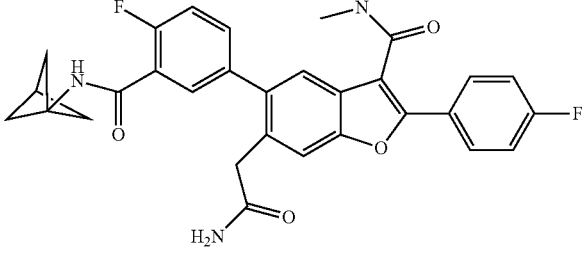 | | 0.01 |
| 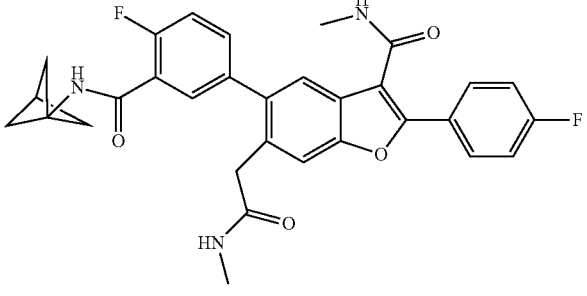 | | 0.05 |

TABLE 2-continued

| Structure | IC$_{50}$ (µM) | *EC$_{50}$ (µM) |
|---|---|---|
| | | 0.01 |
| | | 0.52 |
| | | 0.07 |
| | | 0.04 |
| 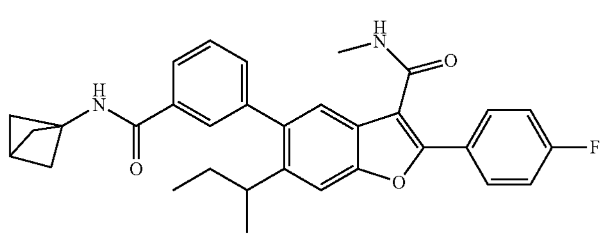 [SMILES: CCC(C)c1cc2oc(-c3ccc(F)cc3)c(C(=O)NC)c2cc1-c1cccc(C(=O)NC23CC(C2)C3)c1] | 5.87E−03 | 0.01 |

TABLE 2-continued

| Structure | IC$_{50}$ (μM) | *EC$_{50}$ (μM) |
|---|---|---|
|  |  | 0.02 |
|  |  | 0.01 |
| 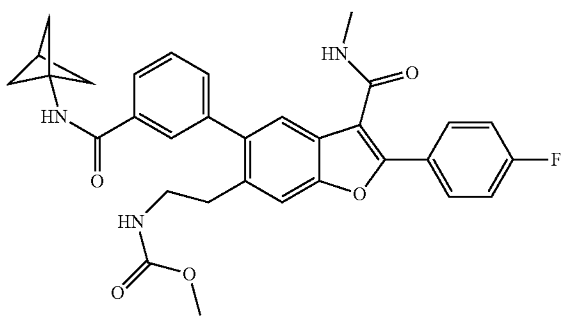 [SMILES: CNC(=O)c1c(-c2ccc(F)cc2)oc2cc(CCNC(=O)OC)c(-c3cccc(C(=O)NC45CC(C4)C5)c3)cc12] | 0.02 | 0.02 |
| 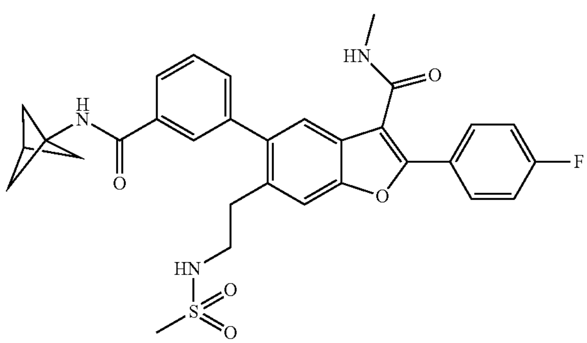 [SMILES: CNC(=O)c1c(-c2ccc(F)cc2)oc2cc(CCNS(C)(=O)=O)c(-c3cccc(C(=O)NC45CC(C4)C5)c3)cc12] | 0.01 | 0.02 |
| 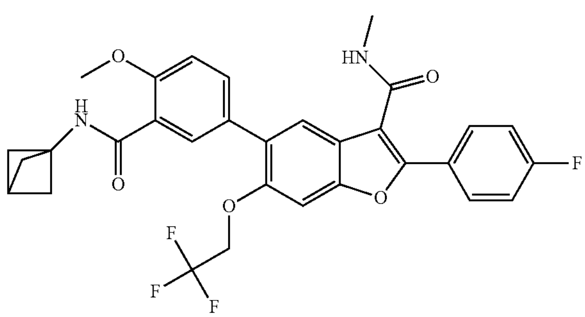 [SMILES: CNC(=O)c1c(-c2ccc(F)cc2)oc2cc(OCC(F)(F)F)c(-c3ccc(OC)c(C(=O)NC45CC(C4)C5)c3)cc12] | 4.55E−03 | 0.01 |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.
We claim:
1. A compound selected from the group consisting of
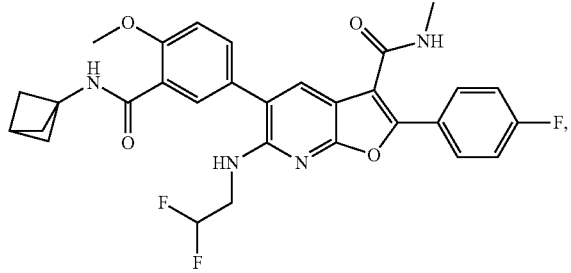
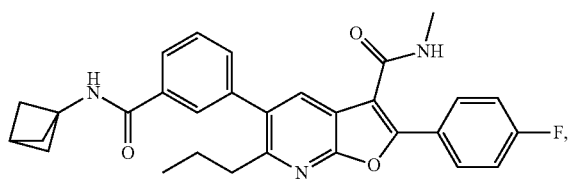
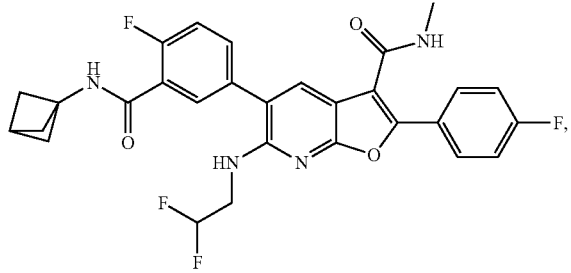
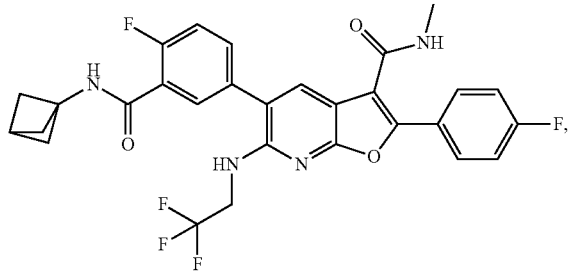
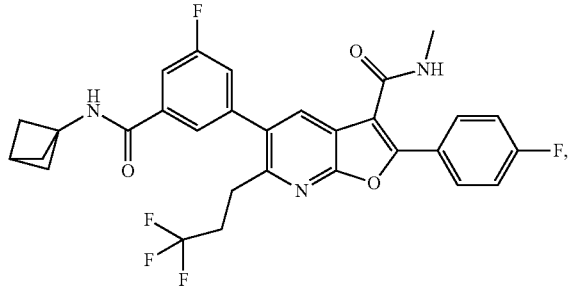
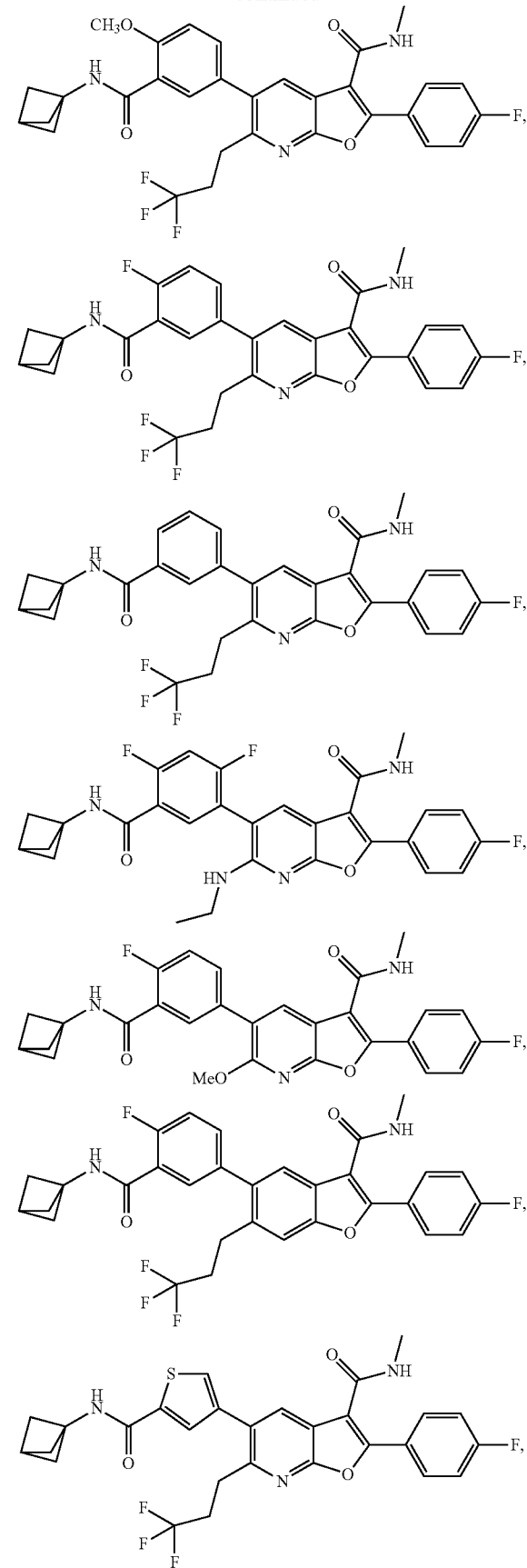

257
-continued
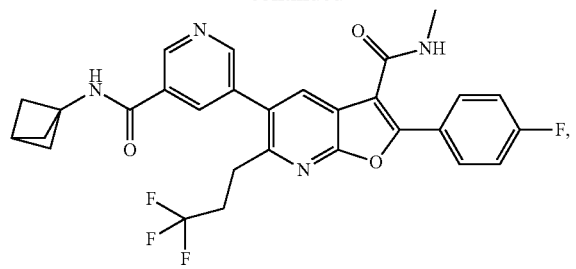
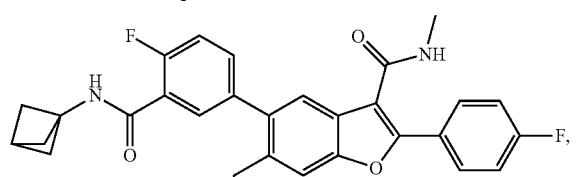
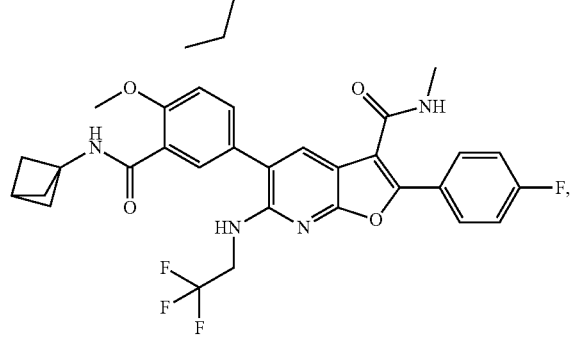
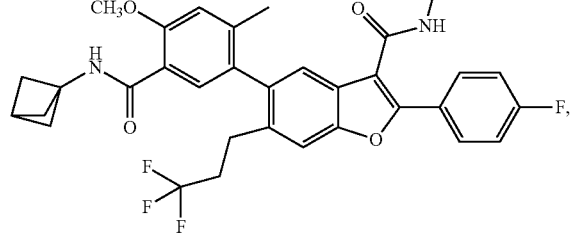
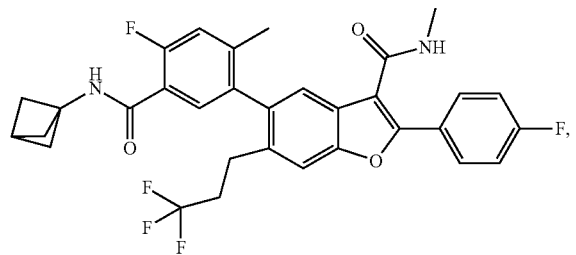
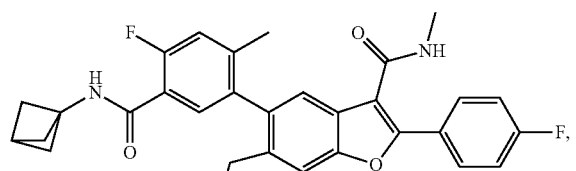
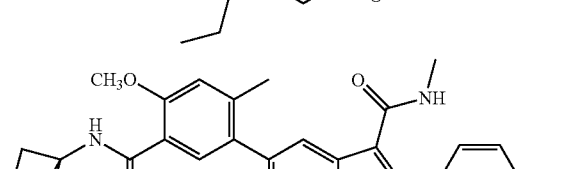
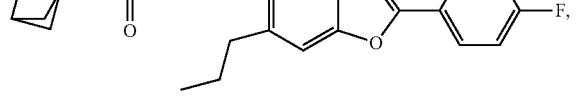
258
-continued
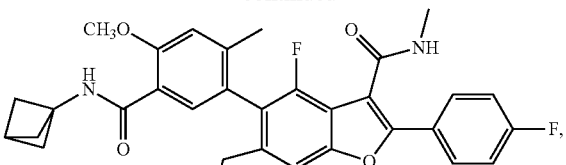
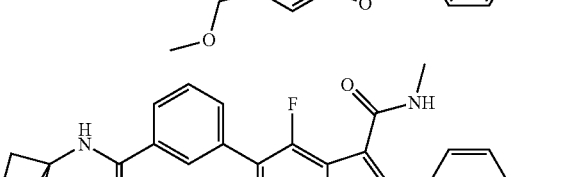
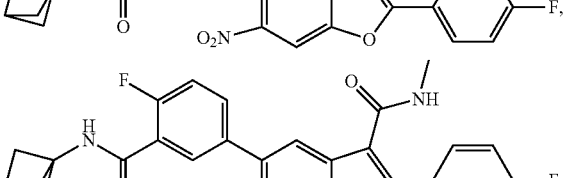
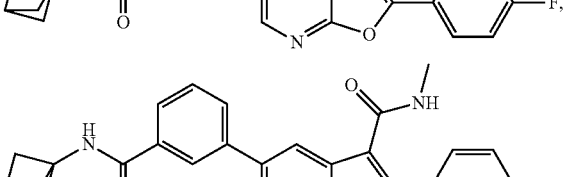
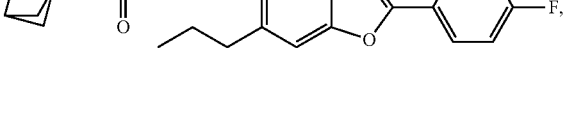
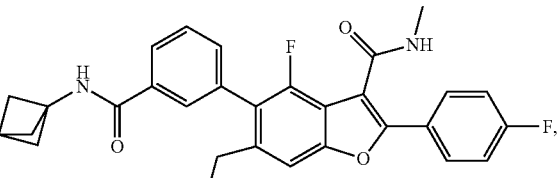
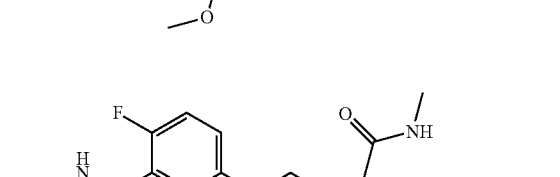
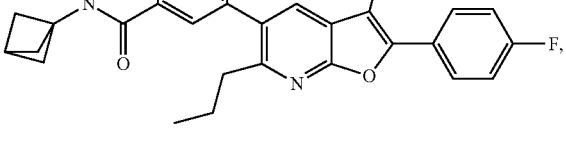
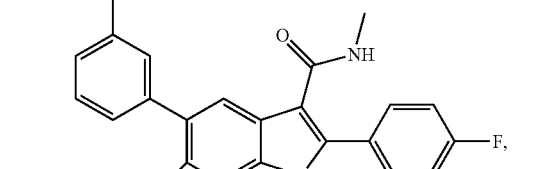
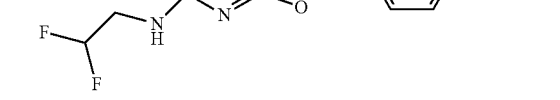

259
-continued
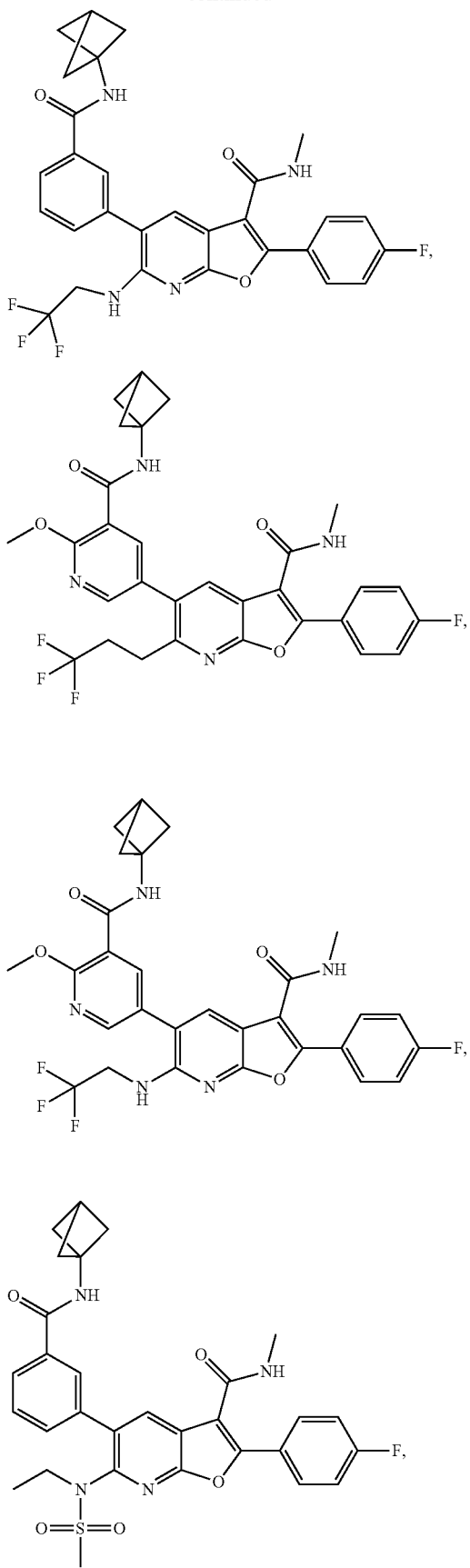
260
-continued
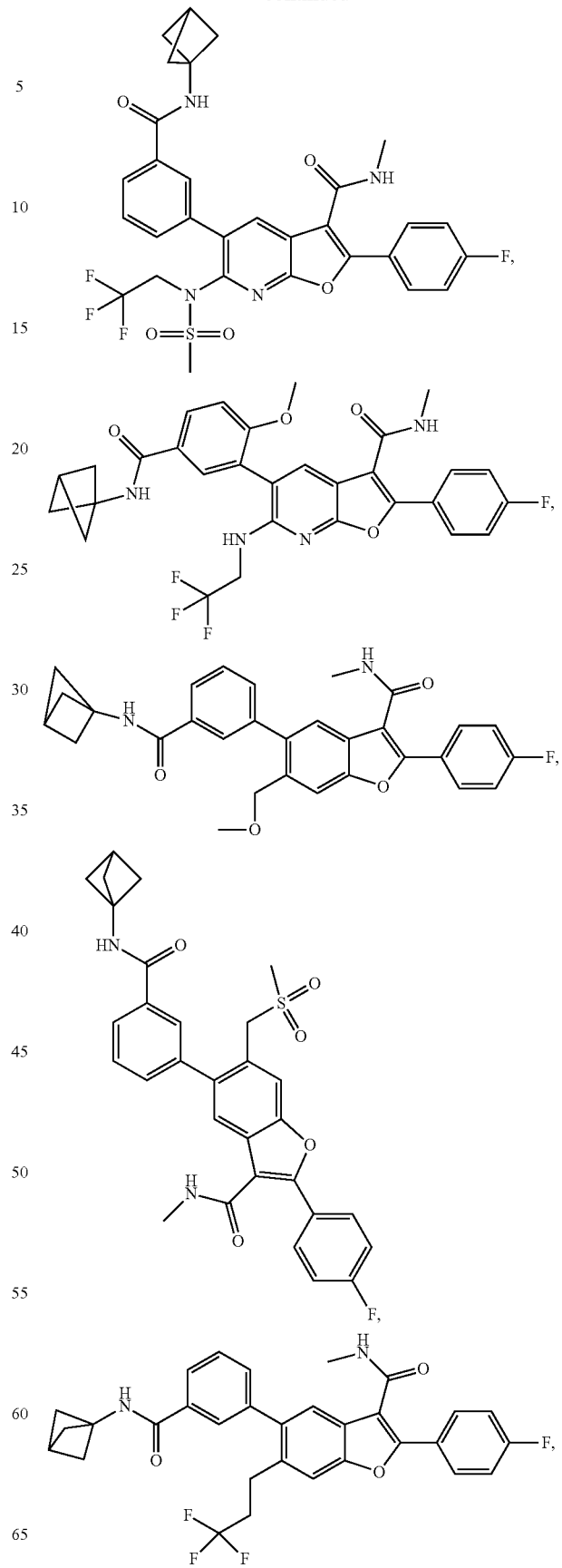

261
-continued
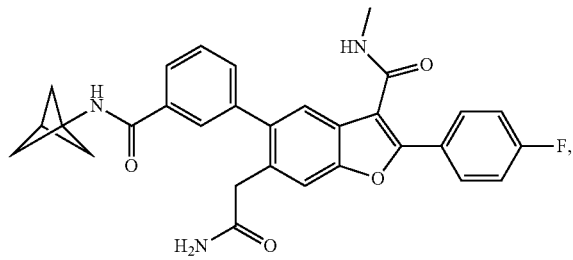
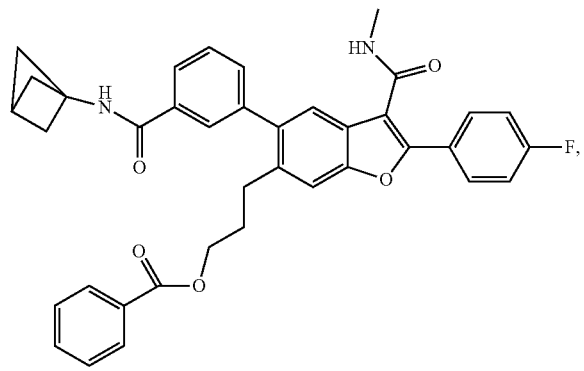
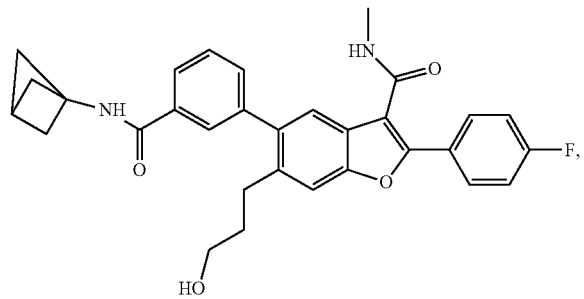
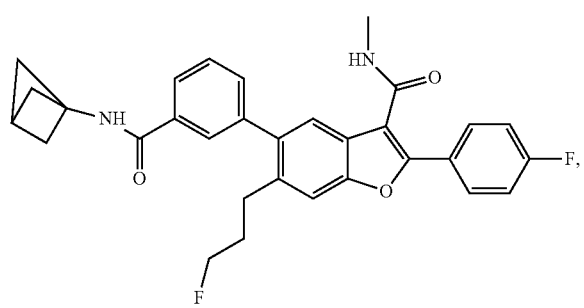
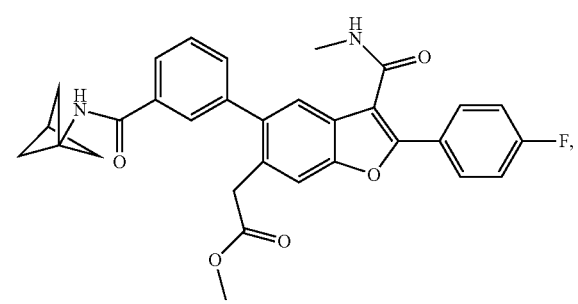
262
-continued
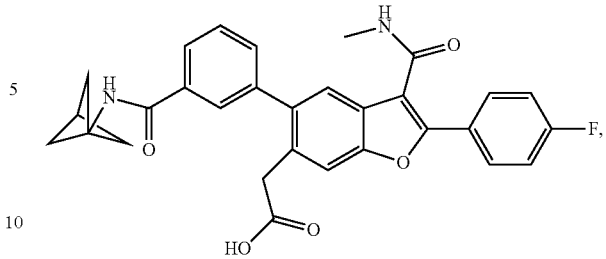
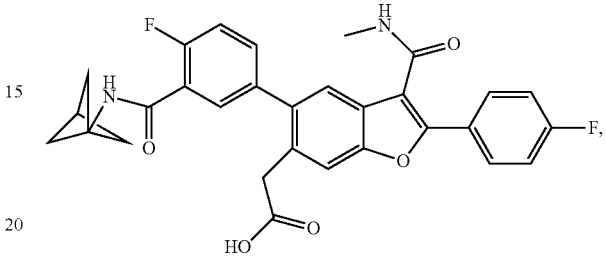
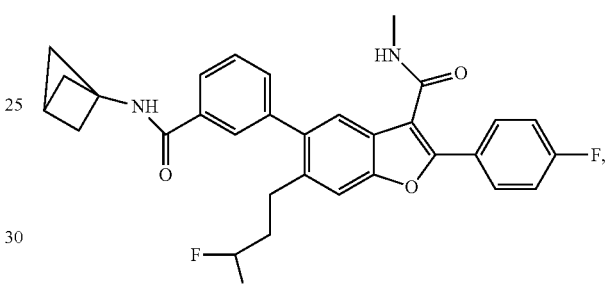
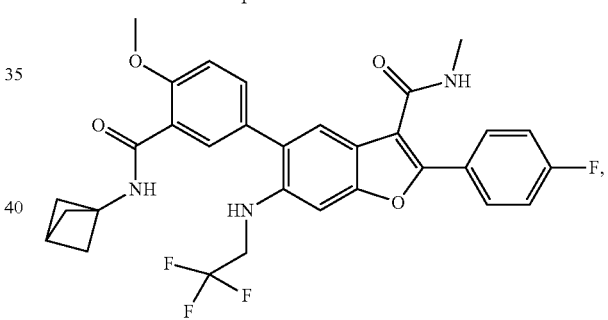
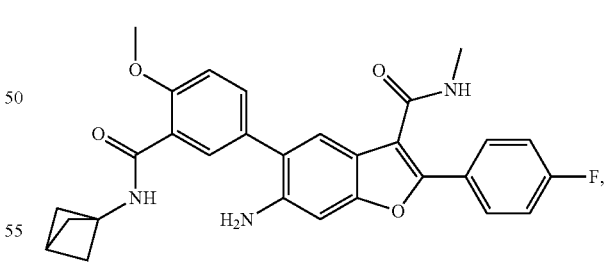
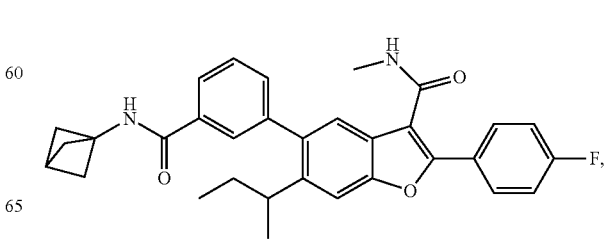

263
-continued
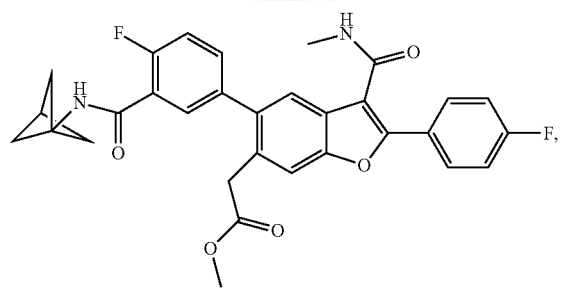
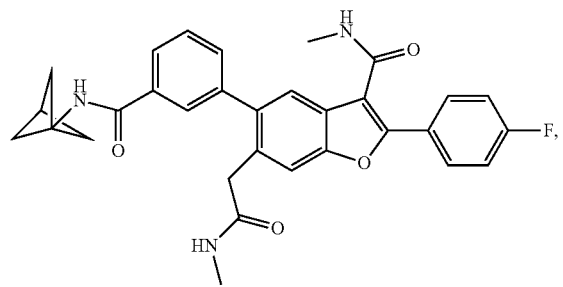
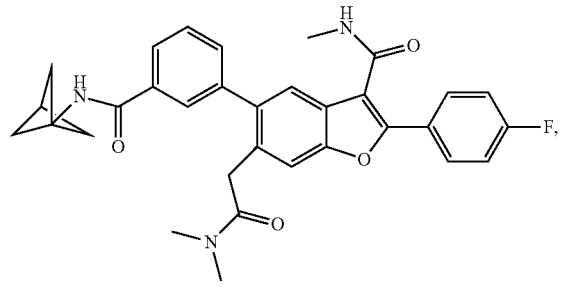
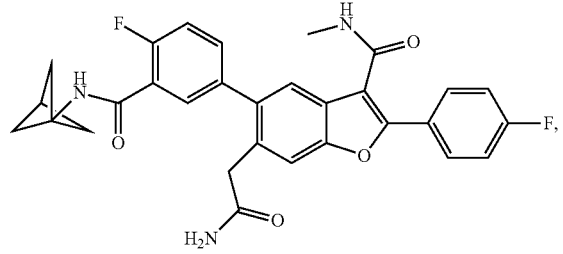
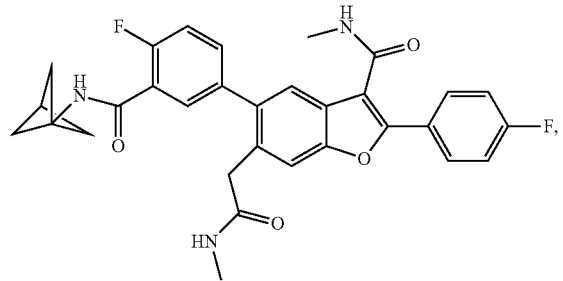
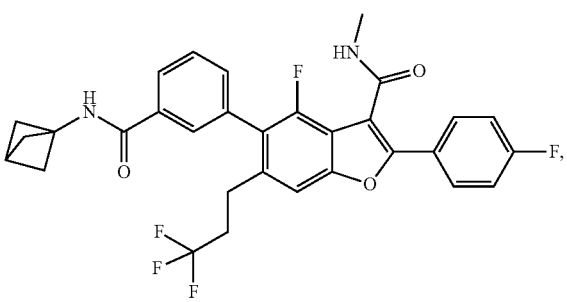
264
-continued
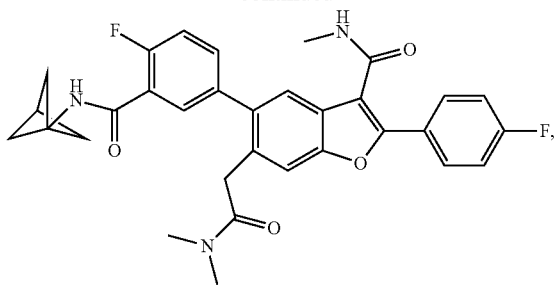
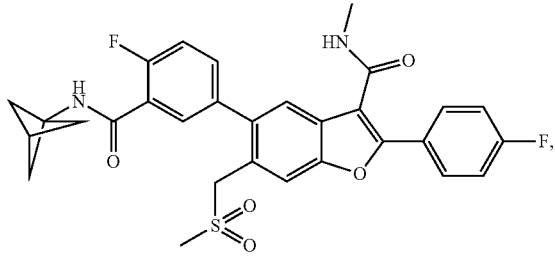
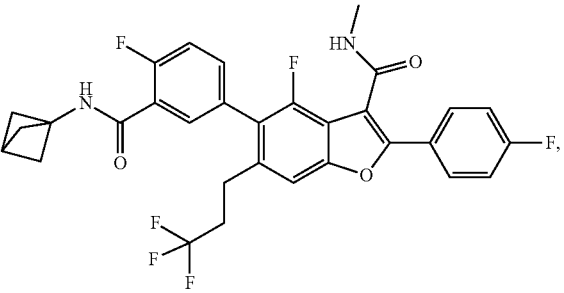
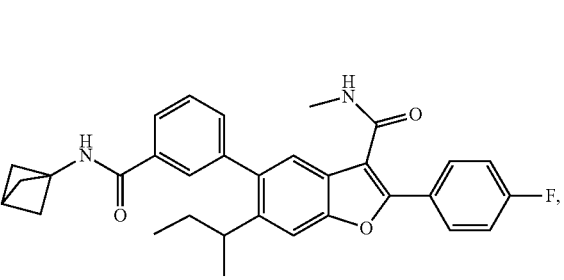
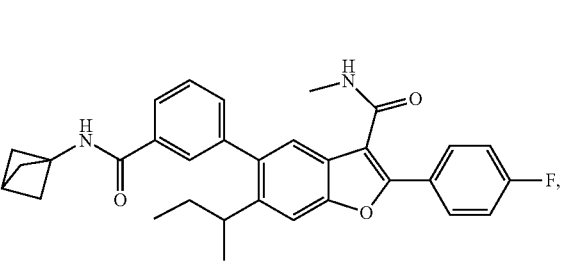
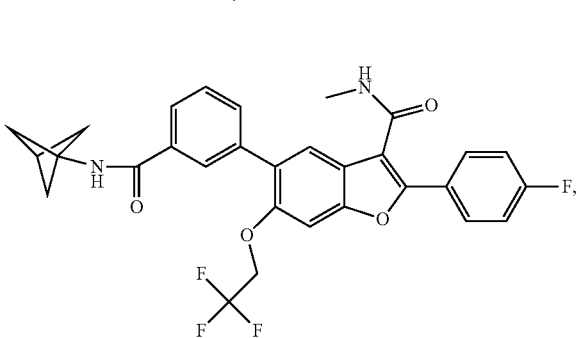

265
-continued
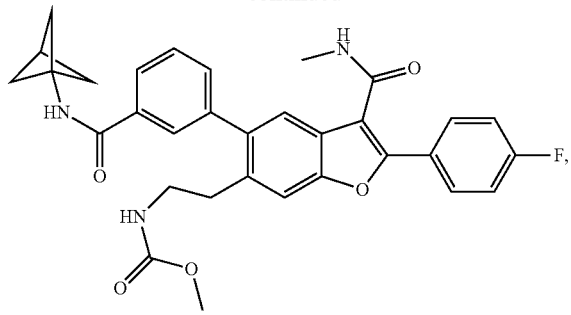
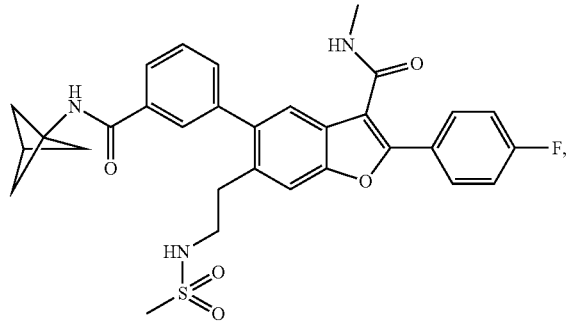
266
-continued
and
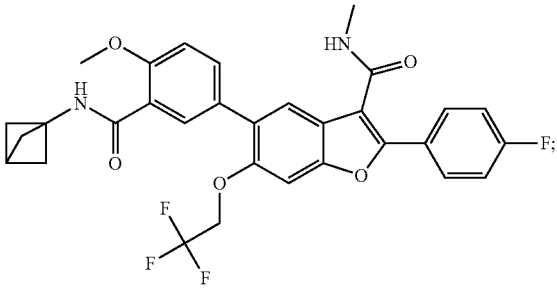
or a pharmaceutically acceptable salt thereof.
2. A composition comprising a compound of claim 1, or a pharmaceutically acceptable salt thereof, and a pharmaceutically acceptable carrier.
3. A method of treating hepatitis C infection comprising administering a therapeutically effective amount of a compound of claim 1 to a patient.
* * * * *

UNITED STATES PATENT AND TRADEMARK OFFICE
CERTIFICATE OF CORRECTION

PATENT NO. : 9,738,653 B2  Page 1 of 1
APPLICATION NO. : 14/773123
DATED : August 22, 2017
INVENTOR(S) : Yeung et al.

It is certified that error appears in the above-identified patent and that said Letters Patent is hereby corrected as shown below:

In the Claims

Claim 1, Column 257, Lines 20-30:

Delete " 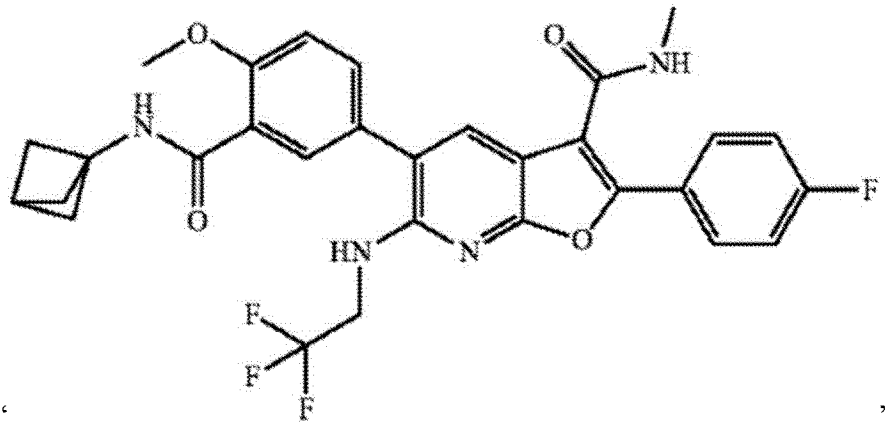 " and insert -- 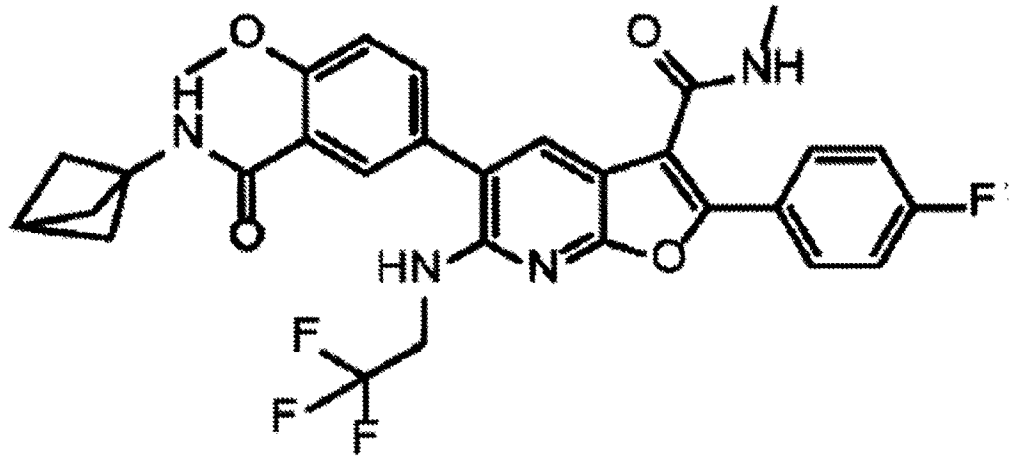 --.

Signed and Sealed this
Ninth Day of October, 2018

Andrei Iancu
*Director of the United States Patent and Trademark Office*